(12) United States Patent
Reeder et al.

(10) Patent No.: US 8,028,355 B2
(45) Date of Patent: Oct. 4, 2011

(54) INTEGRATED BATHROOM ELECTRONIC SYSTEM

(75) Inventors: Ryan A. Reeder, Carmel, IN (US);
Spencer L. Stohler, Anderson, IN (US);
Andrew B. Mendenhall, Mooresville,
IN (US); Paul T. Zink, Indianapolis, IN
(US); Robert W. Rodenbeck,
Indianapolis, IN (US)

(73) Assignee: Masco Corporation of Indiana,
Indianapolis, IN (US)

( * ) Notice: Subject to any disclaimer, the term of this patent is extended or adjusted under 35 U.S.C. 154(b) by 123 days.

(21) Appl. No.: 12/151,769

(22) Filed: May 9, 2008

(65) Prior Publication Data
US 2008/0271238 A1 Nov. 6, 2008

Related U.S. Application Data

(63) Continuation of application No. PCT/US2006/044023, filed on Nov. 13, 2006.

(60) Provisional application No. 60/735,569, filed on Nov. 11, 2005, provisional application No. 60/838,271, filed on Aug. 16, 2006.

(51) Int. Cl.
*E03C 1/05* (2006.01)
(52) U.S. Cl. ..................... 4/623; 4/668; 4/676
(58) Field of Classification Search .............. 4/601, 623, 4/668, 676
See application file for complete search history.

(56) References Cited

U.S. PATENT DOCUMENTS

| | | |
|---|---|---|
| 432,712 A | 7/1890 | Taylor |
| 3,651,989 A | 3/1972 | Westrich |
| 3,987,819 A | 10/1976 | Scheuermann |
| 4,201,518 A | 5/1980 | Stevenson |
| 4,398,789 A | 8/1983 | Pryor |
| 4,406,313 A | 9/1983 | Bennett et al. |
| 4,407,444 A | 10/1983 | Knebel et al. |
| 4,409,694 A | 10/1983 | Barrett, Sr. et al. |
| 4,420,811 A | 12/1983 | Tarnay et al. |
| 4,421,269 A | 12/1983 | Ts'ao |
| 4,563,780 A | 1/1986 | Pollack |
| 4,572,232 A | 2/1986 | Gruber |
| 4,611,757 A | 9/1986 | Saether |
| 4,674,678 A | 6/1987 | Knebel et al. |
| 4,696,428 A | 9/1987 | Shakalis |
| 4,700,884 A | 10/1987 | Barrett et al. |

(Continued)

FOREIGN PATENT DOCUMENTS

CN 2049105 U 12/1989

(Continued)

OTHER PUBLICATIONS

International Search Report and Written Opinion for PCT/US2006/044023, dated Jul. 7, 2008, 10 pgs. Kohler, DTV™ Custom Showering Experience, web pages, circa Apr. 2006, 10 pgs.
The Bold Look of Kohler brochure, Introductions 2006, cover page, pp. 10, 12 and 13, Kohler Co., Kohler, WI.
Got Hot Water, Structured Plumbing® for New Home Construction or Remodeling, retrieved from www.gothotwater.com Dec. 17, 2004, 2 pgs.

(Continued)

*Primary Examiner* — Tuan Nguyen
(74) *Attorney, Agent, or Firm* — Baker & Daniels LLP

(57) ABSTRACT

An integrated bathroom electronic system including a plurality of sensors to detect conditions within a bathroom and to provide signals indicative thereof to a controller. A plurality of distinct and exclusive modules or subsystems are illustratively provided for integration into the system. Such modules may include a quick hot water module, a roman tub module, a custom shower module, a hands free faucet module, and a tub shower module. In certain illustrative shower modules, a user interface includes a plurality of user defined presets, each preset including a shower setting stored in memory.

19 Claims, 88 Drawing Sheets

U.S. PATENT DOCUMENTS

| | | | |
|---|---|---|---|
| 4,700,885 A | 10/1987 | Knebel | |
| 4,742,456 A | 5/1988 | Kamena | |
| 4,756,030 A * | 7/1988 | Juliver | 4/668 |
| 4,842,191 A | 6/1989 | Bergmann | |
| 4,844,333 A | 7/1989 | Davis et al. | |
| 4,854,498 A | 8/1989 | Stayton | |
| 4,869,287 A | 9/1989 | Pepper et al. | |
| 4,869,427 A | 9/1989 | Kawamoto et al. | |
| 4,893,653 A | 1/1990 | Ferrigno | |
| 4,901,915 A | 2/1990 | Sakakibara | |
| 4,909,435 A | 3/1990 | Kidouchi et al. | |
| 4,923,116 A | 5/1990 | Homan | |
| 4,941,608 A | 7/1990 | Shimizu et al. | |
| 4,945,943 A | 8/1990 | Cogger | |
| 4,965,894 A | 10/1990 | Baus | |
| 4,969,598 A | 11/1990 | Garris | |
| 4,976,460 A | 12/1990 | Newcombe et al. | |
| 5,009,572 A | 4/1991 | Imhoff et al. | |
| 5,033,715 A | 7/1991 | Chiang et al. | |
| 5,040,106 A | 8/1991 | Maag | |
| 5,056,712 A | 10/1991 | Enck | |
| 5,058,804 A | 10/1991 | Yonekubo et al. | |
| 5,105,846 A | 4/1992 | Britt | |
| 5,121,511 A | 6/1992 | Sakamoto et al. | |
| 5,124,934 A | 6/1992 | Kawamoto et al. | |
| 5,139,044 A | 8/1992 | Otten et al. | |
| 5,148,824 A | 9/1992 | Wilson | |
| 5,170,361 A | 12/1992 | Reed | |
| 5,170,816 A | 12/1992 | Schnieders | |
| 5,199,639 A | 4/1993 | Kobayashi et al. | |
| D340,279 S | 10/1993 | Mattis | |
| D344,901 S | 3/1994 | Conforti | |
| 5,329,650 A | 7/1994 | Zaccai et al. | |
| 5,351,712 A | 10/1994 | Houlihan | |
| 5,358,177 A | 10/1994 | Cashmore | |
| 5,385,168 A | 1/1995 | Lund | |
| 5,414,879 A | 5/1995 | Hiraishi et al. | |
| 5,419,930 A | 5/1995 | Schucker | |
| 5,428,850 A * | 7/1995 | Hiraishi et al. | 4/601 |
| 5,467,967 A | 11/1995 | Gillooly | |
| 5,482,250 A | 1/1996 | Kodaira | |
| 5,511,579 A | 4/1996 | Price | |
| 5,564,462 A | 10/1996 | Storch | |
| 5,572,985 A | 11/1996 | Benham | |
| 5,577,660 A | 11/1996 | Hansen | |
| 5,595,216 A | 1/1997 | Pilolla | |
| 5,603,344 A | 2/1997 | Hall, Jr. | |
| 5,623,990 A | 4/1997 | Pirkle | |
| 5,627,375 A | 5/1997 | Hsieh | |
| 5,743,511 A | 4/1998 | Eichholz et al. | |
| 5,758,688 A | 6/1998 | Hamanaka et al. | |
| 5,769,120 A | 6/1998 | Laverty, Jr. et al. | |
| 5,829,072 A | 11/1998 | Hirsch et al. | |
| 5,829,467 A | 11/1998 | Spicher | |
| 5,853,130 A | 12/1998 | Ellsworth | |
| 5,868,311 A * | 2/1999 | Cretu-Petra | 4/623 |
| 5,944,255 A | 8/1999 | Shirmohamadi | |
| 5,961,095 A | 10/1999 | Schrott | |
| 5,979,776 A | 11/1999 | Williams | |
| 6,000,429 A | 12/1999 | VanMarcke | |
| 6,019,130 A | 2/2000 | Rump | |
| 6,029,094 A | 2/2000 | Diffut | |
| 6,101,452 A | 8/2000 | Krall et al. | |
| 6,250,558 B1 * | 6/2001 | Dogre Cuevas | 4/676 |
| 6,250,601 B1 | 6/2001 | Kolar et al. | |
| 6,286,764 B1 | 9/2001 | Garvey et al. | |
| 6,315,208 B1 | 11/2001 | Doyle | |
| 6,317,717 B1 | 11/2001 | Lindsey et al. | |
| 6,322,005 B1 | 11/2001 | Kern et al. | |
| 6,341,389 B2 | 1/2002 | Philipps-Liebich et al. | |
| 6,351,603 B2 | 2/2002 | Waithe et al. | |
| D457,442 S | 5/2002 | Schuler | |
| 6,438,770 B1 | 8/2002 | Hed et al. | |
| 6,446,875 B1 | 9/2002 | Brooks et al. | |
| RE37,888 E | 10/2002 | Cretu-Petra | |
| 6,460,735 B1 | 10/2002 | Greenwald et al. | |
| 6,473,917 B1 | 11/2002 | Mateina | |
| 6,474,951 B2 | 11/2002 | Stephan et al. | |
| 6,478,285 B1 | 11/2002 | Bergmann | |
| D469,743 S | 2/2003 | Bergmann | |
| 6,513,787 B1 | 2/2003 | Jeromson et al. | |
| 6,523,193 B2 | 2/2003 | Saraya | |
| 6,598,245 B2 | 7/2003 | Nishioka | |
| 6,629,645 B2 | 10/2003 | Mountford et al. | |
| 6,691,338 B2 | 2/2004 | Zieger | |
| 6,705,534 B1 | 3/2004 | Mueller | |
| 6,892,952 B2 | 5/2005 | Chang et al. | |
| 6,895,985 B2 | 5/2005 | Popper et al. | |
| 6,913,203 B2 | 7/2005 | DeLangis | |
| 6,962,162 B2 | 11/2005 | Acker | |
| 6,962,168 B2 | 11/2005 | McDaniel et al. | |
| 6,964,405 B2 | 11/2005 | Marcichow et al. | |
| 6,996,863 B2 | 2/2006 | Kaneko | |
| 7,099,649 B2 | 8/2006 | Patterson et al. | |
| D528,991 S | 9/2006 | Katsuyama et al. | |
| 7,124,452 B1 | 10/2006 | Bauza | |
| 7,150,293 B2 | 12/2006 | Jonte | |
| 7,475,827 B2 | 1/2009 | Schmitt | |
| D591,182 S | 4/2009 | Schoenherr et al. | |
| 2001/0014835 A1 | 8/2001 | Gauthier et al. | |
| 2001/0044954 A1 | 11/2001 | DiCarlo | |
| 2002/0007510 A1 | 1/2002 | Mann | |
| 2002/0019709 A1 | 2/2002 | Segal | |
| 2003/0088338 A1 | 5/2003 | Phillips et al. | |
| 2003/0089399 A1 | 5/2003 | Acker | |
| 2003/0125842 A1 | 7/2003 | Chang et al. | |
| 2004/0155116 A1 | 8/2004 | Wack et al. | |
| 2004/0193326 A1 | 9/2004 | Phillips et al. | |
| 2004/0204779 A1 | 10/2004 | Mueller et al. | |
| 2004/0206405 A1 | 10/2004 | Smith et al. | |
| 2005/0006402 A1 | 1/2005 | Acker | |
| 2005/0022871 A1 | 2/2005 | Acker | |
| 2005/0044625 A1 | 3/2005 | Kommers | |
| 2005/0072850 A1 | 4/2005 | Cornwall et al. | |
| 2005/0133100 A1 | 6/2005 | Bolderheij et al. | |
| 2005/0150552 A1 | 7/2005 | Forshey | |
| 2005/0151101 A1 | 7/2005 | McDaniel et al. | |
| 2005/0194399 A1 | 9/2005 | Proctor | |
| 2005/0274812 A1 | 12/2005 | Taylor | |
| 2006/0075547 A1 | 4/2006 | Hamilton et al. | |
| 2006/0130908 A1 | 6/2006 | Marty et al. | |
| 2006/0153165 A1 | 7/2006 | Beachy | |
| 2006/0186215 A1 | 8/2006 | Logan | |
| 2006/0200903 A1 | 9/2006 | Rodenbeck et al. | |
| 2006/0201558 A1 | 9/2006 | Marty et al. | |
| 2006/0214016 A1 | 9/2006 | Erdely et al. | |
| 2006/0230772 A1 | 10/2006 | Wacknov et al. | |
| 2006/0231140 A1 | 10/2006 | McNerney | |
| 2008/0000997 A1 | 1/2008 | Smith | |
| 2009/0106891 A1 | 4/2009 | Klicpera | |

FOREIGN PATENT DOCUMENTS

| | | |
|---|---|---|
| CN | 2050951 U | 1/1990 |
| CN | 2056058 U | 4/1990 |
| CN | 2075490 U | 4/1991 |
| CN | 2187917 Y | 1/1995 |
| CN | 2324478 Y | 6/1999 |
| EP | 0 685 604 A1 | 12/1995 |
| EP | 0830482 B1 | 3/1998 |
| EP | 0961067 B1 | 2/2005 |
| EP | 1 657 367 | 5/2006 |
| JP | 64-21129 | 1/1989 |
| JP | 2000-17700 | 1/2000 |
| JP | 2005-105681 | 4/2005 |
| WO | WO 2004/051011 A1 | 6/2004 |
| WO | WO 2004/094990 A3 | 11/2004 |
| WO | WO 2005/056938 A1 | 6/2005 |
| WO | WO 2005/057086 A1 | 6/2005 |
| WO | WO 2006/019635 A2 | 2/2006 |
| WO | WO 2008/130349 | 10/2008 |

OTHER PUBLICATIONS

Got Hot Water, Shopping, retrieved from www.gothotwater.com Dec. 17, 2004, 3 pgs.

* cited by examiner

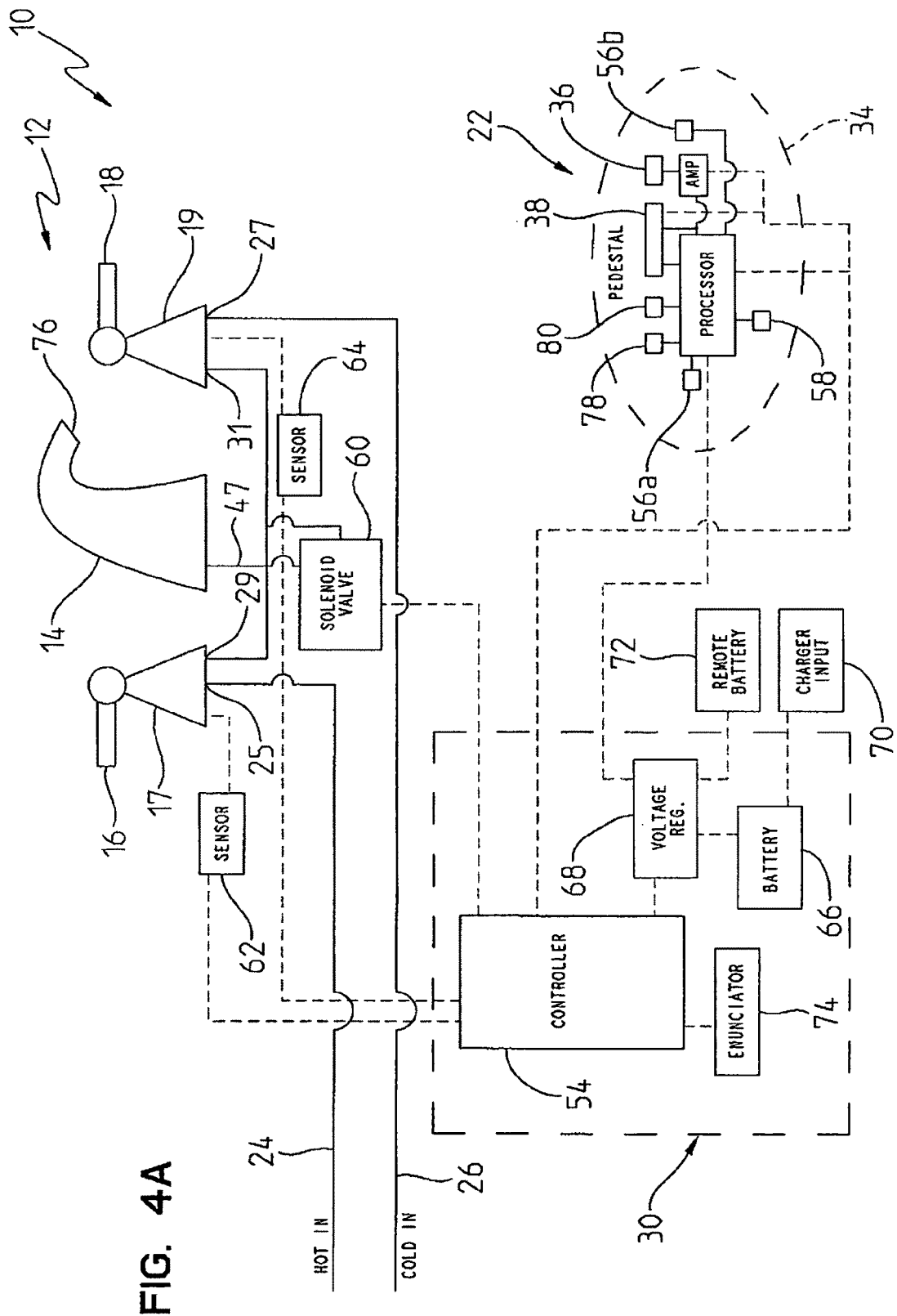

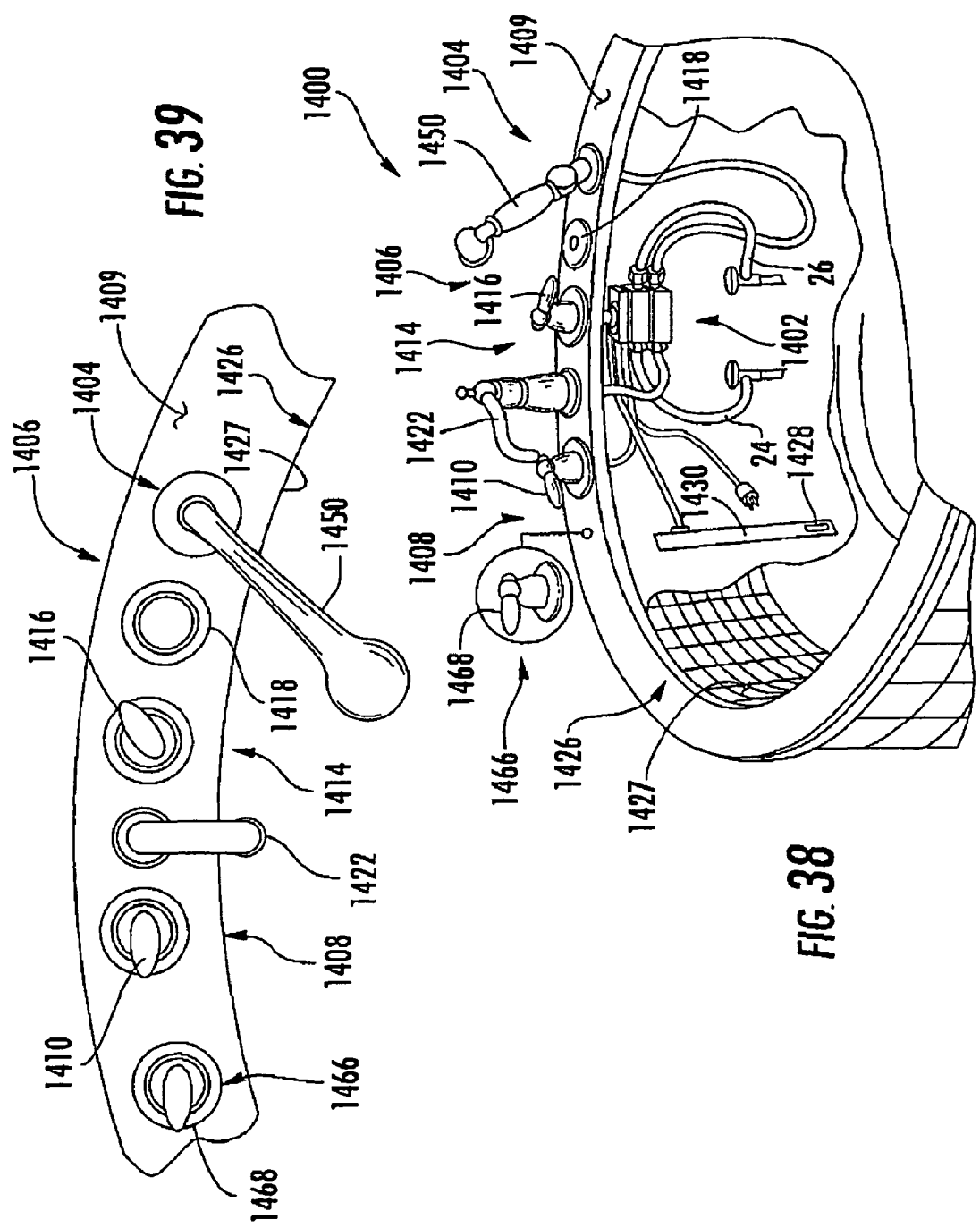

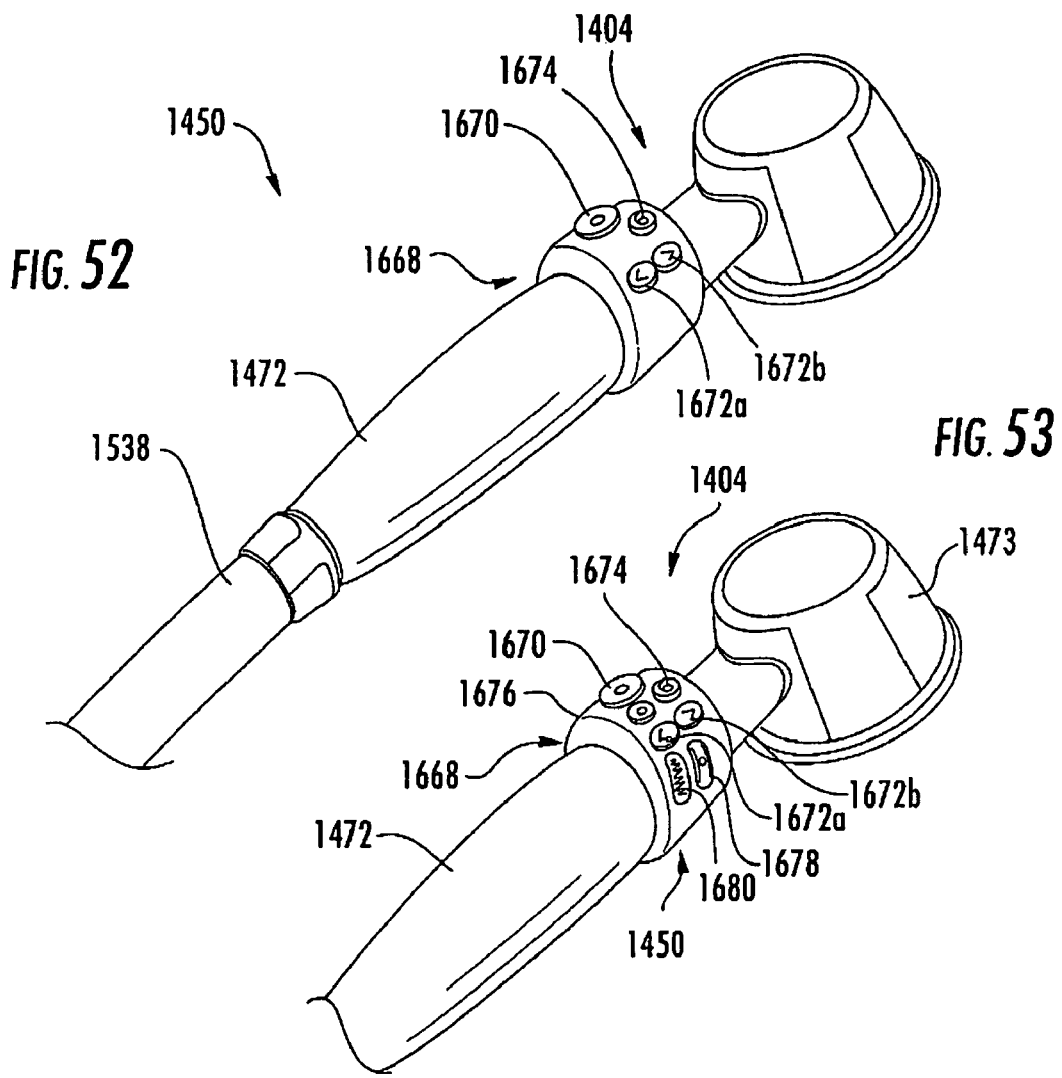

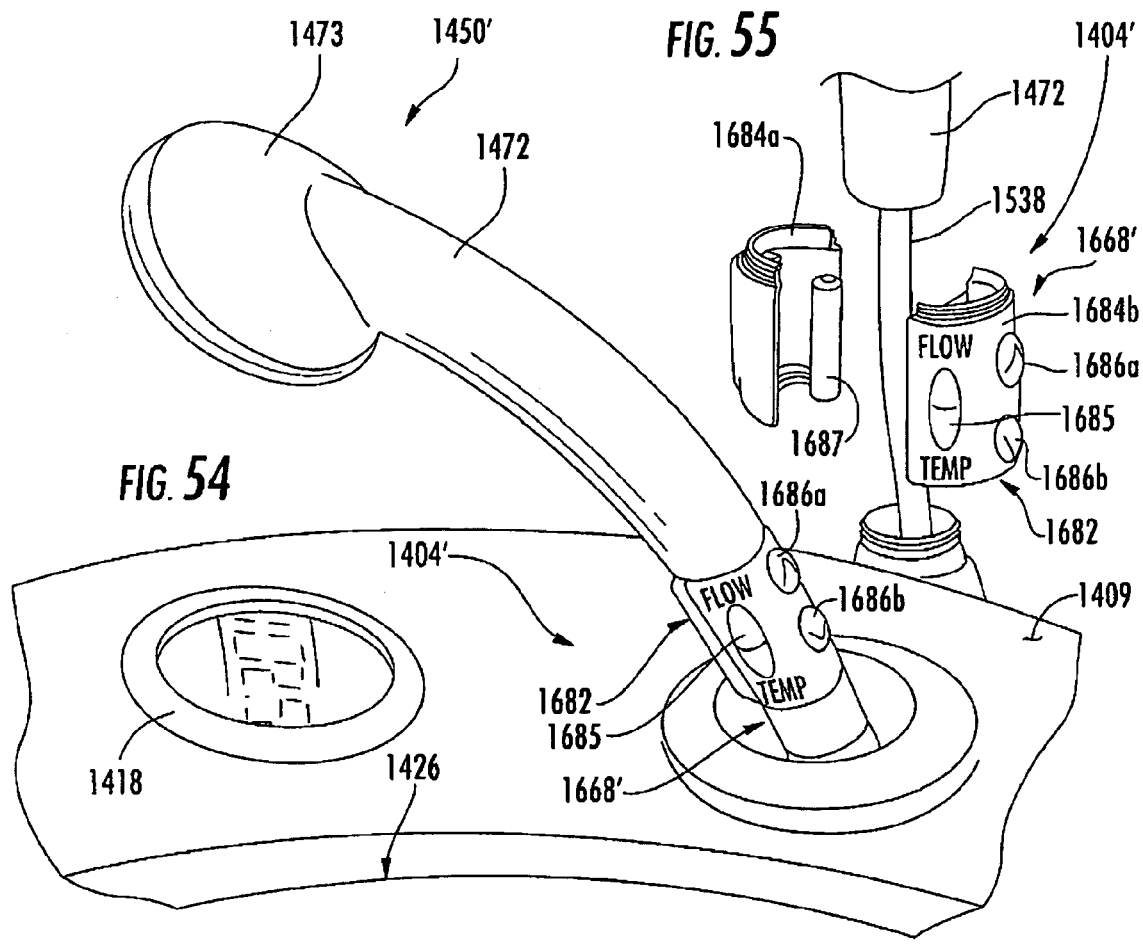

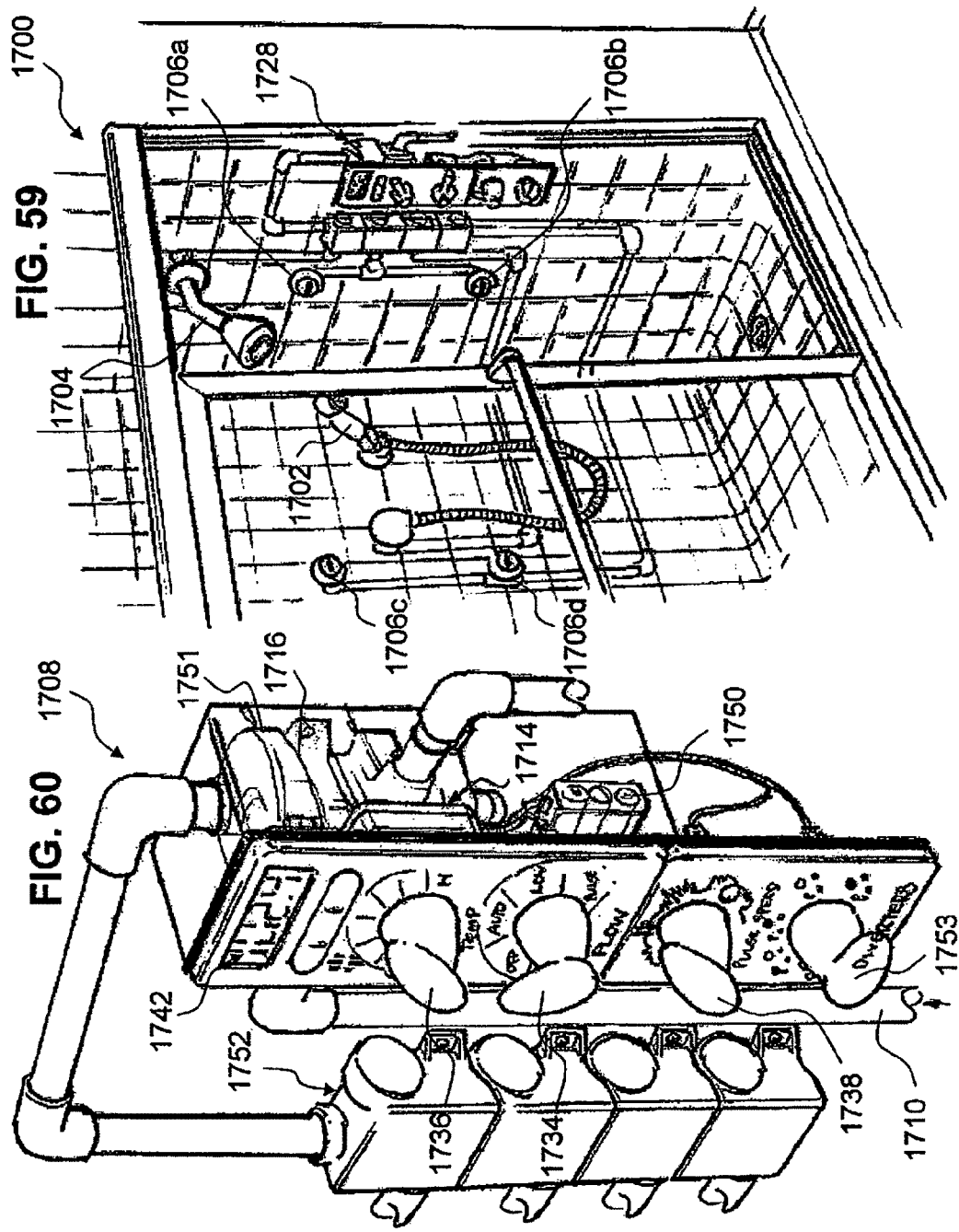

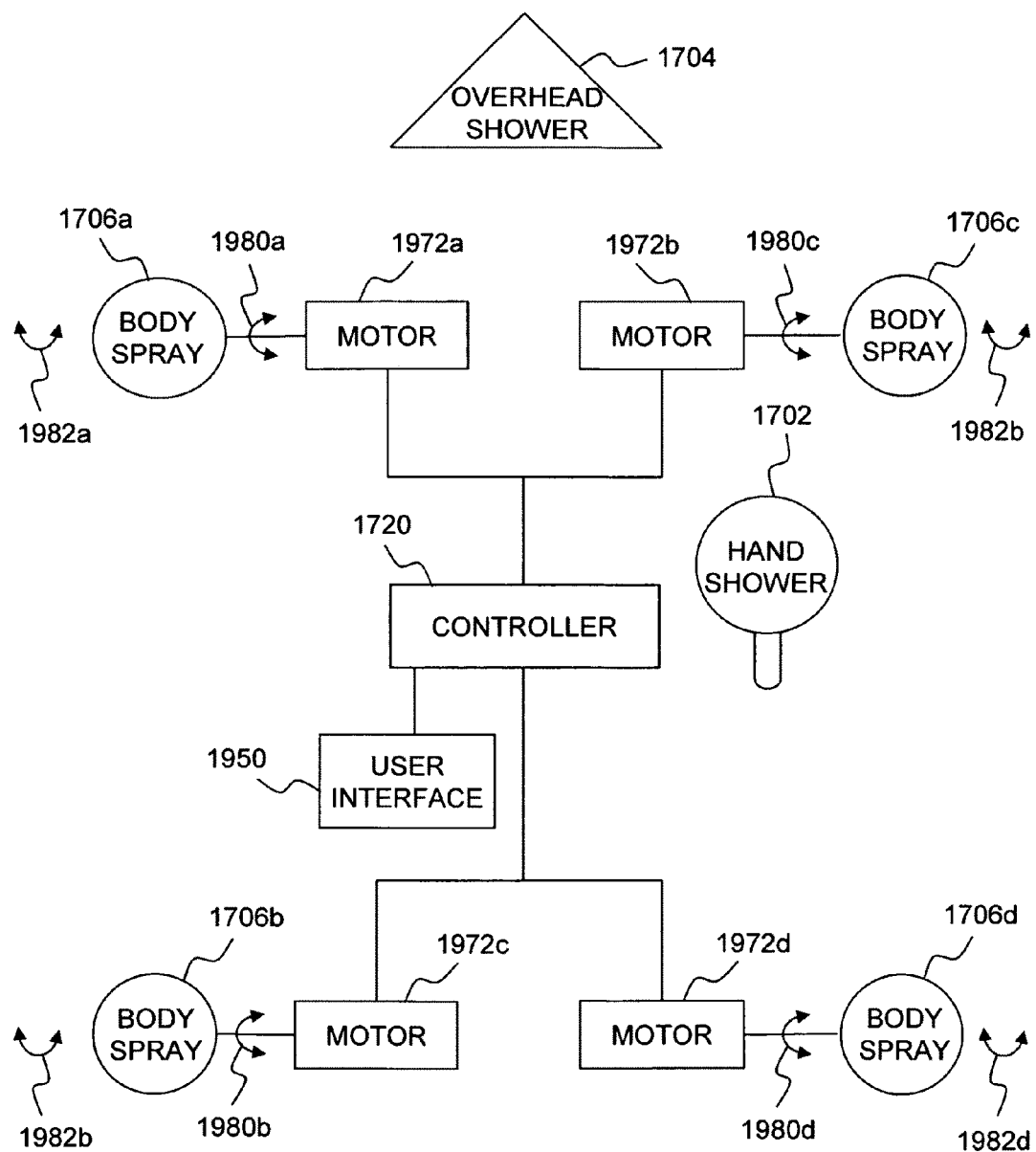
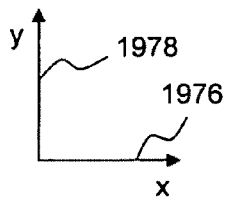
FIG. 81B

INTEGRATED BATHROOM ELECTRONIC SYSTEM

CROSS-REFERENCE TO RELATED APPLICATION

This is a continuation-in-part of International Patent Application No. PCT/US2006/044023 filed Nov. 13, 2006, which claims priority to U.S. Patent Application Ser. No. 60/735,569, filed Nov. 11, 2005, Ser. No. 60/838,271, filed Aug. 16, 2006, and Ser. No. 11/558,118, filed Nov. 9, 2006 now U.S. Pat. No. 7,867,172, the disclosures of which are all expressly incorporated by reference herein.

BACKGROUND AND SUMMARY OF THE INVENTION

The present invention relates generally to plumbing systems and, more particularly, to a plumbing system incorporating integrated technologies to improve operational efficiency.

The integrated bathroom electronic system of the present disclosure illustratively includes a plurality of sensors which are in communication with a controller. The sensors detect various conditions, such as when a person enters the bathroom, when water flow is initiated, when a bathtub is full, etc. The controller illustratively maintains a calendar and utilizes logic to determine how the system performs. The system is networked to multiple sub-systems or modules within the bathroom. For example, in one illustrative embodiment, the system anticipates when hot water is required, and insures that hot water is available when an individual begins his or her shower each morning.

A representative sampling of some of the illustrative features of the integrated system include: hands free operation of a lavatory faucet, quick hot water in a bathroom (including lavatory, tub, and shower), digital water flow and temperature controls, auto fill of a bath tub at a desired temperature, temperature maintenance in the bath tub, remote control of water flow and temperature in the bath tub and shower, and automatic nightlight operation in faucet, tub and shower.

As noted above, the system illustratively comprises a plurality of different modules, such as: a quick hot water module (with presence sensing technology and intelligence); a roman tub module; a custom shower module; a hands free faucet module; and a tub/shower module. The combination of various modules make up a smart bathroom system. The modules may be utilized together or independently.

According to an illustrative embodiment of the present disclosure, a sensor assembly for use with a faucet is provided. The sensor assembly includes a support, and a first sensor coupled to the support and configured to detect a person at a first distance from the faucet. A second sensor is coupled to the support and is configured to detect a person at a second distance from the faucet, wherein the first distance is greater than the second distance.

According to a further illustrative embodiment of the present disclosure, a faucet assembly includes a delivery spout, and an illumination device operably coupled to the delivery spout. A controller is in communication with the illumination device and a sensor. The controller is configured to activate the illumination device when the sensor detects the presence of a person within a predetermined distance of the faucet.

According to another illustrative embodiment of the present disclosure, a faucet assembly includes a mixed water outlet, and a temperature sensor in thermal communication with the mixed water outlet and configured to detect the temperature of water passing therethrough. A controller is in communication with the temperature sensor and a hot water indicator light. A recirculation pump is in communication with the controller and is configured to be deactivated when the temperature sensor detects a temperature greater than a predetermined value. The hot water indicator light is configured to be activated when the temperature sensor detects a temperature greater than the predetermined value.

According to yet another illustrative embodiment of the present disclosure, a water control module is configured to be positioned intermediate hot and cold water supplies and a faucet. The module includes a hands free assembly including a flow control valve. A quick hot assembly includes a recirculation pump positioned upstream from the control valve. A controller is in communication with the hands free assembly and the quick hot assembly.

According to a further illustrative embodiment of the present disclosure, a water faucet includes a delivery spout, a hot water control valve fluidly coupled to the delivery spout, and a cold water control valve fluidly coupled to the delivery spout. A hot water handle is operably coupled to the hot water control valve, and a cold water handle is operably coupled to the cold water control valve. A controller is in communication with the hot water control valve and the cold water control valve. A hot water touch sensor is operably coupled to the hot water handle and is configured to send a hot water signal to the controller in response to the touch of a user. A cold water touch sensor is operably coupled to the cold water handle and is configured to send a cold water signal to the controller in response to the touch of a user.

According to another illustrative embodiment of the present disclosure, a water control system is provided for use with a bath tub. The system includes a fill sensor configured to detect the level of water within the bath tub. A controller is in communication with the fill sensor an audible alarm. The controller is configured to activate the alarm when the fill sensor detects that the level of water has reached a predetermined value.

According a further illustrative embodiment of the present disclosure, a water control system for use with a shower includes a fluid delivery device, and a flow control valve operably coupled to the fluid delivery device. A controller is in communication with the flow control device and a proximity sensor. A temperature sensor is configured to detect the temperature of water exiting the fluid delivery device and is in communication with the controller. The controller is configured to control the flow control valve to stop the flow of water to the fluid delivery device when the proximity sensor detects no user within the predetermined distance of the fluid delivery device and the temperature sensor detects a temperature at least as great as a predetermined value.

According to yet another illustrative embodiment of the present disclosure, a bathroom device control system includes a shower head, a control valve operably coupled to the shower head, and a controller in communication with the control valve. An exhaust fan is in communication with the controller, wherein the controller deactivates the exhaust fan a predetermined time after the control valve stops water flow to the shower head.

According to a further illustrative embodiment of the present disclosure, a shower control interface includes a panel, and a flow control input operably coupled to the panel. A temperature control input and an audio listening device are operably coupled to the panel.

According to a further illustrative embodiment of the present disclosure, a roman tub assembly includes a tub, a jet system including a plurality of nozzles in communication with the tub, and a water reservoir in fluid communication with the nozzles. A heat transfer fluid line is in thermal communication with the reservoir of the jet system, the heat transfer fluid line extending between the cold water supply line and the hot water supply line of a building facility. A recirculation pump is fluidly coupled to the heat transfer fluid line and is configured to pump water from the hot water supply line, through the heat transfer fluid line, and into the cold water supply line.

According to an illustrative embodiment of the present disclosure, a faucet includes a spout, a first water inlet, and a first manual valve positioned intermediate the first water inlet and the spout. The first manual valve is configured to control the flow of water from the first water inlet to the spout during a manual mode of operation. An electrically operable valve is positioned intermediate the first water inlet and the spout. The electrically operable valve is configured to control the flow of water from the first water inlet to the spout during a hands-free mode of operation. The first manual valve is configured to control the flow of water to the spout independent of the electrically operable valve. A controller is in communication with the electrically operable valve. A mode sensor is in communication with the controller and is configured to provide a mode signal to the controller. A proximity sensor is in communication with the controller and is configured to provide a proximity signal to the controller. The controller is configured to select between the manual mode of operation and the hands-free mode of operation in response to the mode signal. The controller is further configured to control the electrically operable valve in response to the proximity signal during the hands-free mode of operation.

According to a further illustrative embodiment of the present disclosure, a faucet includes a spout, a water inlet, and a manual valve positioned intermediate the water inlet and the spout. An electrically operable valve is positioned intermediate the water inlet and the spout. A controller is in communication with the electrically operable valve. A mode sensor is in communication with the controller and is configured to detect when water is flowing through the spout. A proximity sensor is in communication with the controller and is configured to detect the presence of an object within a detection zone, wherein the controller controls the electrically operable valve in response to input from both the mode sensor and the proximity sensor.

According to another illustrative embodiment of the present disclosure, a faucet includes an outlet, a hot water line, and a cold water line. An electrically operable valve is positioned intermediate at least one of the hot water line and the cold water line and the outlet. A controller is in electrical communication with the electrically operable valve. A first proximity sensor is in electrical communication with the controller. A cross-over line is in fluid communication with the hot water line and the cold water line. A first cross-over valve is positioned within the cross-over line. A pump is in communication with the controller and is configured to cause water to flow from the hot water line through the cross-over line and to the cold water line.

According to yet another illustrative embodiment of the present disclosure, a faucet includes a spout, a hot water inlet, and a cold water inlet. At least one electrically operable valve is positioned intermediate the hot water and cold water inlets and the spout. A controller is in communication with the at least one electrically operable valve. A proximity sensor is in communication with the controller and is configured to provide a proximity signal to the controller. A touch sensor is in communication with the controller and is configured to adjust the mixture of hot and cold water flowing from the spout.

According to a further illustrative embodiment of the present disclosure, a shower system includes a plurality of water outlets configured to discharge water when active, a controller configured to control the discharge of water through the plurality of water outlets, and a user interface in communication with the controller and including a plurality of user defined presets. Each preset includes a shower setting stored in memory by a user, and defines an arrangement of active water outlets and a set temperature of water discharged from the active water outlets.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 4A is a schematic view of an illustrative hands free system for use with the faucet of FIG. 1;

FIG. 38 is perspective view, with a partial cut-away, of an illustrative embodiment roman tub system;

FIG. 39 is a top plan view of the user interface of the roman tub system of FIG. 38;

FIG. 52 is a perspective view of an illustrative embodiment hand shower configured to be supported by the deck of a roman tub;

FIG. 53 is a perspective view of another illustrative embodiment hand shower;

FIG. 54 is a perspective view of a further illustrative embodiment hand shower;

FIG. 55 is a partially exploded perspective view of the hand shower of FIG. 54;

FIG. 59 is a perspective view of an illustrative embodiment custom shower system;

FIG. 60 is a perspective view of an illustrative embodiment custom shower control module of the shower of FIG. 59;

FIG. 81B is a partial schematic view of another illustrative embodiment custom shower system;

DESCRIPTION OF INVENTION

Figure 1:
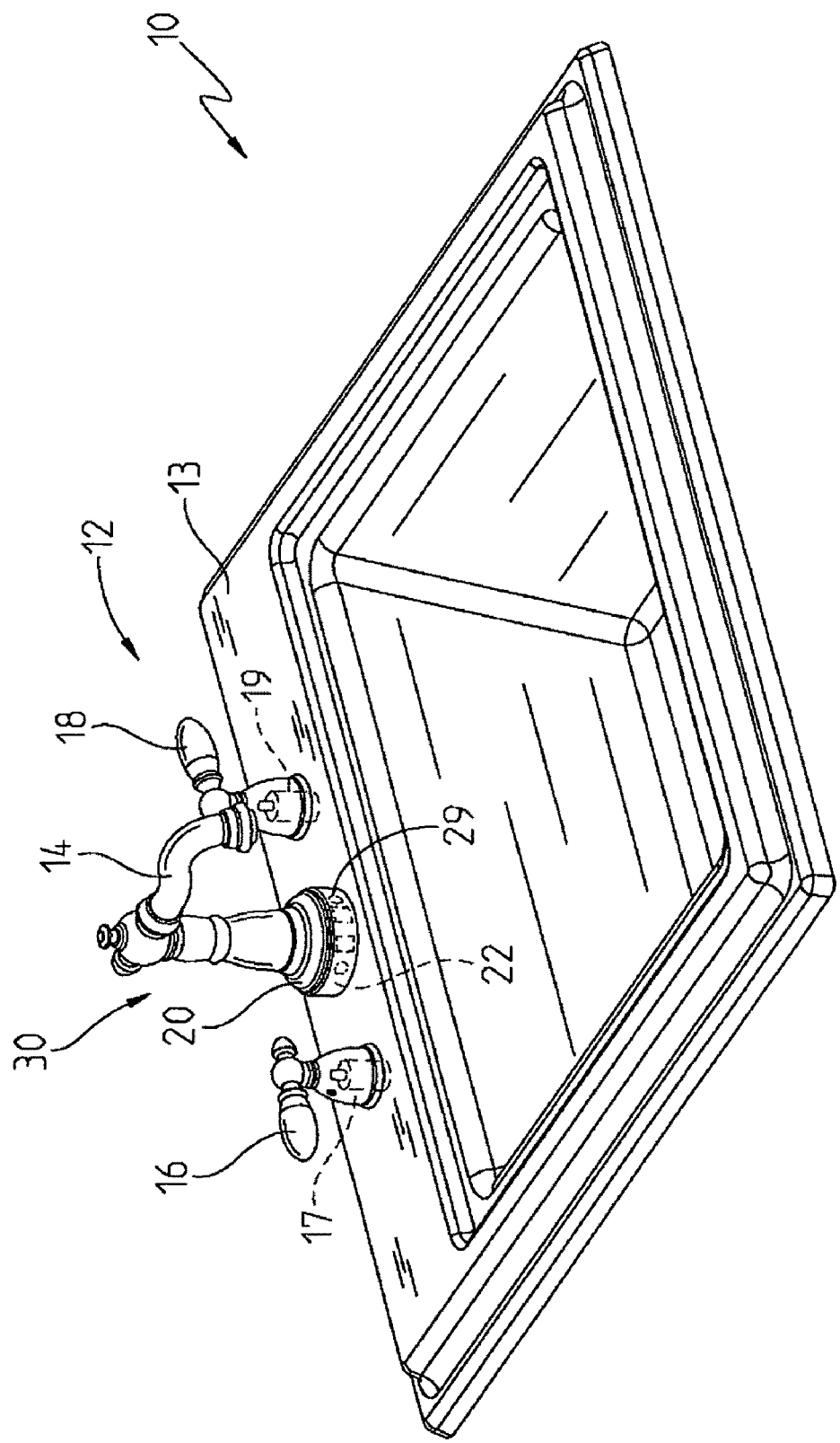
FIG. 1 is a perspective view of an illustrative faucet including a pedestal sensor assembly, showing the faucet coupled to a sink deck.
Figure 2:
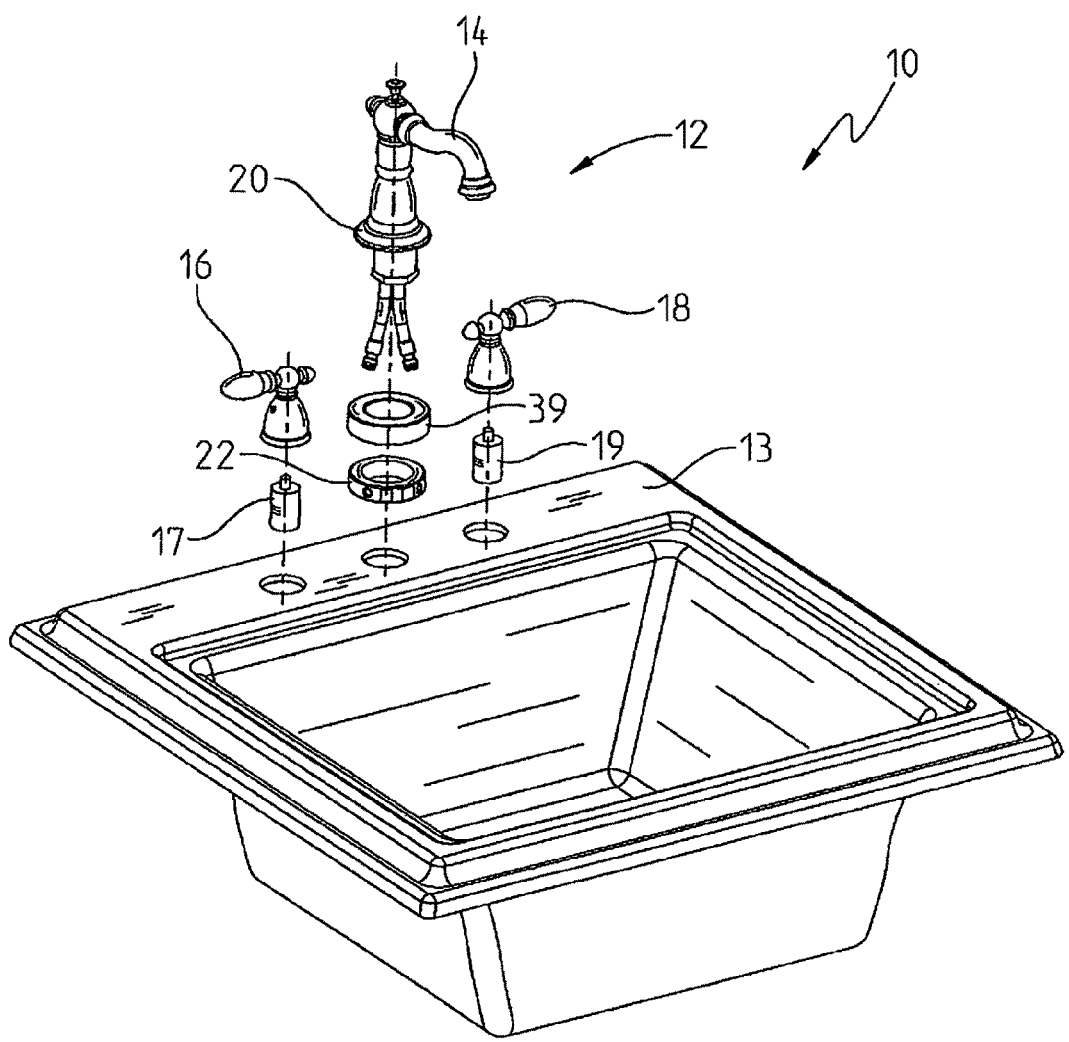
FIG. 2 is an exploded perspective view of the faucet of FIG. 1, showing the pedestal sensor assembly positioned for mounting between the delivery spout and the sink deck.

The integrated bathroom electronic system 10 of the present disclosure illustratively includes a plurality of different modules or subsystems which may be utilized independently or in various combinations with each other. Referring initially to FIGS. 1 and 2, an illustrative embodiment of the system 10 includes a faucet assembly 12 configured for hands free operation. The faucet assembly 12 is shown mounted to a sink deck 13 and illustratively includes a delivery spout 14 positioned intermediate a first, or hot water handle 16 and a second, or cold water handle 18. An escutcheon 20 supports the delivery spout 14 above a pedestal or sensor module 22. The faucet assembly 12 is sometimes referred to as a widespread faucet since the spout 14 and handles 16 and 18 are spread apart for direct mounting in separate holes within the sink deck 13. While the illustrative embodiment shows a faucet assembly 12 including two handles 16 and 18, it should be appreciated that aspects of the invention may find equal applicability with a single handle or lever type faucet.

Figure 4B:
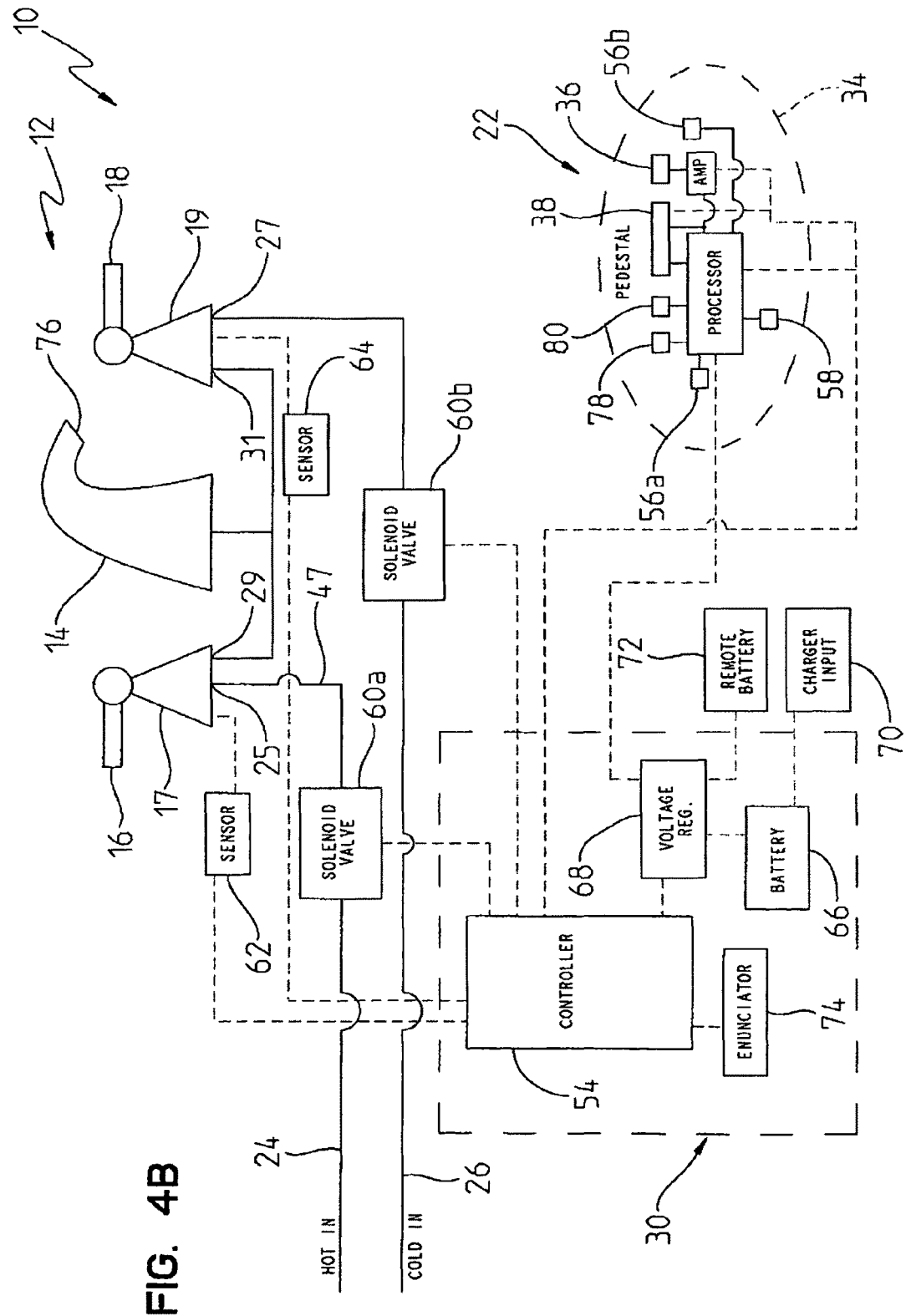
FIG. 4B is a schematic view of a further illustrative hands free system for use with the faucet of FIG. 1.

With reference to FIGS. 1, 2, 4A and 4B, the hot water handle 16 is operably coupled to a conventional hot water manual valve 17, while the cold water handle 18 is operably coupled to a cold water manual valve 19. A hot water line 24 is in fluid communication with a hot water inlet 25 of the manual valve 17, and a cold water line 26 is in fluid communication with a cold water inlet 27 of the manual valve 19 (FIGS. 4A and 4B). Water flows from the valves 17 and 19 through outlets 29 and 31, respectively.

With reference now to FIGS. 1-4A, hands free operation is illustratively provided by a hands free module 30 which includes the pedestal 22. The pedestal 22 includes a body 34 supporting a first or room sensor 36 for detecting when a person enters a first detection zone, illustratively the room containing the faucet assembly 12. The pedestal 22 further includes a second or hands free sensor 38 for detecting when a person places his or her hands within a second detection zone in proximity to the faucet assembly 12, illustratively immediately below the delivery spout 14. In other words, the first sensor 36 is configured to detect when a person is within a first distance to the faucet assembly 12, while the second sensor 38 is configured to detect when a person is within a second distance to the faucet assembly 12. As may be appreciated, the first distance is greater than the second distance. While two sensors 36 and 38 are utilized in the illustrative embodiment, the number of sensors may vary. In fact, a single sensor could be used in combination with proper control logic to differentiate different distances from the faucet assembly 12.

The body 34 of the pedestal 22 may include a locating element, such as a key (not shown), which is configured to properly orient the sensors 36 and 38 for proper operation. Further, while the pedestal 22 is shown to support the sensors 36 and 38 directly below the faucet spout 14, it should be appreciated that they may be located in other positions, such as below the handles 16 and 18.

Figure 3:
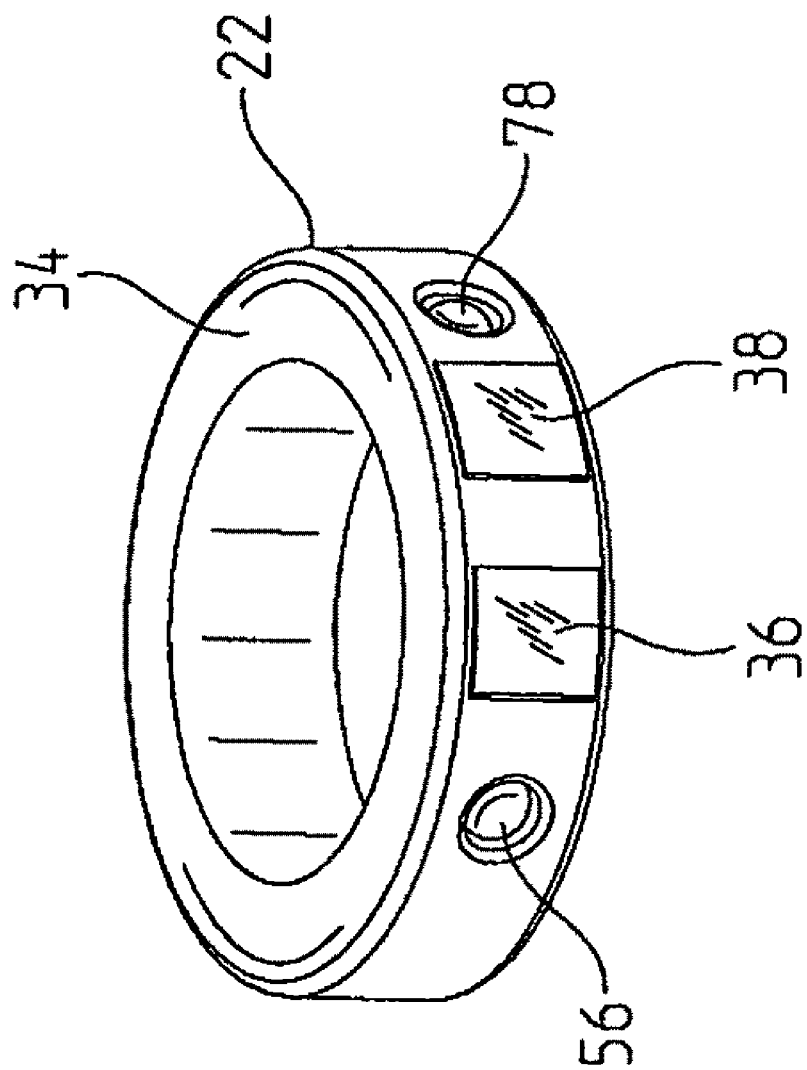
FIG. 3 is a perspective view of the pedestal sensor assembly of FIG. 1; showing internal components thereof including a first sensor, a second sensor, a nightlight, and a temperature indicator light.

The body 34 of the pedestal 22 in FIGS. 1-3 is in the form of an annular ring or puck and may be formed of a thermoplastic. In one illustrative embodiment, the pedestal 22 is molded from a transparent thermoplastic such that the sensors 36 and 38 may function therethrough. In a further illustrative embodiment, a transparent protective outer ring or cover 39, which may also be formed of a transparent thermoplastic, is received over the pedestal 22 (FIG. 2).

Figure 5:
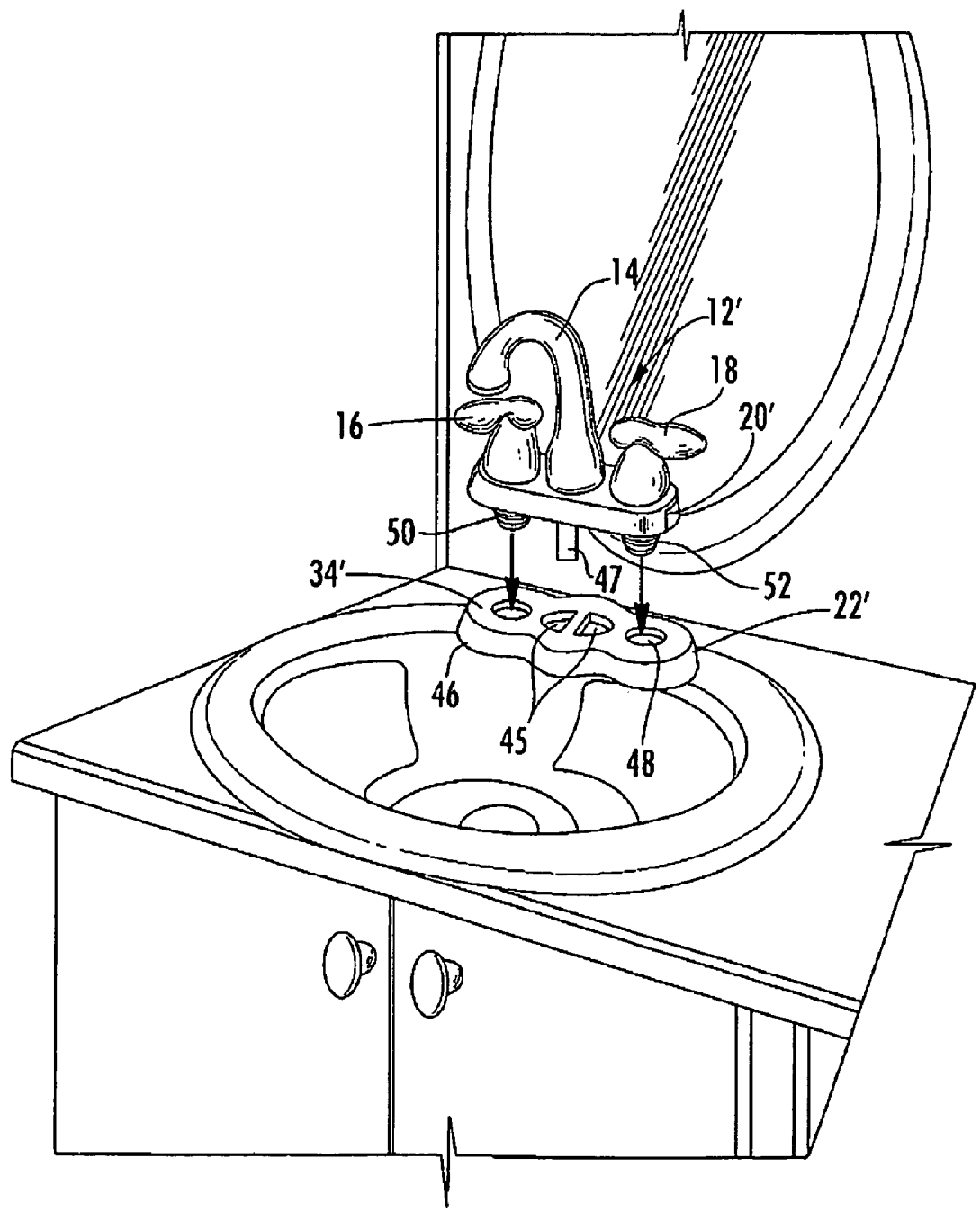
FIG. 5 is an exploded perspective view showing a further illustrative embodiment faucet including a pedestal sensor assembly.
Figure 6:
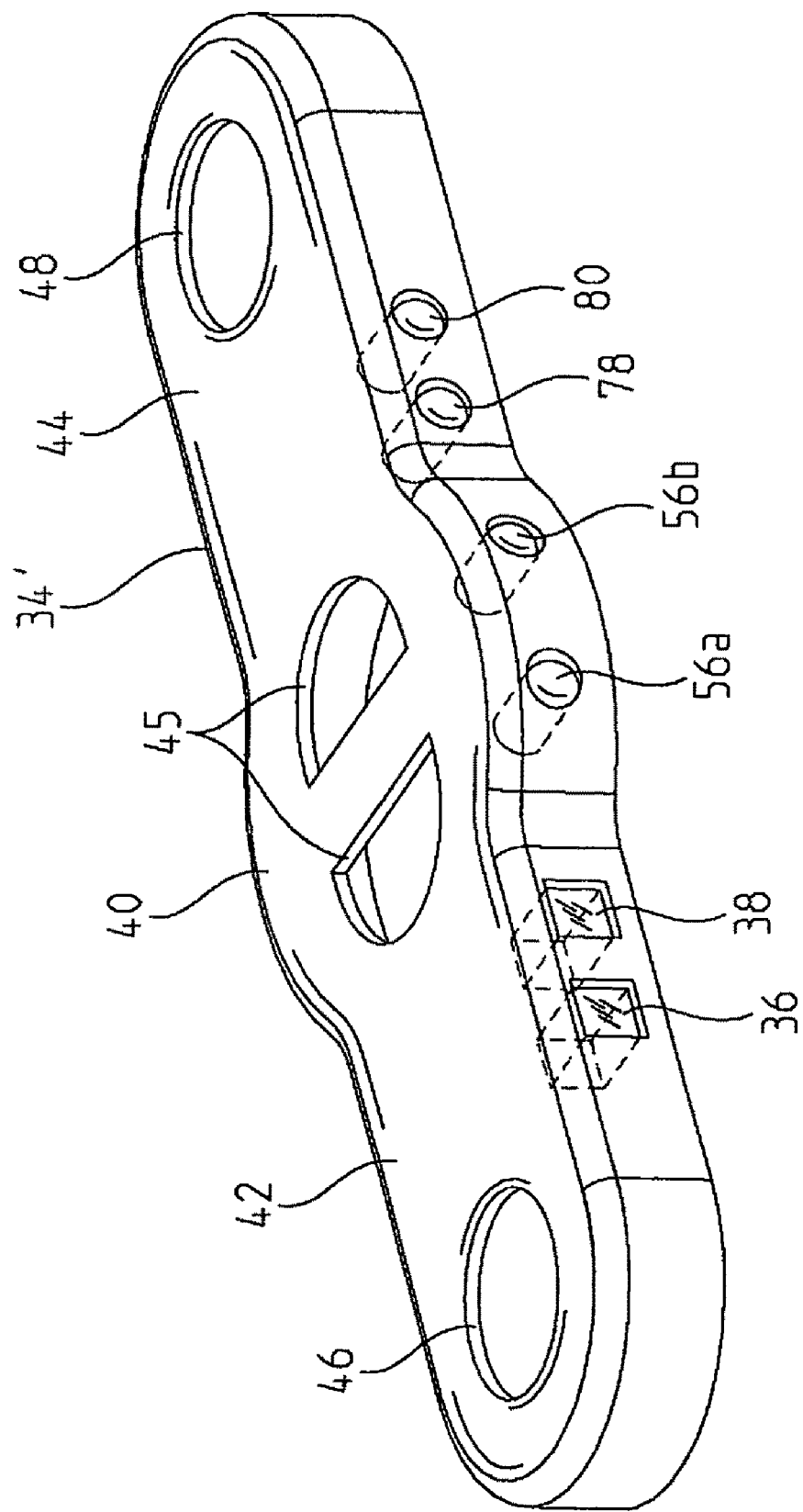
FIG. 6 is a perspective view of the pedestal sensor assembly of FIG. 4, showing internal components thereof including a first sensor, a second sensor, nightlights, and temperature indicator lights.

As shown in FIGS. 5 and 6, a further illustrative embodiment pedestal 22' is configured for use beneath the escutcheon 20' of a center set faucet assembly 12'. The pedestal 22' includes a body 34' having center portion 40 and a pair of outwardly extending arms 42 and 44. The center portion 40 includes at least one opening 45 to receive a water outlet conduit 47. Each arm 42 and 44 includes an opening 46 and 48 to receive the hot and cold water supply conduits 50 and 52, respectively.

With further reference to FIGS. 3-4B, the first sensor 36 comprises a passive infrared sensor, such as a pyroelectric sensor which is configured to detect moving infrared radiation. As such, the first sensor 36 uses reduced power as compared to many other conventional sensors. The sensor 36 is configured to send a detection signal to a controller 54 when it detects that a person has entered the room (i.e., first detection zone) and is within the first distance to the faucet assembly 12. In response, the controller 54 activates at least one illumination device, illustratively a nightlight 56 which is received in the body 34, 34' of the pedestal 22, 22'. In a further illustrative embodiment, a visible light sensor 58 is in communication with the controller 54 and is configured to detect ambient light (FIGS. 4A and 4B). During low light conditions as detected by the sensor 58, the controller 54 permits activation of the nightlight 56. As shown in FIG. 6, multiple nightlights 56a and 56b may be included within the pedestal 22'. Illustratively, the first nightlight 56a may be illuminated whenever a person is detected by the first sensor 36 thereby providing an indication of proper system operation. The second nightlight 56b may be illuminated only when a person is detected by the first sensor 36 and low light conditions are detected by the visible light sensor 58, in the manner detailed herein.

Illustratively, the nightlights 56 comprise light emitting diodes (LEDs). However, other conventional illuminating devices may be used, such as light pipes, luminescent materials and fiber optics.

The second sensor 38 illustratively comprises a position sensing device (PSD), such as an infrared emitter and an infrared receiver. As a user's hands are placed within the second detection zone under the spout 14, the sensor 38 sends a detection signal to the controller 54. In response, the controller 54 activates an electrically operable valve, illustratively, a solenoid valve 60, which permits water flow from valve outlets 29 and 31 to the spout 14. While only a single solenoid valve 60 is shown in FIG. 4A, separate solenoid valves 60a and 60b for the supply of hot and cold water to the delivery spout 14 may be substituted therefor, as shown in FIG. 4B.

The second sensor 38 may be configured to sense only human hands in order to prevent false activations. Illustratively, the second sensor 38 is configured to respond within 250 milliseconds and to operate under low power conditions.

Touch or tap sensors 62 and 64 are illustratively associated with the hot water control handle 16 and the cold water control handle 18, respectively. The tap sensors 62 and 64 are configured to provide a signal to the controller 54 in response to a user touching either handle 16 and 18. The tap sensors 62 and 64 may comprise conventional capacitive touch sensors, such as a Q-Prox™ sensor manufactured by Quantum Research Group of Hamble, United Kingdom. The tap sensors 62 and 64 may operate in a manner similar to that detailed in any one of U.S. Provisional Patent Application Ser. No. 60/662,106, filed Mar. 14, 2005, titled "VALVE BODY ASSEMBLY WITH ELECTRONIC SWITCHING"; U.S. Provisional Patent Application Ser. No. 60/661,982, filed Mar. 14, 2005, titled "POSITION-SENSING DETECTOR ARRANGEMENT FOR CONTROLLING A FAUCET", and U.S. patent application Ser. No. 10/755,581, filed Jan. 12, 2004, titled "MULTI-MODE HANDS FREE AUTOMATIC FAUCET"; the disclosures of which are expressly incorporated by reference herein. It should be further appreciated that touch sensors may be positioned within other portions of the faucet assembly 12, such as the delivery spout 14 or the escutcheon 20.

While tap sensors 62 and 64 are illustratively capacitance sensors, it should be appreciated that other sensors may be substituted therefor. For example, the tap sensors 62 and 64 may comprise vibration sensors or acoustic sensors, such as microphones. In another illustrative embodiment, the tap sensors 62 and 64 may be replaced with a piezoelectric sensor in the form of a thin film configured to detect force applied to the faucet assembly, such as to the spout 14, by a user.

The controller 54 is illustratively powered by a battery 66. A voltage regulator 68 may be positioned intermediate the battery 66 and the controller 54. The battery 66 illustratively includes a charger input 70 for electrically coupling with a conventional alternating current (AC) outlet (not shown). A remote battery 72 may be electrically coupled with the voltage regulator 68 to provide additional or supplemental power to the system 10. An audible alarm or enunciator 74 is coupled to the controller 54 and is configured to provide audible signals to the user. For example, the enunciator 74 may provide an audible signal to the user when operation modes (manual, hands free (proximity), and touch) are activated.

During a manual mode of operation, rotation of the handles 16 and 18 causes operation of valves 17 and 19, respectively, in a conventional manner. More particularly, the valves 17 and 19 control the flow of hot and cold water to the solenoid valve 60 and, in turn, the flow of mixed water to the outlet 76 of the delivery spout 14. During a proximity or hands free mode of operation, the second sensor 38 causes operation of the solenoid valve 60 when it detects an object adjacent to the delivery spout 14 (i.e., within the second detection zone). Illustratively, the second sensor 38, that senses the presence of an object under the spout 14, causes the controller 54 to cease the flow of water approximately one second after the object has been removed from the detection zone. Finally, during the touch mode of operation, the touch sensors 62 and 64 control the operation of the solenoid valve 60 in response to user contact with the handles 16 and 18.

The first sensor 36 may also cooperate with the controller 54 to automatically shut off water flow when the user leaves the room. More particularly, the sensor 36 sends a signal to the controller 54 when no user is detected in the room for a predetermined deactivation time after water flow activation, regardless of whether being activated by manual mode, proximity mode, or touch mode. In response, the controller 54 deactivates the solenoid valve 60, thereby preventing water flow to the delivery spout 14. The turn-off or deactivation time is based on the activity in and out of the infrared activation and motion zones. An auto time-out feature exists to disable water flow after a defined period of time (illustratively 120 seconds) to prevent water from flowing indefinitely. This will occur regardless of the criteria for activation or motion.

For tap operation, the touch sensors 62 and 64 are operably coupled to the handles 16 and 18 such that when the handle 16, 18 is touched, the water will stay on for a predetermined time, illustratively a maximum of three minutes. When the handle 16, 18 is touched again, the water will shut off. Grasping or touching the handle 16, 18 will turn the water on. When released, the water will continue to flow, thereby mimicking a manual mode of operation. Touching the handle 16, 18 again, will turn the water off. The sensors 36 and 38 are configured to operate such that if water is not flowing, touching the handle 16, 18 will result in water flow activation. If water is flowing, touching the handle 16, 18 will result in water flow activation. If water is flowing, touching the handle 16, 18 will result in the cessation of water flow. Illustratively, grasping the handle 16, 18 will always result in water flow activation. A time-out feature illustratively exists to disable water flow after five minutes from either a "tap" on or "handle grab" on mode of operation. This is to prevent indefinite water flow. Sensors 62 and 64 are configured to distinguish between tap activation and grab activation. Tap activation is illustratively considered to be of a duration between 20 milliseconds to 250 milliseconds. Grab activation is illustratively considered to be greater than 250 milliseconds.

The touch sensors 62 and 64 are configured to work with both copper and plastic piping. The touch sensors 62 and 64 are designed to minimize false touches caused by water splashing on sensitive areas. Further, the touch sensors 62 and 64 are configured to detect touches from both direct skin contact and through rubber gloves. The sink, water line, and connections with the faucet handles 16 and 18 are non-conductive.

As noted above, the pedestal 22 permits any style faucet to be used with the system 10. With reference to FIGS. 3-4B and 6, the pedestal 22, 22' also illustratively includes a hot water indicator 78. More particularly, the hot water indicator 78 may comprise a light emitting diode (LED), illustratively red, to be implemented into the pedestal body 34, 34' to indicate when hot water is ready. The hot water indicator 78 is activated by the controller 54 when the temperature of hot water available to the solenoid valve 60 and the delivery spout 14 reaches a predetermined value, illustratively approximately 90° Fahrenheit. This feature is illustratively functional with the integration of a quick-hot module as further detailed herein. The pedestal 22, 22' may also include a cold water indicator 80, illustratively a blue LED, which may be activated by the controller 54, for instance, when the available hot water temperature has reached the predetermined value. A conventional temperature sensor, such as a thermistor (not shown) may be used to detect the temperature of hot water available to the spout 14 and provide a signal thereof to the controller 54.

The hands-free faucet module 30 is designed to work with multiple sink configurations and sink finishes. The module 30 is configured to adapted to its environment to eliminate unintended activations caused by standing water or highly reflective objects. Finally, the module 30 is tolerant of extraneous infrared sources, such as sunlight, fluorescent lighting, etc.

Figure 7:
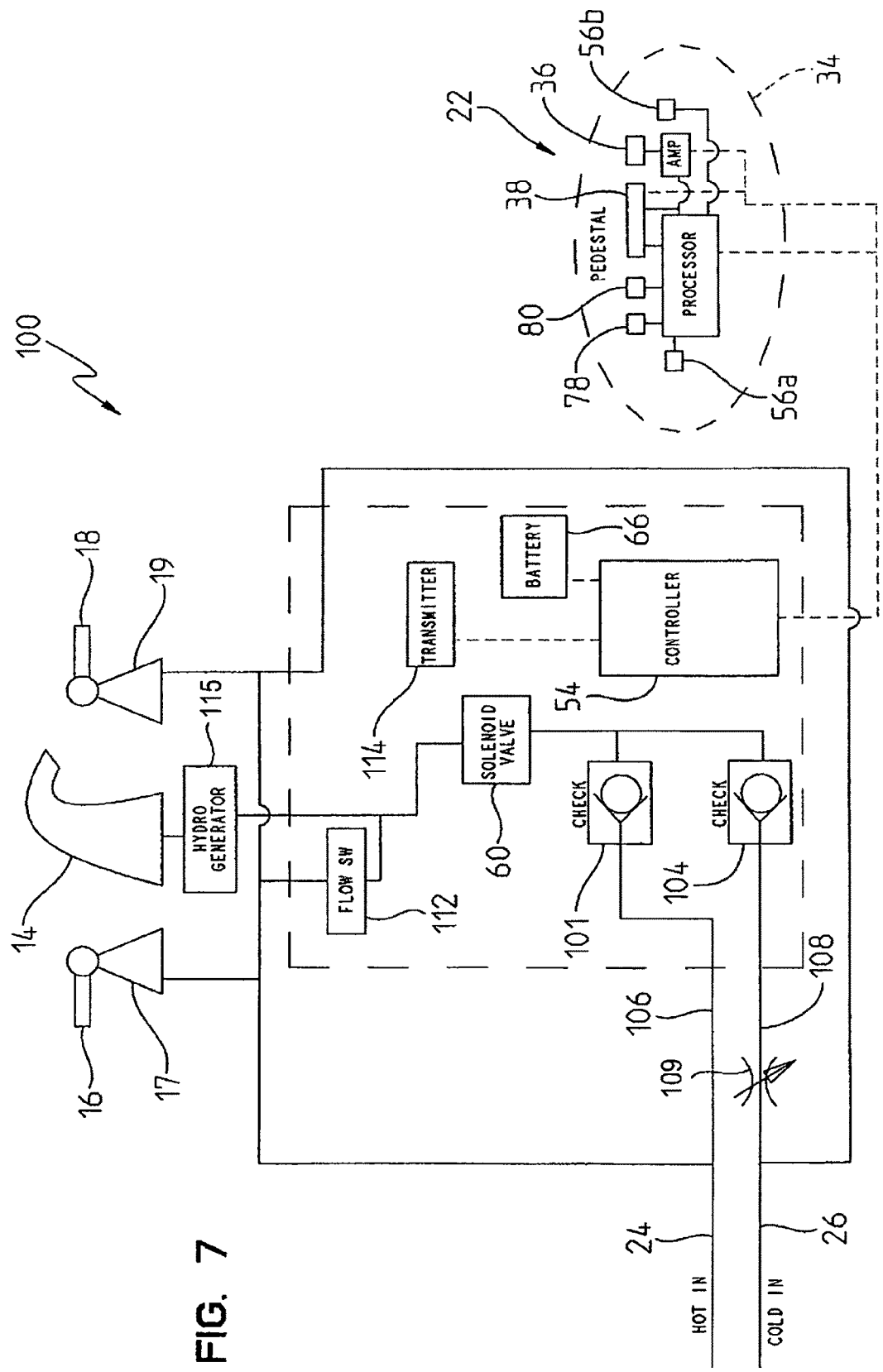
FIG. 7 is a schematic view of a further illustrative hands free system for use with the faucet of FIG. 1.

FIG. 7 illustrates a hands-free no tap system 100 which is similar to system 30. First and second check valves 101 and 104 are positioned upstream from an electrically operable valve 60 to prevent unintended cross flow between the hot and cold water lines 106 and 108. An adjustable restrictor 109 may be positioned within the cold water supply line 108 to vary the ratio of cold to hot water supplied to the valve 60. A flow switch or sensor 112 is positioned intermediate the manual valves 17 and 19 and the spout 14 and provides a flow signal to the controller 54 indicating that water is flowing through the manual valves 17 and 19. As detailed herein, the flow signal provided to the controller 54 provides an indication that the system 100 is in the manual mode of operation and the controller 54 deactivates the hands-free sensor 38 in response thereto. In the illustrative embodiment, a transmitter 114 is in communication with the controller 54. Further, a hydro-generator 115 may be provided in line with solenoid valve 60 in order to generate power in response to water flow through the spout 14 for charging the battery 66.

Figure 8:
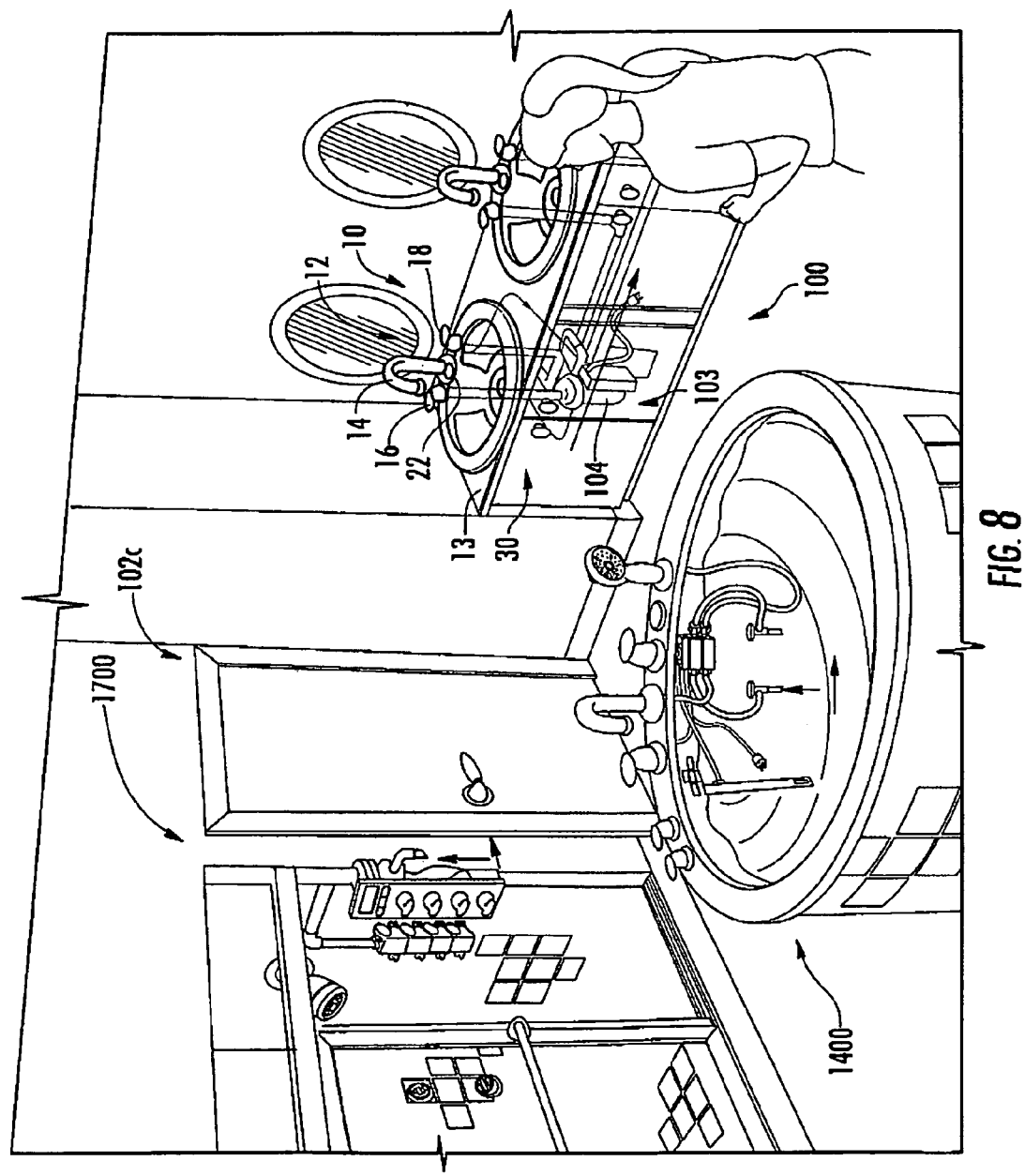
FIG. 8 is a perspective view of a bathroom coupled to a quick hot water system.
Figure 9:
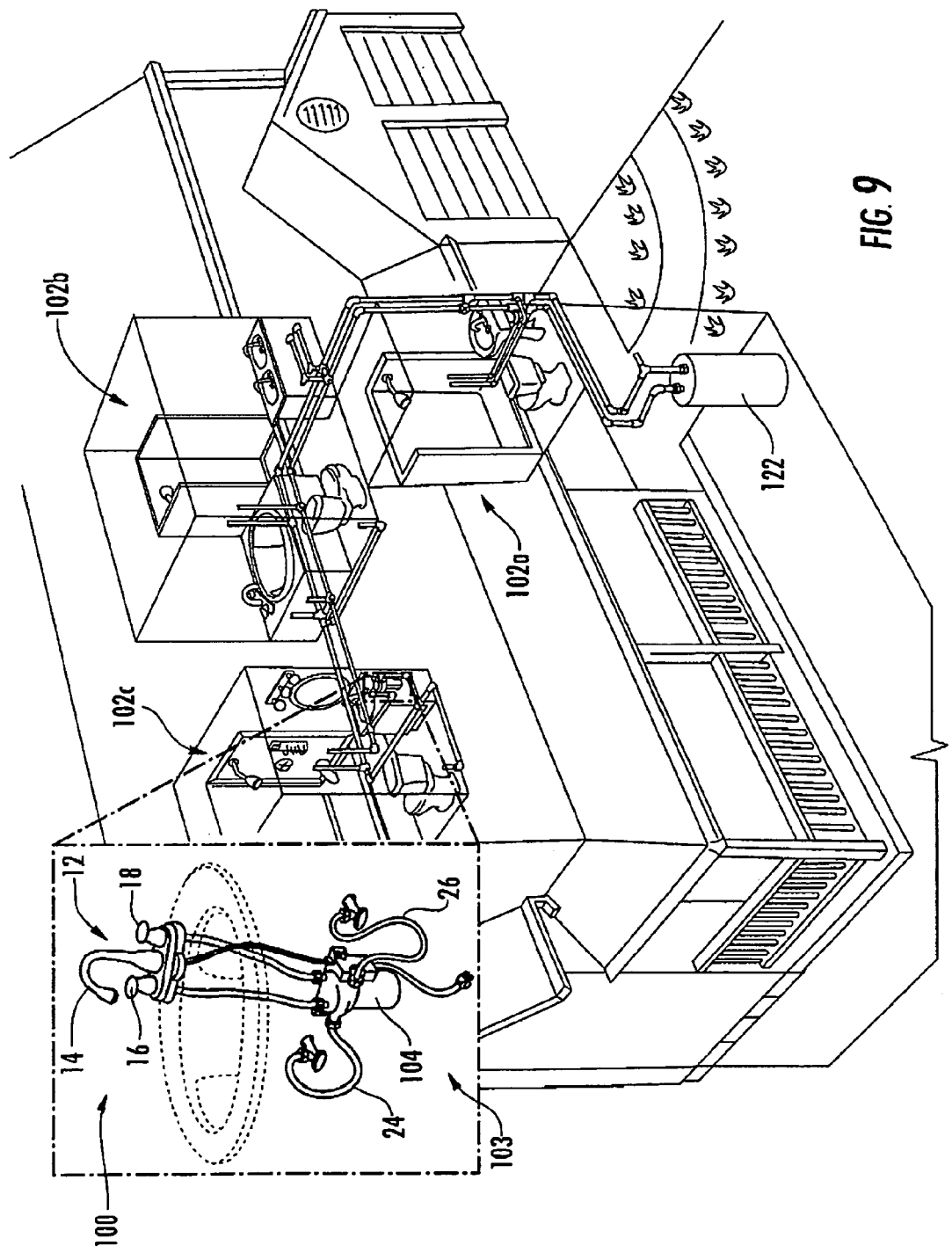
FIG. 9 is a perspective view, in partial schematic, of a house including an integrated quick hot water system.

With reference now to FIGS. 8 and 9, an integrated quick hot or recirculation system 100 is shown within a bathroom 102c. In one illustrative embodiment of the system 100, human presence is detected and results in the delivery of hot water to at least one fluid delivery device or fixture in the bathroom 102c. More particularly, the hands free faucet assembly 12, including the module 30 detailed herein, may be included within the quick hot system 100. In a further illustrative embodiment, the integrated quick hot system 100 includes system intelligence which predicts when hot water is required based on usage patterns. In the integrated quick hot system 100, all components are illustratively located in the bathroom 102c of interest. The components of the recirculation pump module 103 are illustratively combined and mounted as a package under the lavatory or sink deck 13.

Figure 10:
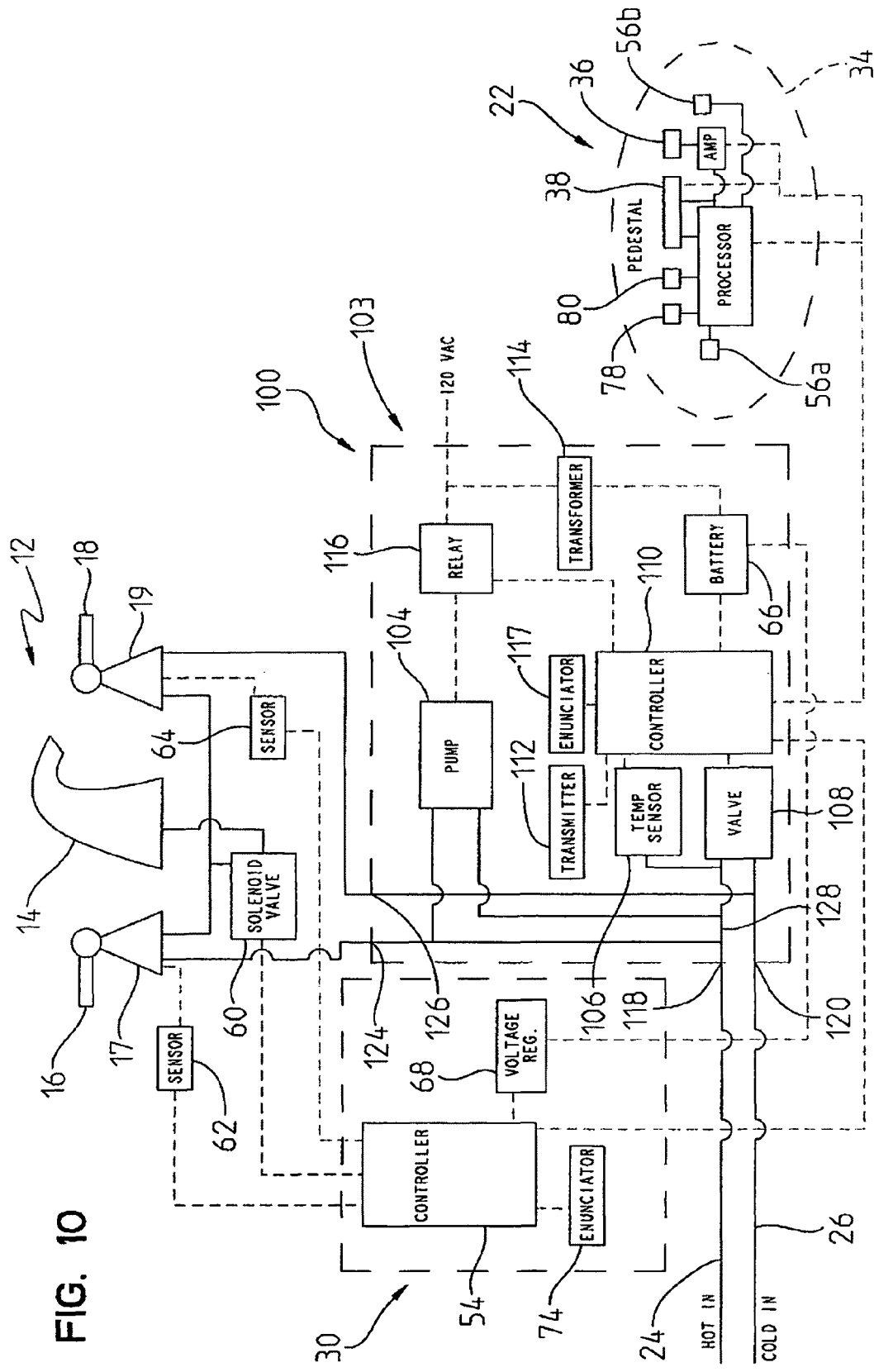
FIG. 10 is a schematic view of an illustrative hands free system incorporating the integrated quick hot water system of FIG. 9.

With reference to FIG. 10, the recirculation pump module 103 illustratively includes a recirculation pump 104, a temperature sensor 106, a cross-over valve 108, and a controller 110. The controller 110 may be combined with the controller 54 of the hands free module 30. Transmitter 114 is in communication with controller 110, while a battery 66 provides power to the controller 110. A relay 116 is positioned intermediate the controller 110 and the pump 104. The pump 104 is illustratively operated at 120 VAC and provides fluid flow at a rate of 2 gpm at 6 ft. head (3 psi). An enunciator 117 may be instructed by the controller 110 to provide an audible signal under certain conditions (e.g., desired hot water temperature reached as detected by temperature sensor 106).

The recirculation pump module 103 is illustratively positioned intermediate the hot water line 24 and the cold water line 26. More particularly, the pump module 103 includes a hot water inlet 118 and a cold water inlet 120, which are fluidly coupled to the hot water supply line 24 and the cold water supply line 26, respectively. The hot water supply line 24 is fluidly coupled to a hot water supply, such as a hot water heater 122. A hot water outlet 124 and a cold water outlet 126 are fluidly coupled to a fluid delivery device, such as the spout 14 of faucet 12.

In operation, the pump 104 draws water from the hot water line 24 through the hot water inlet 118. The pump 104 then forces the water through a transfer, connecting, or cross-over line 128, through the cross-over valve 108, and out into the cold water line 26. The temperature sensor 106 senses the temperature of the water in the cross-over line 128 and sends a signal indicative thereof to the controller 110.

Illustratively, the pump 104 is configured to shut off after three minutes of continuous operation, or by operation of the temperature sensor 106. More particularly, the temperature sensor 106 is configured to shut off the pump 104 after detecting a water temperature of at least a predetermined value, illustratively 95° F. The cross-over valve 108 may comprise a hot-to-cold water check valve illustratively having a cracking pressure of approximately 1 psi. Alternatively, the cross-over valve may comprise a thermostatic valve or an electrically operable valve, such as a solenoid valve, coupled to the controller 110.

As detailed above in connection with the pedestal 22, the motion sensor 36 illustratively communicates with the controller 110 and is configured to detect a person's entrance and exit from an area proximate the faucet 12 (i.e., first detection zone). The sensor 36 is configured to communicate either via hard wire or radio frequency with the controller 110. When a human is detected within the first detection zone of the faucet 12, the electronics are activated. When the user has left the first detection zone, the electronics are de-activated. Upon detection of an individual in the first detection zone (bathroom), the sensor 36 is configured to transmit a start signal to the controller 110 for activating the pump 104.

In one illustrative embodiment, the sensor 36 may be wall mounted. Alternatively, the sensor 36 may be positioned behind an escutcheon or under the faucet 132. As detailed above, the sensor 36 may also be positioned within the pedestal 22 of the faucet 12.

As detailed herein, the sensor 36 is configured to detect a person's entrance and exit from the bathroom. The sensor 36 is configured to communicate, illustratively via radio frequency, with a plurality of smart fluid delivery devices, such as hands-free faucet systems 30, roman tub systems 1400, custom shower systems 1700, and tub shower systems 2000. When a human is detected in the bathroom 102, the electronics are activated. When the user has left the bathroom 102, the electronics are deactivated. Finally, when a user enters the bathroom 102 and it is dark, illumination devices are activated. The illumination devices may include nightlights 56 associated with the faucet 12, along with nightlights associated with the other systems 1400, 1700, and 2000. It should be appreciated that the illuminated displays for the various systems may define illumination devices.

When the user enters the bathroom 102, the tub 1426 of the roman tub module 1400 is full, and the maintain temperature mode of operation is initiated, the recirculation pump 104 operates to maintain the availability of hot water. Additional details of the maintain temperature mode of operation are provided herein.

Illustratively, the controller 110 may utilize system intelligence by tracking usage patterns over a given time period. After an initial learning period, the system will initiate desired operation within a predetermined period, illustratively five to ten minutes prior to the learned usage window.

Figure 11:
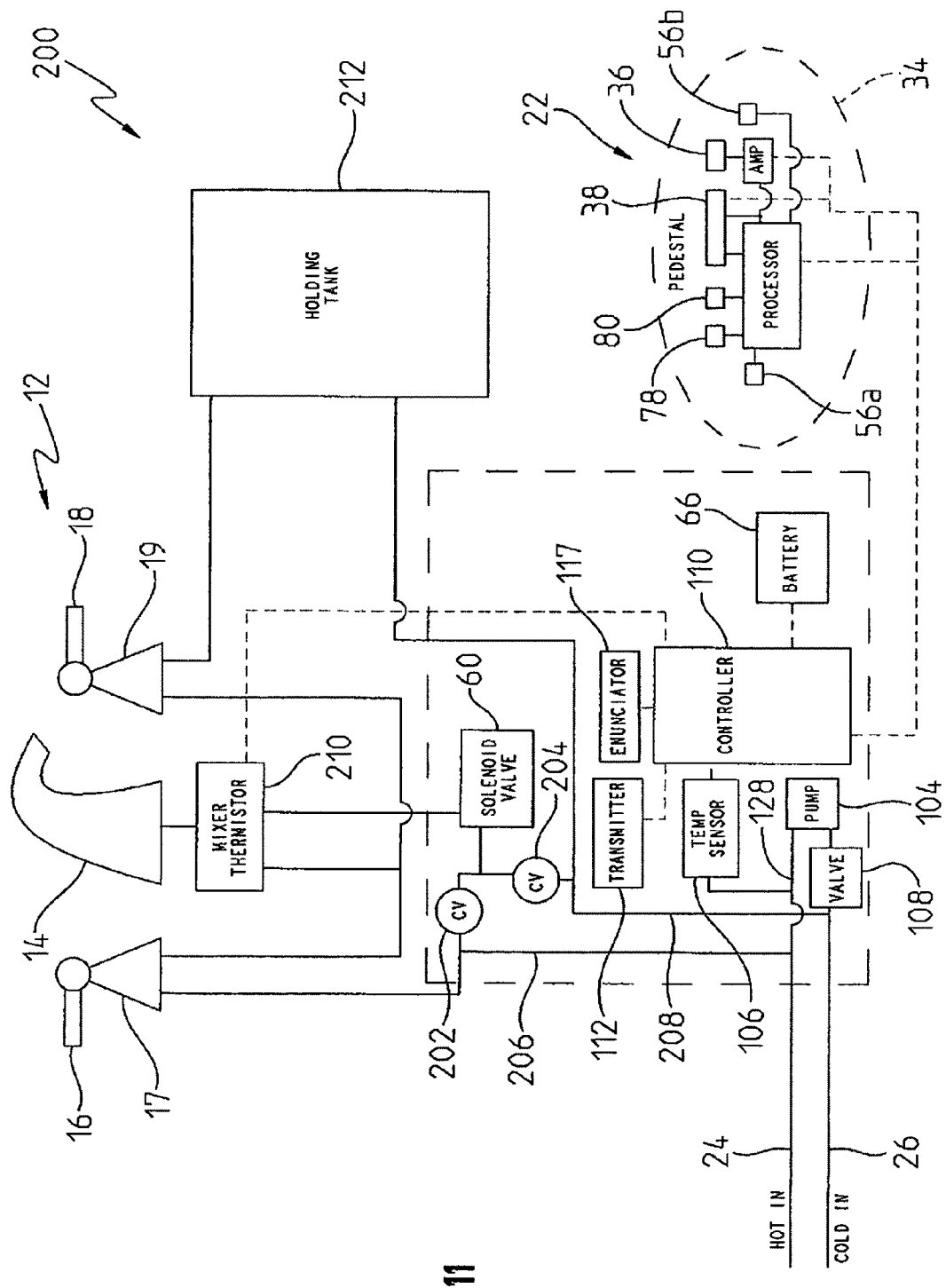
FIG. 11 is a schematic view of a further illustrative hands free system incorporating an integrated quick hot water system.

Turning now to FIG. 11, a further illustrative embodiment integrated hands-free quick hot system 200 is illustrated. Many of the components of the illustrated system 200 are the same as those detailed above with respect to the system 100 of FIG. 10 and, as such, are identified with like reference numbers. However, the electrically operable valve 60 of the system 200 is positioned in parallel to manual valves 17 and 19, as opposed to being positioned in series to valves 17 and 19, as shown in FIG. 10. A pair of check valves 202 and 204 are positioned upstream from the valve 60 in order to prevent unintended cross-flow between the hot and cold water lines 206 and 208. Additionally, a mixer thermistor 210 is positioned immediately upstream from the spout 14 and is configured to detect the temperature of mixed temperature water supplied to the spout 14, while facilitating the mixing of hot and cold water. Recirculation pump 104 is positioned within cross-over line 128 and is in series with cross-over valve 108.

Illustratively, a holding tank 212 is fluidly coupled with the cold water line 208 upstream from the cold water manual valve 19 and may provide for a quick-cold functionality. More particularly, the holding tank 212 may contain an amount, illustratively one quart, of cold or room temperature water which may be supplied to the spout 14 through operation of the manual valve 19. This may prevent the unintended supply of tempered or mixed temperature water immediately after operation of the recirculation pump 104. Moreover, immediately after operation of recirculation pump 104, the cold water supply line 26 will contain mixed temperature water. The holding tank 212 provides a predetermined supply of cold water to delay this water from being supplied to valve 19.

As may be appreciated, the quick hot system 200 of FIG. 11 eliminates the tap sensors 62 and 64 of the prior described control system 100 and also allows for the faucet 12 to be used manually independent of the valve 60. As such, the user gains control over the flow and temperature of water, and starts a flow when his or her hands are proximate the spout 14 and when the valves 17 and 19 are turned off. This "no tap" functionality, or manual mode of operation, is facilitated by the positioning of the electrically operable valve 60 parallel with the manual valves 17 and 19, as detailed above. A sensor is used to detect when the faucet 12 is in use manually. In the illustrative embodiment, the mixer thermistor 210 defines the sensor which provides an indication of water flowing to the spout 14. The detection of flow to the spout 14 in combination with the position of the solenoid valve 60 provides the controller 110 with information necessary to determine whether the manual valves 17 and 19 are open or closed.

Figure 12:
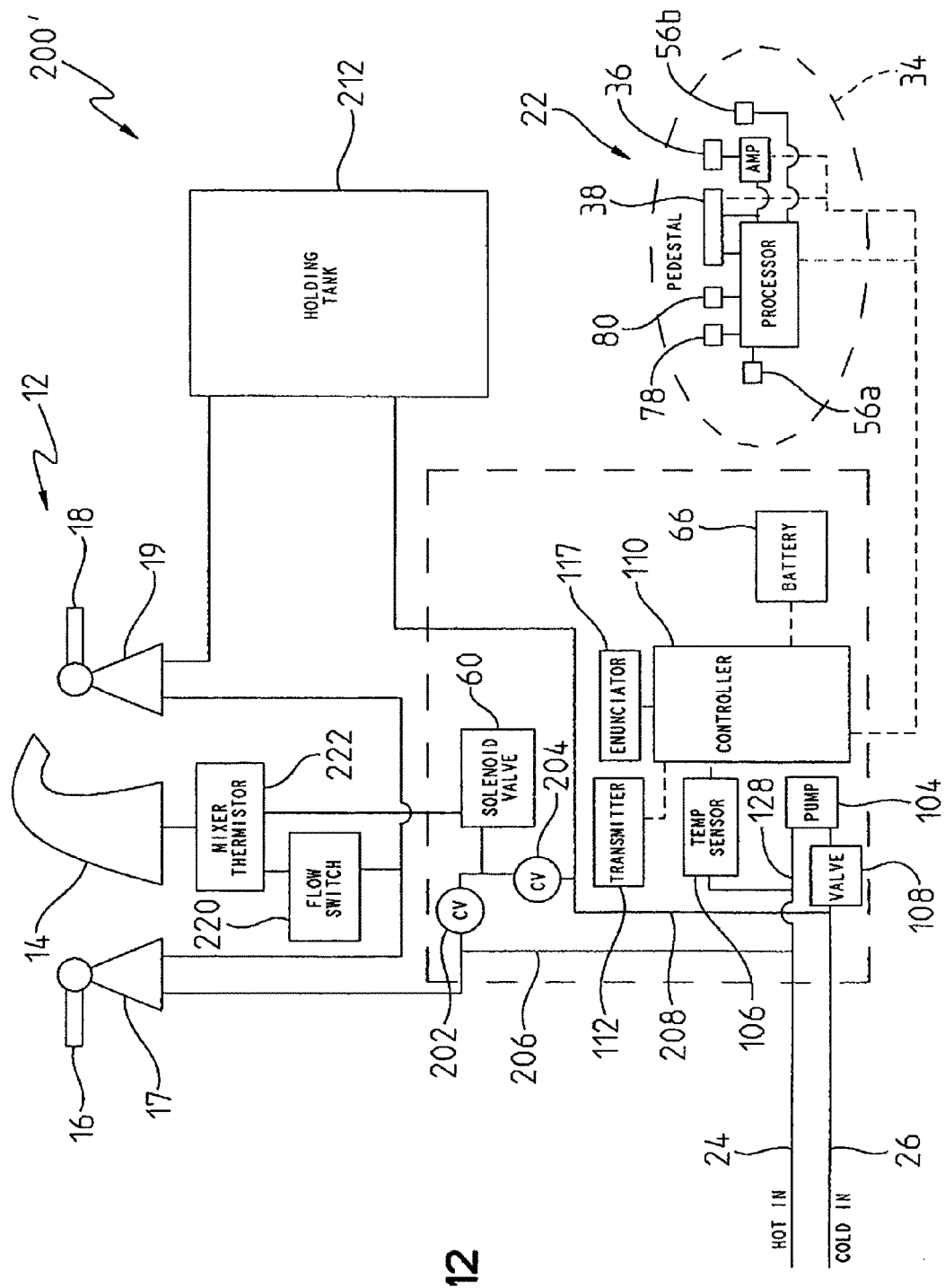
FIG. 12 is a schematic view of a further illustrative hands free system incorporating an integrated quick hot water system.

With reference now to the illustrative embodiment quick hot system 200' of FIG. 12, the mixer thermistor 210 of FIG. 11 may be replaced with a flow switch 220 for detecting water flow to the spout 14, and a mixer 222 for mixing hot and cold water into a blended mixed temperature water.

The flow switch 220 is operably coupled to the controller 110 to inhibit flow from hands-free operation through electrically operable valve 60 when the manual valves 17 and 19 are open. However, this arrangement allows hands-free operation through valve 60 when the manual valves 17 and 19 are closed. Moreover, the controller 110 keeps the valve 60 closed when the flow switch 220 detects flowing water, and permits the valve 60 to open when the flow switch 220 does not detect flowing water. Again, the holding tank 212 is positioned intermediate the point where tempered water is returned back through the cold line 208 and the cold manual valve 19. This provides a quick cold feature as detailed above. Adjustable flow restrictors (not shown) may be positioned after the check valves 202 and 204 that feed the solenoid valve as a means for adjusting the hot/cold water mix resulting from the hands-free operation.

Figure 13:
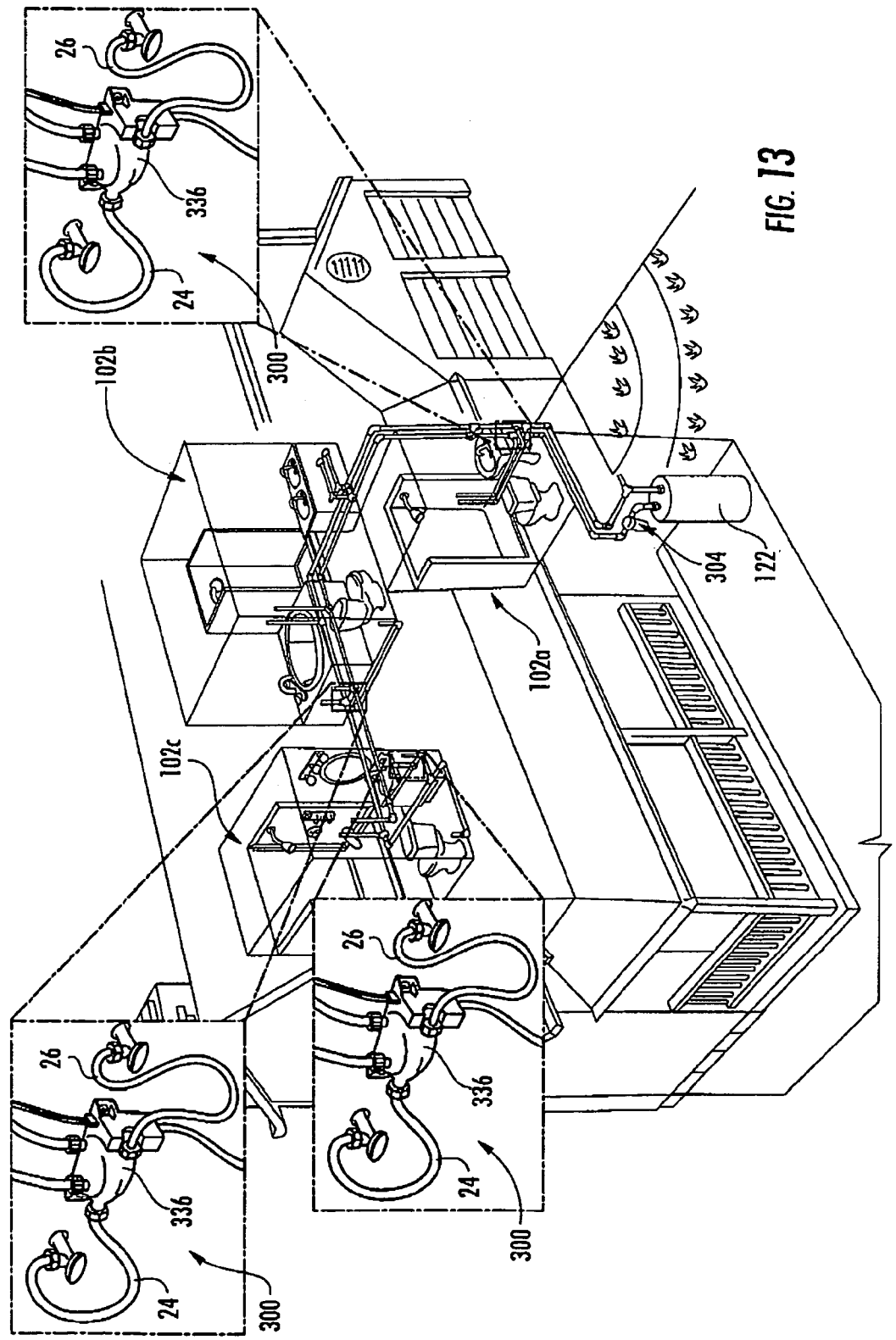
FIG. 13 is a perspective view similar to FIG. 9 of a house including a distributed quick hot water system.
Figure 14:
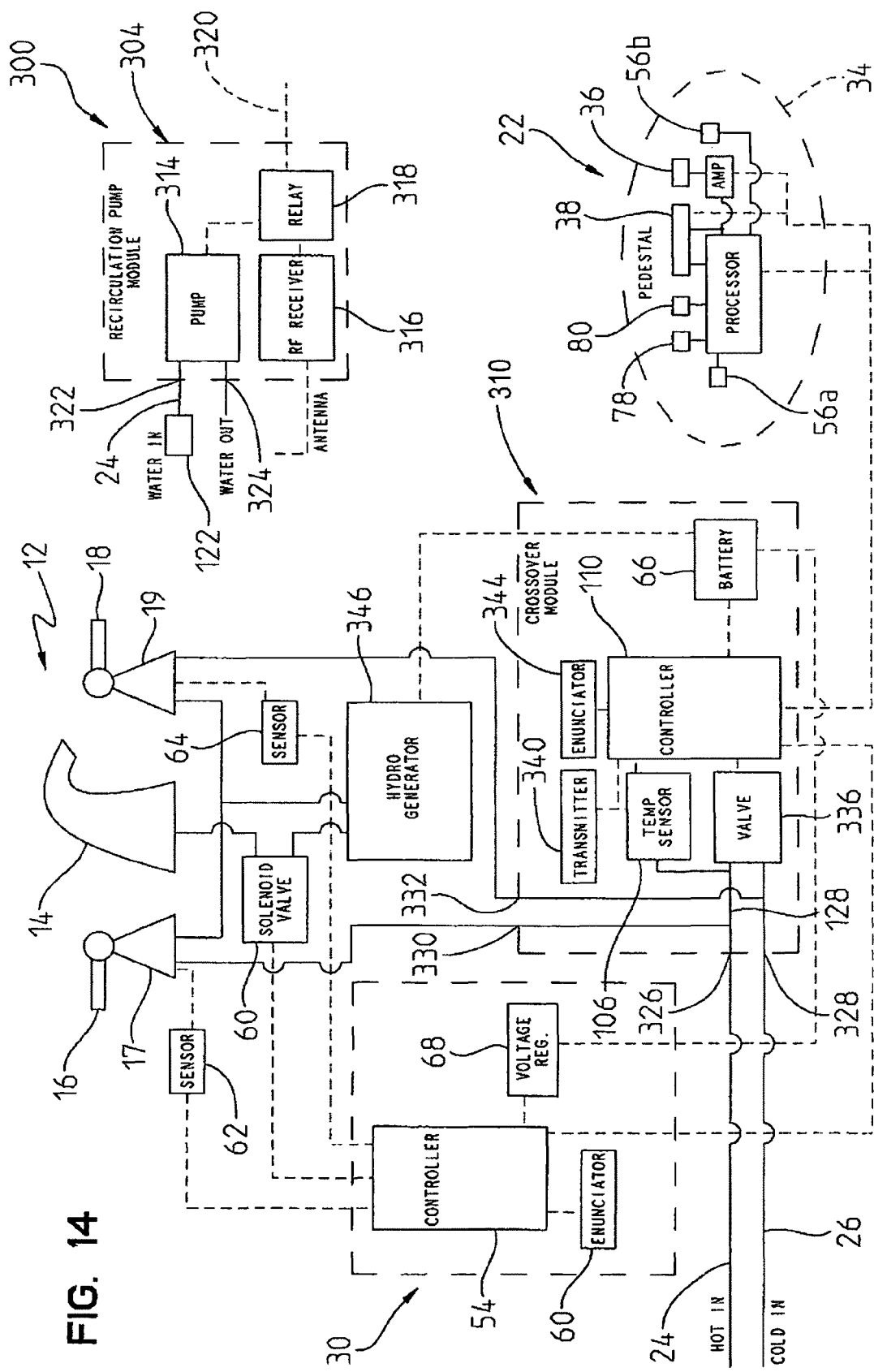
FIG. 14 is a schematic view of an illustrative hands free system incorporating the distributed quick hot water system of FIG. 13.

Turning now to FIGS. 13 and 14, an illustrative embodiment distributed quick hot, or recirculation system 300 is shown for use with bathrooms 102a, 102b, and 102c. In one illustrative embodiment of the distributed quick hot system 300, human presence is detected and results in the delivery of hot water to a least one fluid delivery device or fixture in the bathroom 102, such as the faucet 12. In a further illustrative embodiment, the distributed quick hot module 300 includes system intelligence which predicts when hot water is required based on usage patterns. In the distributed quick hot system 300, a recirculation pump module 304 is located proximate the hot water supply, illustratively hot water heater 122. In the illustrative embodiment, a cross-over valve module 310 is located below the lavatory or sink deck 13, remote from the pump module 304. As with the control system 100 of FIG. 10, a hands free module 30 is located in each bathroom. In one illustrative embodiment, a cross-over valve module 310, including temperature sensor 106, is located in each bathroom 102. In an alternative embodiment, a cross-over valve module 310, including temperature sensor 106, is located only within the bathroom 102c furthest from the recirculation pump module 304. In a further embodiment, a cross-over valve module 310 is located in each bathroom 102a, 102, and 102c, but the temperature sensor 106 is located only within the bathroom 102c furthest from the recirculation pump module 304. In the illustrative embodiments, a sensor 36 is located within each bathroom 102 in order to detect the presence of a person within the first detection zone.

As noted above, the recirculation pump module 304 is mounted adjacent to the water heater 122 and illustratively includes a pump 314 and a receiver 316, illustratively an RF receiver. A relay 318 couples the receiver 316 to the pump 314 and a power supply 320. The pump 314 illustratively operates at 2 gpm at 6 ft. head (3 psi). The recirculation pump module 304 receives RF communications from the sensor module or pedestal 22 for activation (on) and from the cross-over valve module 310 for deactivation (off).

The cross-over valve module 310 includes a hot water inlet 326 and a cold water inlet 328, which are fluidly coupled to the hot water supply line 24 and a cold water supply line 26, respectively. A hot water outlet 330 and a cold water outlet 332 are fluidly coupled to a fluid delivery device, such as a faucet 12.

Both the recirculation pump module 304 and the cross-over valve module 310 may be powered by conventional power supplies, such as 120 VAC power line 320 or a battery 66. Illustratively, the battery 66 may be automatically recharged through the 120 VAC house current. If recharged, the battery 66 illustratively has a life of approximately 7 years. If not, the battery 66 illustratively has a life of approximately 2 years. In the illustrative embodiment, a hydro-generator 346 may be provided in line with the valve 60 in order to generate power in response to water flow through the spout 14 for charging the battery 66.

The cross-over valve module 310 further includes a temperature sensor 106, a cross-over valve 336, and a controller 110 in communication with the temperature sensor 106. The cross-over valve 336 illustratively comprises an electrically operated valve, such as a solenoid valve, controlled by the controller 110. Alternatively, the cross-over valve 336 may comprise a hot-to-cold check valve as further detailed herein. A transceiver 340 is in communication with the controller 110. The battery 66 may provide power to the controller 110 and the transceiver 340. An enunciator 344 is illustratively in communication with the controller 110. Illustratively, the cross-over valve module 310 is located in the furthest bathroom 102c from the water heater 122. As such, the hot water is recirculated through the upstream bathrooms 102a and 102b prior to reaching the furthest bathroom 102c.

In operation, the pump 314 draws water from the hot water heater 122, through inlet 322, and forces the water out through outlet 324 through the hot water supply line 24 and the hot water inlet 326 of the cross-over valve module 310. Controller 110 opens valve 336 such that water passes therethrough and out into the cold water supply line 26 by passing through the cold water inlet 328. The temperature sensor 106 senses the temperature of the water passing through the valve 336 and sends a signal indicative thereof to the controller 110.

Illustratively, the pump 314 is configured to shut off after three minutes of continuous operation, or by operation of the temperature sensor 106. More particularly, the temperature sensor 106 is configured to cause the pump 314 to shut off when the water temperature reaches a predetermined value, illustratively approximately 95° F.

The sensor module 22 may be similar to that identified above with the integrated quick hot module 100. More particularly, the sensor module 22 is configured to detect the entrance and exit of a person from the bathroom 102. The sensor module 22 is configured to communicate with a plurality of smart fluid delivery device modules, including hands-free faucet modules, custom shower modules, roman tub modules, and tub/shower modules. For example, the detector 36 may communicate with the controller 54 of the hands free module 30. When a person is detected in the room 102, the electronics are activated. When the person has left the room 102, the electronics are deactivated. Finally, when a person enters the room 102 and it is dark, nightlights may be activated.

When the user leaves the room 102 and water flow to the shower or tub is initiated, the enunciator 344 illustratively sounds an alarm of a higher volume when the task is completed. When the user enters a room 102, the tub is full and the maintain temperature operation is initiated, the recirculation pump 314 delivers hot water to a heat transfer mechanism, as further detailed herein.

The motion detector 36 transmits a start signal to the pump 314 and illustratively operates at 433 MHz or 900 MHz frequency. The detector 36 also receives instructions from the "smart" roman tub, custom shower, and/or tub shower module.

Illustratively, the controller 110 may utilize system intelligence by tracking usage patterns over a given time period. After an initial learning period, the system will initiate five to ten minutes prior to the learned usage window.

Figure 15:
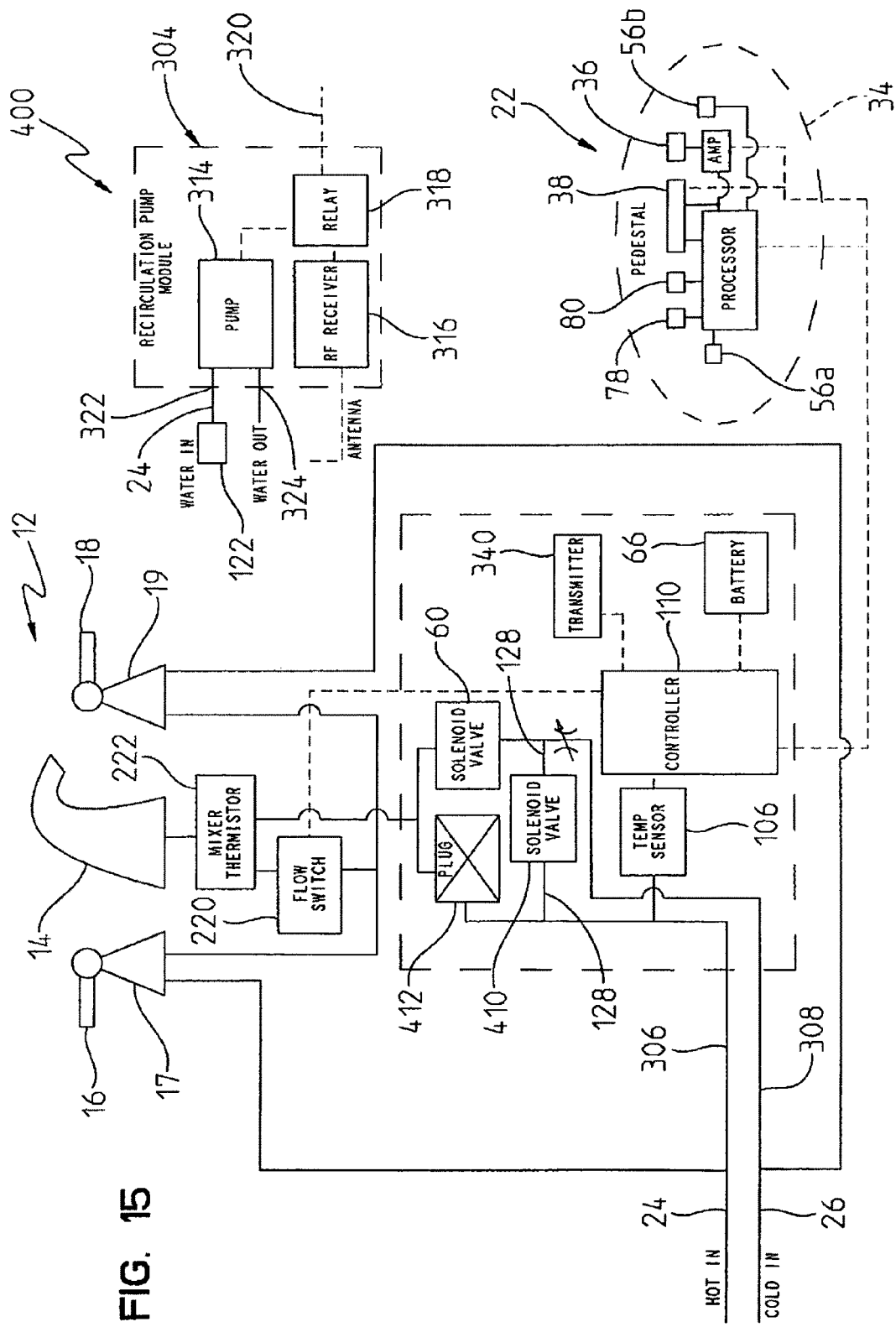
FIG. 15 is a schematic view of a further illustrative hands free system incorporating a distributed quick hot system.

With reference now to FIG. 15, a further illustrative hands-free distributed quick hot system 400 is illustrated. The system 400 of FIG. 15 is similar to the system 300 of FIG. 14 in that the recirculation pump 314 is positioned proximate the hot water heater 122, as opposed to proximate the faucet 12 (i.e., distributed system versus integrated system). As such, transmitter 340 is coupled to the microcontroller 110 for communicating with the receiver 316 coupled to the pump 314. An electrically operable cross-over valve 410 within the cross-over line 128 is in communication with the controller 110 and operates in cooperation with the recirculation pump 314. More particularly, during the recirculation mode of operation, the pump 314 is activated and the valve 410 is opened to permit the flow of water from the hot water supply line 24 through the cross-over line 128 to the cold water supply line 26. A plug 412 is positioned downstream from the cross-over valve 410 and upstream from the spout 14 in order to prevent water flow therethrough. As explained in further detail herein, the plug 412 may also be utilized when a common manifold is present.

Figure 16:
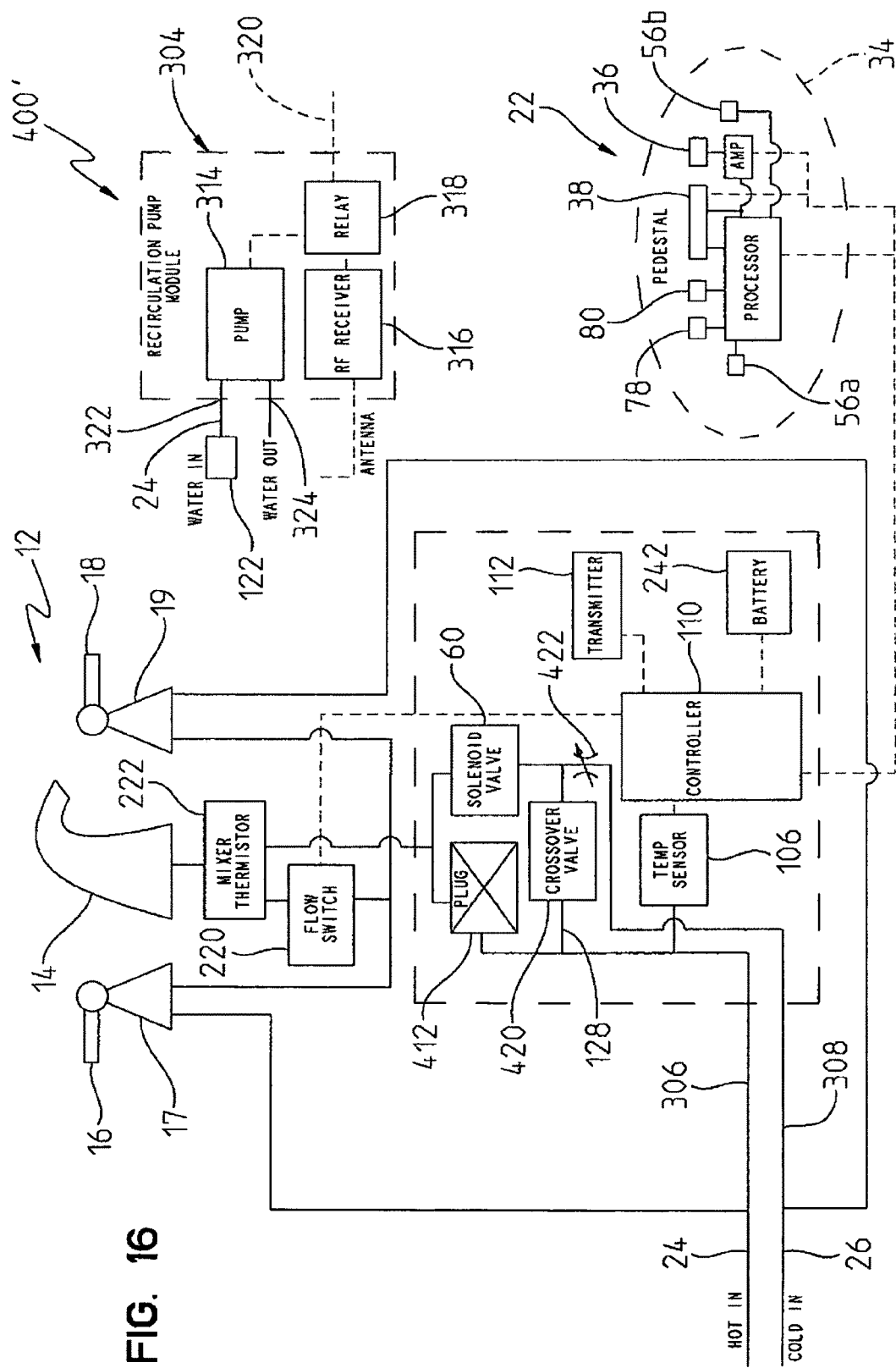
FIG. 16 is a schematic view of a further illustrative hands free system incorporating a distributed quick hot system.

With reference now to FIG. 16, a further illustrative embodiment control system 400' is shown. The system 400' of FIG. 16 is similar to the system of FIG. 15, however a check valve 420 replaces the electrically operable valve 410 within the cross-over line 128. The check valve 420 is illustratively configured to crack or open when pressure in the hot water line 306 increases a predetermined amount due to operation of the recirculation pump 314. An adjustable flow restrictor 422 is illustratively positioned within cold water line 308 for facilitating adjustment of the mixed water temperature supplied by the spout 14.

Figure 17:
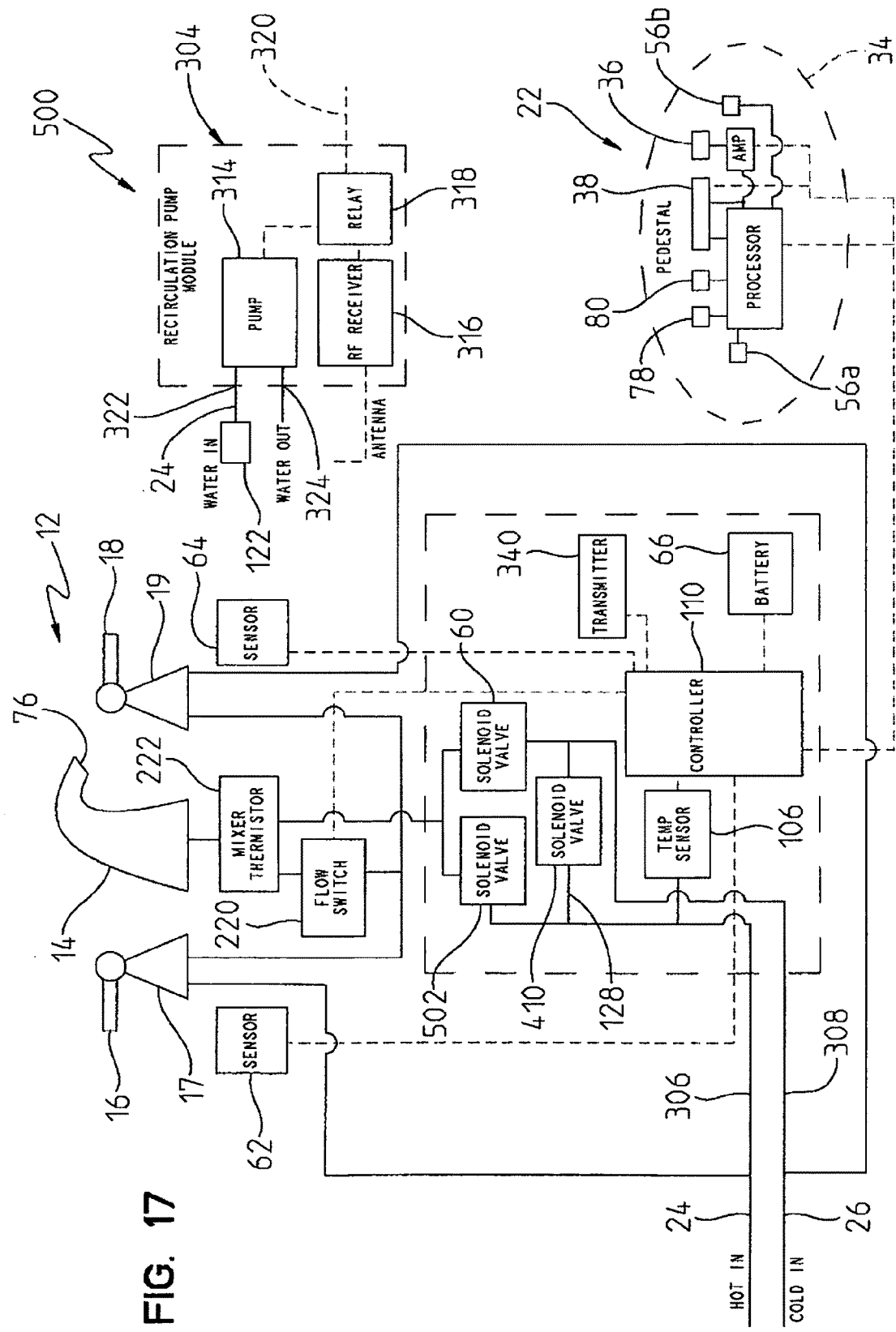
FIG. 17 is a schematic view of a further illustrative hands free system incorporating a distributed quick hot system, and including hot tap and cold tap functionality.

With reference now to FIG. 17, a further illustrative hands-free distributed quick hot system 500 is shown. The system 500 is similar to system 400 illustrated in FIG. 15, but includes an electrically operable valve 502, illustratively a solenoid valve replacing the plug 412. Additionally, touch or tap sensors 62 and 64 are operably coupled with the handles 16 and 18. In an illustrative embodiment, the tap sensors 62 and 64 may provide for the adjustment of water temperature when operating in the hands-free mode. More particularly, tapping of hot and cold handles 16 and 18 may incrementally increase the flow of hot and cold water, respectively.

In a further illustrative embodiment, the tap sensors 62 and 64 may be utilized in an independent mode of operation from the hands-free or the manual modes. More particularly, tapping the hot or cold sensors 62 and 64 may activate the respective valves 502 and 60 for permitting hot or cold water to flow through the spout 14. Such operation is independent from the other modes of operation.

In this illustrative mode of operation, initial tapping of the hot water handle 16 is detected by tap sensor 62 which causes the controller 110 to open the hot water valve 502. A second tap of the hot water handle 16 causes the controller 110 to close the hot water valve 502. Tapping the cold water handle 18 after the hot water handle 16 has been tapped causes the controller 110 to open the cold water valve 60 such that mixed hot and cold water flows through the spout 14. After either of the hot or cold handles 16 and 18 have been tapped once, subsequent tapping of the same handle 16 and 18 will turn off the water flow. In a similar manner, initial tapping of the cold water handle 18 is detected by tap sensor 64 which causes the controller 110 to open the cold water valve 60. Subsequent tapping of the hot water handle 16 causes a mixture of hot and cold water to flow through the spout 14. After either of the hot and cold handles 16 and 18 have been tapped once, subsequent tapping of the same handle 16 and 18 will turn off the water flow.

It should be appreciated that the tap sensors 62 and 64 may be utilized in other manners depending upon the logic contained within the controller 110. More particularly, subsequent taps of the hot or cold handles 16 and 18 may incrementally adjust the temperature of the water flowing from either the hot or cold valves 502 and 60. In other words, tapping the hot water handle 16 a second or third time may incrementally increase hot water supplied to the spout 14.

Similarly, incrementally tapping the cold water handle 18 may cause incremental increases in cold water supplied to the spout 14.

Figure 18:
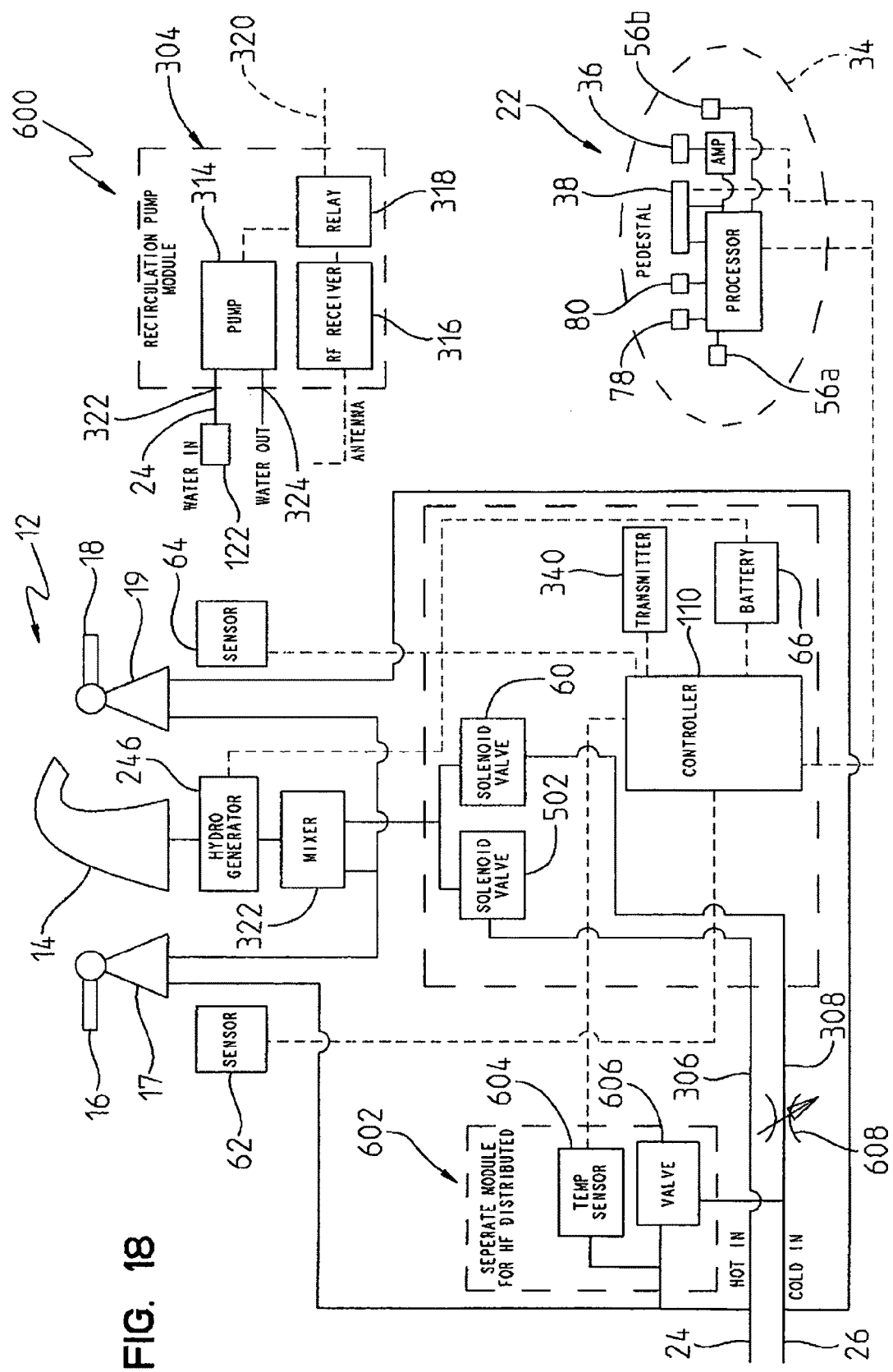
FIG. 18 is a schematic view of a further illustrative hands free system incorporating a distributed quick hot system, and including hot tap and cold tap functionality.

Turning now to FIG. 18, a further illustrative hands-free distributed quick hot system 600 is illustrated as having a separate module 602 configured to provide distributed quick hot functionality. In other words, the quick hot features have been made optional with respect to the hands-free features. The module 602 includes a temperature sensor 604 in communication with the controller 110. A cross-over valve 606 is also provided, while the recirculation pump module 304, including pump 314, is located adjacent the hot water heater 122. An adjustable restrictor 608 may be provided in cold water line 308 to adjust the ratio of cold water to hot water supplied to mixer 322.

Figure 19:
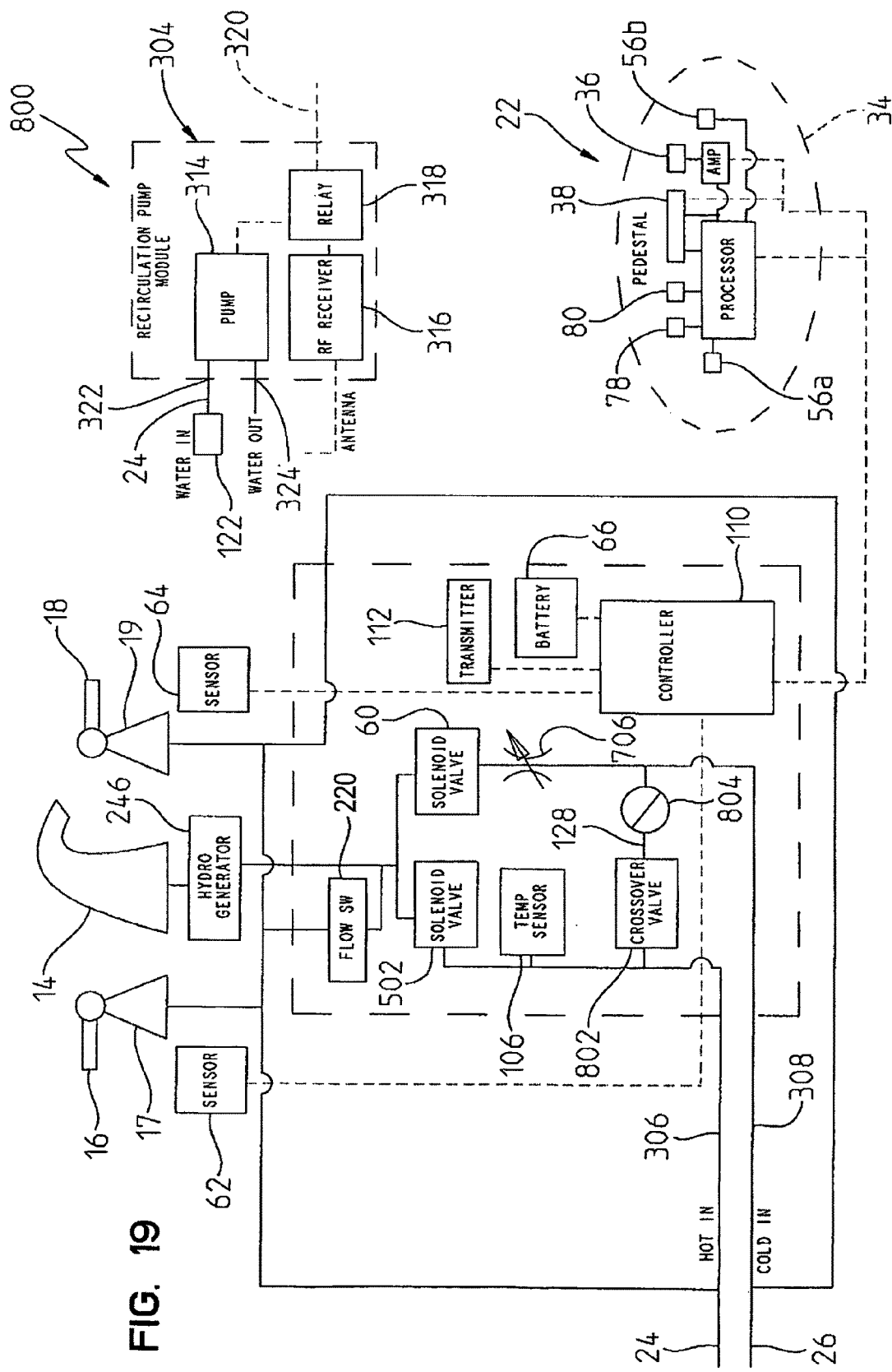
FIG. 19 is a schematic view of a further illustrative hands free system incorporating a distributed quick hot system, and including hot tap and cold tap functionality.

FIG. 19 illustrates a further illustrative hands-free distributed quick hot system 800 which is a variation of the system 600 as shown in FIG. 18. The system 800, as with system 600 detailed above, includes first and second electrically operable valves 502 and 60 to control the flow of hot and cold water to the spout 14 in a hands-free mode of operation. A cross-over valve 802, illustratively an electrically operable or check valve, is positioned within the cross-over line 128 and is configured to allow water flow from the hot water line 306 to the cold water line 308 when the recirculation pump adjacent the hot water heater 122 is operating. A valve 804, illustratively a ball valve, is positioned downstream from the cross-over valve 802 and is configured to selectively close the cross-over line 128. More particularly, the ball valve 804 may be in a closed positioned for all installations except for the fixture (i.e., faucet 12) furthest from the hot water heater 122, which provides for the effective recirculation of hot water to the fixture furthest from the hot water heater 122.

Figure 20:
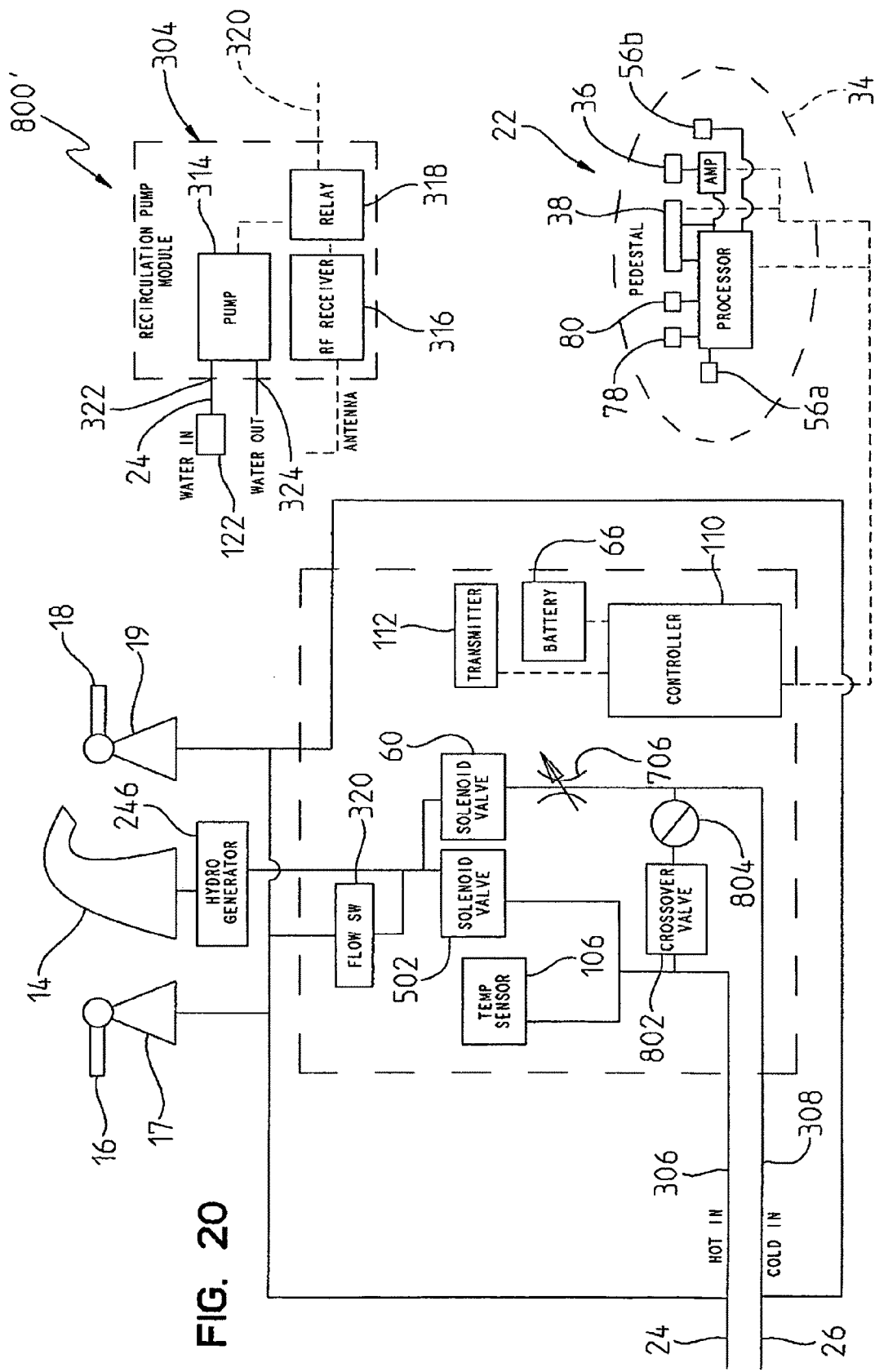
FIG. 20 is a schematic view of a further illustrative hands free system incorporating a distributed quick hot system.

FIG. 20 illustrates a hands-free distributed system 800' which is similar to the system of FIG. 19, but without tap sensors 62 and 64.

Referring now to FIGS. 21-31, an illustrative modular system 900 including a housing 902 is shown. The system 900 may include components of the hands free module 30 (FIGS. 4A and 4B), the recirculation pump module 103 (FIG. 10), and/or the cross-over module 310 (FIG. 14), which are combined in order to minimize the physical size of a housing 902. The design permits integration of hands-free and quick hot modules 30 and 103, 310 into a compact, easily installed unit. It should be noted that the system 900 is modular such that the housing 902 may incorporate the hands free module 30 alone, the quick hot module 103, 310 alone, or a combination of modules 30, 103, and 310. More particularly, the system 900 may be provided with electrical connections and fluid couplings configured such that the modules 30 and 103, 310 may be added and/or removed as desired, thereby providing for a modular "plug and play" capability.

Figure 21:
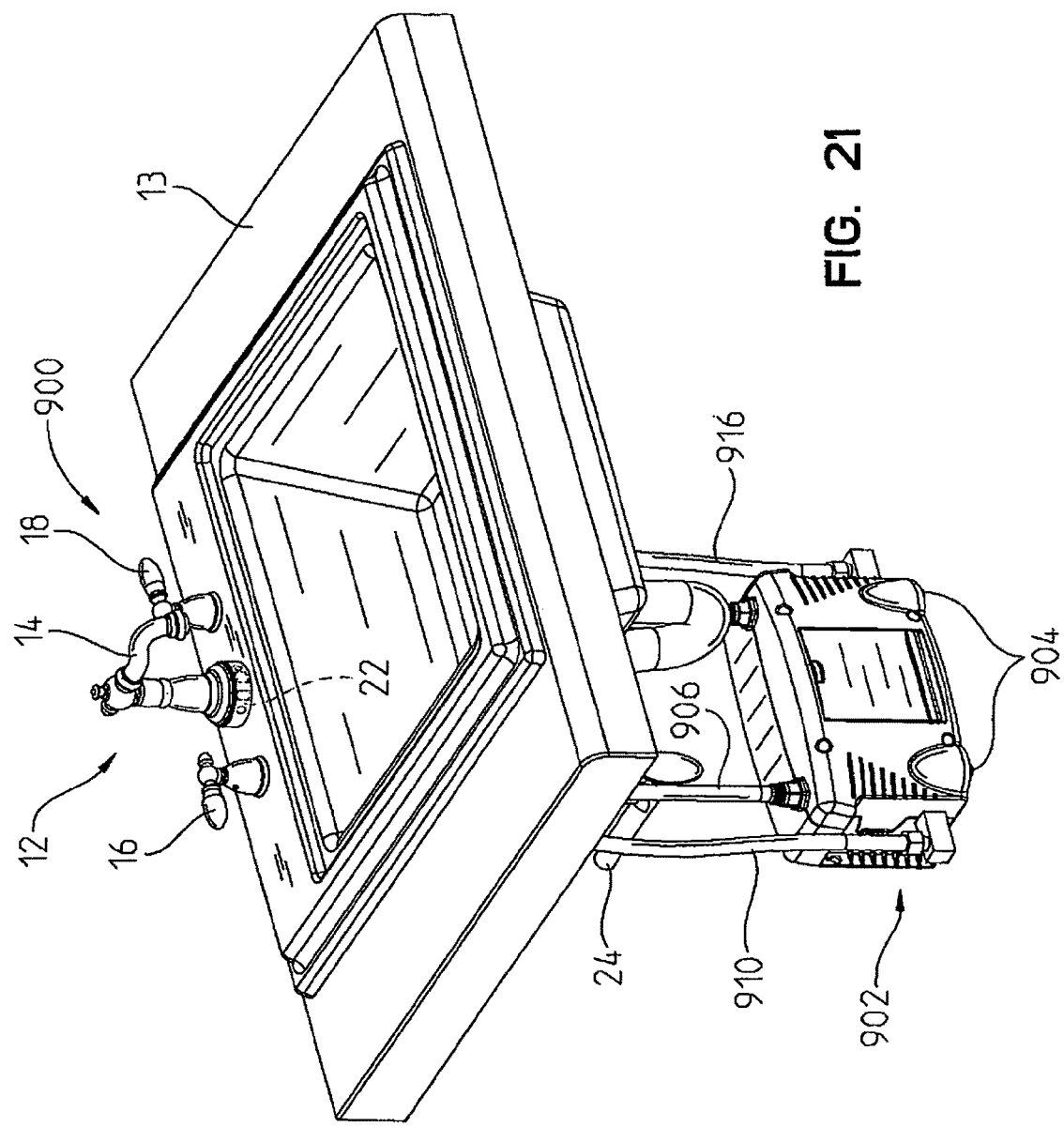
FIG. 21 is a perspective view of a modular hands free water system positioned under a sink deck.
Figure 22:
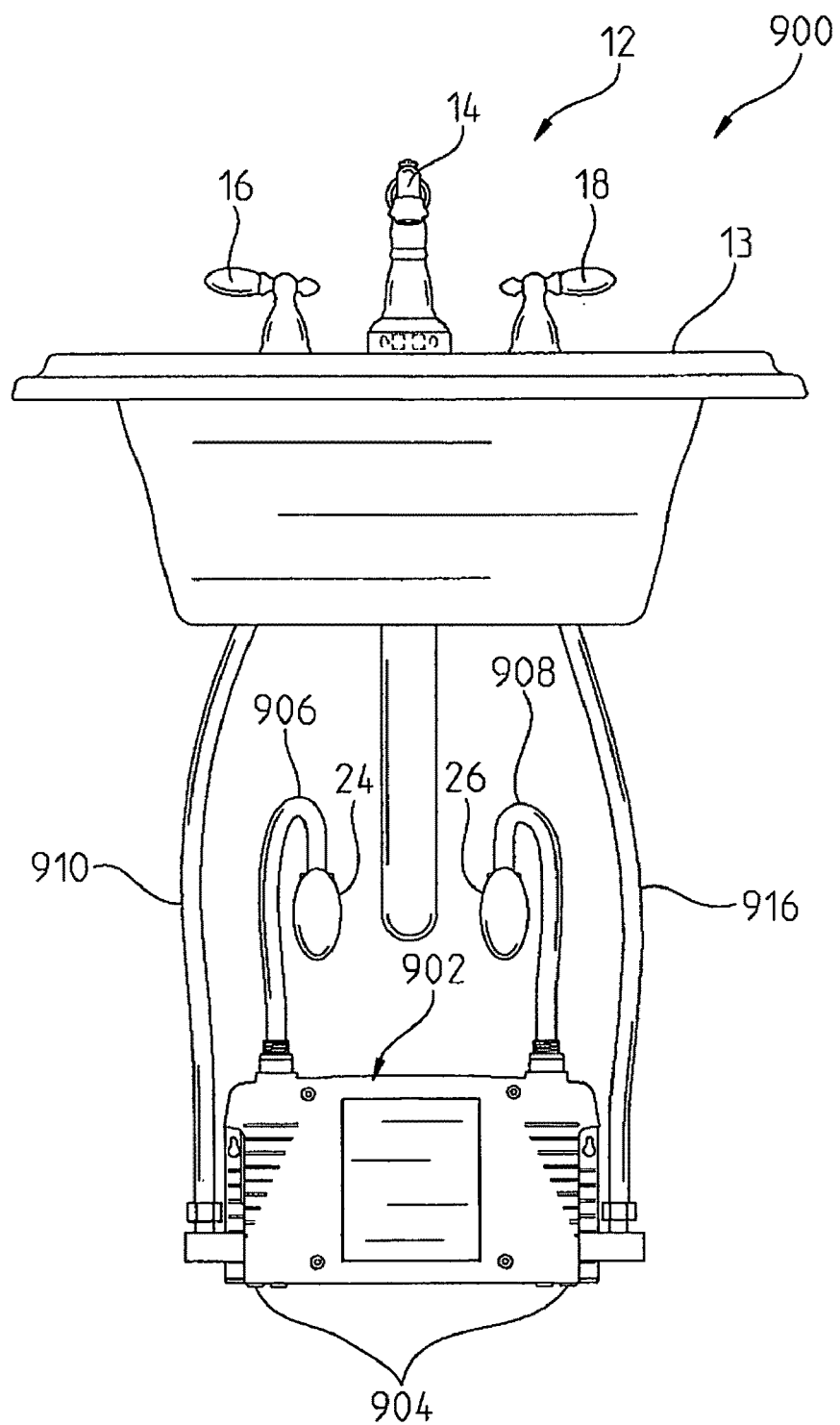
FIG. 22 is a front view of the system of FIG. 21.
Figure 23:
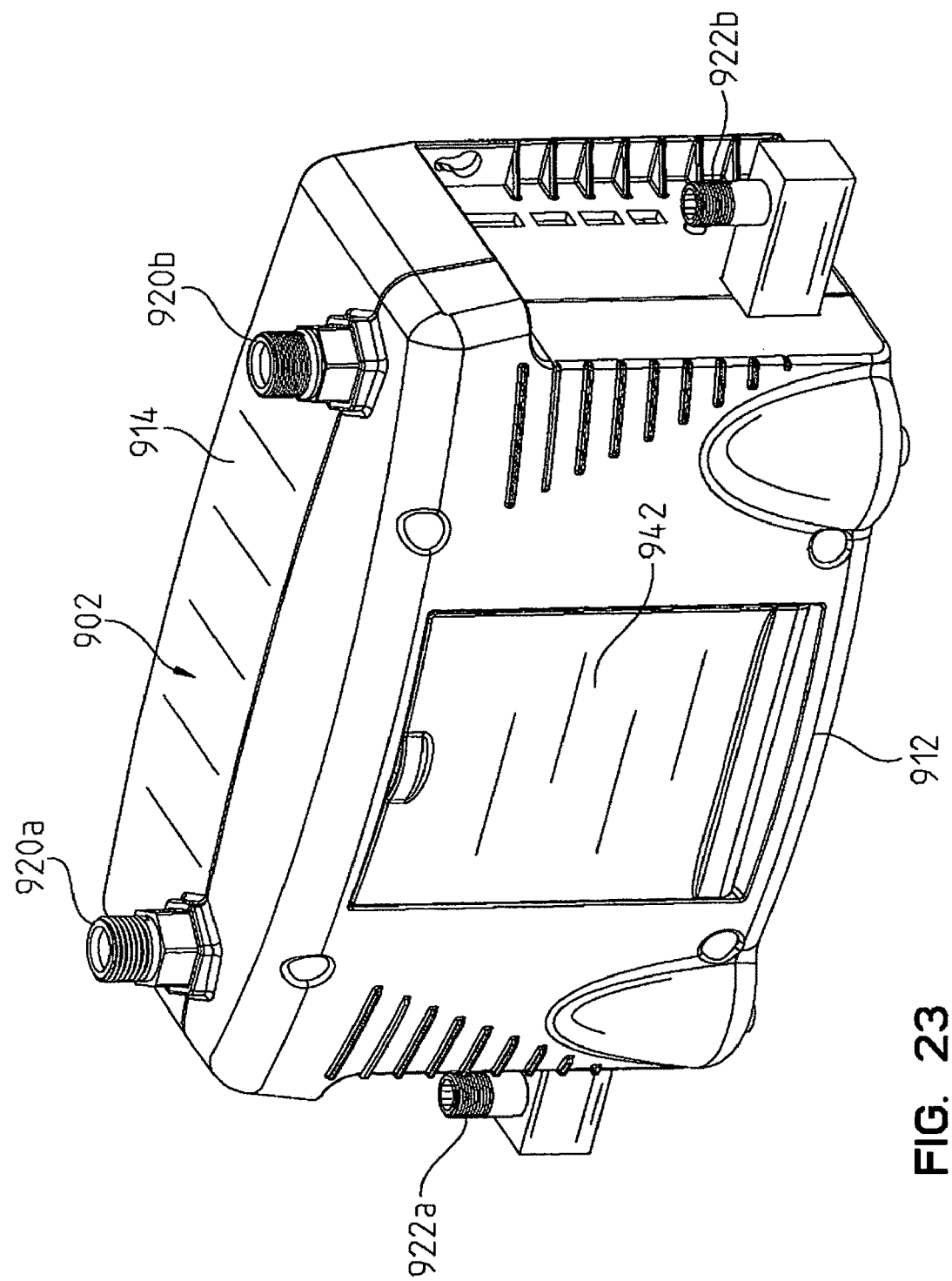
FIG. 23 is a right front perspective view of the system of FIG. 21.
Figure 24:
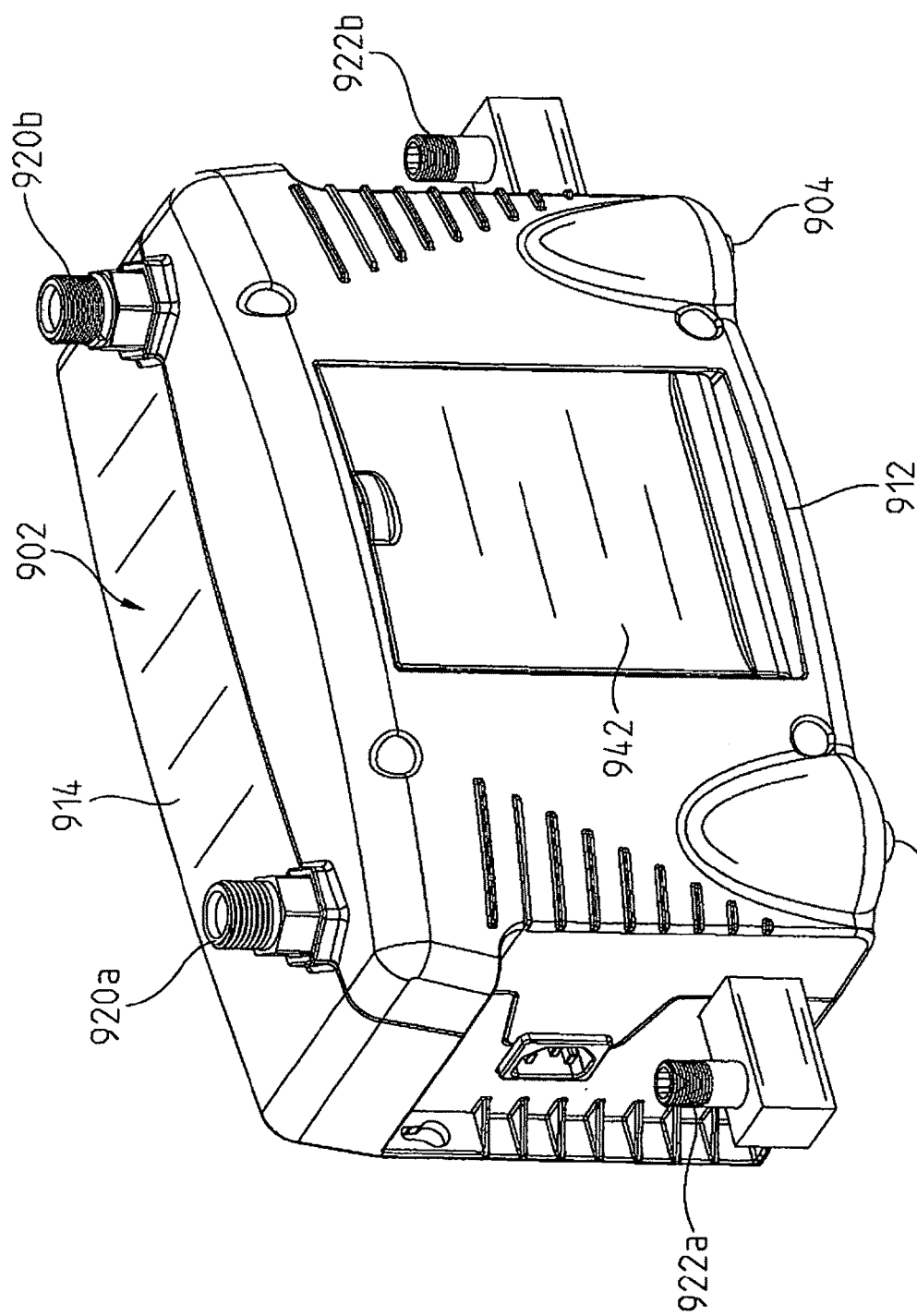
FIG. 24 is a left front perspective view of the system of FIG. 21.

FIGS. 21 and 22 show the housing 902 located beneath a conventional sink deck 13 and supported by feet 905. The hot water supply 24 is coupled to the system 900 through a hot water inlet tube 906, while the cold water supply 26 is coupled to the system 900 through a cold water inlet tube 908. A hot water outlet tube 910 couples the system 900 to the hot water inlet 25 of the faucet 12. Similarly, a cold water outlet tube 916 couples the system 900 to the cold water inlet 27 of the faucet 12. FIGS. 23 and 24 show threaded connections 920 and 922 for coupling the inlet tubes 906 and 908 and outlet tubes 910 and 916 to the system 900. It should be appreciated that the threaded connections 920 and 922 may be replaced with other conventional connections, such as quick connect couplings.

The housing 902 illustratively includes a front portion 912 coupled to a rear portion 914. Both portions 912 and 914 may be formed of a molded thermoplastic.

Figure 25:
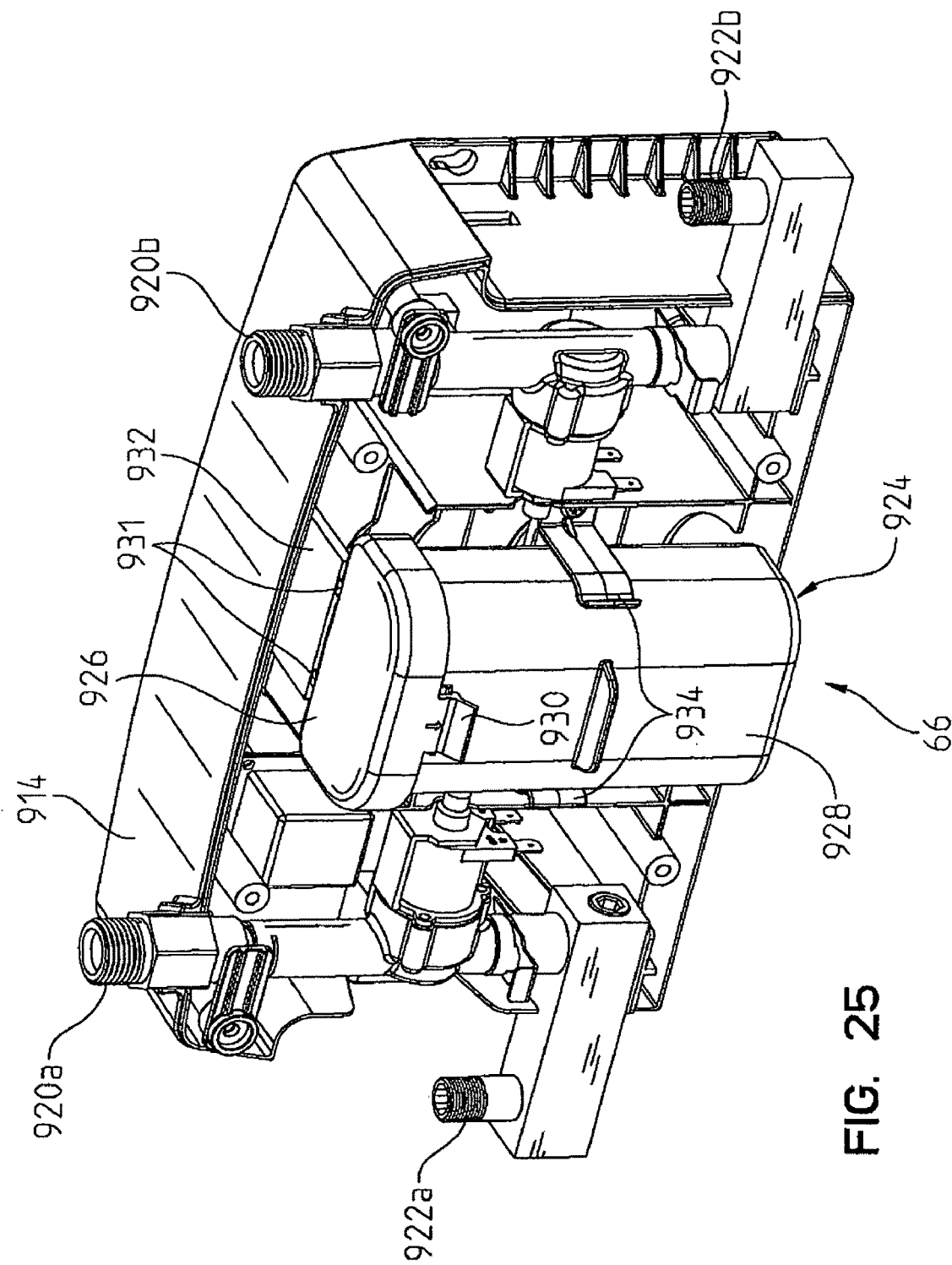
FIG. 25 is a perspective view similar to FIG. 23, with the outer cover removed to show the internal components for use as a hands free system.

With reference to FIGS. 4B and 25, battery 66 may be received within a battery pack or compartment assembly 924 and placed in communication with the controller 54 for powering operation of the hands-free module 30, including the hands free sensor 38 and the solenoid valves 60a and 60b. The battery compartment assembly 924 illustratively includes a lid 926 and a housing 928, which are formed of a non-conductive material and together define an interior space. The lid 926 may be hingedly coupled to the housing 928 and illustratively includes a latch 930. In one illustrative embodiment, a pair of contacts 931 extend rearwardly from the lid 926 and are configured to be slidably received within a pair of receiving slots supporting electrical contacts (not shown) and in electrical communication with a power module circuit board 932. A pair of resilient arms 934 are configured to engage the housing 928 and facilitate securing the battery compartment assembly 924 to housing 902.

The interior space of the housing 928 is configured to receive a plurality of batteries 66. In the illustrative embodiment, the interior space is configured to receive four (4) D-cell batteries (not shown). However, it should be appreciated that the housing 928 may be configured to receive different numbers and sizes of batteries (i.e., AA, AAA, C, and/or D-cell). The battery compartment assembly 924 may be of the type detailed in U.S. Provisional patent application Ser. No. 11/324,901, filed Jan. 4, 2006, titled "BATTERY BOX ASSEMBLY," the disclosure of which is expressly incorporated by reference herein.

Figure 26:
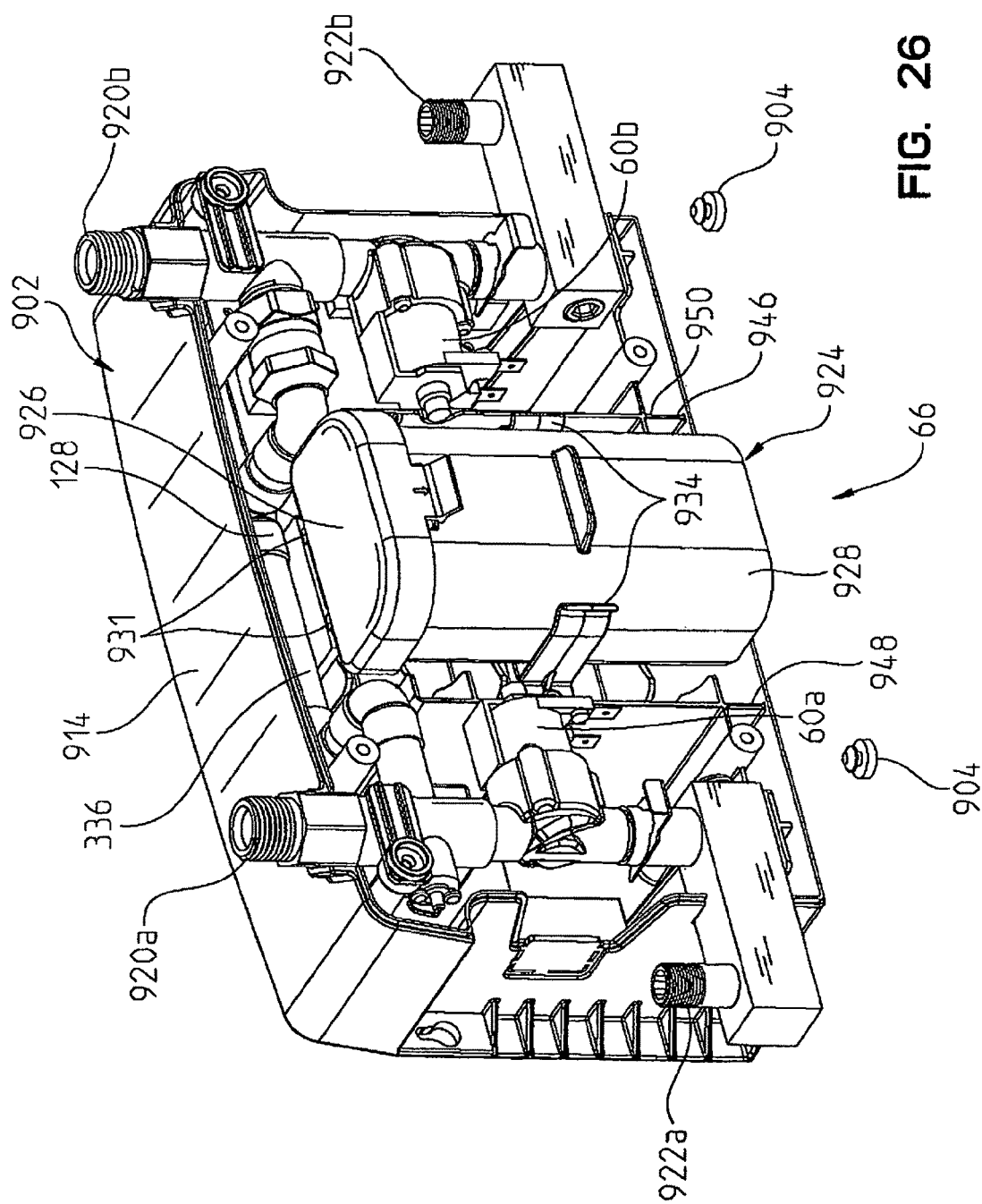
FIG. 26 is a perspective view similar to FIG. 25 showing a cross-over line for use as a hands free quick hot distributed system.
Figure 27:
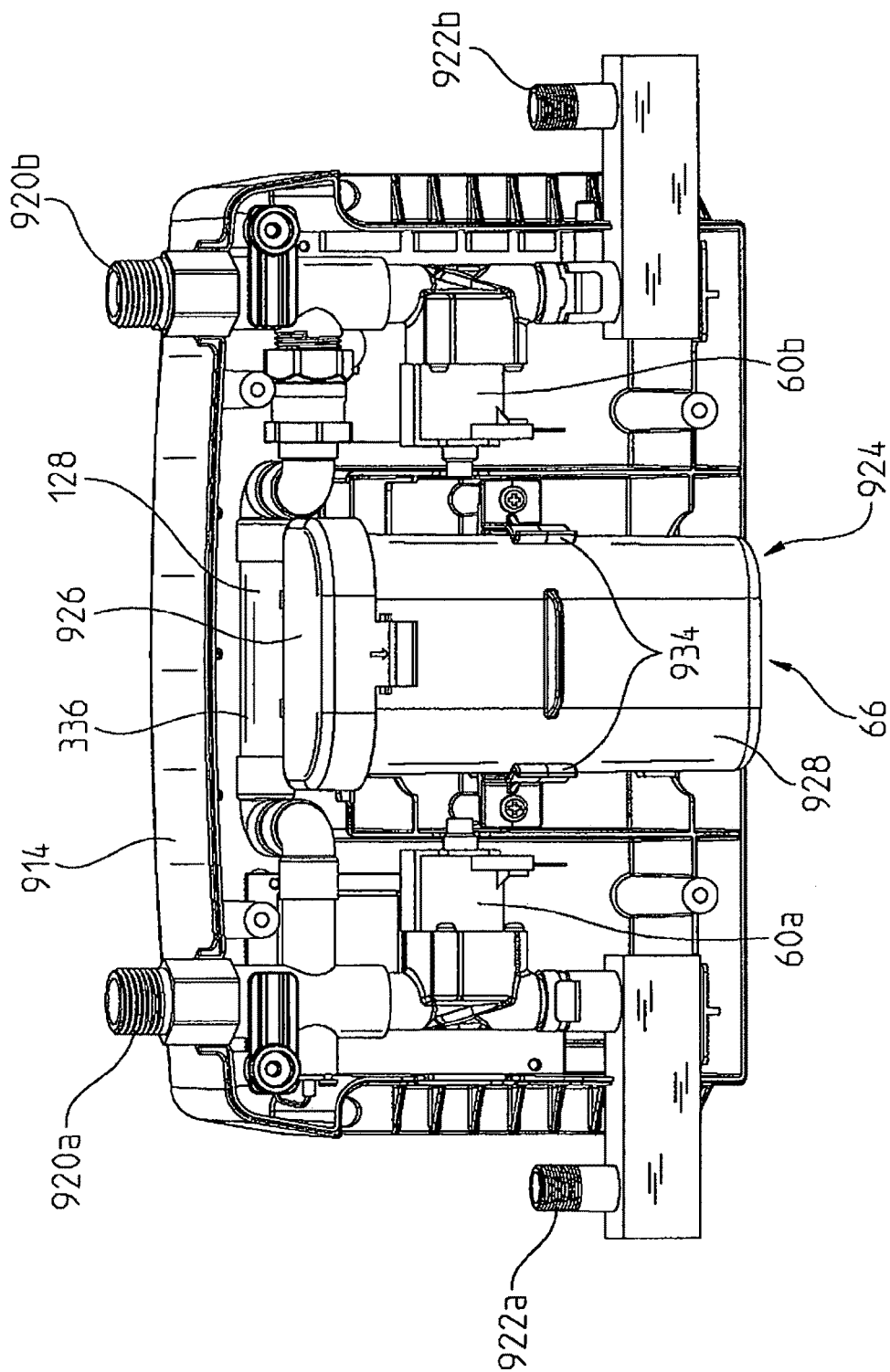
FIG. 27 is a front elevational view similar to FIG. 26.
Figure 28:
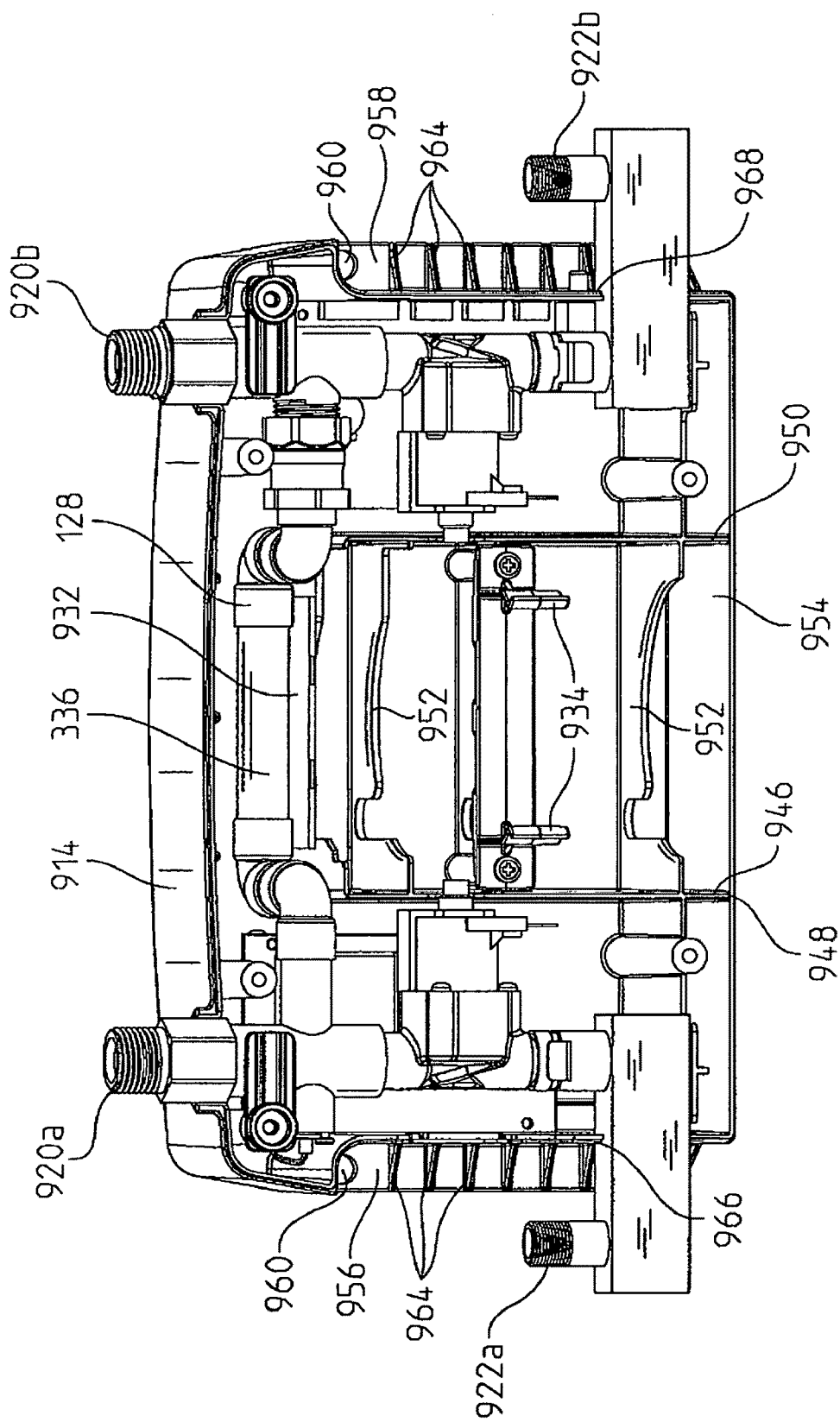
FIG. 28 is a front elevational view similar to FIG. 27, showing the battery pack removed.

In the illustrative embodiment of FIGS. 26-28, a cross-over line 128 and valve 336 are provided to form cross-over module similar to module 310 of hands-free distributed quick hot system 300 of the type illustrated in FIG. 14.

Figure 29:
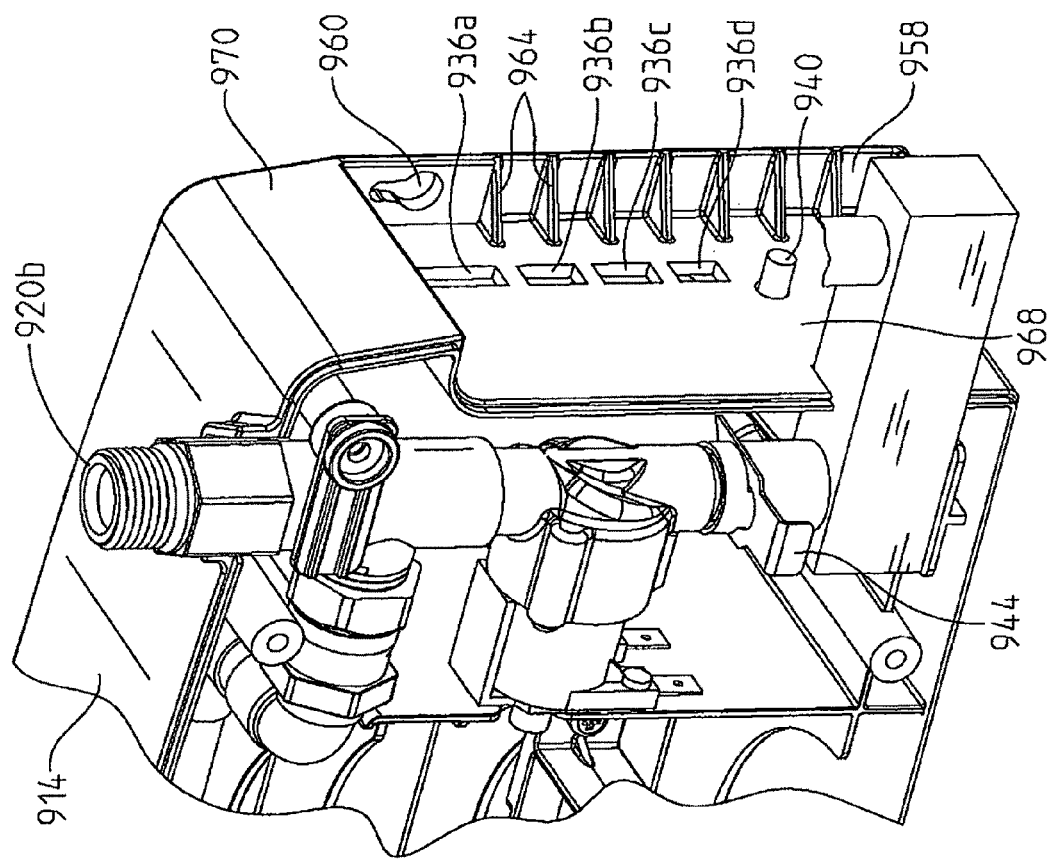
FIG. 29 is a partial perspective view similar to FIG. 28, showing the various connections to external components.

As shown in the detail view of FIG. 29, a plurality of electrical connections 936 to the controller 54 are provided in the sidewall 938 of rear portion 914 of housing 902. These connections 936 may be defined by conventional electrical connectors or plugs. More particularly, connection 936a is provided to the pedestal 22, connections 936b and 936c are provided to the left and right capacitance touch sensors 62 and 64, and connection 936d is provided to an external thermistor (not shown). The external thermistor illustratively may be placed in fluid communication with mixed water exiting the faucet 12 and is configured to provide a signal indicative of temperature to the controller 54. The controller 54 uses the signal to deactivate water flow if the detected temperature is too great (illustratively above 105° F.), thereby providing for scald protection. In one illustrative embodiment, when the thermistor detects that the water temperature at the spout 14 exceeds 105° F., the hot water solenoid valve 60a is closed. When the thermistor detects the water temperature reaches 98° F., the solenoid valve 60a is again opened. As such, the solenoid valve 60a may be "pulsed" (i.e., opened and closed in succession) to adjust temperature. A potentiometer 940 is provided to adjust the shut-off temperature (for scald protection) or the desired hot water temperature as controlled by the controller 54.

Figure 30:
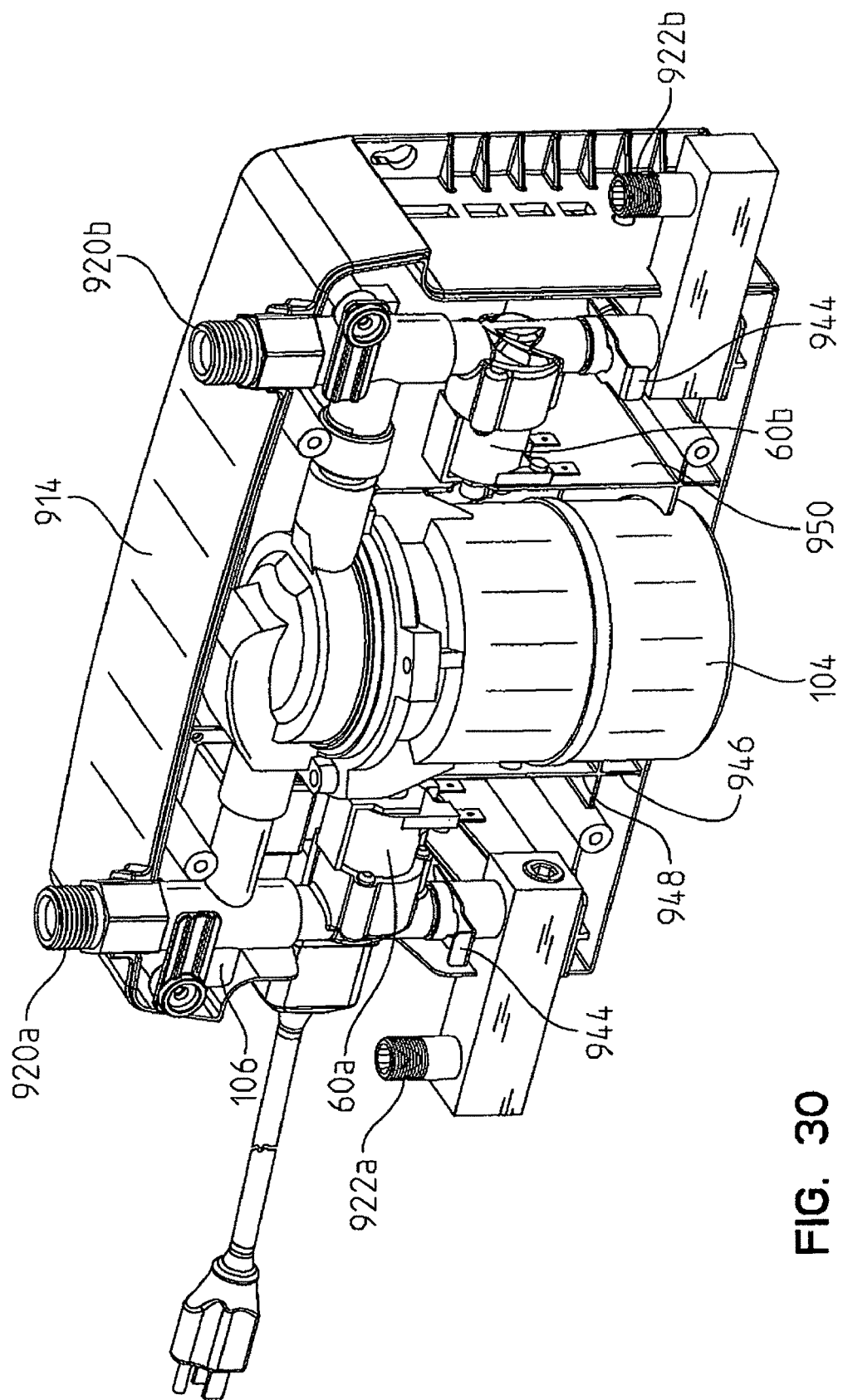
FIG. 30 is a perspective view similar to FIG. 26, showing the battery pack replaced with a recirculating pump for providing a hands free quick hot integrated system.
Figure 31:
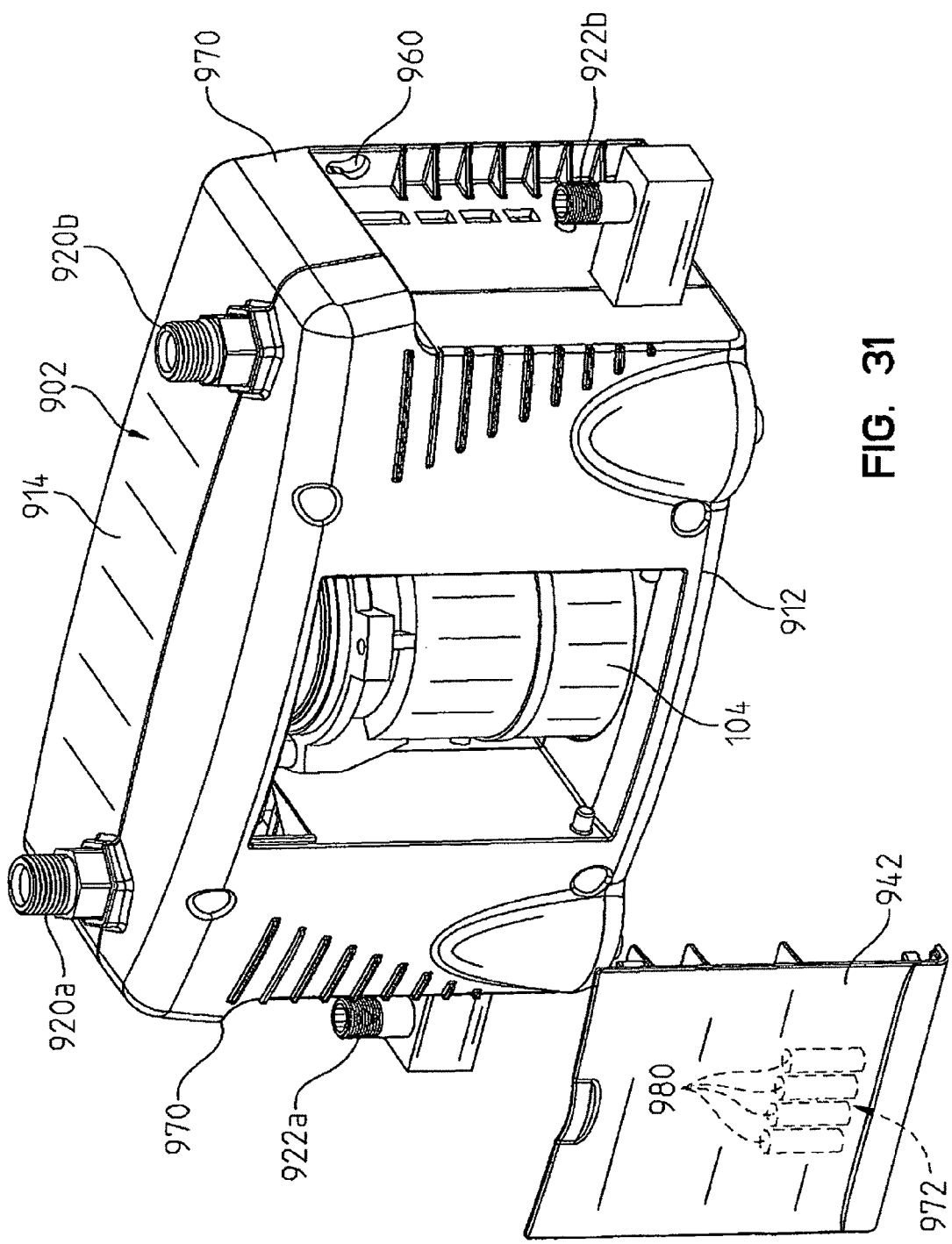
FIG. 31 is a perspective view similar to FIG. 30, showing the outer cover supporting an access door having a battery backup.

As shown in FIGS. 30 and 31, a recirculation pump 104 is positioned within the housing 902 and is fluidly coupled to the inlet tubes 906 and 908. The pump 104 may replace the battery compartment assembly 924 for providing a hands free integrated quick hot system 100 of the type shown in FIG. 10. The pump 104 may be accessed through an access door 942. Solenoid valves 60a and 60b are positioned intermediate the inlet tubes 906 and 908 and outlet tubes 910 and 916, respectively, while the pump 104 is positioned intermediate the inlet tubes 906 and 908. U-shaped quick connect clips 944 are illustratively used to couple the connections 922 to the solenoid valves 60a and 60b. Thermistor 106 is in communication with water passing through the hot water inlet tube 906 and is configured to provide a signal to controller 110 indicative of water temperature passing through the pump 104.

With reference to FIGS. 26, 28 and 30, a support 946 is illustratively positioned inside the housing 902. Illustratively, the support 946 is integrally formed with the rear portion 914 of molded thermoplastic. First and second vertical webs 948 and 950 support the solenoid valves 60a and 60b, respectively. Cross members 952 and a base 954 alternatively support the battery compartment assembly 924 and the pump 104 (FIG. 28). Flanges 956 and 958 are formed on opposing sides of the rear portion 914 and include keyholes 960 (FIG. 29) to facilitate mounting of the housing 902 to a vertical surface through conventional fasteners, such as screws (not shown). A plurality of gussets 964 extend between each flange 956, 958 and a respective sidewall 966, 968 to provide improved structural rigidity. A water shield 970 extends between the flanges 956 and 958 is configured to prevent water from entering the housing 902 and from contacting the electrical connections extending through the sidewalls 966 and 968.

With further reference now to FIG. 31, a battery backup assembly 972 may be provided for operating the system in the event of a power failure. More particularly, the battery backup assembly 972 is configured to operate both the hands free module and the quick hot module should power from the main power supply be interrupted. In the illustrative embodiment, the battery backup assembly 972 is supported by a rear surface of the access door 942 and includes a housing (not shown) integrally formed therewith. Electrical contacts (not shown) are supported by the housing for receiving a plurality of batteries, illustratively four (4) AAA-cell batteries 980. Again, it should be appreciated that different numbers and sizes of batteries may be used.

Figure 32:
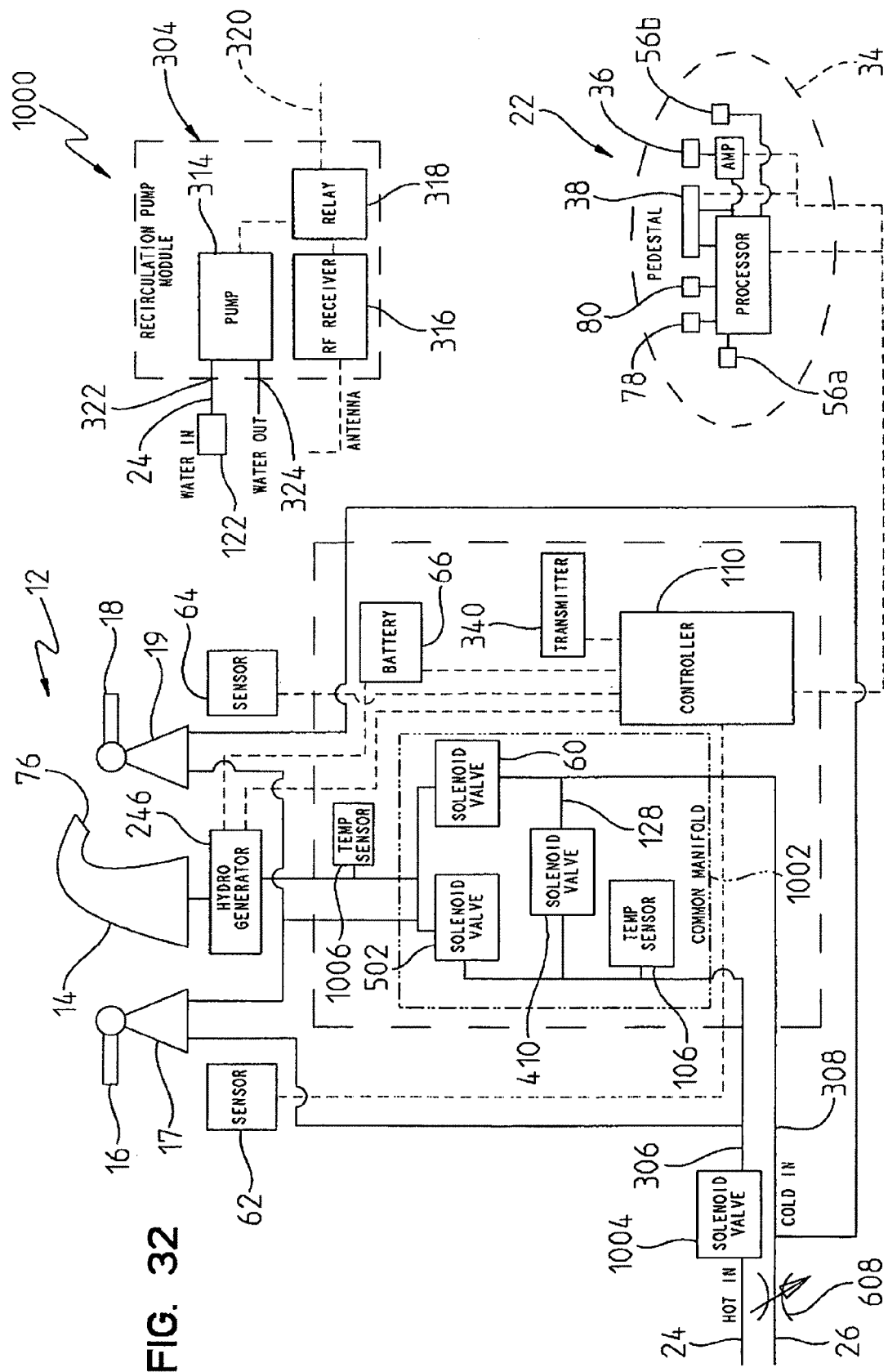
FIG. 32 is a schematic view of a further illustrative hands free system incorporating a distributed quick hot system, and including a manifold for supporting electrically operable valves.

With reference now to FIG. 32, a further illustrative embodiment hands-free distributed quick hot system 1000, similar to system 500 illustrated in FIG. 17, is shown. In system 1000, the flow sensor 220 is incorporated within hydro-generator 246. More particularly, operation of the hydro-generator 246 provides a signal to the controller 110 indicating that water is flowing through the spout 14. During initial faucet use, the controller 110 can determine whether water is flowing through the manual valves 17 and 19 or the electrically operable valves 502 and 60 by receiving a flow sense signal from the hydro-generator 246 and determining the relative positions of the valves 502 and 60. As with the system 800 of FIG. 19, a ball valve 804 may be incorporated within the cross-over line 128, as desired. The valves 60, 410, and 502, and temperature sensor 106 may all be received within a common manifold 1002. A scald protection solenoid valve 1004 may be positioned in series with the hot water line 24 to provide scald protection. More particularly, the controller 110 is configured to close the valve 1004 if a temperature sensor 1006 detects that the mixed water temperature at the spout 14 exceeds a predetermined temperature. By closing valve 1004, hot water cannot be supplied through either the manual valve 17 or the solenoid valve 502.

Figure 33:
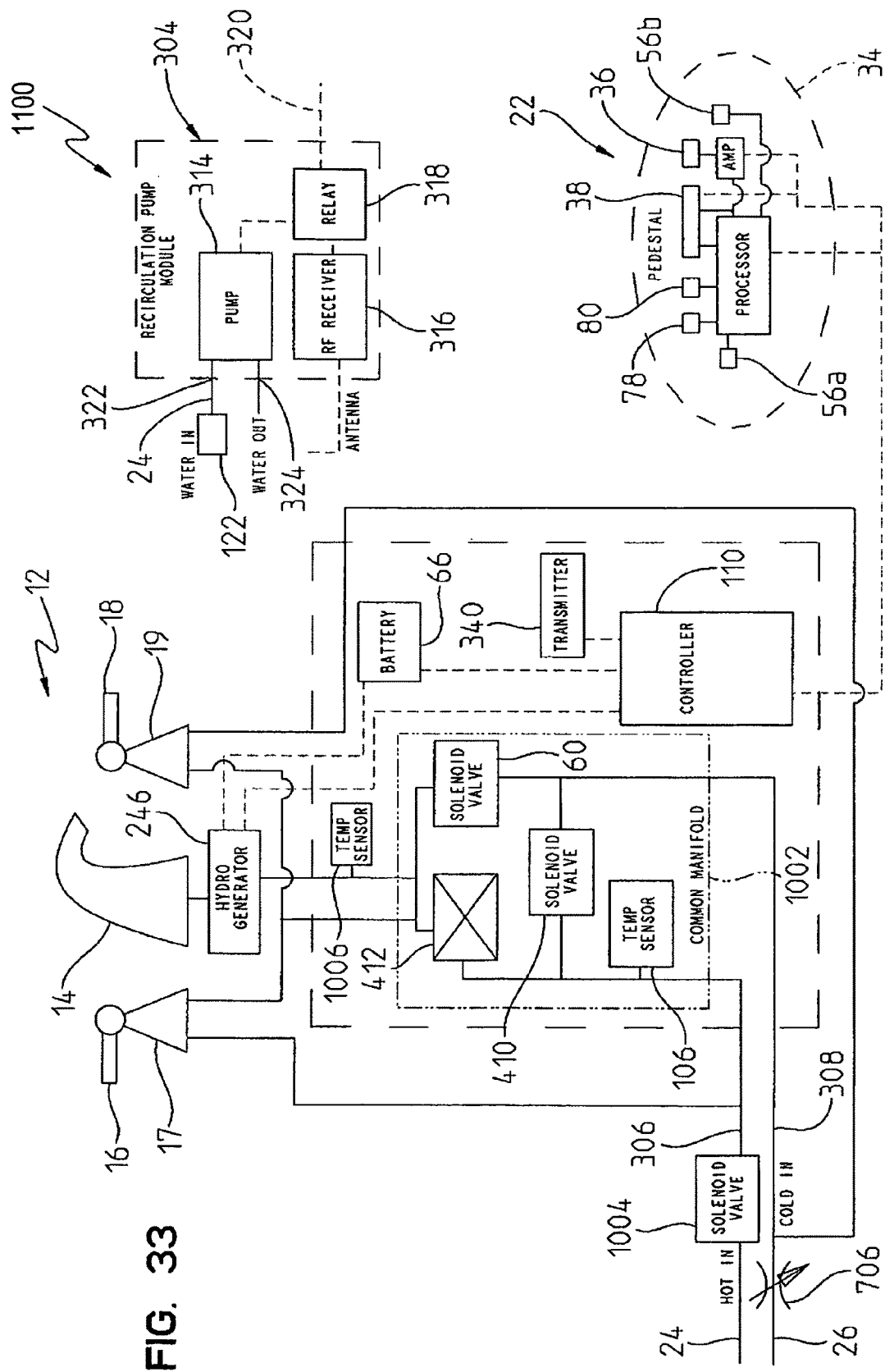
FIG. 33 is a schematic view of a further illustrative hands free system incorporating a distributed quick hot system, and including a manifold for supporting electrically operable valves.

With reference now to FIG. 33, a hands-free distributed quick hot system 1100 is illustrated. This system 1100 is similar to system 1000 illustrated in FIG. 32, but for the removal of the touch sensors 62 and 64 and electrically operable valve 502. In other words, operation is through either a manual mode (through manual valves 17 and 19) or a hands-free mode (through electrically operable valve 60). The hot water valve 502 is replaced with a plug 412.

Figure 34:
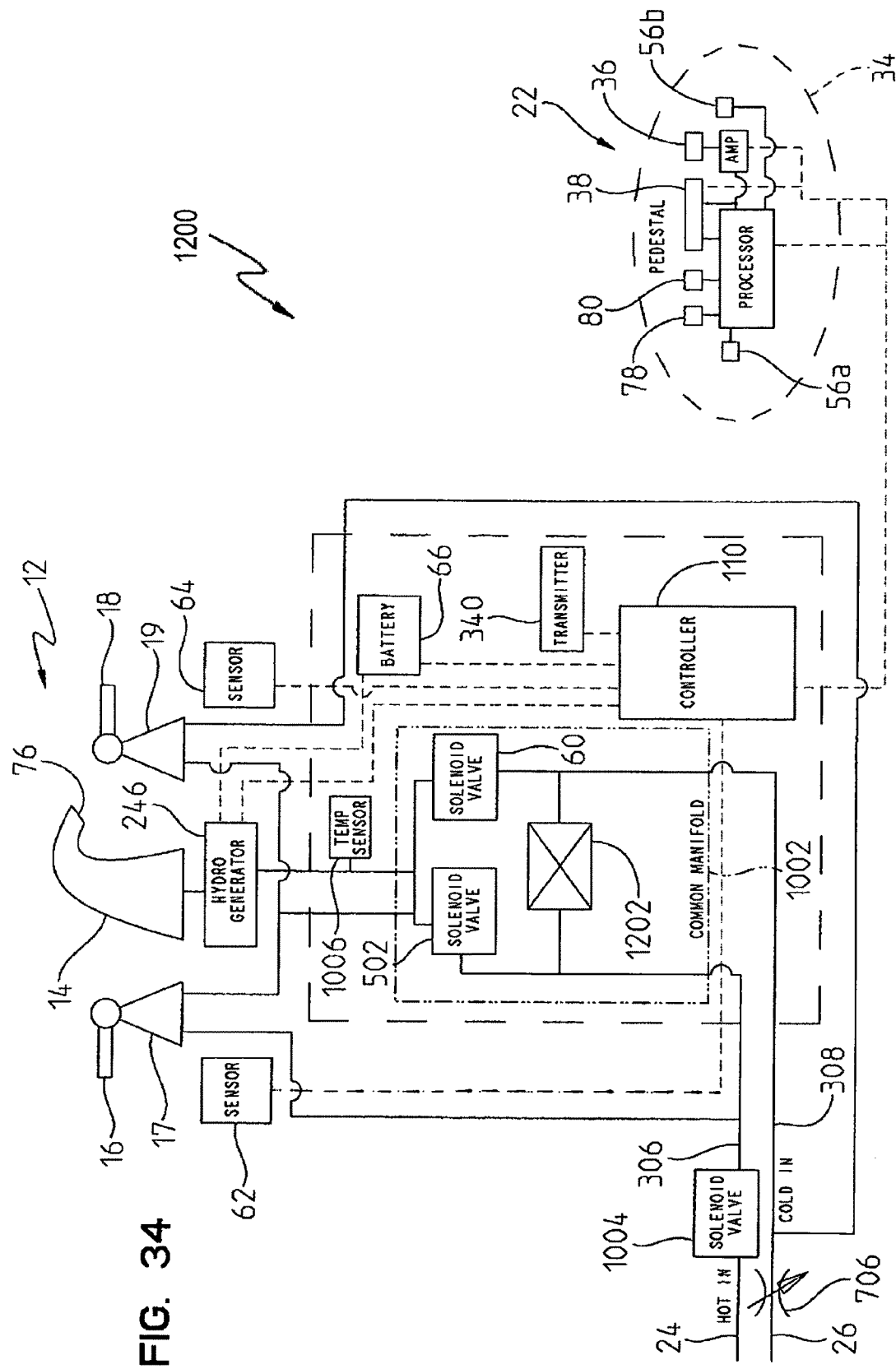
FIG. 34 is a schematic view of a further illustrative hands free system including a manifold for supporting motorized valves.

FIG. 34 illustrates a hands-free system 1200 which is similar to the system of FIG. 33, but does not include the distributed quick hot, or recirculation feature. The system 1200 also includes tap sensors 62 and 64 for operation similar to system 500 of FIG. 17. However, given removal of the quick hot functionality, the cross-over solenoid valve 410 has been replaced with a plug 1202 and the temperature sensor 106 has been removed.

Figure 35:
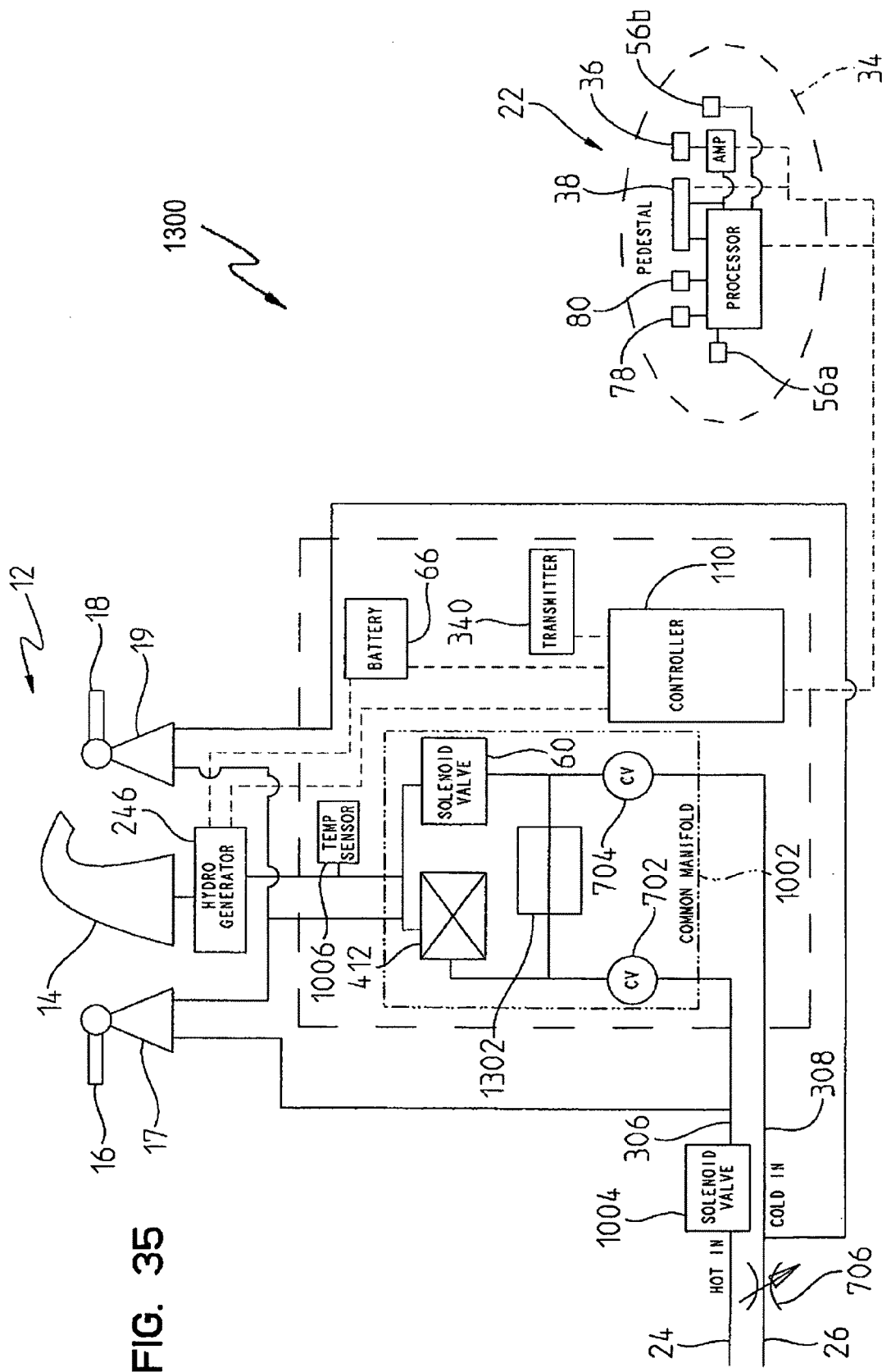
FIG. 35 is a schematic view of a further illustrative hands free system including a manifold for supporting motorized valves.

FIG. 35 illustrates a hands-free "no tap" system 1300. This system 1300 is similar to the system 1200 of FIG. 34, but does not include the touch sensors 62 and 64 for controlling water flow. In other words, operation is through either a manual mode (through manual valves 17 and 19) or a hands-free mode (through electrically operable valve 60). The hot water valve 502 has been replaced with a plug 412. Similarly, the plug 1202 of FIG. 34 has been replaced with a through line 1302. Check valves 702 and 704 are illustratively placed upstream from the electrically operable valve 46 to prevent unintended cross flow between the hot and cold water lines 306 and 308.

Figure 36:
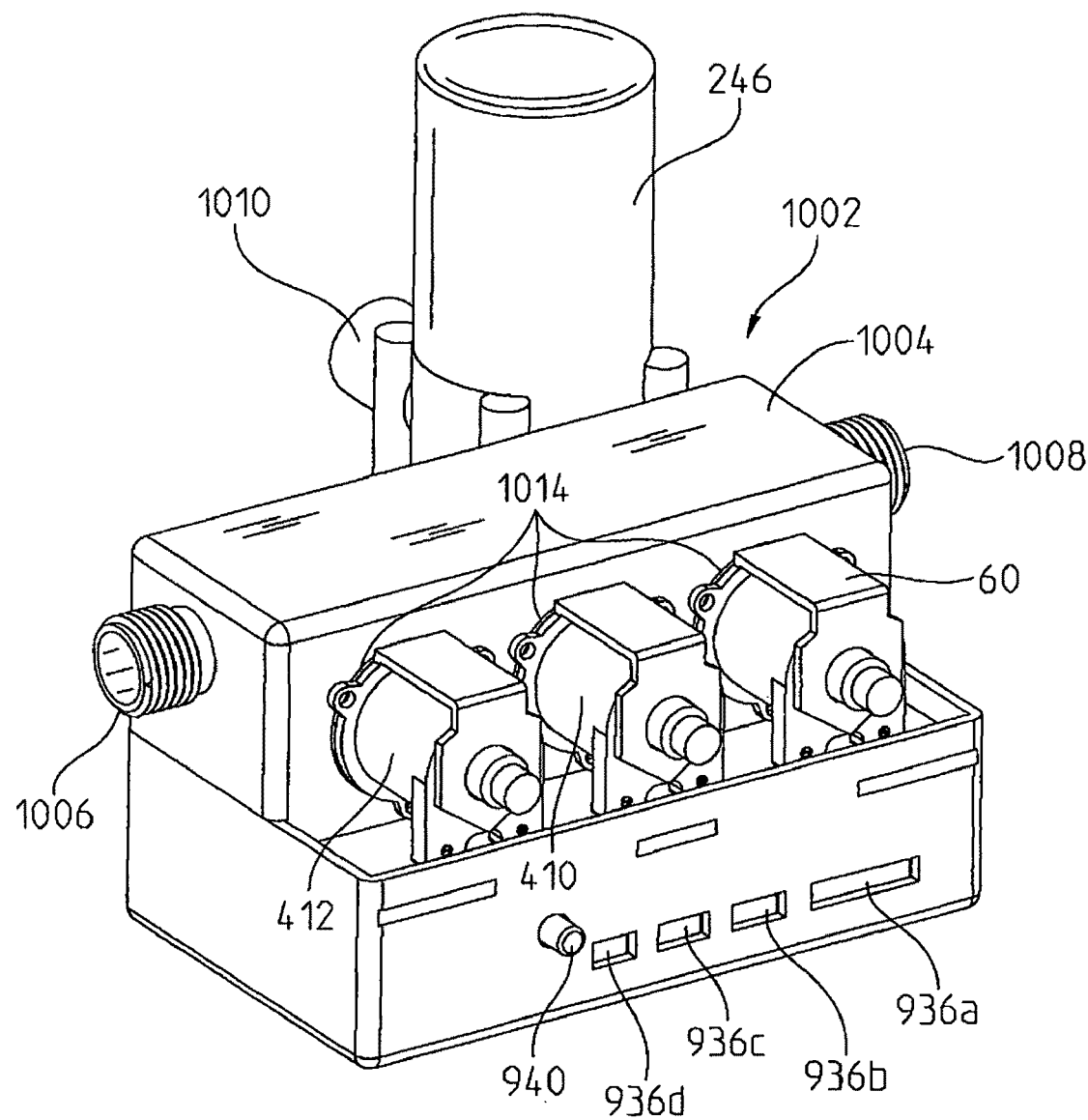
FIG. 36 is a front perspective view of an illustrative manifold for use with the system of FIG. 32.
Figure 37:
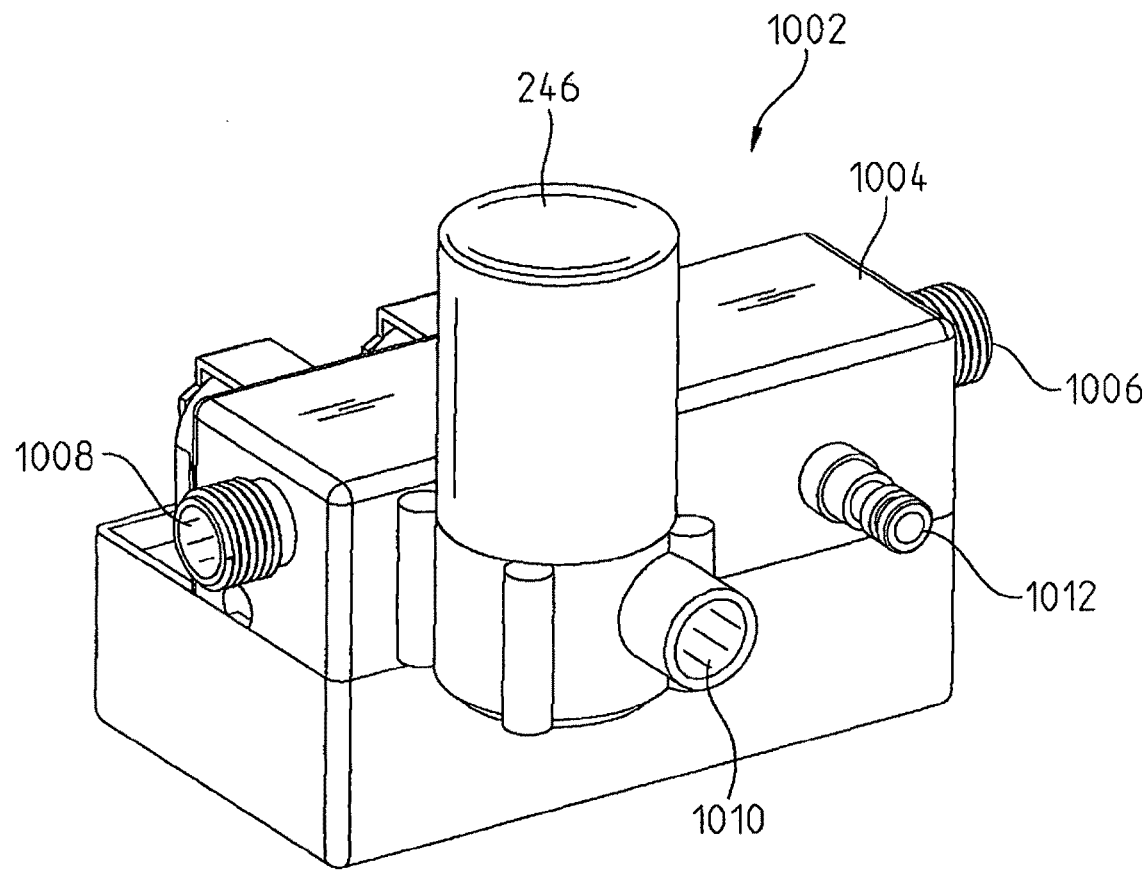
FIG. 37 is a rear perspective view of the illustrative manifold of FIG. 36.

Referring now to FIGS. 36 and 37, an illustrative manifold 1002 for use in connection with the systems 1000, 1100, 1200, and 1300 of FIGS. 32-35 is shown. The manifold 1002 includes a body 1004 supporting a hot water inlet 1006 and a cold water inlet 1008. The hydro-generator 246 is coupled to the body 1004 and includes a first outlet 1010 coupled to the spout 14. A second outlet 1012 is supported by the body 1004 and is fluidly coupled to the manual valves 17 and 19.

The manifold 1002 supports a plurality of electrical connections 936, and potentiometer 940, similar to those detailed above in connection with system 900. The manifold 1002 includes a plurality of openings 1014 configured to receive various combinations of solenoid valves, plugs, and through lines in order to provide flexibility and the ability to customize systems such as those shown in FIGS. 32-35.

In an illustrative embodiment, the controller may have a system intelligence function. More particularly, the controller 110 "learns" of desired user actions over a time period and in response thereto predicts future behavior. For example, based upon a learned use pattern, the controller 110 may activate the nightlights 56 and recirculation pump 104, 314 at a certain time when such devices are typically activated by the user. In one embodiment, the devices may be activated a certain time period before typically activated by the user in anticipation of use. For example, the recirculation pump 104, 314 may be activated 15 minutes before typical activation by the user to ensure the availability of hot water at the desired time.

The controller 110 illustratively maintains a database for tracking when people enter the bathroom 102 and use hot water. The system uses trend analysis to predict when hot water will be required. For example, if the system identifies Monday through Friday shower usage at 6:30 a.m., the system may initiate the recirculation pump 104, 314 at 6:15 to ensure that hot water is available at 6:30. Logic in software accessed by the controller 110 determines trends and anticipated hot water needs.

Figure 40:
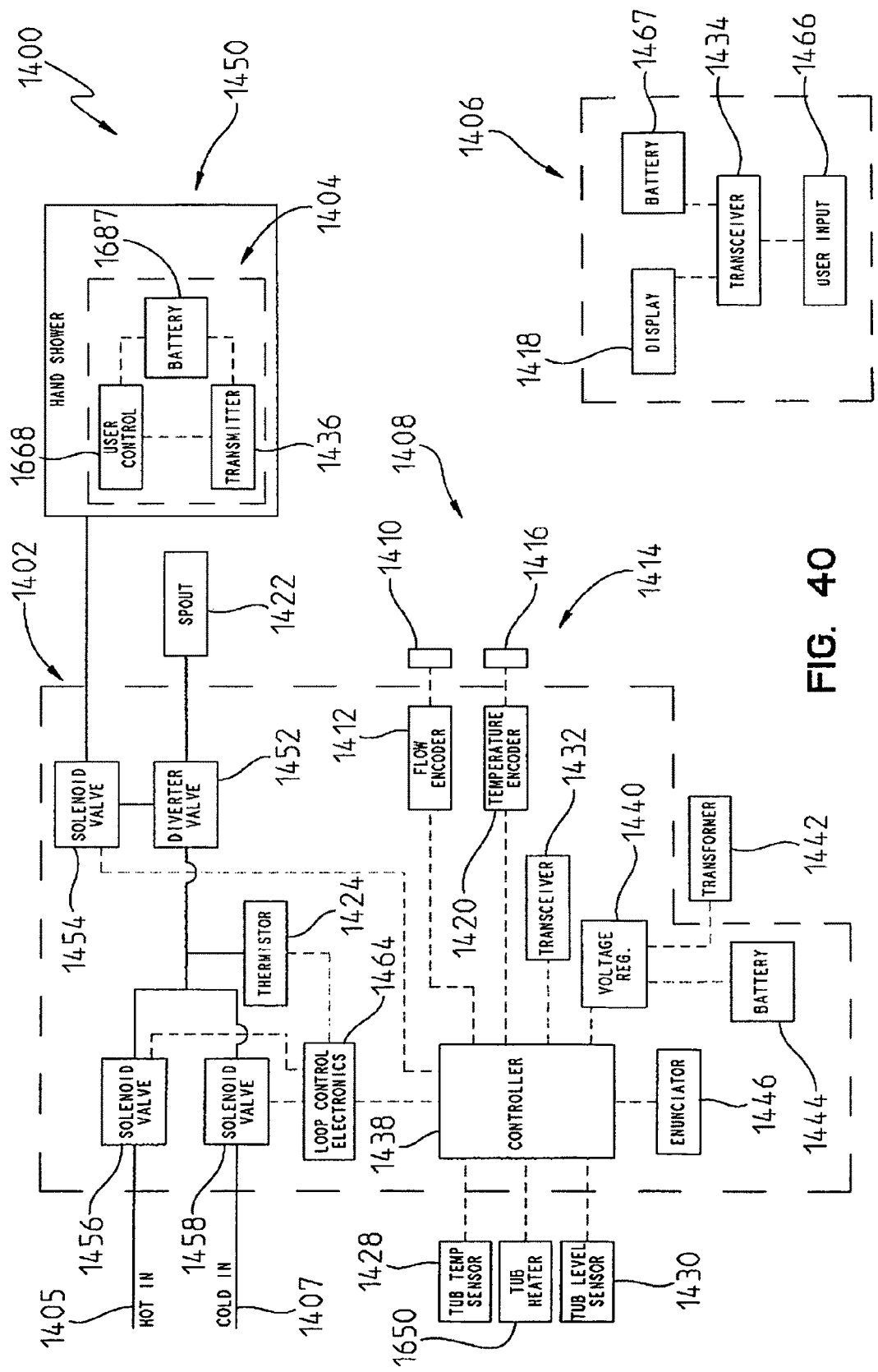
FIG. 40 is a schematic view of an illustrative roman tub system.

An illustrative embodiment roman tub system 1400 is shown in FIGS. 38-40. The roman tub system 1400 includes a roman tub control module 1402, a hand shower control module 1404, and a user interface module 1406. The control module 1402 is fluidly coupled to a hot water supply line 1405 and a cold water supply line 1407. A flow select device 1408 is supported by the tub deck 1409 and permits the user to select a desired flow rate with a tub knob or handle 1410. The handle 1410 provides tactile feedback during rotation and is operably coupled to a flow encoder 1412. A temperature select device 1414 is also supported by the tub deck 1409 and permits the user to select a desired temperature with a tub knob or handle 1416, while a display 1418 provides visual feedback. The handle 1416 provides tactile feedback during rotation and is operably coupled to a temperature encoder 1420. The desired set temperature increases with counter-clockwise rotation and decreases with clockwise rotation of the handle 1416.

The display 1418 is configured to display temperature set and tub temperature, illustratively ranging from 60 to 180° F. The display 1418 is configured to show the temperature in 4 digits with one decimal point. As detailed herein, the display 1418 further includes fill level present icons, showing low, medium, and high fill levels. A flow control indicator is configured to display low and high settings. A low battery indicator includes an icon which illuminates to indicate low life of battery. The enunciator 1446 sounds an alarm when the tub reaches a desired fill setting. A louder alarm sounds when a tub overfill is detected.

The display 1418 illustratively toggles between the temperature of water delivered by a spout 1422, as measured by a thermistor 1424, and the desired tub temperature while drawing a bath. Alternatively, the display 1418 may toggle between the temperature of water within the tub 1426, as measured by a tub temperature sensor 1428, and the desired tub temperature. The temperature sensor 1428 may comprise a sensing strip or tape mounted to the sidewall 1427 of the tub 1426. A fill level sensor 1430, configured to sense the level of water within the tub 1426, may also be supported by the sidewall 1427 of the tub 1426. Illustratively, the temperature sensor 1428 and fill level sensor 1430 may be formed as a single unit and incorporated within the same sensing strip. In one illustrative embodiment, the sensor 1430 may generate a magnetic field which changes as water passes in proximity thereto. Alternatively, the fill level of the tub basin 1426 may be determined by a flow meter (not shown) coupled to the spout 1422.

The roman tub control module 1402 illustratively includes a transceiver 1432 configured to communicate with a transceiver 1434 of the user interface module 1406 and with a transmitter 1436 of the hand shower control module 1404. The roman tub control module 1402 may also communicate with other smart fluid delivery devices, such as a quick hot module 100.

With reference to FIG. 40, the flow encoder 1412 and the temperature encoder 1420 are in communication with a controller 1438. The controller 1438 may comprise a conventional micro-controller powered by a 120 VAC power line coupled to a voltage regulator 1440 and transformer 1442. An optional battery 1444 may be provided for back-up power. An enunciator 1446 is in communication with the controller 1438 and is configured to provide audible signals under certain conditions.

The thermistor 1424 is configured to detect the temperature of water supplied to either the spout 1422 or a hand shower 1450. A flow operated diverter valve 1452 directs flow to either the spout 1422 or the hand shower 1450. An electrically operable valve 1454, illustratively a solenoid valve, is configured to control water flow to the hand shower 1450.

Hot and cold water electrically operable valves 1456 and 1458, illustratively solenoid valves, are coupled to hot and cold water supply lines 1405 and 1407, respectively. The valves 1456 and 1458 are in communication with the controller 1438 and loop control electronics 1464, which together control the temperature and flow of mixed water supplied to the diverter valve 1452. More particularly, the thermistor 1424 senses the temperature of the mixed water and provides a signal indicative thereof to the loop control electronics 1464 and controller 1438 which, in turn, control the valves 1456 and 1458. A user may rotate the handle 1416 until a desired set temperature appears on the display 1418. Once set, the controller 1438 operates the valves 1456 and 1458 to supply water at the set temperature in the manner detailed above.

The user interface module 1406 may be supported by the tub deck 1409 and illustratively includes display 1418 and a user input 1466. The user interface module 1406 may receive power from the control module 1402 or from a separate battery 1467. The display 1418 may toggle between showing the set temperature and the tub water temperature as detected by the tub temperature sensor 1428. Alternatively, the display 1418 may toggle between showing the outlet water temperature, as supplied to the spout 1422 or the hand shower 1450 and detected by the thermistor 1424, and the tub water temperature, as detected by the tub temperature sensor 1428. Illustratively, the display 1418 comprises a liquid crystal display (LCD) 1466 providing a digital readout.

The user may also rotate the handle 1410 to a desired set fill level. Once set, the controller 1438 operates the valves 1456 and 1458 to supply water to the tub 1426 until the set fill level is detected by the fill level sensor 1430. Once the set fill level is detected, the controller 1438 closes the valves 1456 and 1458.

The user input 1466 may further include a preset control, illustratively a knob or handle 1468 rotatable to a plurality of positions having preset values stored in the memory associated with the controller 1438. Illustratively, these values may be any combination of preset flow rates and fluid temperatures.

Figure 41A:
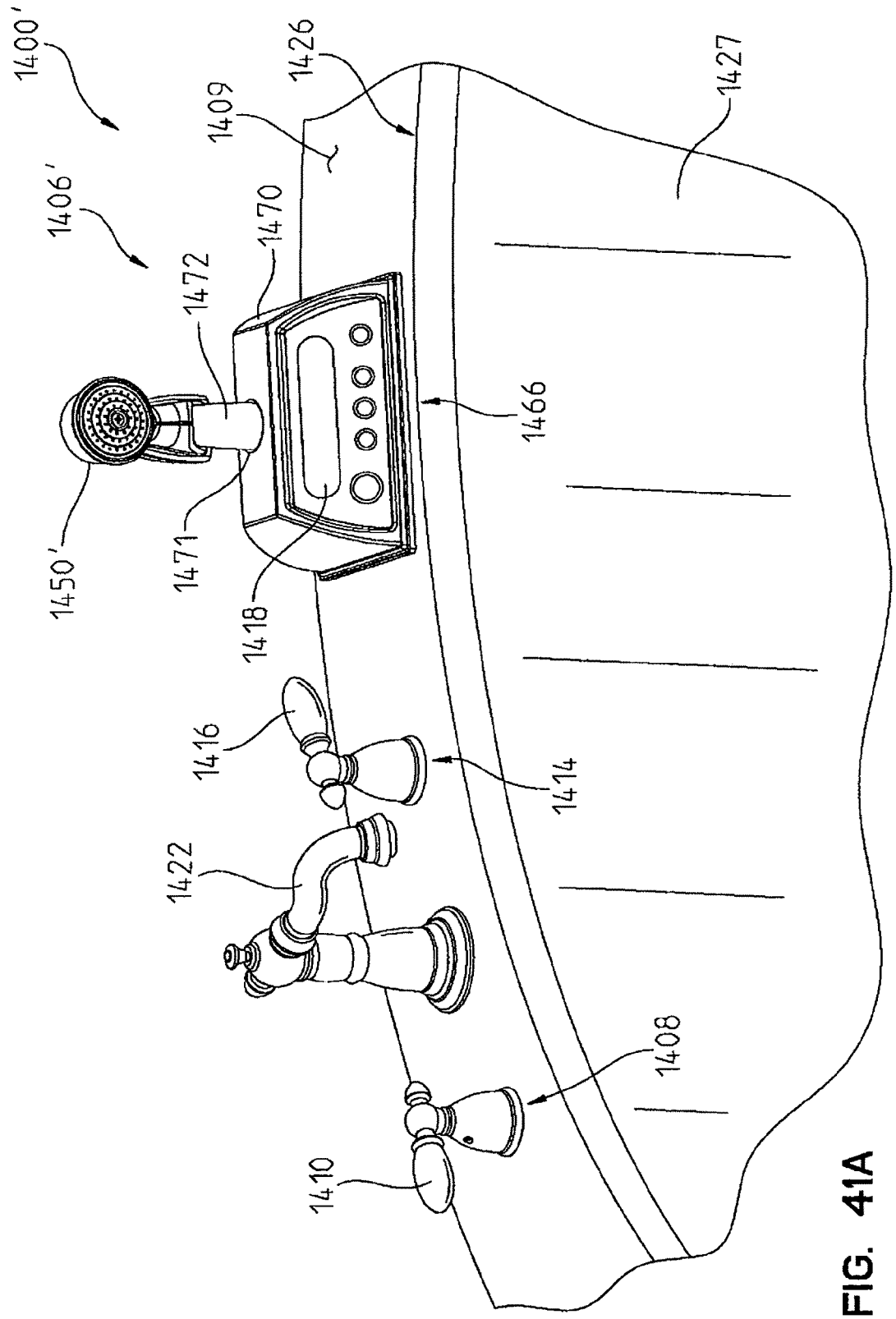
FIG. 41A is a perspective view similar to FIG. 38 showing a further illustrative user interface.
Figure 41B:
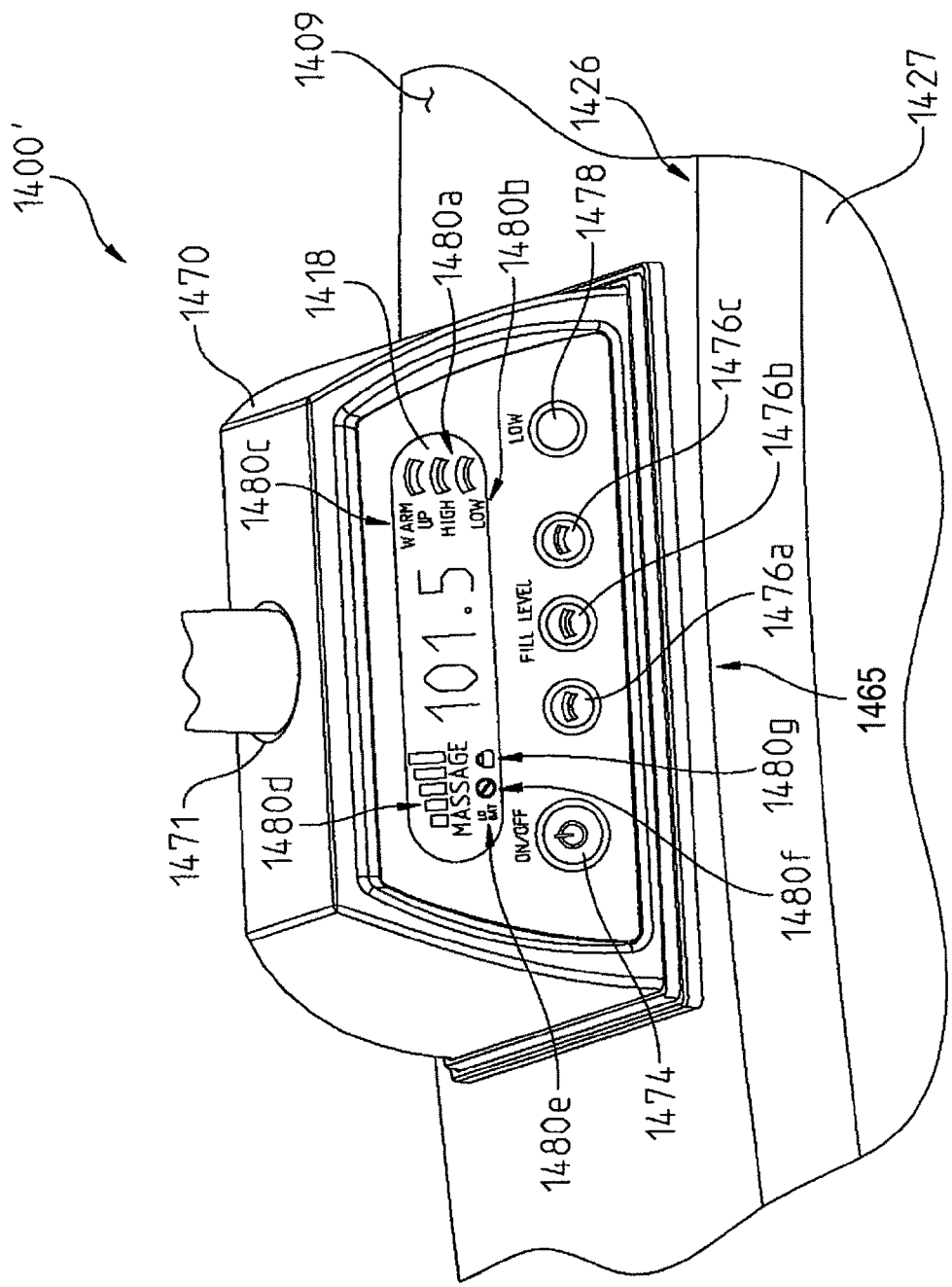
FIG. 41B is a detail perspective view of FIG. 41A.

Referring now to FIGS. 41A and 41B, in a further illustrative embodiment roman tub system 1400', the user interface module 1406' includes a housing 1470 supporting the display 1466. The housing 1470 is coupled to the tub deck 1409 and includes a docking collar 1471 configured to slidably receive the handle 1472 of the hand shower 1450'.

With reference to FIG. 41B, the housing 1470 supports preset controls 1465 including a push ON/OFF button 1474 and fill level buttons 1476a, 1476b, and 1476c. The ON/OFF button 1474 is utilized to activate and deactivate the flow of water in the roman tub system 1400'. In one illustrative embodiment, the ON/OFF button 1474 causes the valves 1456 and 1458 to activate and deactivate all flow to the diverter valve 1452, and therefor to either the spout 1422 or the hand shower 1450. In a further illustrative embodiment, the button 1474 controls water only to the hand shower 1450 by activating and deactivating the solenoid valve 1454.

The fill level buttons 1476a, 1476b, and 1476c cause the controller 1438 to open valves 1456 and 1458 until a predetermined amount of water is supplied to the tub 1426, illustratively in the manner detailed herein. As shown in FIG. 41B, fill level buttons 1476a, 1476b, and 1476c provide for increasing water levels within the tub 1426. A low flow button 1478 is also provided for reduced water flow. Upon depressing the low flow button 1478, the controller 1438 reduces flow through each of the valves 1456 and 1458 while maintaining a substantially consistent mixture of hot and cold water and thereby maintaining a substantially constant mixed water temperature as measured by the temperature sensor 1424. In a further illustrative embodiment, a dedicated solenoid valve may provide a low flow rate by directing water through a parallel fluid line including a flow restriction (not shown).

As shown in FIG. 41B, the display 1418 may provide an indication of temperature as measured by the temperature sensor 1424. As indicated above, the display 1418 provides a digital readout of the measured temperature. In one illustrative embodiment, the temperature as set by the user through operation of the knob 1416 is displayed in a flashing manner until the measured temperature is within a predetermined range of the set temperature. In a further illustrative embodiment, the set temperature and the measured temperature are alternatively shown on the display 1418 until stable. The display 148 may also provide indicators 1480 showing additional elements of system status. For instance, indicators 1480a may provide an indication of measured fill level, indicators 1480b may provide an indication of high or low flow rates, indicator 1480c may provide an indication of warm-up status, and indicators 1480d may provide an indication of massage settings. Additional indicators 1480e, 1480f, and 1480g may provide indications of low battery, alarm mute, and lock-out mode, respectively. The lock-out mode disables the keys 1465 to prevent unwanted activation thereof, for instance, when cleaning the housing 1470.

In an illustrative embodiment, when a user has left the room 102, the controller 1438 puts the electronics to sleep. When a user enters the room 102, the controller 1438 activates the electronics. Further, when a user enters a dark room, illumination devices may be activated. When the user leaves the room 102 after the illumination devices have been activated, the illumination devices are subsequently deactivated.

In a further illustrative embodiment, when a user leaves the room 102 and a tub fill mode has been initiated, an audible alarm of task completion is provided by the enunciator 1446 at a higher audible volume than if the user is detected to be in the room. In a further illustrative embodiment, when a user is within the room 102 and the tub 426 has been filled with water, a recirculation pump 314 maintains hot water available for use by the hand shower 1450.

Figure 42:
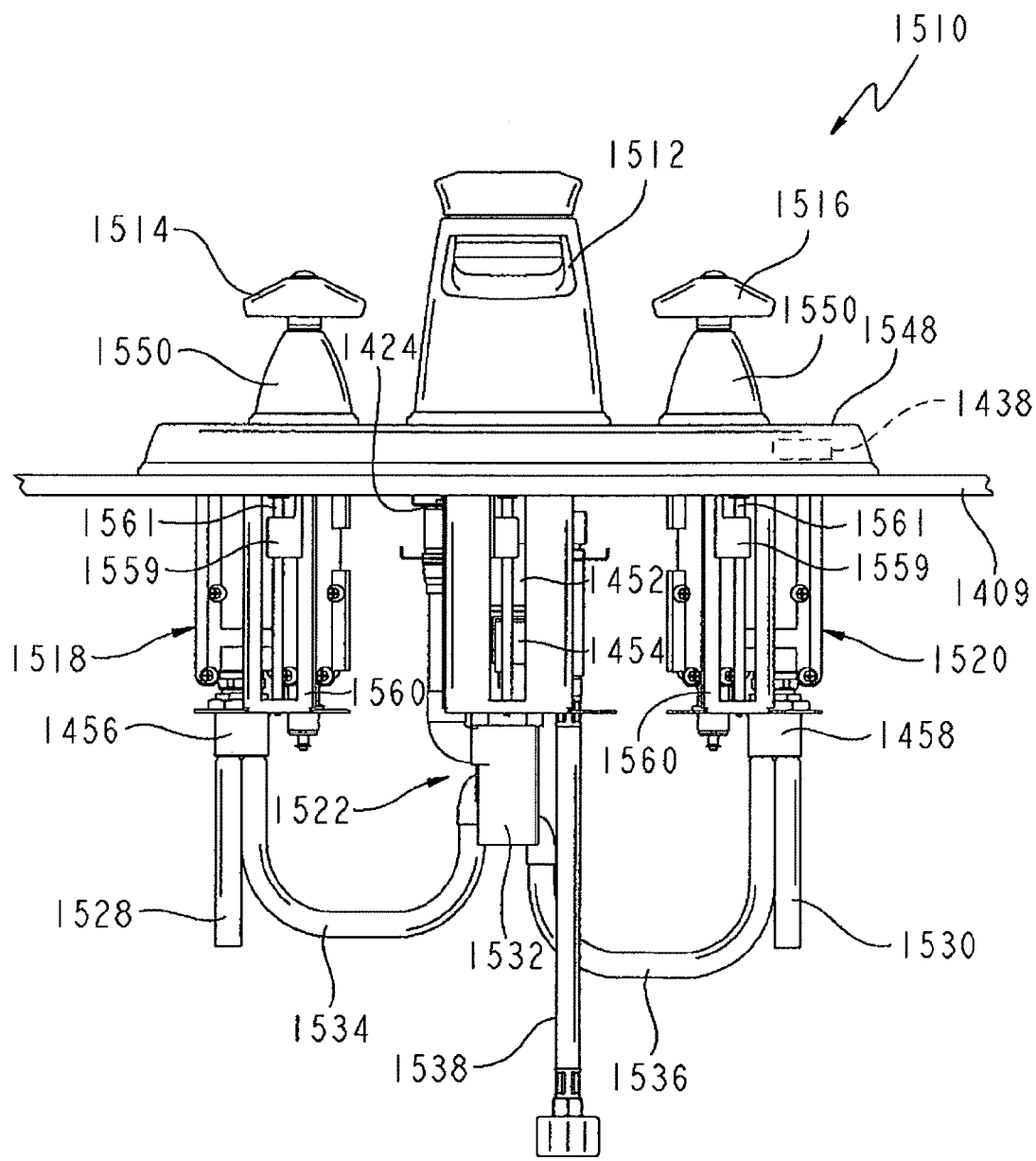
FIG. 42 is a front view of an illustrative faucet assembly for use with a roman tub that is operable both automatically and manually.

Referring now to FIG. 42, a further illustrative faucet assembly 1510 for use with the roman tub module 1400 includes a spout 1512, a first control member, illustratively a knob or handle 1514, and a second control member, illustratively a knob or handle 1516. The first handle 1514 controls a first power, or control module 1518, and the second handle 1516 controls a second power, or control module 1520. The first power module 1518 includes first fluid control valve 1456 and the second power module 1520 includes second fluid control valve 1458. The first fluid control valve 1456 controls water flow from a hot water inlet 1528 to an outlet 1534. The second fluid control valve 1458 controls water flow from a cold water inlet 1530 to an outlet 1536. It should be appreciated that the hot water inlet 1528 and the cold water inlet 1530 may be reversed based on installation and controller programming.

The outlets 1534 and 1536 feed water to a mixing module 1522. The mixing module 1522 includes a mixing valve 1532 that provides for substantially uniform mixing of hot and cold fluids. The mixing valve 1532 may be similar in functionality to the mixer detailed in U.S. patent application Ser. No. 11/109,283, filed Apr. 19, 2005, which is expressly incorporated by reference herein. Temperature sensor 1424 is illustratively disposed within the mixing module 1522 to obtain information indicative of fluid temperature passing therethrough to the spout 1512. The mixing module 1522 further illustratively includes flow triggered diverter valve 1452, and solenoid valve 1454 that operates to direct water through an outlet hose 1538 to hand shower 1450 (FIG. 40).

The illustrative faucet assembly 1510 is mounted on the deck 1409 and includes controller 1438 which may be housed within a cover or escutcheon 1548. It should be appreciated that the controller 1438 may be positioned at other locations, including below the deck 1409. Each handle 1514, 1516 is supported above the deck 1409 by a respective handle support 1550. Mounting frames 1560 extend downwardly from the deck 1409 and support the power modules 1518 and 1520. An adjustable clamp 1559 is supported for movement along a threaded post 1561 for coupling each mounting frame 1560 to the deck 1409. Since the clamp 1559 is adjustable, the mounting frame 1560 may be coupled to decks 1409 having varying thicknesses.

The controller 1438 is programmed to provide instructions to each of the power modules 1518, 1520 for controlling fluid flow rate and temperature, and to the solenoid valve 1454 for controlling or directing flow between the spout 1512 and the outlet hose 1538 of the hand shower 1450. More particularly, in the automatic control position, the controller 1438 receives inputs from rotation of the handles 1514 and 1516 to establish set fluid flow rate and temperature, respectively.

The controller 1438 also illustratively receives input from temperature sensor 1424 indicative of the outlet or mixed water temperature, thereby providing control feedback for maintaining the set fluid temperature through control of power modules 1518, 1520. The temperature sensor 1424 may also be utilized to provide for scald protection, wherein the first fluid control valve 1456, and in certain embodiments also the second fluid control valve 1458, are closed by respective motors 1566 (FIG. 43) when a predetermined temperature is exceeded. In one illustrative embodiment, the predetermined temperature is 120° F. A flow sensor (not shown) may also be in communication with the controller 1438 for providing control feedback for maintaining the set fluid flow rate. The power modules 1518 and 1520 are selectively operable in an automatic (or electric) control mode or position, and a manual control mode or position. The illustrative first power module 1518 and the second power module 1520 operate in a similar manner.

Operation of the faucet assembly 1510 in the automatic control position provides for separate and automatic control of fluid flow and temperature. The first handle 1514 provides the input to the controller 1438 utilized to set a desired fluid flow rate. The second handle 1516 provides the input to the controller 1438 utilized to set a desired fluid temperature. It should be appreciated that the first handle 1514 and the second handle 1516 could be reversed, such that the first handle 1514 is utilized to control fluid temperature and the second handle 1516 is utilized to control fluid flow rate. The controller 1438 receives inputs from both the first and second handles 1514 and 1516 and translates those inputs into the appropriate actuation of electric motors 1566 and respective valves 1456 and 1458 (FIGS. 43-45) within each of the power modules 1518 and 1520. Operation of the first handle 1514 to control fluid flow thereby provides an input to the controller 1438 that results in actuation of the electric motors 1566 in each of the power modules 1518 and 1520, such that the set or desired flow rate is achieved. Similarly, operation of the second handle 1516 to control fluid temperature provides the input to the controller 1438 that results in selective operation of electric motors 1566 in each power module 1518 and 1520 to supply a mixture of hot and cold water that provides the set or desired temperature of fluid output from the spout 1512.

Figure 43:
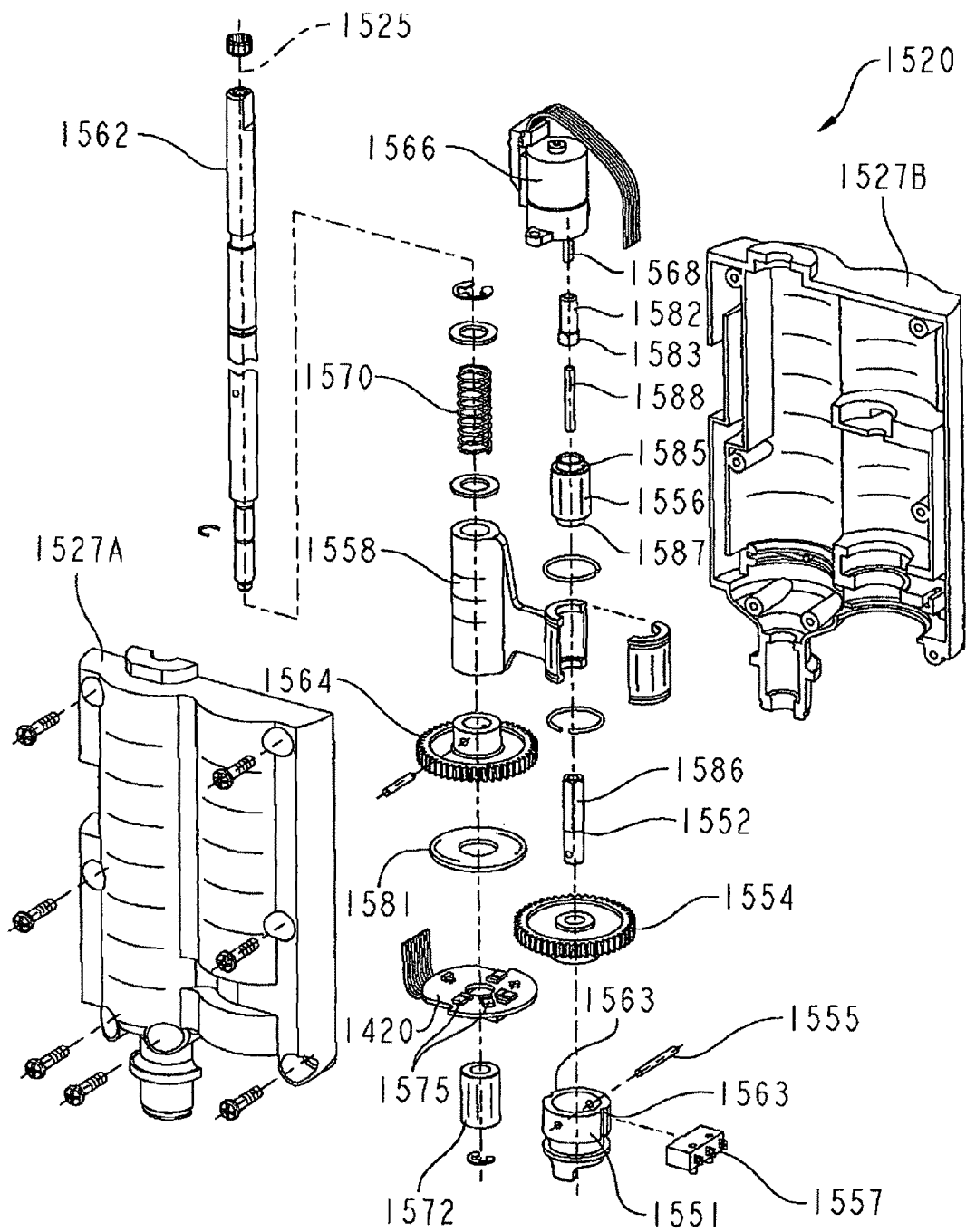
FIG. 43 is an exploded perspective view of an illustrative power control module of the faucet assembly of FIG. 42.
Figure 44:
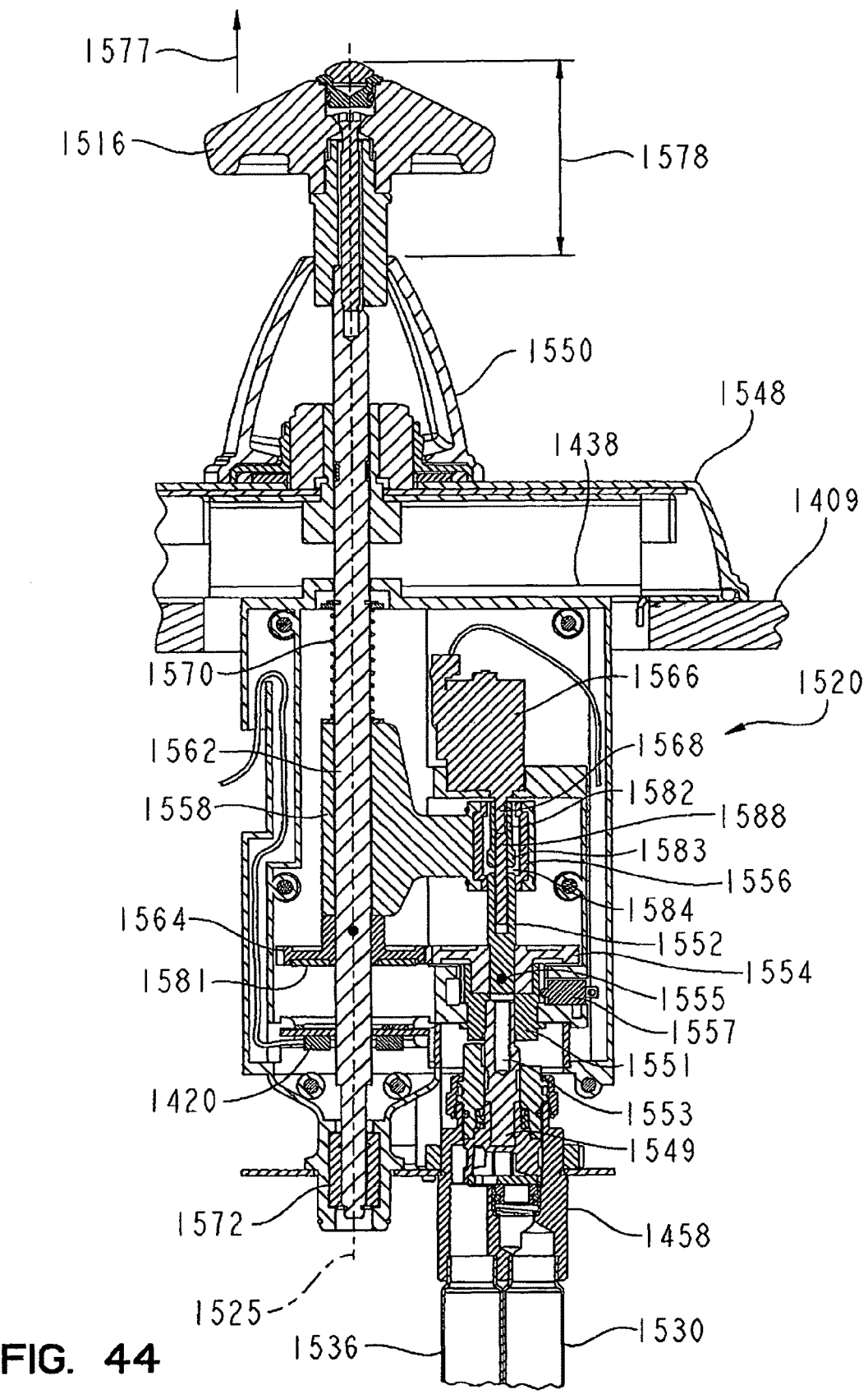
FIG. 44 is a cross-section of the illustrative power control module of FIG. 42 in a manual operation position.
Figure 45:
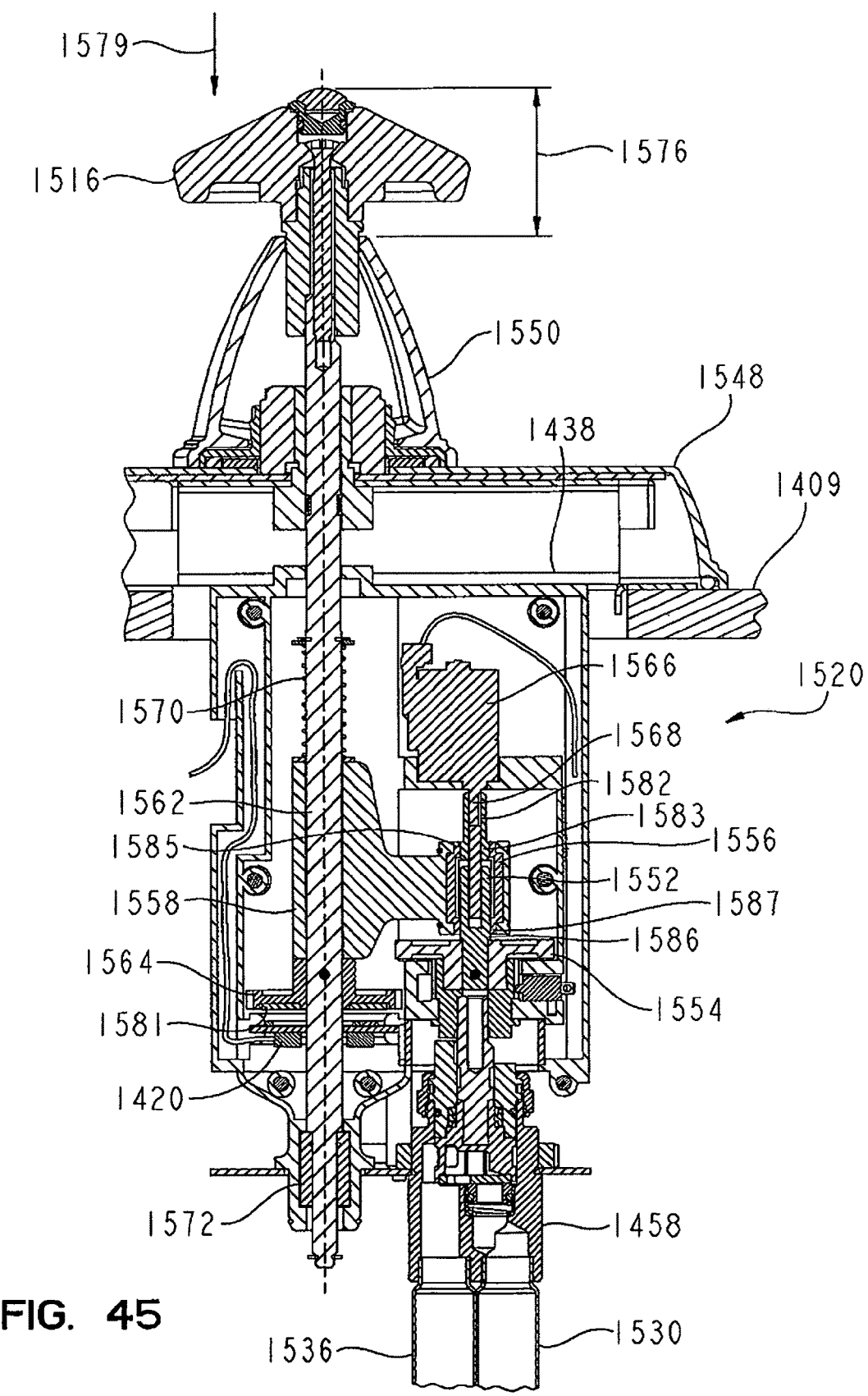
FIG. 45 is a cross-section of the illustrative power control module of FIG. 42 in an automatic operation position.

Referring to FIGS. 43-45, the operation and features of the illustrative first and second power modules 1518 and 1520 are described with reference to the second power module 1520. As noted above, the second power module 1520 is substantially identical to the first power module 1518. The illustrative second power module 1520 includes the second handle 1516 attached to rotate a stem 1562 about an axis 1525. The stem 1562 extends within front and rear housing portions 1527A and 1527B, and is supported for rotational movement within a drive coupling support member 1558. The stem 1562 supports a stem gear 1564 which is rotatable about the axis 1525 and is also movable axially with the stem 1562 to selectively engage a first valve gear 1554. More particularly, the stem gear 1564 is engageable with the valve gear 1554, which is operably coupled to a valve shaft 1549 of the second fluid valve 1458, when the stem 1562 is moved axially upward or outward (in the direction of arrow 1577) to the illustrated manual operation position 1578 of FIG. 44. A valve coupler 1551 receives an upper end 1553 of the valve shaft 1549, wherein the upper end 1553 of the valve shaft 1549 has a flat defining a "D" cross-section to prevent relative rotation between the valve shaft 1549 and the valve coupler 1551. A connecting shaft 1552 is coupled to the valve coupler 1551 and the valve gear 1554 through a pin 1555.

The connecting shaft 1552 is operably coupled to a drive shaft coupler or second valve gear 1556 that is engageable with a motor shaft 1568 of the electric motor 1566. The coupling support member 1558 mounted to the stem 1562 rotatably supports the drive shaft coupler 1556. The coupling support member 1558 moves with axial movement of the stem 1562 to selectively engage the drive shaft coupler 1556 with the motor shaft 1568 such that the motor 1566 can drive the fluid control valve 1458 (FIG. 45). The stem gear 1564 (in the manual operation position) and the motor shaft 1568 (in the automatic operation position) are alternatively engageable (i.e., manually coupled or electrically coupled) to drive the valve shaft 1549 and provide control over actuation of the fluid control valve 1458. An end of travel switch 1557 is configured to provide a signal to the controller 1438 when the valve 1458 reaches a point of maximum rotation. Illustratively, the switch 1557 comprises a snap switch configured to trigger off of grooves 1563 formed in the outer surface of the valve coupler 1551.

The stem 1562 is held in the manual operation position 1578 (illustratively, axial displacement of approximately 0.5 inches) by a detent assembly 1572. The detent assembly 1572 holds the stem 1562 in the manual operation position 1578 against the biasing force provided by a return spring 1570. In the manual operation position, the stem gear 1564 is coupled to the valve gear 1554, and the motor shaft 1568 is decoupled from the drive shaft coupler 1556. More particularly, a drive member 1582 is coupled to the motor shaft 1568. The drive member 1582 illustratively includes an engagement or hex portion 1583 having a hexagonal cross-section, which is free to rotate within an inner chamber 1584 of the drive shaft coupler 1556. Rotation of the handle 1516 and stem gear 1564 is transmitted to rotation of the first valve gear 1554 that, in turn, rotates the valve coupler 1551 and the valve shaft 1549 to control fluid flow. The control of fluid flow in the manual operation position 1578 provides for the manual control of fluid flow and temperature by controlling the flow of fluid from the inlet 1530 to the outlet 1536.

When in the manual operation position 1578, magnetic encoder or switch 1420 is disengaged such that the controller 1438 does not operate the motors 1566 of respective first or second power modules 1518 or 1520. More particularly, the magnetic encoder 1420, illustratively including a plurality of Hall-effect sensors 1575 (FIG. 43), is configured to detect a magnet 1581 supported by the stem gear 1564 only when the stem 1562 is in the automatic operation position.

Referring to FIG. 45, the second power module 1520 is shown in the automatic operation position 1576. The handle 1516 and the stem 1562 are moved axially downward or inward (in the direction or arrow 1579) such that in the automatic operation position 1576, the stem gear 1564 is disengaged from the first valve gear 1554. The downward movement and position of the stem 1562 includes a corresponding movement of the stem gear 1564 such that the magnet 1581 actuates the magnetic encoder 1420. Actuation of the magnetic encoder 1420 signals the controller 1438 that the power module 1520 is in the automatic operation position 1576.

Downward axial movement of the stem 1562 disengages the stem gear 1564 from the valve gear 1554, and concurrently moves the coupling support member 1558 and the drive shaft coupler 1556 into an engaged position. More particularly, the drive or hex portion 1583 of the drive member 1582 operably couples with a cooperating hex portion or lip 1585 of the drive shaft coupler 1556. The illustrative connecting shaft 1552 and drive shaft coupler 1556 include cooperating engagement portions 1586 and 1587, respectively, that provide for transmission of motor shaft rotation to the valve shaft 1549 while at the same time providing for axial sliding movement of the drive shaft coupler 1556 between coupled and decoupled positions. The engagement portions 1586 and 1587 may comprise of cooperating hex portions or splines.

An alignment pin 1588 may extend between the connecting shaft 1552 and the drive member 1582 to facilitate axial alignment therebetween but without transmitting rotational movement. The return spring 1570 provides a downward bias on the coupling support member 1558 such that if the drive portion 1583 of the drive member 1582 and the lip 1585 of the drive shaft coupler 1556 are not aligned, initial rotation of the electric motor 1566 relative to the drive shaft coupler 1556 will operate to engage once in a proper position. Further, the return spring 1570 maintains the stem 1562 and the handle 1516 in the automatic position 1576 until the detent assembly 1572 is engaged.

The magnetic encoder 1420 mounted relative to the stem 1562 generates a signal indicative of rotation of the stem 1562 that is provided to the controller 1438. More particularly, the encoder 1520 provides an indication of the relative angular positions of the poles of the magnet 1581 supported by the stem gear 1564. While a single ring magnet 1581 is illustrated in FIG. 43, it should be appreciated that multiple angularly spaced magnets could be substituted therefor. Detected rotation of the stem 1562 is thereby translated into a corresponding rotation of the electric motors 1566 within each of the power modules 1518 and 1520. The rotation of the electric motors 1566 responsive to rotation of the stem 1562 provides for actuation of the fluid control valves 1456 and 1458 to provide the desired fluid flow output necessary to accomplish the desired fluid flow and temperature from the spout 1512.

In the absence of electric power to the faucet assembly 1510, or in the event of motor failure, operation can be changed from automatic to manual. The first and second knobs 1514 and 1516 would be pulled axially upwardly, or away from the deck 1409, to engage the corresponding detent assemblies 1572. With the axial upward movement, the electric motor 1566 is decoupled from the valve shaft 1549 by disengaging the hex portion 1583 of the drive member 1582 from the drive shaft coupler 1556. Further, the magnetic encoder or switch 1420 is disengaged to signal manual operation to the controller 1438 that, in turn, discontinues operation of the motors 1566. The disengaged magnetic encoder or switch 1420 provides for manual operation even with available electric power, if desired. The stem gear 1564 is then coupled to the valve gear 1554 and provides for manual actuation and adjustment of the first and second valves 1456 and 1458 (FIG. 42). Operation is thereby provided without power to the faucet assembly 1510 or activation of the motors 1566.

Figure 46:
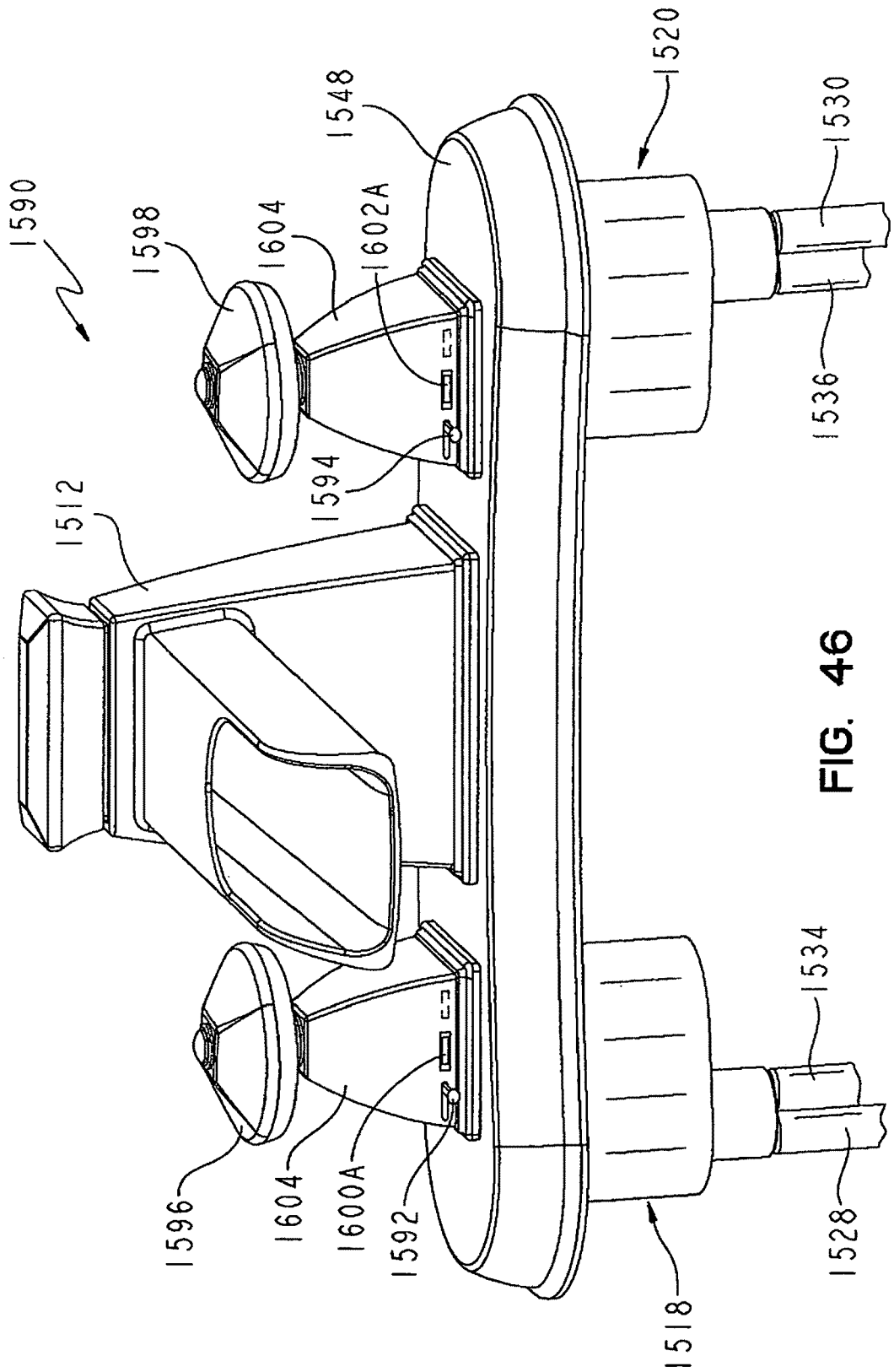
FIG. 46 is a perspective view of another illustrative faucet assembly including displays indicating operating position.
Figure 47:
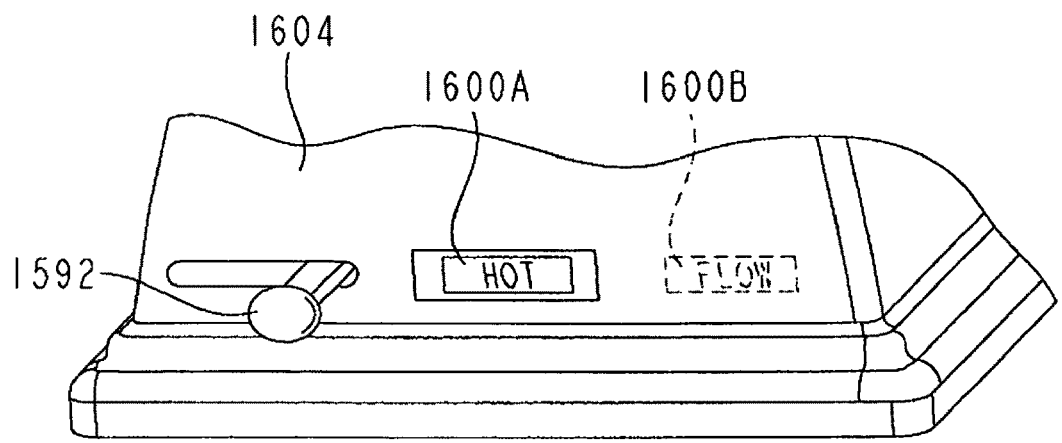
FIG. 47 is a detail view of the first handle of FIG. 46.
Figure 48:
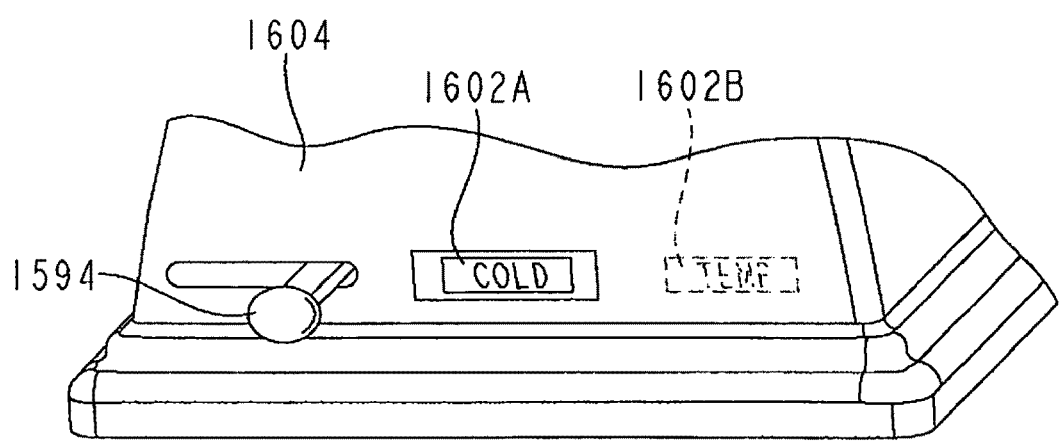
FIG. 48 is a detail view of the second handle of FIG. 46.

Referring to FIGS. 46-48, another example faucet assembly 1590 includes selection levers 1592 and 1594 disposed at a base of a first knob or handle 1596 and a second knob or handle 1598, respectively. Movement of the selection levers 1592 and 1594 moves the handle stem 1562 axially between the automatic and mechanical positions 1576 and 1578 (FIGS. 44-45). Movement of the levers 1592 and 1594 provides for indication of an operating mode within first and second displays 1600A and 1602A supported by handle supports 1604. The first and second displays 1600A and 1602A are shown in a manual operating position where the first and second handles 1596 and 1598 (FIG. 46) control hot and cold water flow (FIGS. 47 and 48). Selection of an automatic operating position would change the displays to indicate that the first handle 1596 controls flow 1600B, and that the second handle 1598 controls temperature 1602B. The first and second knobs 1596 and 1598 may illustratively be illuminated by way of a power source separate from the main power supply. In the illustrative faucet assembly 1590, the displays 1600A and 1602A are illuminated in response to a power failure, thereby illuminating faucet knobs 1596 and 1598 to aid in the use and selection of the manual operation mode.

Figure 49:
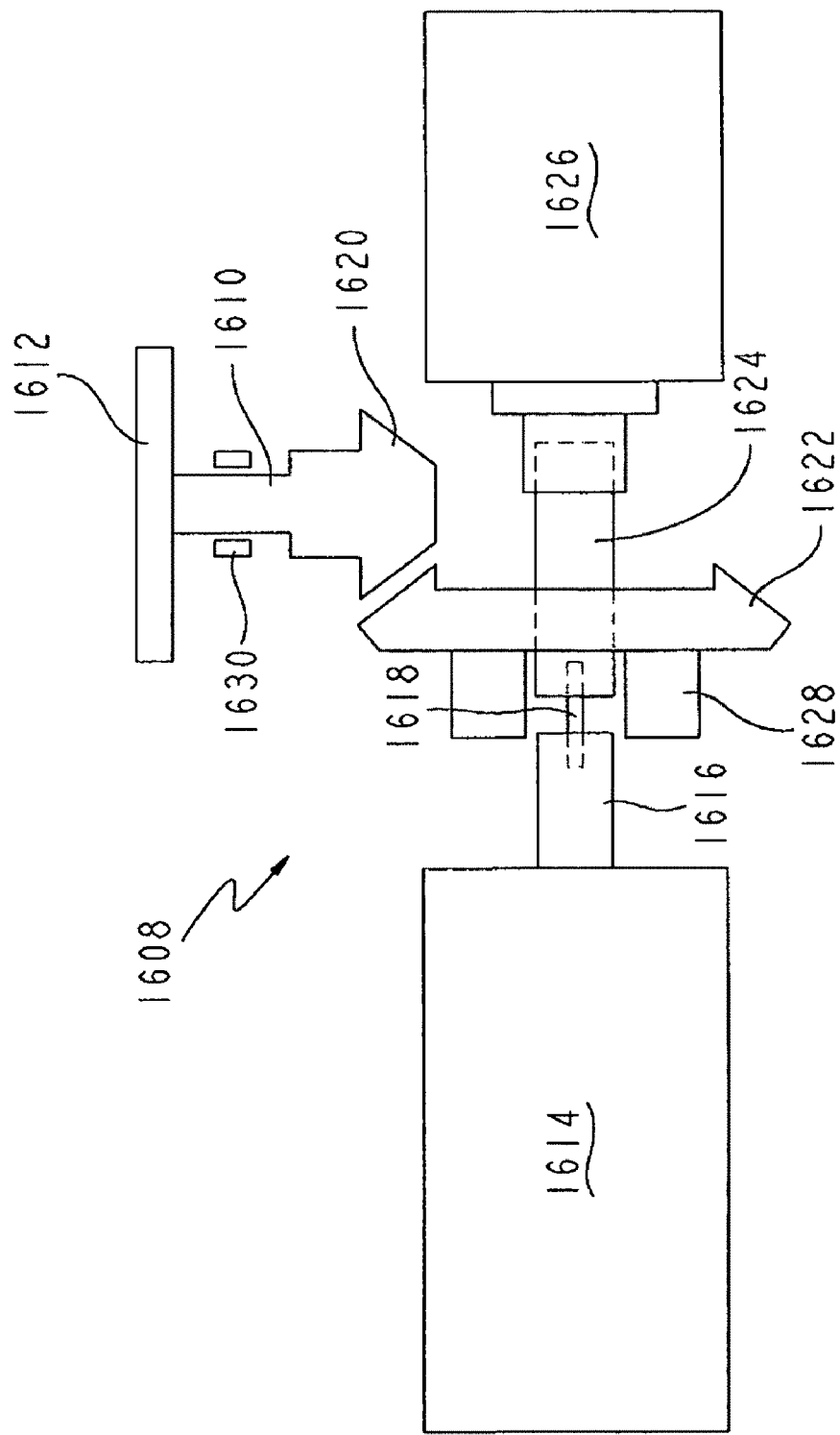
FIG. 49 is a cross-sectional view of another illustrative control module for switching a faucet assembly between automatic and manual operation.

Referring to FIG. 49, another illustrative faucet assembly 1608 includes a handle stem 1610 that extends from a handle 1612. A bevel gear 1620 is mounted at the end of the handle stem 1610. In manual mode, a manual gear 1622 is moved axially to engage the bevel gear 1620. The manual gear 1622 includes a collar 1628 that includes splines to transfer rotational movement to the valve shaft 1624 while still providing for axial movement of the manual gear 1620. Axial movement of the collar 1628 causes a decoupling of the collar 1628 with the motor shaft 1616. The motor shaft includes corresponding splines that engage the splines of the collar 1628. An alignment pin 1618 may be provided between the motor shaft 1616 and the valve shaft 1624 to facilitate alignment therebetween.

An automatic mode is provided by moving the manual gear 1622 out of engagement with the bevel gear 1620. The axial movement of the manual gear 1622 causes the collar 1628 to span a gap between the motor shaft 1616 and the valve shaft 1624. This coupling of the motor shaft 1616 to the valve shaft 1624 provides for the transmission of rotational movement of the motor 1614 to the valve 1626. The collar 1628 can only couple the motor shaft 1616 with the valve shaft 1624 when the manual gear 1620 is spaced apart from the bevel gear 1620.

Rotation of the handle stem 1610 is sensed by magnetic encoders 1630 to provide the desired input utilized to control the electric motor 1614, and thereby the valve 1626.

Figure 50:
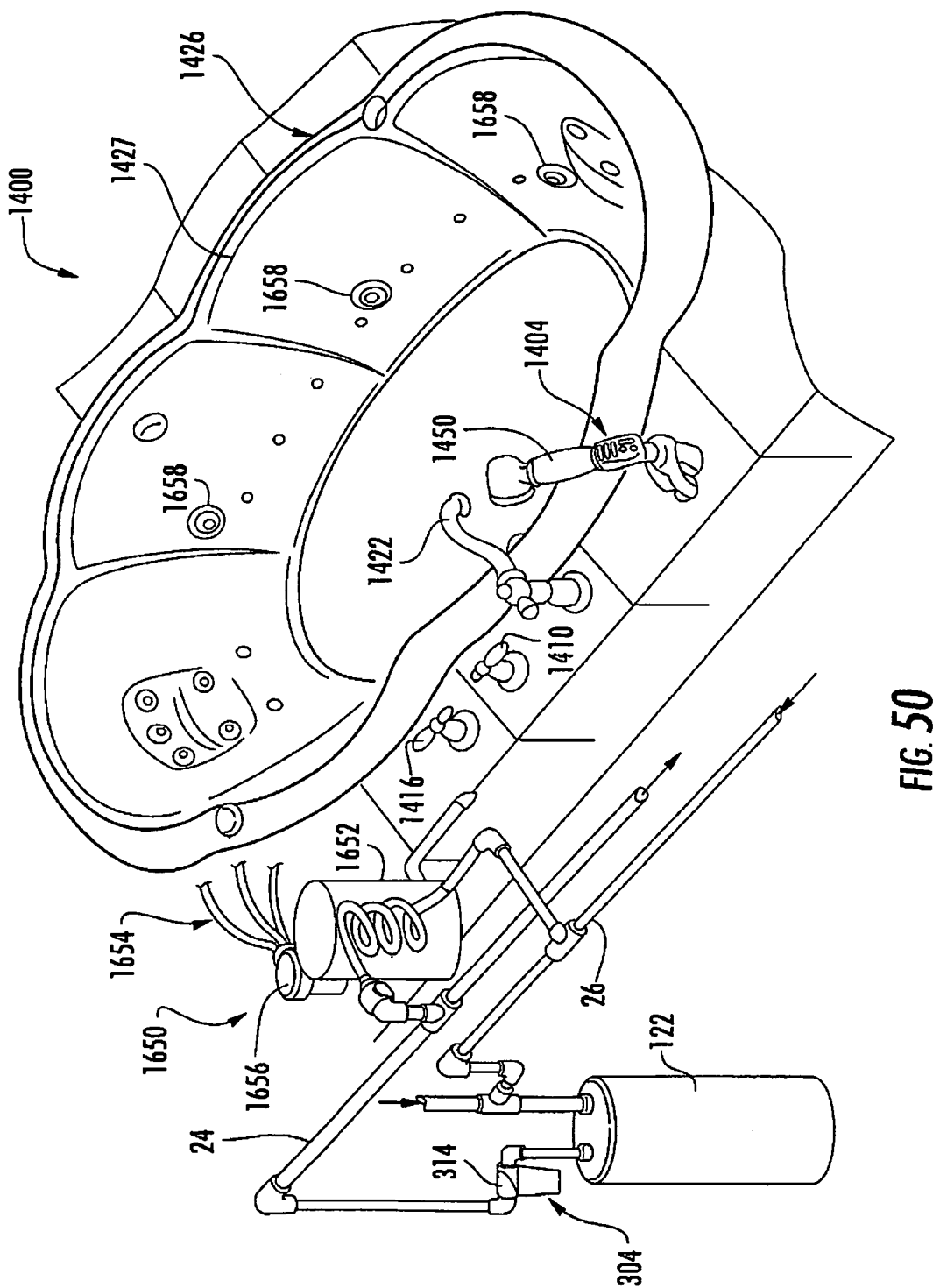
FIG. 50 is a perspective view of an illustrative roman tub having a whirlpool temperature maintain system.

As shown in FIG. 50, the roman tub system 1400 may include a tub heater or heat transfer device 1650. An illustrative embodiment tub heater 1650 is shown in FIG. 50. When a user is within the room 102, the tub 1426 has water present, and a maintain temperature command is initiated (for example, through a button in the control module 1402), the recirculation pump 314 delivers hot water from hot water heater 122 to heat transfer device 1650. The heat transfer device 1650 may be fluidly coupled to a quick hot module, such as the distributed quick hot module 300 detailed herein. The hot water recirculated by the quick hot module 300 is configured to heat water within a reservoir 1652 of a whirlpool jet system 1654. Water from the reservoir 1652, as heated from the hot water supply line 24, is then circulated via a pump 1656 to a plurality of jets 1658 positioned within the sidewall 1427 of the roman tub 1426.

Figure 51:
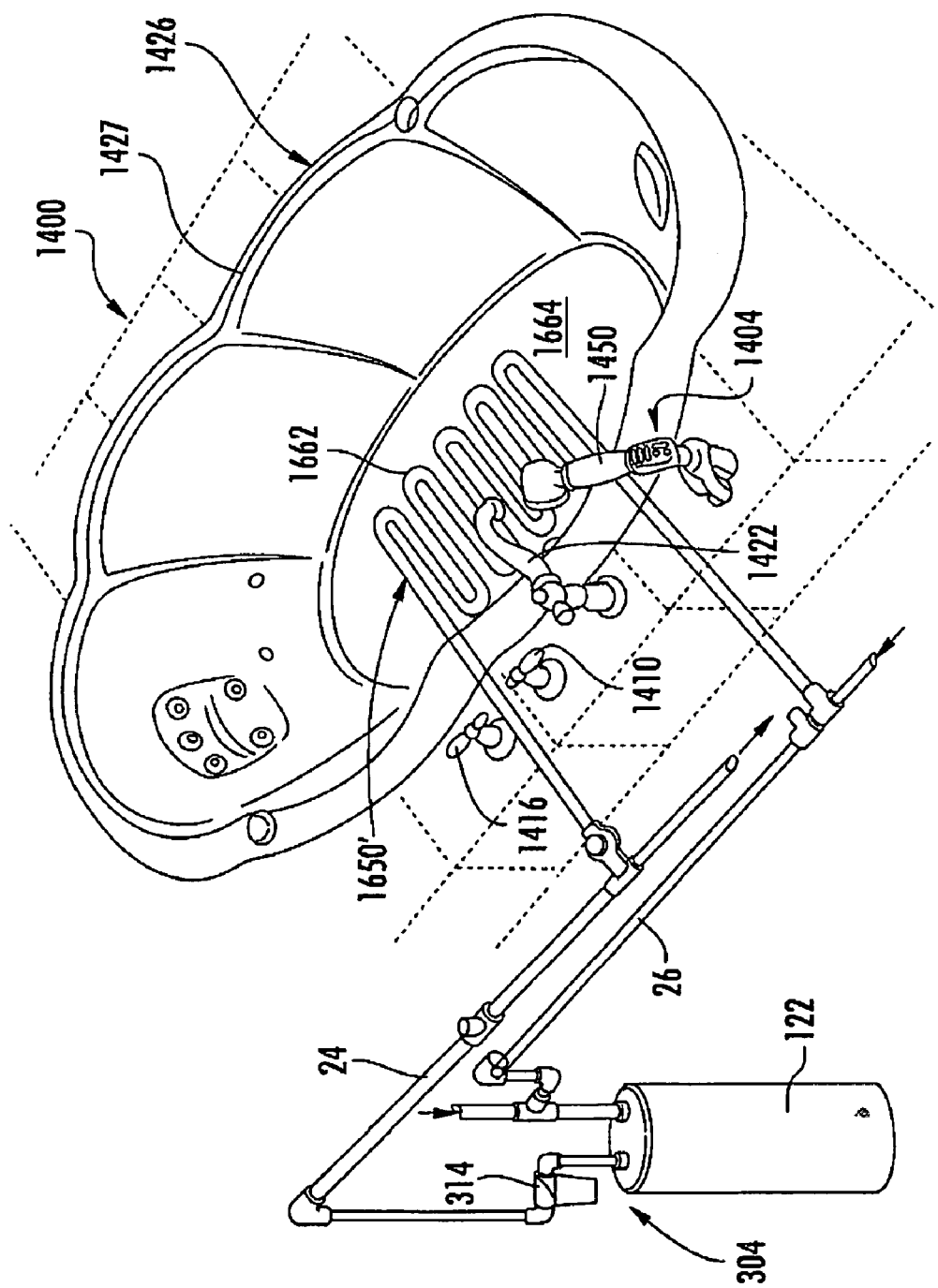
FIG. 51 is a perspective view of an illustrative roman tub having a radiant temperature maintain system.

In a further illustrative embodiment shown in FIG. 51, a heat transfer device 1650' comprises radiant heat tubes 1662 positioned in thermal communication with the base 1664 of the roman tub 1426. Pump 314 recirculates hot water from the hot water heater 122 through the hot water supply line 24, through tubes 1662, and back to the hot water heater 122 through cold water return line 26. Heat is transferred from the tubes 1662 through the base 1664 and to the water in the tub 1426. The controller 1438 controls operation of the pump 314 in order to maintain the desired temperature of water in the tub 1426.

The hand shower 1450 includes handle 1472 supporting a spray head 1473. Than handle 1472 and spray head 1473 may be of conventional design. With reference to FIGS. 52 and 53, the illustrative hand shower 1450 includes a remote control module 1404 having a plurality of user controls 1668. The user controls 1668 transmit signals to the controller 1438 via transmitter 1436 and transceiver 1432. The user controls 1668 illustratively include flow on/off button 1670, temperature up and down buttons 1672a and 1672b, and a low flow button 1674. A separate high flow button (not shown) may be provided, or the low flow button 1674 may toggle between low and high flows. As shown in FIG. 53, the hand shower controls 1668 may also include a light on/off button 1676, a whirlpool jets on/off button 1678, and a massage control slide switch 1680.

The hand shower remote control module 1404 may be retrofit to an existing hand shower 1450. More particularly, the hand shower 1450' includes a shower module 1404' of FIGS. 54 and 55, illustratively having a housing 1682 including a battery portion 1684a and a transmitter portion 1684b. The portions 1684a and 1684b may be secured together or clamped in a conventional manner at the base of the hand shower 1450 around the handle 1472 or the flexible water hose 1538. At least one battery 1687 is supported in the battery portion 1684a, while an RF transmitter 1436 is supported by the transmitter portion 1684b. The transmitter 1436 communicates with the transceiver 1432 of the roman tub module 1402, and hence the display module 1406, wherein the display 1418 may present a digital readout of the desired or set water temperature. In the hand shower module 1404', the user controls 1668' include a toggle button 1685, an up button 1686a, and a down button 1686b. The toggle button 1685 is configured to switch operation of the buttons 1686a and 1686b from between flow and temperature of water flowing through the sprayhead 1473.

Figure 56:
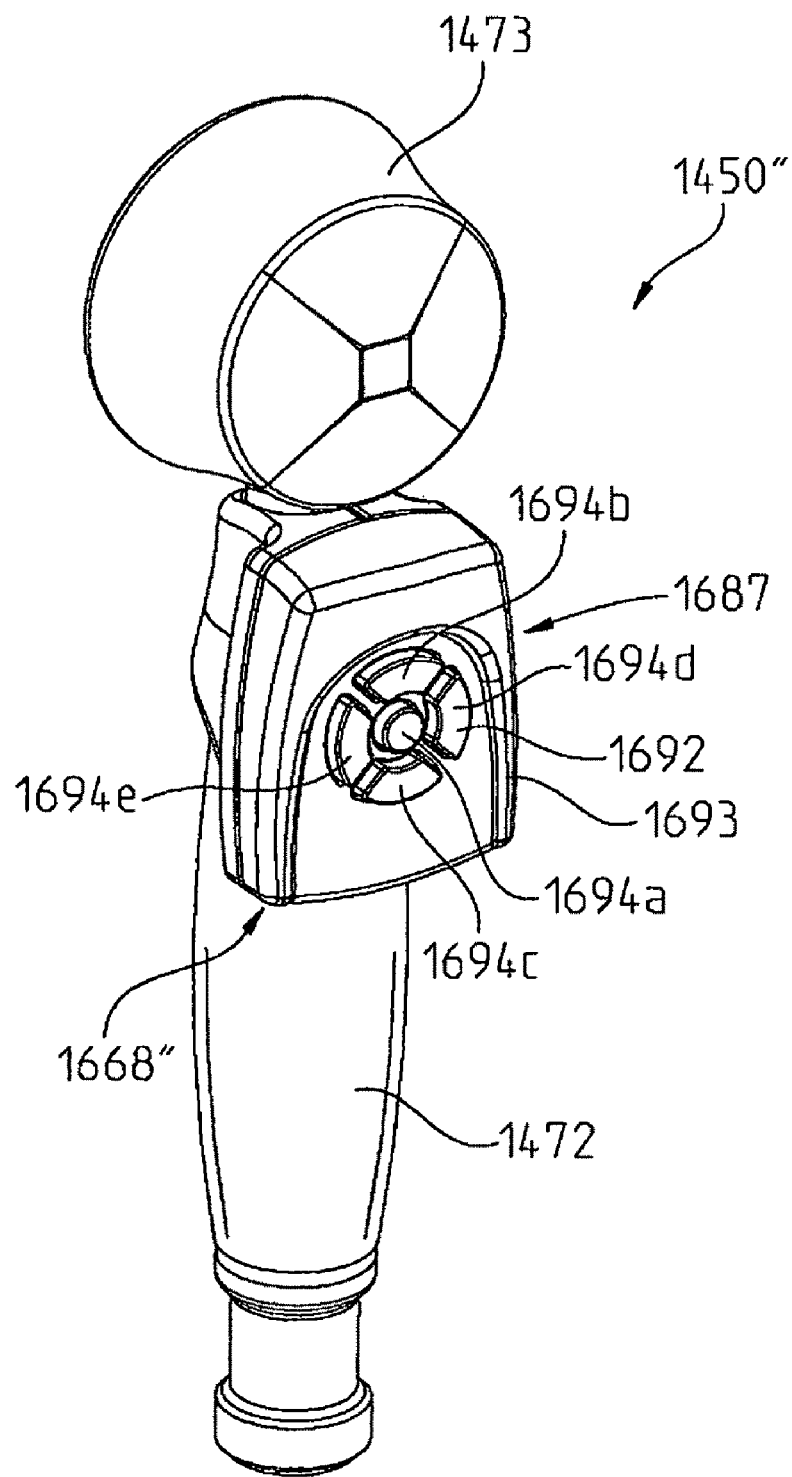
FIG. 56 is a perspective view of a further illustrative embodiment hand shower.
Figure 57:
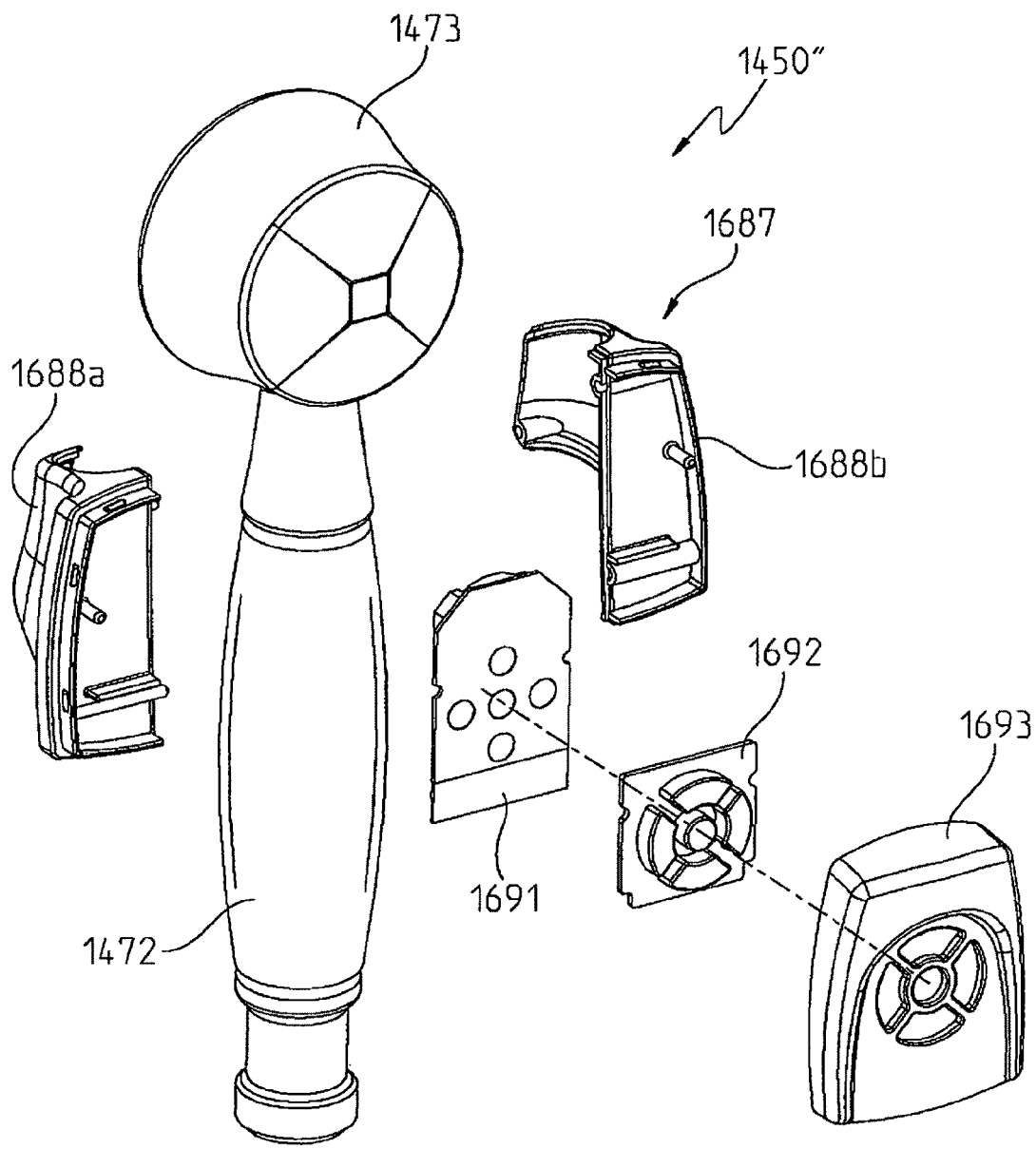
FIG. 57 is a partially exploded perspective view of the hand shower of FIG. 56.

Referring now to FIGS. 56 and 57, a further illustrative embodiment hand shower remote control module 1404" is shown. The module 1404" includes a housing 1687 having first and second housing portions 1688a and 1688b configured to be secured around the handle 1472 of the hand shower 1450". A circuit board 1691 and button assembly 1692 is received intermediate the housing 1687 and an outer faceplate or cover 1693. The button assembly 1692 defines controls 1668" push buttons including an ON/OFF button 1694a, flow control high button 1694b, flow control low button 1698c, temperature control up button 1694d, and temperature control down button 1694e. As with the remote control module 1404", the module 1404' is configured to communicate with the controller 1438 in a wireless manner, illustratively through RF signals.

Figure 58:
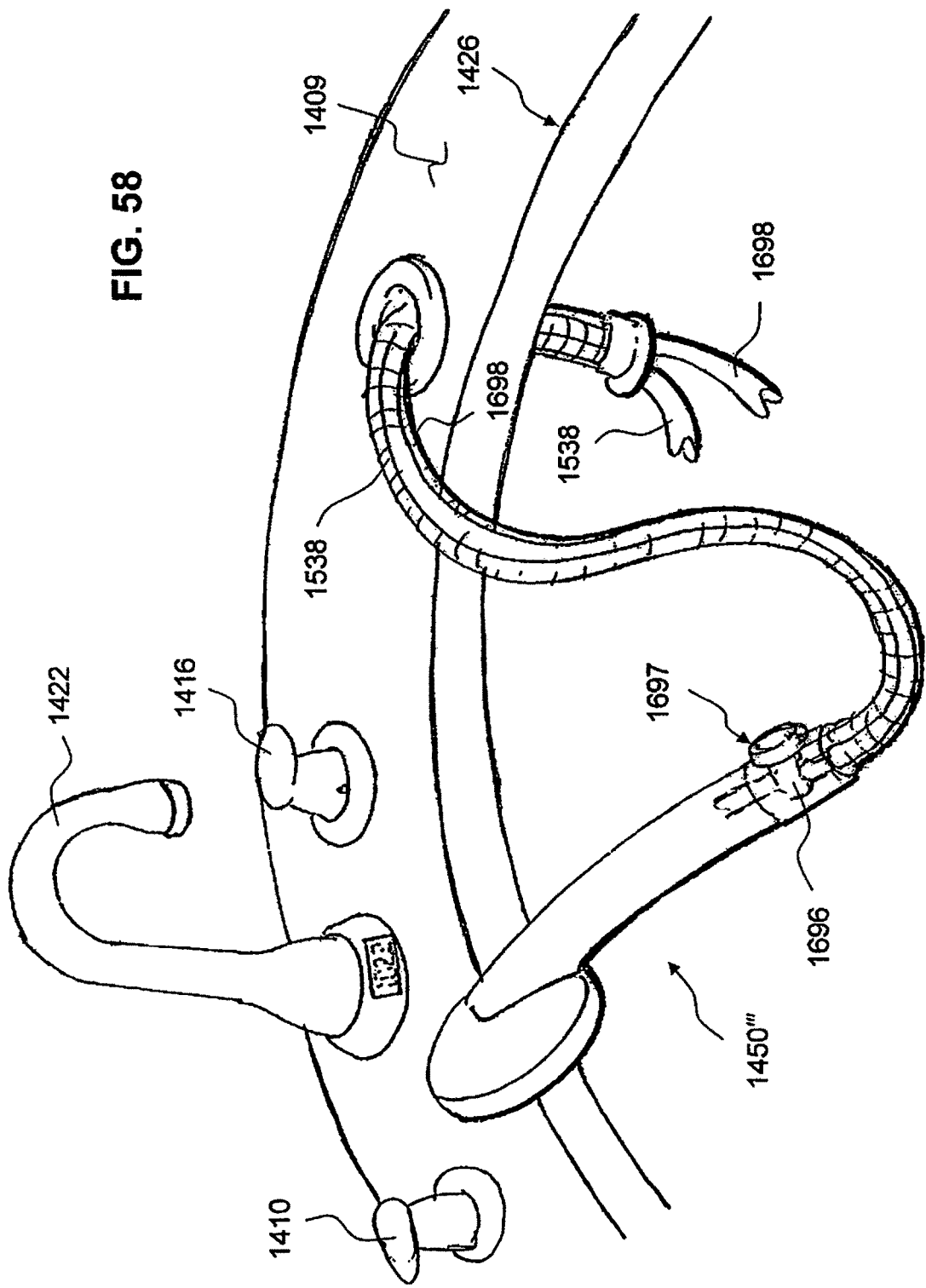
FIG. 58 is a perspective view of a further illustrative embodiment hand shower, shown coupled to the deck of a roman tub and including a cold water purge device.

FIG. 58 shows a further illustrative embodiment hand shower 1450'" which includes a purge valve 1696. The purge valve 1696, when activated by a push button 1697, causes cold water remaining within the flexible inlet hose 1538 to purge out through a flexible return hose 1698. In other words, the purge valve 1696 causes water to flow through the inlet hose 1538 and out through the return hose 1698. As such, cold or tempered water sitting within the inlet hose 1538 may be eliminated or purged.

As noted above, control module 1402 is located near the valve components and is illustratively hidden below a deck.

The control module 1402 includes user interface components to control water flow, water temperature (actual and desired), tub fill levels, hand shower valve, and the temperature maintain system. The control module 1402 is illustratively in radio-frequency communication with the user interface module 1406 and the hand shower remote control module 1404 through use of the transceiver 1432.

The user interface module 1406 may be activated only when the user performs certain actions, such as pushing the on/off button, adjusting the temperature control in the tub or on the hand shower, or adjusting the flow control in the tub or on the hand shower. Similarly, the user interface module 1406 may be deactivated when the user performs, or fails to perform, certain actions. For example, the user interface module 1406 may be deactivated when the user pushes the on/off button in the tub, or after a predetermined time period (e.g. 15 seconds) after the user adjusts temperature, flow, and the tub is not on.

The user interface module 1406 may be free standing and illustratively communicates with the control module 1402 through radio frequency. Alternatively, the user interface module 1406 may be hard wired to the control module 1402. The user interface module 1406 may also includes a backlight for the display. The backlight illustratively blinks or flashes when the tub is full.

The user interface module 1406 provides tactile feedback through the user interface. The user interface module 1406 may be powered through battery 1750 or through 120 VAC.

The transceiver 1434 of the user interface module 1406 transmits signals in order to operate in a temperature maintain mode. A button may be provided within the user interface module 1406 to activate the temperature maintain mode of operation. The temperature maintain function is provided by a combination of components, including tub water temperature sensor 1428 and heating device 1650. Illustratively, the temperature of the tub water is maintained by a recirculating pump (i.e., jetted tub) in the manner detailed above. Alternatively, the temperature maintain function is achieved by radiated heating coils in thermal communication with the tub water, or by recirculation of hot water. The transceiver illustratively receives signals indicative of the desired tub temperature setting, the current tub temperature setting, the spout temperature setting, the hand shower temperature setting, the tub fill setting, the tub flow setting, and the overfill sensor.

The mechanical interface may include the flow/fill control knob 1410 which is symmetrical and includes no pointer or indicator. The flow/fill control handle 1410 may be continuously adjustable (i.e., no stops) and may be pushed for on/off activation. The flow/fill knob illustratively selects low and high flow modes, and also selects low, medium, and high tub fill settings. The handle 1410 provides tactile feedback and a backlight is provided for facilitation knob location.

As with the flow/fill handle 1410, the temperature control knob or handle 1416 may be symmetrical, having no pointer or indicator and that is continuously adjustable (i.e., no stops). The temperature handle 1416 is configured to be rotated counterclockwise for hot and clockwise for cold. The handle 1416 illustratively provides tactile feedback and a backlight indicator is provided to facilitate knob location.

A battery backup may be provided within the roman tub module. Illustratively the battery backup is charged from AC power and has a minimum life expectancy of approximately 5 years. A hydro-generator may also be used to charge the battery.

As detailed above, a water level sensor 1430 may be provided for detecting the depth of water within the tub 1426. Illustratively, the water level sensor 1430 detects various water depths, such as low, medium, high, and overfilled. The sensor 1430 transmits a signal to the controller 1438 when the depth setting is reached. The controller 1438, in turn, activates the alarm 1446 and deactivates the valves 1456 and 1458. The alarm 1446 may also be triggered to indicates a drain open condition. In another embodiment, the drain may be automatically closed when the automatic fill mode is selected.

The temperature maintain selection is transmitted via radio frequency from the user interface module 1406 to the control module 1402. Button selections of the hand shower 1450 are likewise transmitted via radio frequency to the control module 1402. Diagnostic status, temperature setting, and flow setting are transmitted via radio frequency from the control module 1402 to the display module 1406. Illustratively, the various transmission components have a range of approximately 50 feet and operate at 433 or 900 MHz.

Figure 61A:
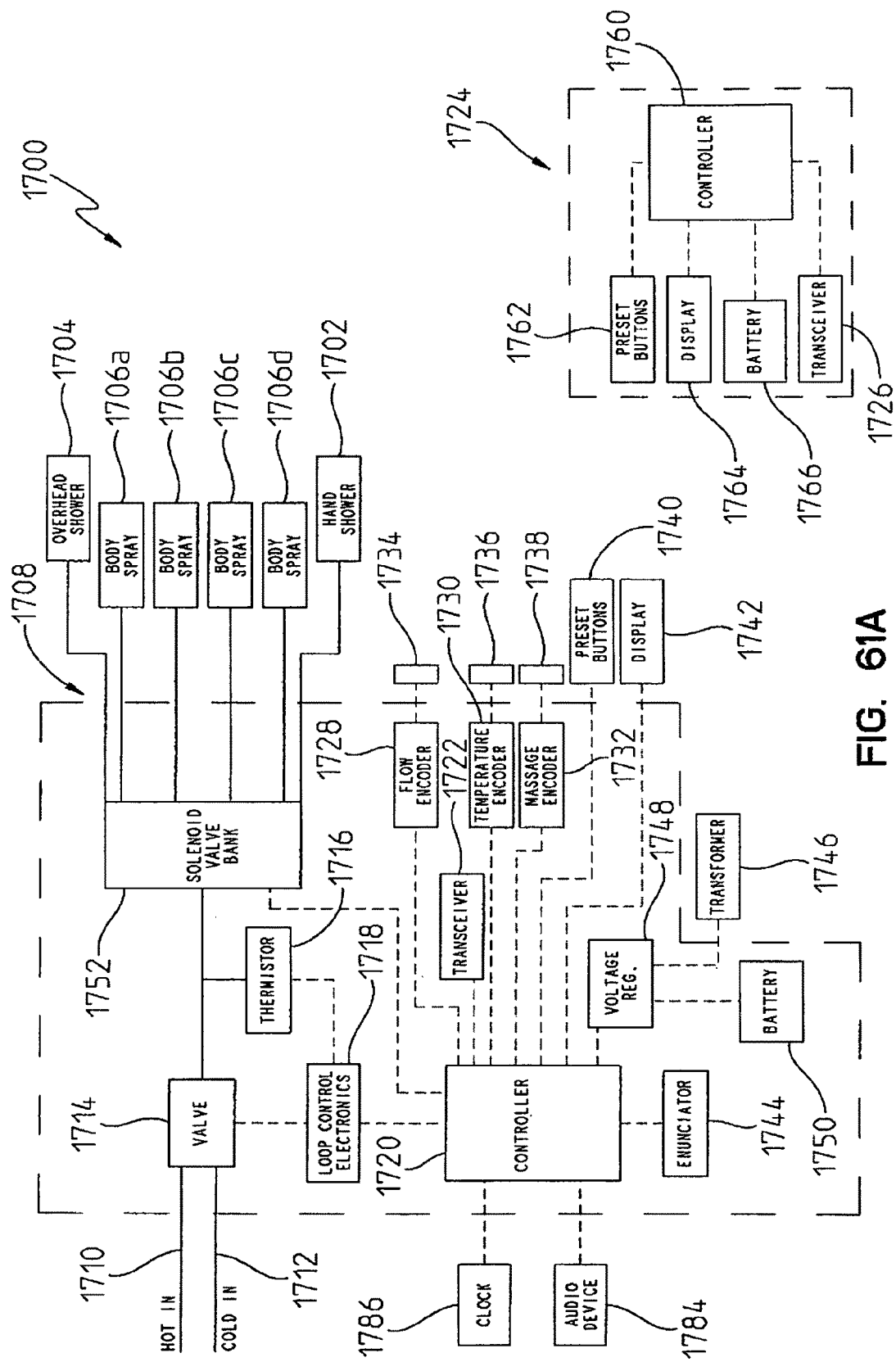
FIG. 61A is a schematic view of an illustrative custom shower system.
Figure 61B:
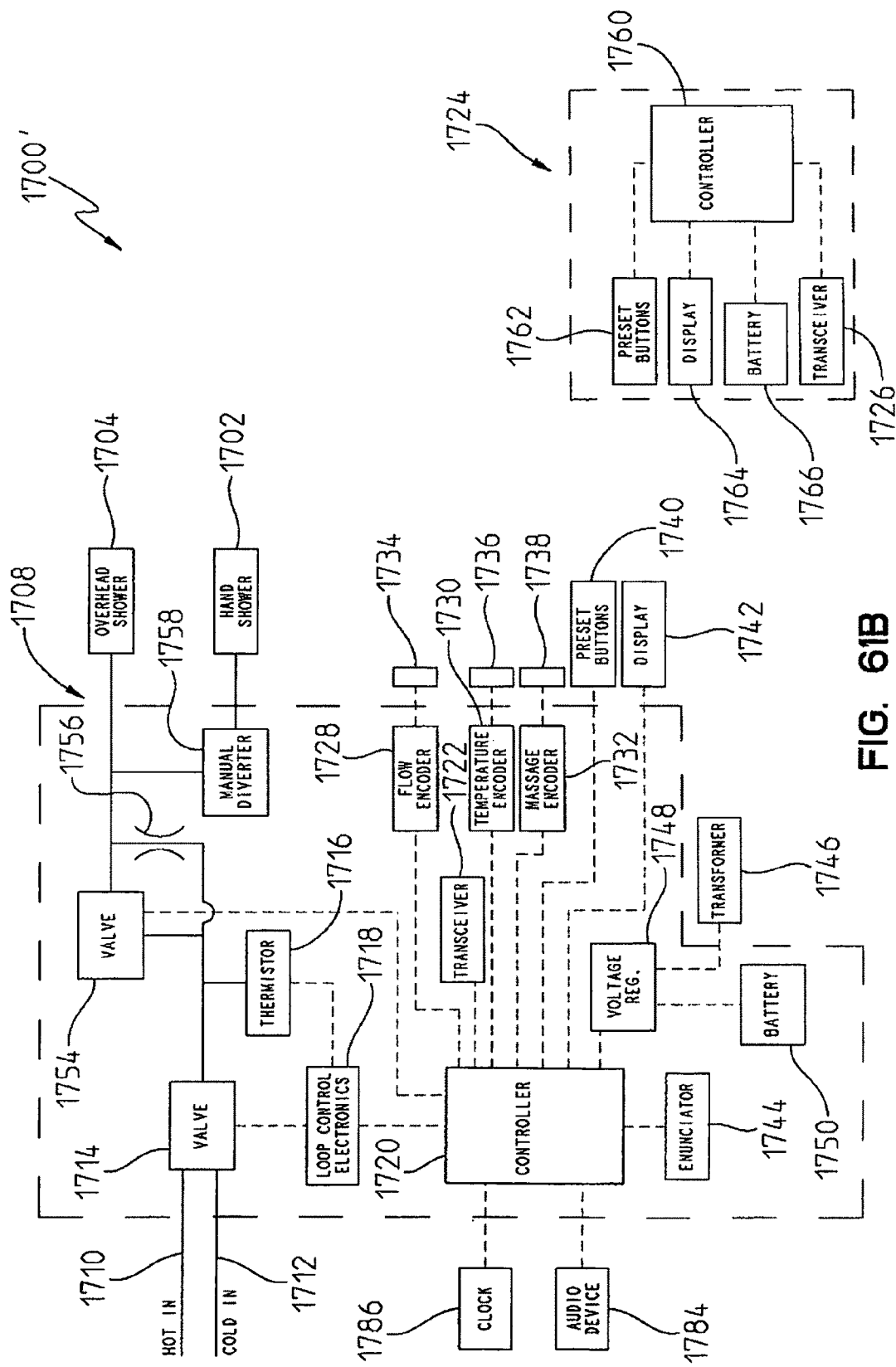
FIG. 61B is a schematic view of a further illustrative custom shower system.

An illustrative custom shower system 1700 is shown in FIGS. 59-61B. One illustrative embodiment custom shower system 1700 includes a hand shower 1702, an overhead shower 1704, and a plurality of body sprays 1706 (FIG. 61A) configured to discharge water when active. In an alternative embodiment shower system 1700', the body sprays 1706 may be eliminated (FIG. 61B). A custom shower control module 1708 is fluidly coupled to a hot water supply line 1710 and a cold water supply line 1712 are in fluid communication with an electrically operable, or motorized temperature control valve 1714. A thermistor 1716 is in thermal communication with the outlet of the motorized valve 1714 and is in electrical communication with loop control electronics 1718. More particularly, the thermistor 1716 provides a signal to the electronics 1718 indicative of outlet water temperature. The electronics 1718 compare the outlet water temperature to a set temperature and controls operation of the motorized valve 1714 in response thereto. The loop control electronics 1718 are in electrical communication with a controller 1720 which is configured to receive input from a transceiver 1722. The transceiver 1722 is configured to be in communication with a remote control module 1724 through a transceiver 1726.

The controller 1720 is also configured to receive input from a flow encoder 1728, a temperature encoder 1730, and a massage encoder 1732 which are operably coupled to flow control knob or handle 1734, temperature control knob or handle 1736, and massage control knob or handle 1738, respectively. A plurality of preset buttons 1740 may also be provided to supply input signals to the controller 1720. A display 1742 is in electrical communication with the controller 1720 to provide visual indications to a user, while an enunciator 1744 is likewise in electrical communication with the controller 1720 to provide audible indications to the user.

A transformer 1746 is illustratively in electrical communication with a voltage regulator 1748 for supplying power to the controller 1720 from a conventional 120 VAC power supply. A battery 1750 may also be provided for back-up power. Illustratively the battery backup is charged from AC power and has a minimum life expectancy of approximately 5 years. A hydro-generator 1751 (FIG. 60) may also be used to charge the battery 650.

In the body spray embodiment shower system 1700 of FIG. 61A, a solenoid valve bank or manifold 1752 is provided in fluid communication with the outlet of the motorized valve 1714. The valve bank 1752 controls the flow of water to the hand shower 1702, the overhead shower 1704, and the plurality of body sprays 1706a-1706d. A shower/body spray selector 1753 (FIG. 75) activates individual solenoid valves for the shower/body spray selected. In an illustrative embodiment, the spray selector 1753 includes a plurality of buttons 1956 which are illustratively backlit when selected and are configured to independently control the solenoid valves of valve bank 1752, and thereby the discharge of water to the individual body sprays 1706, overhead shower 1704, and/or hand shower 1702.

With reference to the shower system 1700' of FIG. 61B, a solenoid valve 1754 is in fluid communication with the outlet of the motorized valve 1714 and a restriction 1756 is placed in parallel thereto. A manual diverter 1758 is configured to control the flow of water from the valve 1714 to one of the hand shower 1702 and the overhead shower 1704. The manual diverter 1758 may include a conventional pull knob (not shown) of conventional design.

The remote control module 1724 illustratively includes a controller 1760 in communication with the transceiver 1726, a plurality of preset buttons 1762, and a display 1764. A battery 1766 illustratively powers the controller 1760.

The display 1764 illustratively provides feedback on system conditions. A first illustrative embodiment remote module 1724 is shown in FIG. 62, while a second illustrative embodiment remote module 1724' is shown in FIGS. 63 and 64.

Figure 62:
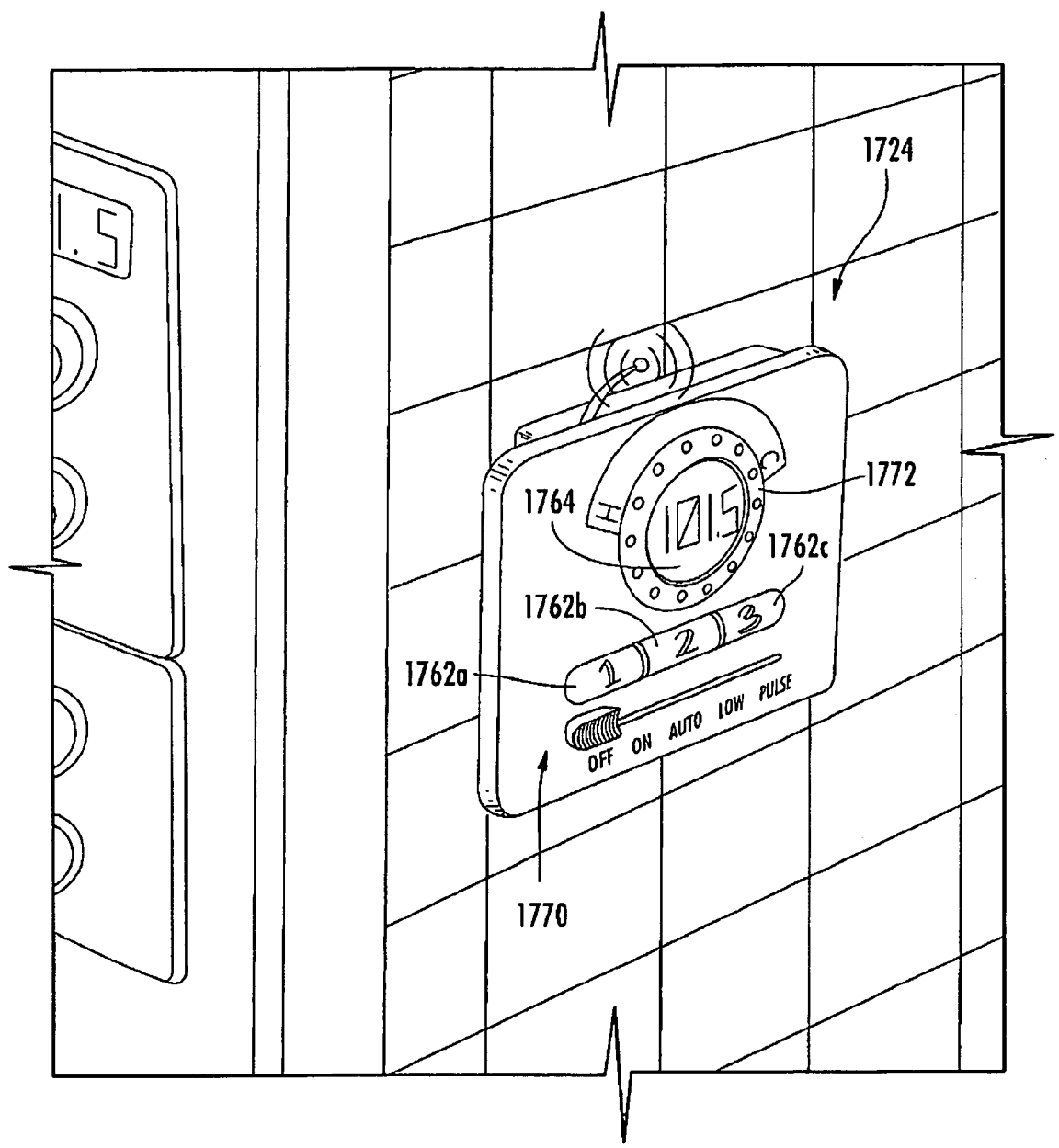
FIG. 62 is a perspective view of an illustrative remote shower control module.

With reference to FIG. 62, the remote module 1724 include a slide switch 1770 which can be used to select flow off, flow on, auto flow, low flow, and pulse massage. A switch ring 1772 is received around the display 1764 and may be rotated to adjust the desired set temperature. In another illustrative embodiment, the switch ring 1772 may include at least one capacitive touch sensor (not shown) which may be utilized by a user to adjust temperature. The present buttons 1762a, 1762b, and 1762c may be used to recall previously stored settings. For instance, a user can store his or her desired temperature, flow setting, massage setting, and shower selection by pressing and holding a numbered preset button 1762 for a predetermined time period, illustratively 2 seconds. The stored preset may then be recalled by pressing and releasing the preset button 1762.

Figure 63:
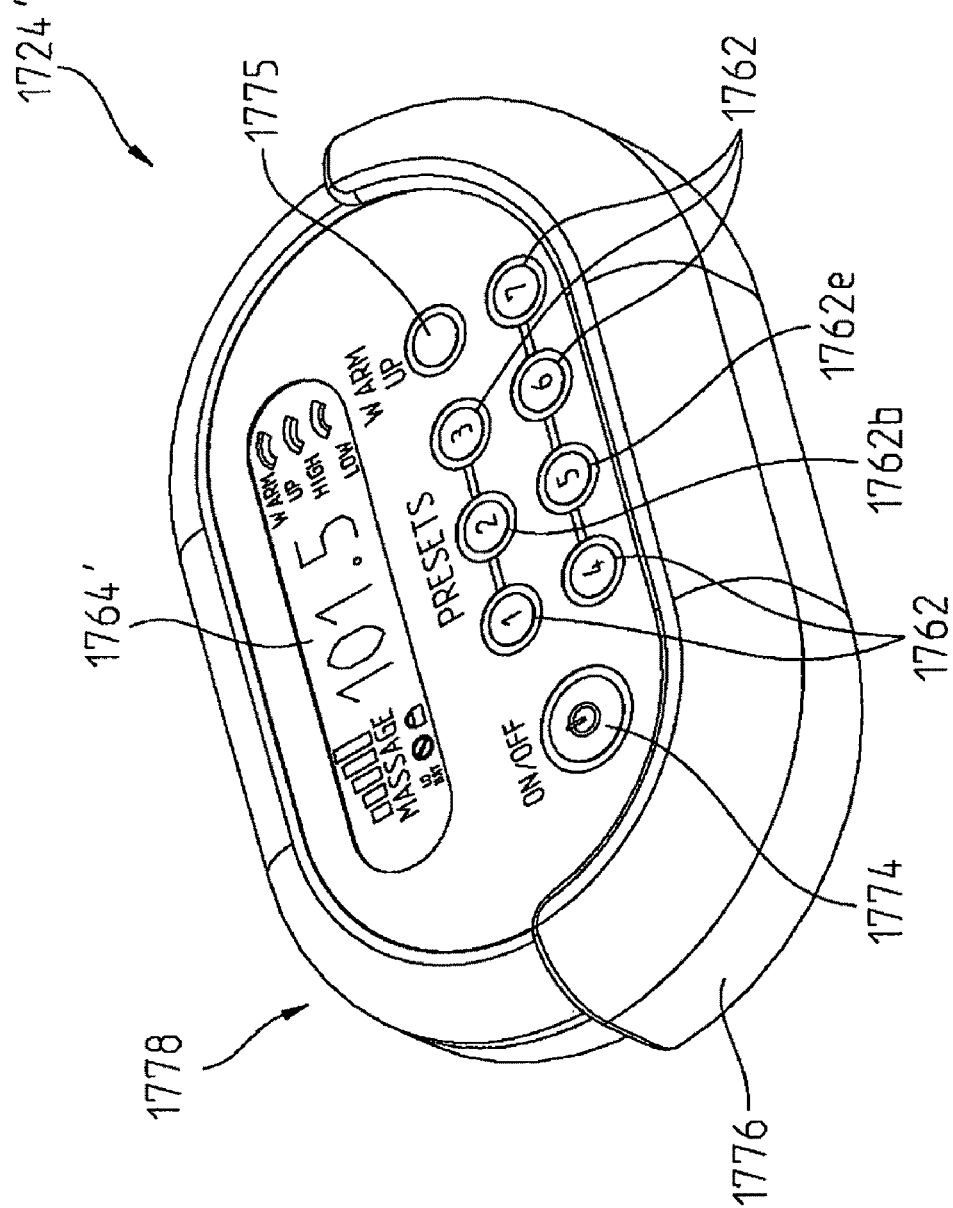
FIG. 63 is a perspective view of a further illustrative remote shower control module.
Figure 64:
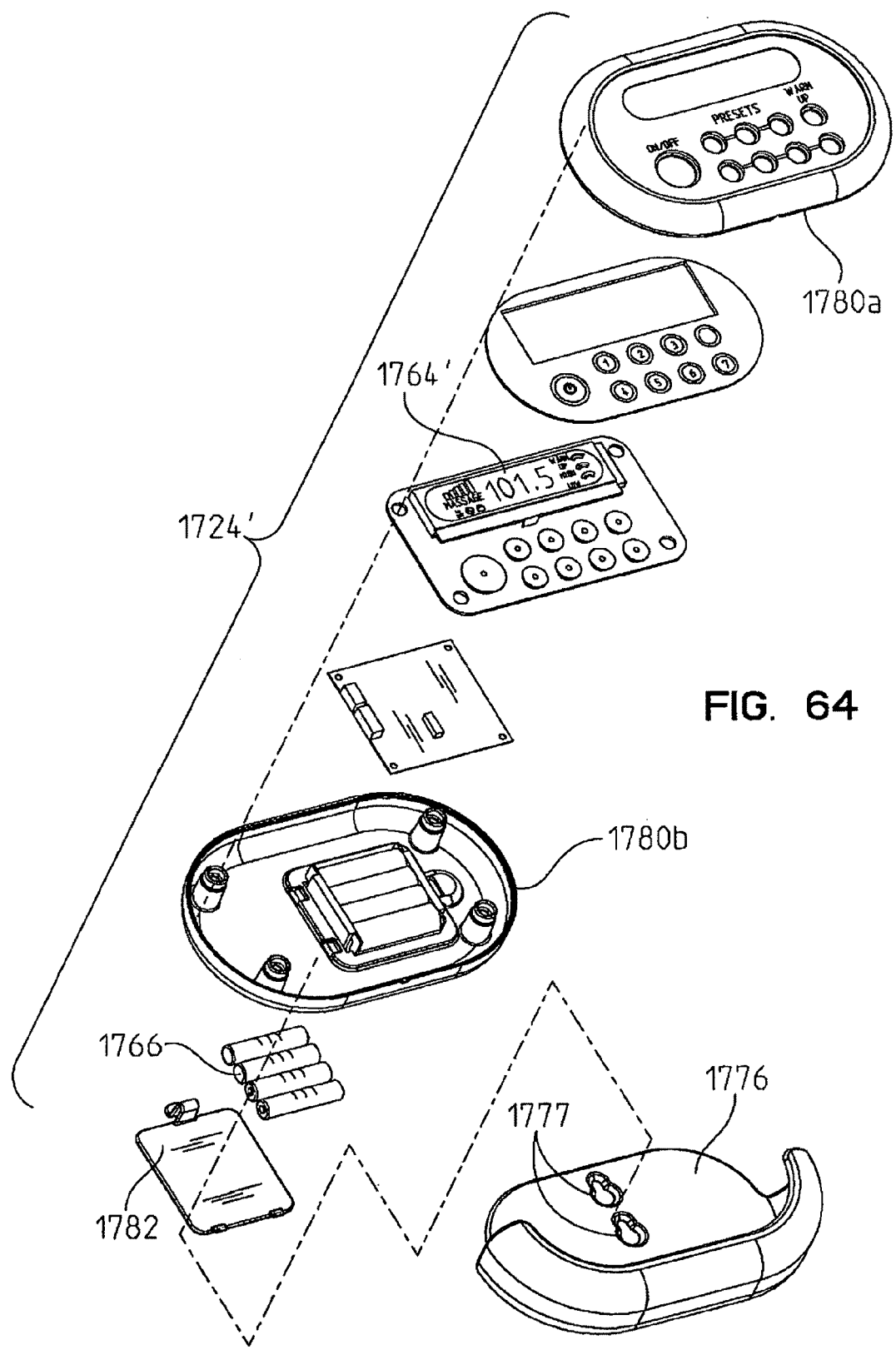
FIG. 64 is an exploded perspective view of the remote shower control module of FIG. 63.

Referring now to FIGS. 63 and 64, the remote module 1724' includes a plurality of push buttons including an on/off button 1774. The remote module 1724' includes display 1764' which is configured to substantially match the shower display module 1742. The preset buttons 1762 operate as detailed above in connection with the remote control module 1724. Buttons 1762 on the remote may be used to recall already established presets. The user illustratively programs the presets with the shower display module. Illustratively, there are seven (7) button presets 1762, but this number may vary. A warm up button 1775 is also provided and is configured to instruct the controller to activate the valve 1714 until a predetermined temperature is reached as measured by the thermistor 1716. The buttons 1762, 1774 and 1775 are illustratively backlit when activated and provide tactile-feedback. In one illustrative embodiment, pressing and holding preset button 1762b (for 2 seconds) causes the temperature setting to increase. Similarly, pressing and holding preset button 1762e (for 2 seconds) causes the temperature setting to decrease. Remote button activation is illustratively transmitted via radio frequency to the shower control module 1708. Similarly, the remote control module 1724 receives preset information from the shower control module 1708 via radio frequency by transceiver 1726.

The remote control module 1724' may be wall mounted. As shown in FIGS. 63 and 64, the remote control module 1724' is removably received within a cradle 1776. The cradle 1776 includes keyhole shaped openings 1777 configured to receive fasteners (not shown) for fixing the cradle 1776 to a wall. The remote control module 1724' includes a housing 1778 defined by front rear housing portions 1780a and 1780b. Batteries 1766 are supported within the rear housing portion 1780b and accessible through an access door or cover 1782.

The control module 1708 allows a user to adjust temperature with a handle 1736 while the shower display 1742 provides visual feedback. The handle 1736 provides tactile feedback during rotation. The desired set temperature increases with counterclockwise rotation and decreases with clockwise rotation. A backlight (not shown) may be provided to facilitate identification and location of the knob 1736.

In one illustrative embodiment, the flow control knob 1734 may be pushed to turn the shower on/off. A full flow setting sets the water to full flow, a low flow setting sets the water to low flow, while an auto flow setting sets the water to full flow and causes the enunciator 1744 to sound when the set temperature has been detected by the thermistor 1716. The flow control knob 1734 provides for tactile feedback and illustratively includes a indicator (not shown) to facilitate identification and location of the knob 1734. For the body spray module 1700, the programmable massage setting sets the intensity and the frequency of pulsing from the body sprays 1706. Again, the programmable massage knob 1738 provides tactile feedback and includes a backlight (not shown) for knob identification. The shower/body spray selection activates the desired overhead shower 1704, hand shower 1702, and/or body sprays 1706 as desired.

As further detailed herein, a manual valve override 1790 enables the user to manually adjust temperature and flow in the event of a power or electronics failure. Illustratively, the temperature knob 1736 is pulled out to activate the manual override mode, while the temperature knob 1736 is pushed in to return to the normal use mode. When activated, the manual valve override 1790 operates through mechanical operation. Moreover, the on/off activation of the flow is controlled by rotating the temperature knob 1736 clockwise. The knob 1736 is rotated counterclockwise to decrease temperature and is rotated clockwise to increase temperature.

The shower display 1742 is illustratively activated when the user performs certain actions. For example, the display 1742 may be activated if the user adjusts or pushes any of the controls on the shower control module 1708 or the remote control module 1724. The display 1742 is illustratively deactivated when the user performs or fails to perform certain actions. For example, the display 1742 may be deactivated when the user pushes the on/off button in the shower or on the remote to turn the flow off. Additionally, the display times out and is deactivated after a predetermined time period, illustratively 15 seconds, from the last user adjustment of the temperature, flow, massage, or shower/body spray and the shower is not on.

The set temperature and the actual temperature are illustratively displayed on a liquid crystal display (LCD) within a range, illustratively 60-110° F. and are shown with 4 digits having one decimal place. In the massage mode, an icon illuminates to indicate the massage setting. Indicators are also provided for off, low, medium, and high frequency massage settings. A low battery indicator includes an icon which illuminates to provide an indication of low battery life, illustratively less than approximately 20% of battery life remaining. A flow control indicator displays low, full, and auto modes. An audio transducer sounds an audible alarm when the shower reaches the desired set temperature.

An audio device 1784 and/or clock 1786 may be integrated with the shower control module 1708. For example, a radio or MP3 device may be provided for control from within the shower. The display 1742 may show audio listening information and/or time to the user.

The temperature knob 1736 may be symmetrical, having no pointer or indicator, and is continuously adjustable (i.e., no stops). The temperature knob 1736 is configured to be rotated counterclockwise for hot and clockwise for cold. The knob 1736 provides tactile feedback and a backlight indicator is provided to facilitate knob location.

The flow/fill control knob 1734 may also be symmetrical and include no pointer or indicator. The flow/fill control knob 1734 is continuously adjustable (i.e., no stops) and may be pushed for on/off activation. The flow/fill knob 1734 selects low and high flow modes, and also selects low, medium, and high tub fill settings. The knob 1734 provides tactile feedback and a backlight is provided for facilitation knob location.

Massage knob 1738 may also be symmetrical and include no pointer or indicator. The massage knob 1738 is continuously adjustable (i.e., no stops). The user may select off or different frequency pulse modes. The knob 1738 provides tactile feedback and a backlight is provided for facilitating knob location.

The valve control permits flow of 9 gpm at 60 psi. Closed loop motor control (60-110° F.) includes a thermistor sensor and a relative mechanical encoder set point.

The massage control includes one solenoid per spray head and a DC latching valve. The body sprayer illustratively has a capacity of 1.6 gpm, while the overhead sprayer has a rating of 2.2 gpm.

In one illustrative embodiment when the user places the custom shower module 1700 in an "auto" mode, water flows and the enunciator 1744 sounds an alarm when the set temperature is reached. In a further illustrative embodiment, water flows when the custom shower module 1700 is placed in an "on" mode. However, once the desired set temperature is reached, water flow stops to save water. The alarm may also be sounded by the enunciator 1744.

Figure 65:
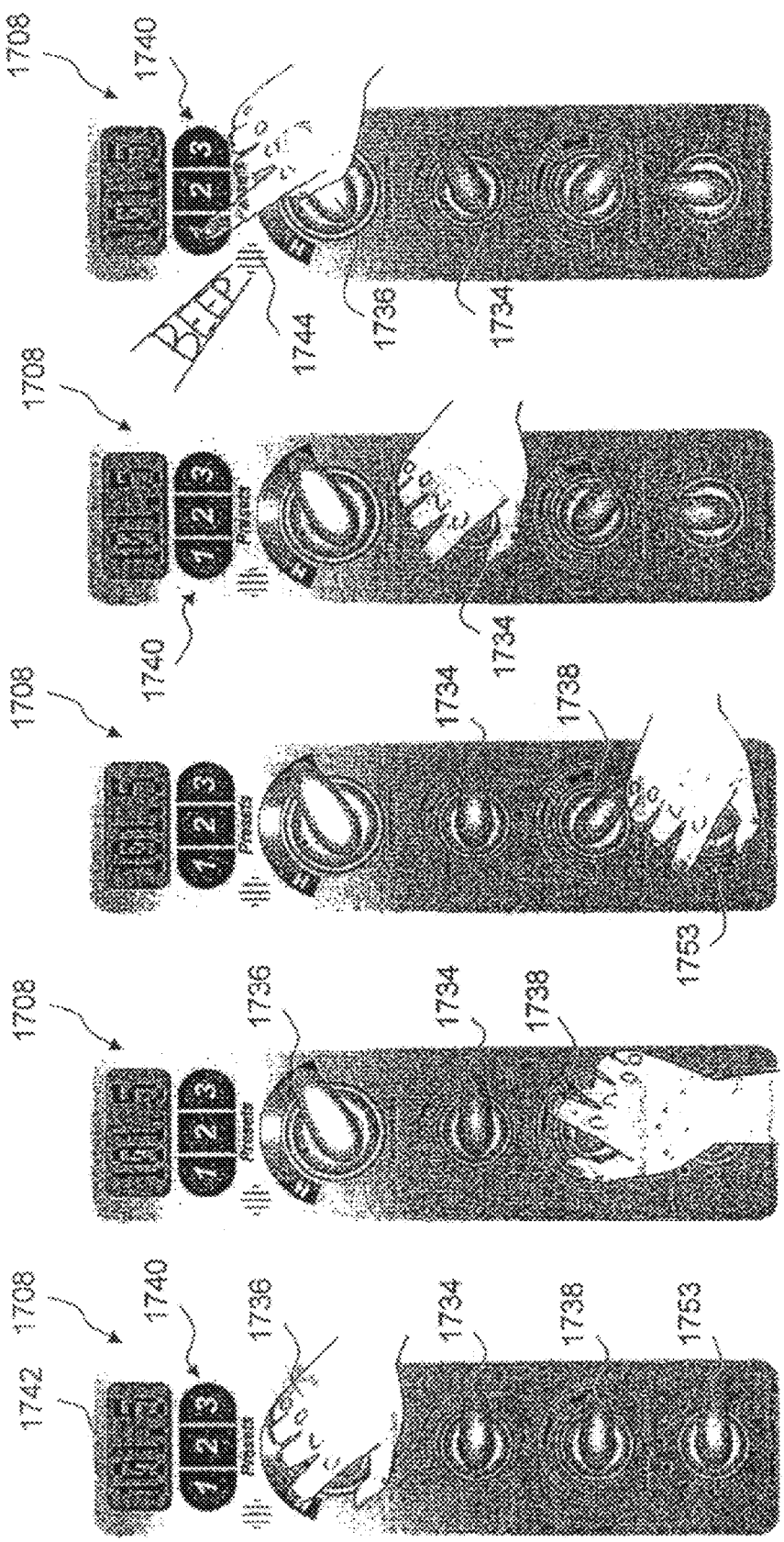
FIGS. 65A-65E are front elevational views of an illustrative user interface for a shower control module, showing steps for setting a memory preset.

As with the roman tub module, the shower module 1700 may operate in low flow mode, which may be advantageous when a user is lathering with soap or shampoo. As detailed herein, various representative programmable massage settings may be used in the custom shower module 1700. FIGS. 65A-65E show various illustrative methods of setting memory presets. More particularly, in FIG. 65A the user selects a desired temperature by operating temperature control handle 1736. In FIG. 65B, the user selects a desired massage control by operating massage control handle 1738. Desired sprayheads are selected in FIG. 65C by operating shower/body spray selector 1753, while a desired flow rate is selected in FIG. 65D by operating flow control handle 1734. Finally, the user associates and stores the selected settings by depressing one of the present buttons 1740 for a predetermined time. An audible signal may be provided to indicate the storing of the settings.

Figure 66:
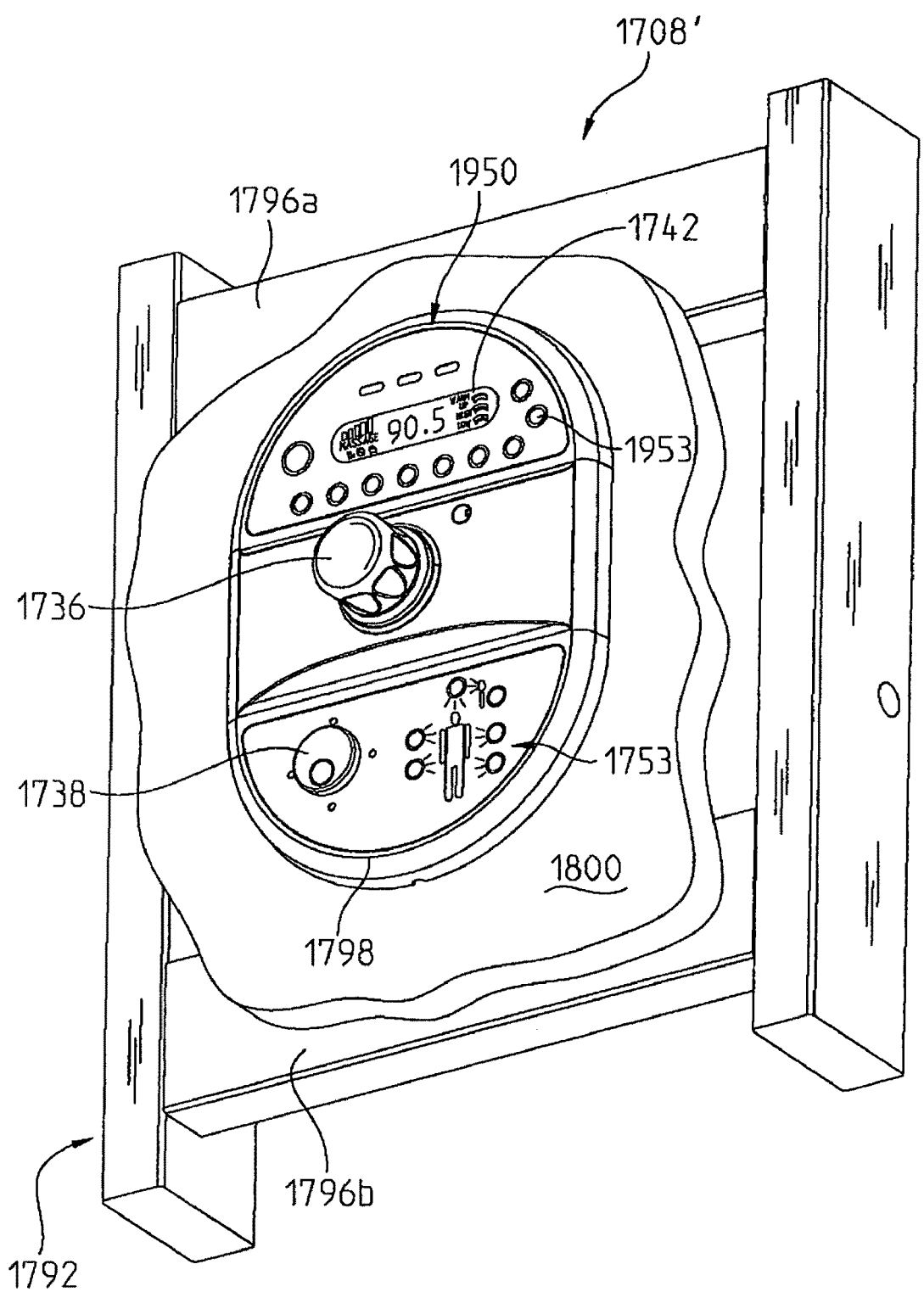
FIG. 66 is a perspective view of an illustrative embodiment custom shower control module mounted within a wall.

A further illustrative custom shower control module 1708' is shown in FIGS. 66-70. FIG. 66 shows the module 1708' mounted to a shower wall 1792. More particularly, a mounting bracket 1794 supports the module 1708' between crossmembers 1796a and 1796b of the wall 1792. A user interface plate 1798 is supported on the outer surface 1800 of the wall 1792 and illustratively includes a seal or gasket (not shown) positioned therebetween.

Figure 67:
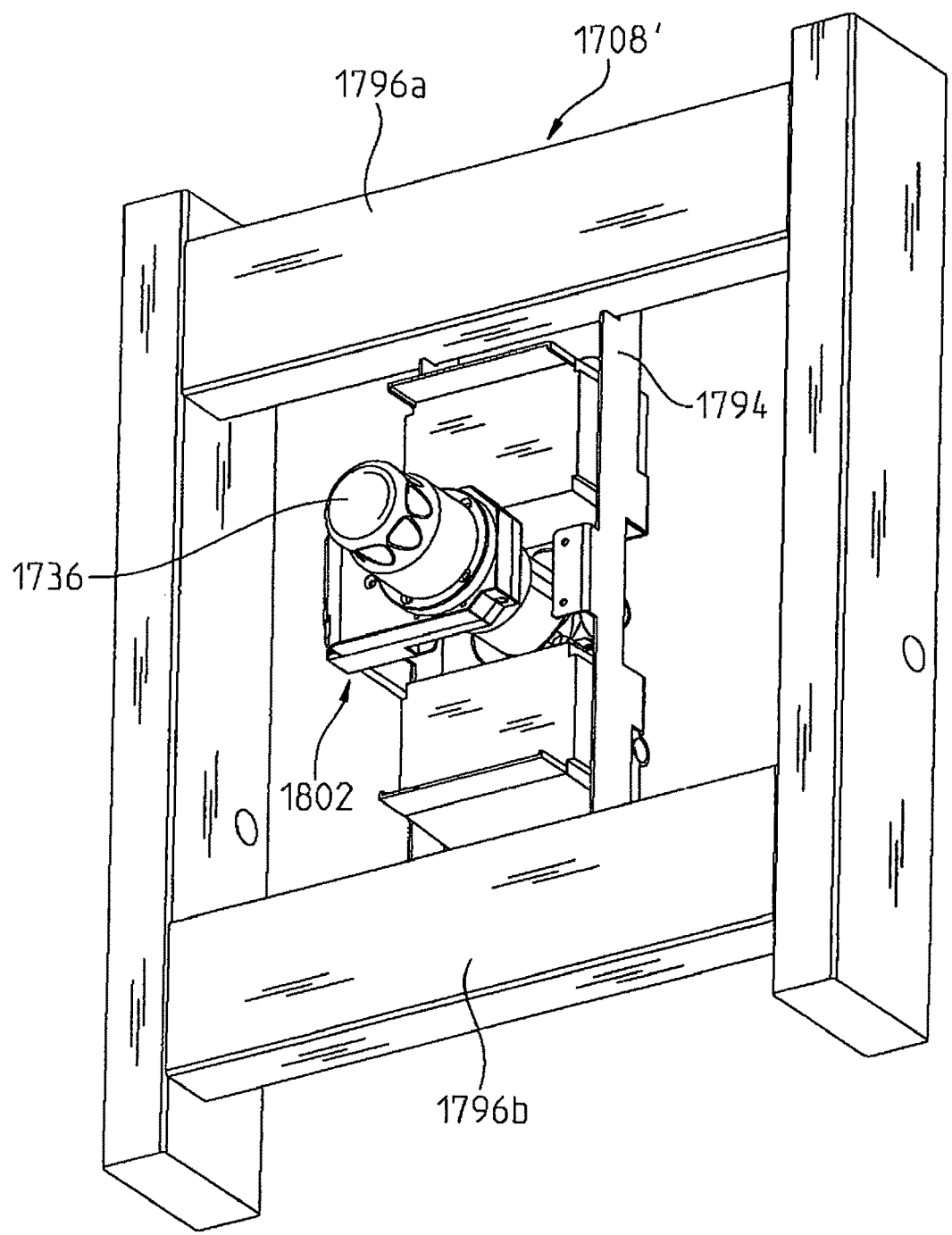
FIG. 67 is a perspective view similar to FIG. 66, with the user interface plate and the outer wall removed.
Figure 68:
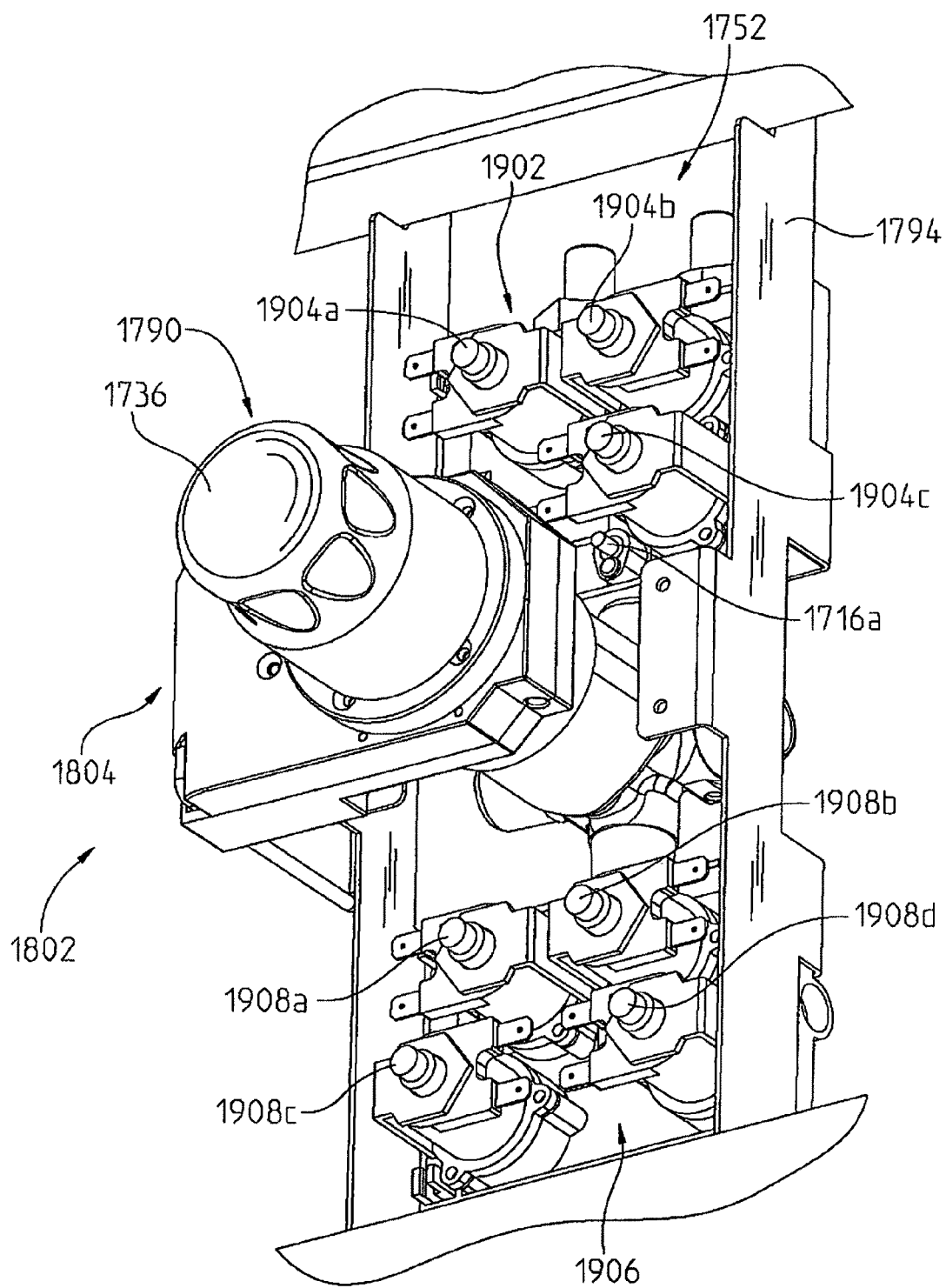
FIG. 68 is a front perspective view showing the control valves of the control module of FIG. 67.

In the illustrative embodiment of FIGS. 66-68, the flow encoder 1728 and cooperating handle 1734 have been removed. Instead, flow is controlled by the low flow button as further detailed herein. The temperature encoder 1730 is incorporated within a magnetic encoder gear box 1802, as also further detailed herein.

Figure 71A:
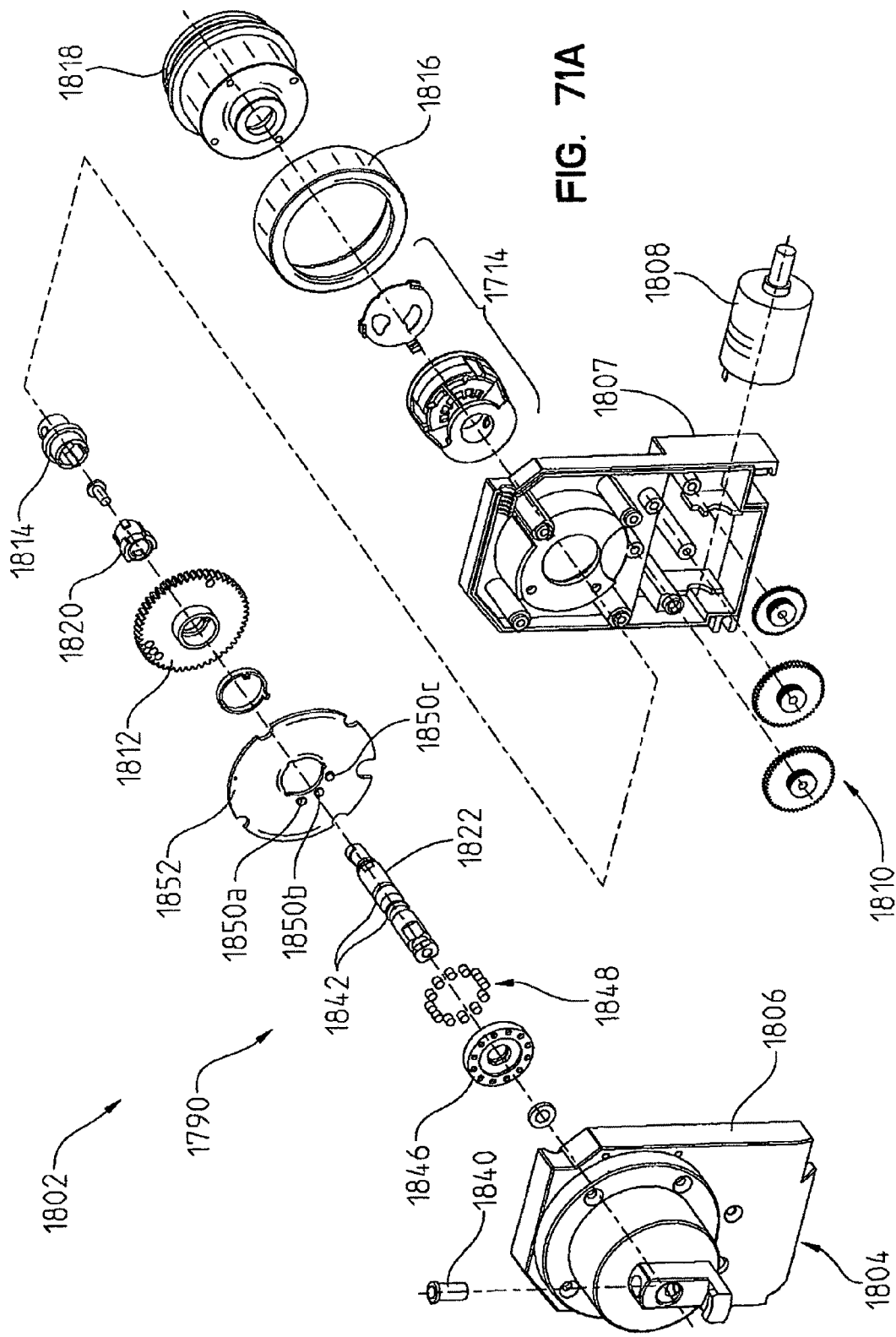
FIG. 71A is an exploded perspective view of a magnetic encoder gear assembly, including a manual override, of the control module of FIG. 67.
Figure 72:
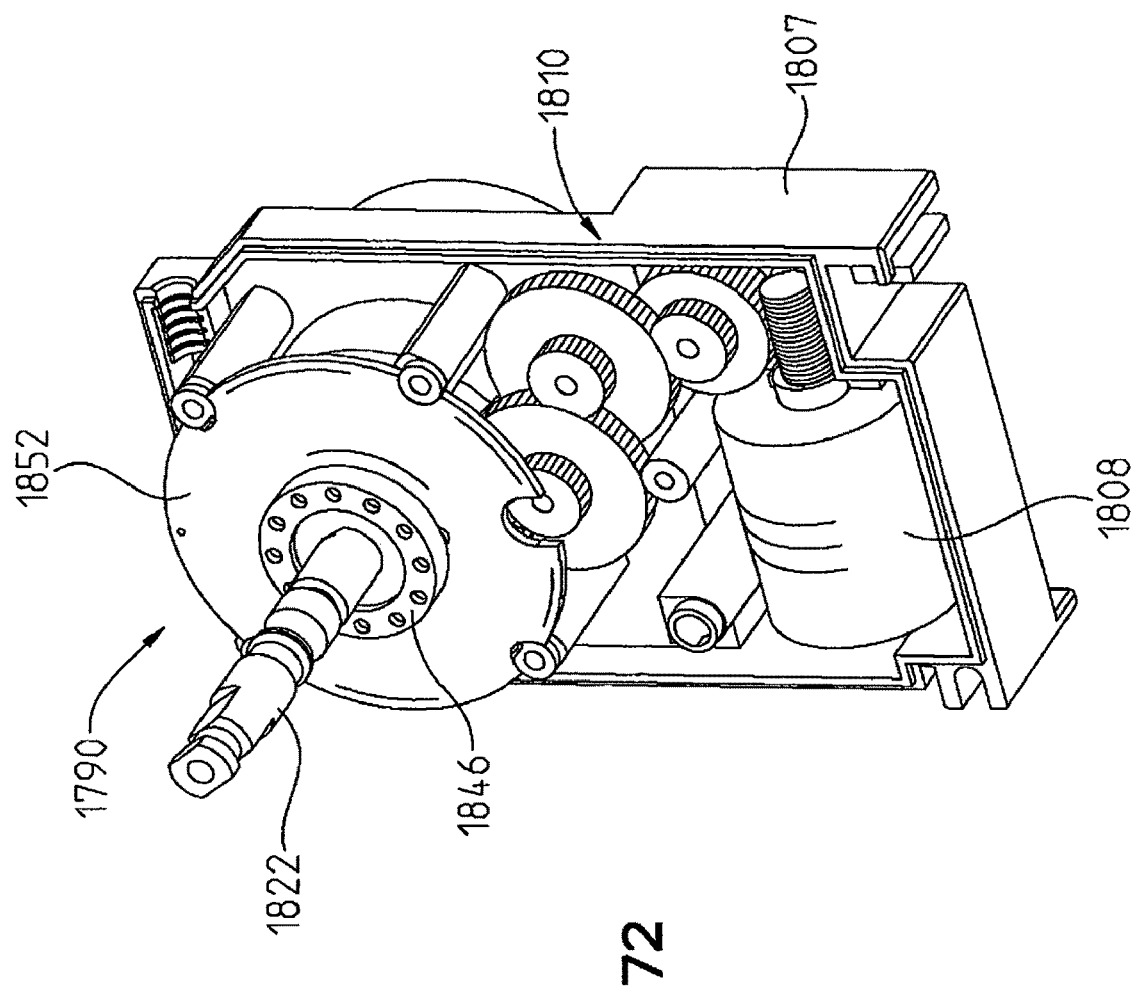
FIG. 72 is a perspective view of the magnetic encoder gear assembly of FIG. 71A.

With reference now to FIGS. 68, 71A, and 72, an illustrative embodiment manual valve override 1790 is coupled to magnetic encoder gear box 1802 and handle 1736 independent from other controls. The gear box 1802 includes a housing 1804 having a front portion 1806 coupled to a rear portion 1807. A motor 1808 is supported within the housing 1804 and is configured to drive a gear assembly 1810 including a drive gear 1812. Valve components, including a valve shaft or drive member 1814, a ring 1816, and a bushing 1818, are selectively coupled to the drive gear 1812. The valve shaft 1814 is coupled to the valve 1714 and is configured to rotate internal valve components to control the mixing of water from the supply lines 1710 and 1712.

Figure 71B:
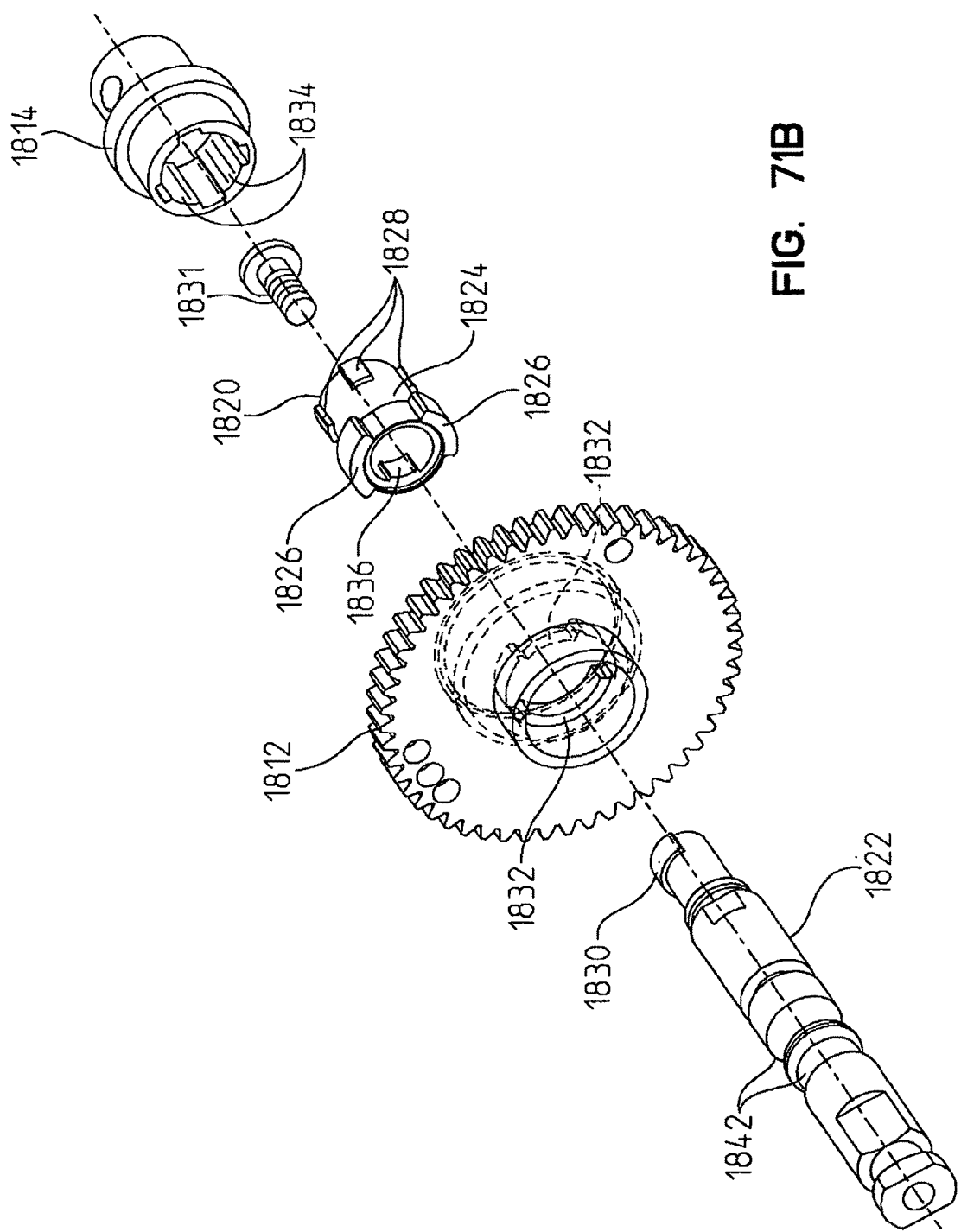
FIG. 71B is a detail exploded perspective view of FIG. 71A.
Figure 73:
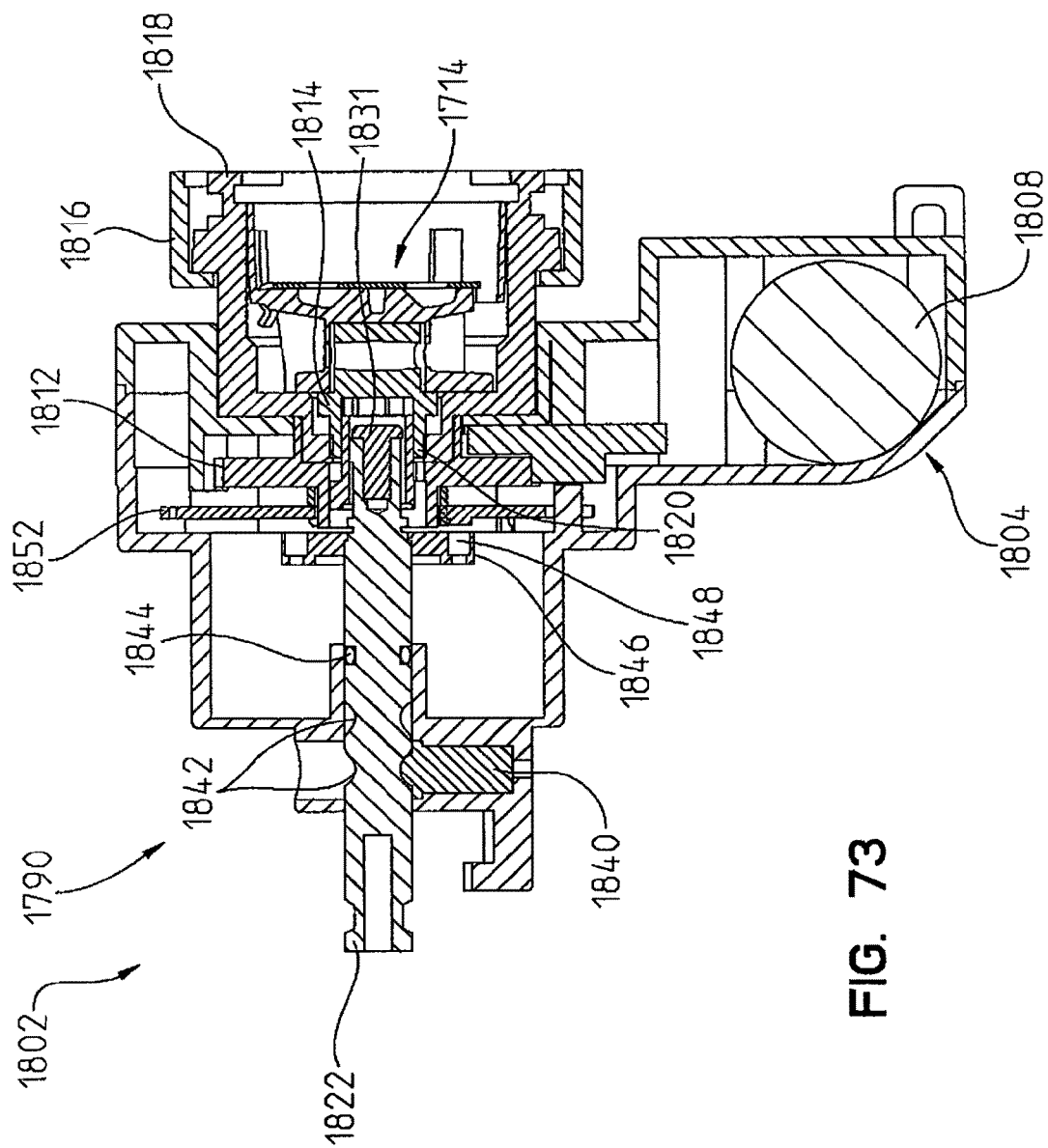
FIG. 73 is a cross-sectional view of the magnetic encoder gear assembly of FIG. 72, showing the system in an electronic or automatic mode of operation.
Figure 74:
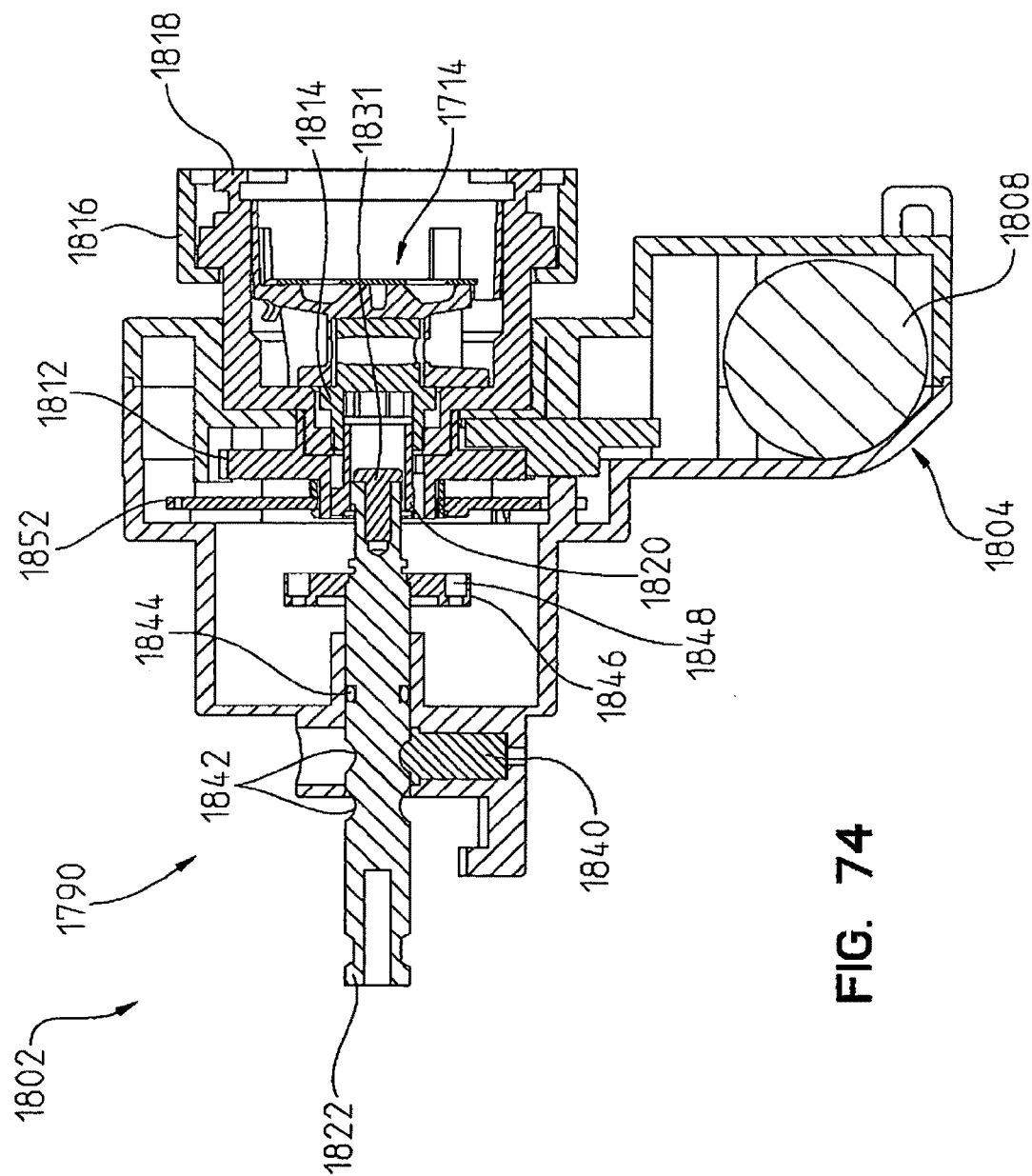
FIG. 74 is a cross-sectional view similar to FIG. 73, showing the system in a manual mode of operation.

With further reference to FIGS. 71A and 71B, a shuttle 1820 selectively couples the drive gear 1812 to the valve shaft 1814. The shuttle 1820 is operably coupled to a control shaft 1822 is movable therewith. FIG. 73 illustrates the shuttle 1820 in a first position rotationally coupled to the drive gear 1812, while FIG. 74 illustrates the shuttle 1820 in a second position uncoupled from the drive gear 1812 but rotationally coupled to the control shaft 1822. With reference now to FIG. 71B, the shuttle 1820 includes a cylindrical body 1824 having external end tabs 1826 and 1828 formed on the outer surface at opposing ends. The control shaft 1822 also includes an external tab 1830 extending radially outwardly at an inner end thereof. The tabs 1826 are configured to alternatively engage internal tabs 1832, supported by drive gear 1812, and the external tab 1830, supported by the control shaft 1822. An internal tab 1836 is also supported on the inner surface of the body 1824 and is configured to be axially engaged by an end fastener 1831 supported by the inner end of the control shaft 1822.

When the control shaft 1822 is in a first position (FIG. 73), the external tabs 1826 of the body 1824 cooperate with the internal tabs 1832 of the drive gear 1812 to rotatably couple the shuttle 1820 and the drive gear 1812. When the control shaft 1822 is in a second position (FIG. 74), axially moved away from the housing 1804, the external tabs 1826 of the shuttle 1820 uncouple from the tab of the drive gear 1812. However, in the second position, the external tab of the control shaft 1822 operably couple with the internal tabs 1836 of the shuttle 1820. As such, the control shaft 1822 is rotatably coupled with the shuttle 1820. In both the first and second positions, the external tabs 1828 of the body 1824 of the shuttle 1820 are rotatably coupled with the internal tabs 1834 of the valve shaft 1814.

A ball plunger 1840 is supported by the housing 1804 and is configured to be received within detents or annual grooves 1842 formed within the control shaft 1822. More particularly, the detents 1842 define the first and second positions of the control shaft 1822.

As noted above, the control shaft 1822 is supported by the housing 1804 for axial sliding movement. An o-ring 1844 is provided to seal between the control shaft 1822 and the housing 1804. A carrier 1846, illustratively formed of thermoplastic, is coupled to the control shaft 1822 for movement therewith. The carrier 1846 supports a plurality of magnets 1848 which are configured to cooperate with Hall-effect sensors 1850 supported by a circuit board 1852. The magnets 1848 in the carrier 1846 have alternating north and south poles. Illustratively, three (3) Hall-effect sensors 1850 are supported by the circuit board 1852. The lower two Hall-effect sensors 1850b, 1850c generate a 0,1,3,2 sequence when the control shaft 1822 is rotated clockwise, and generate a 0,2,3,1 sequence when the control shaft 1822 is rotated counterclockwise. Hall-effect sensor 1850a produces the opposite phase output from the bottom Hall-effect sensor 1850c, thus insuring that there is a signal at all positions of the control shaft 1822. When the shaft 1822 is pulled out for mechanical override, the magnets 1848 are far enough away from the Hall-effect sensors 1850 that no signal is detected. Based upon the signal detected, or not detected, the controller 1720 determines if the system is in a manual override mode.

Figure 69:
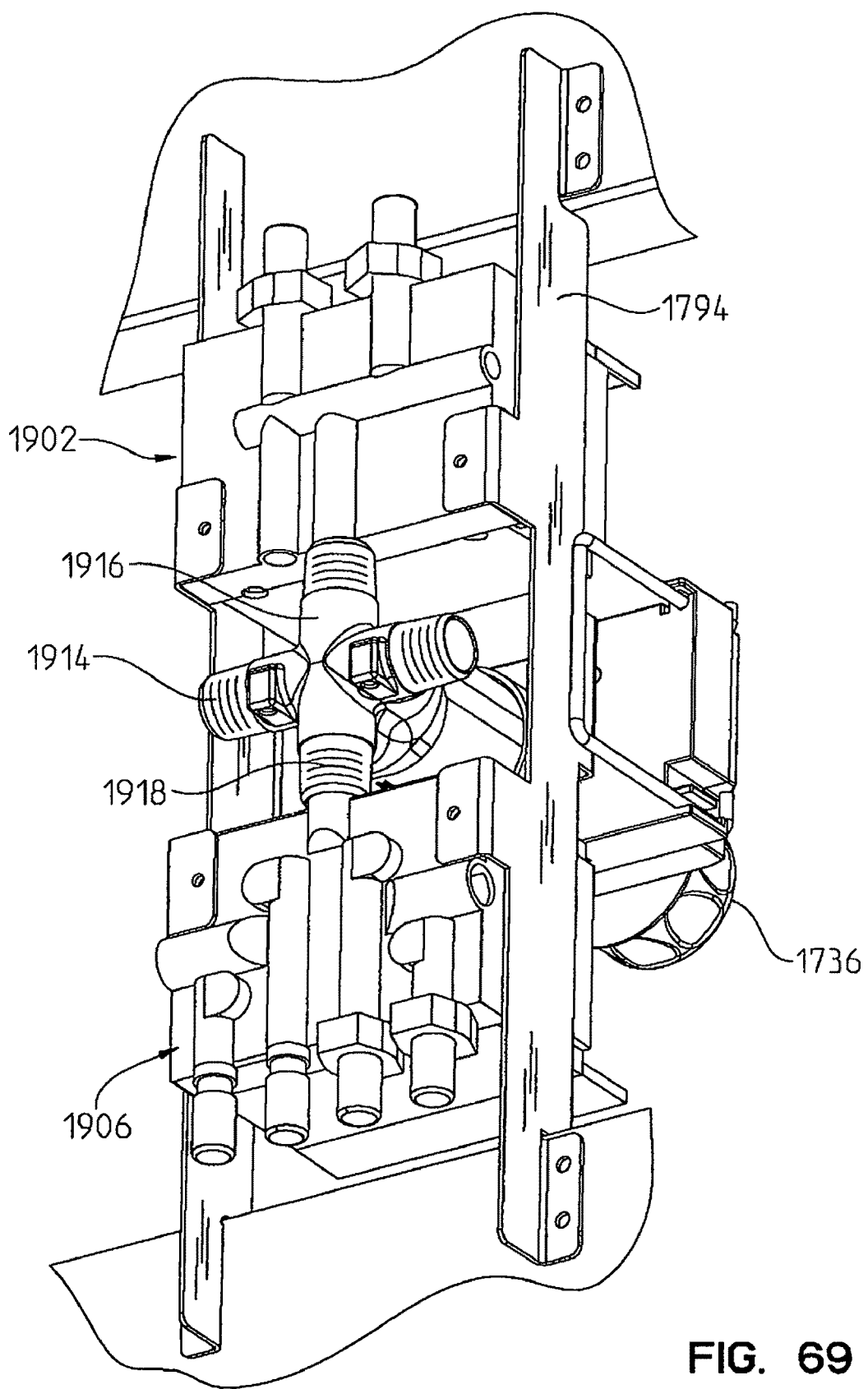
FIG. 69 is a rear perspective view of the control module of FIG. 67.
Figure 70:
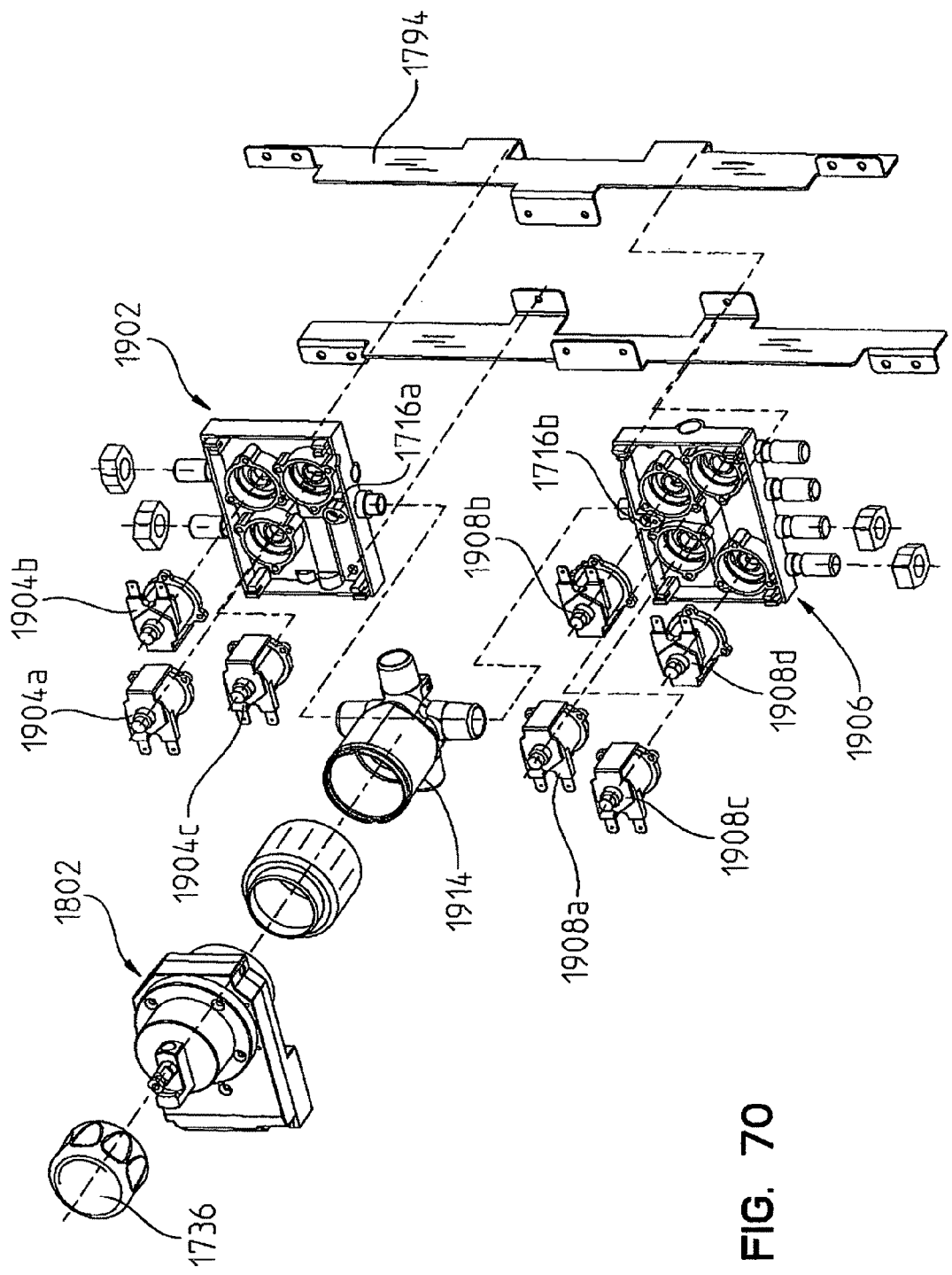
FIG. 70 is an exploded perspective view of the control module of FIG. 67.

With further reference to FIGS. 68-70, the valve bank assembly 1752 illustratively includes an upper manifold 1902 which is in fluid communication with the overhead shower 1704 and the hand shower 1702. A first electrically operable valve 1904a is configured to supply water to the overhead shower 1704, a second electrically operable valve 1904b is configured to supply water to the hand shower 1902, while a third electrically operable valve 1904c is configured to select between high and low water flows. When the valve 1904c is closed for low flow, the water is ported to the shower heads 1702 and 1704. The third valve 1904c is illustratively configured to open for high flow when the body sprays 1706 are active. During low flow, the valve 1904c directs water through a bypass duct having a restriction, such as a small diameter orifice, thereby reducing flow to the hand shower 1702 and the overhead shower 1704.

A lower manifold 1906 includes electrically operable valves 1908 configured to each selectively couple to one of four body sprays 1706. A releasable coupling, such as a bayonet coupling, illustratively secures each valve 1904, 1908 to one of the respective manifolds 1902, 1906. Illustratively, each electrically operable valve 1904, 1908 comprises a conventional solenoid (not shown) operably coupled to the controller 1720.

A first thermistor 1716a is operably coupled to the upper manifold 1902, while a second thermistor 1716b is operably coupled to the lower manifold 1906. More particularly, the first and second thermistors 1716a and 1716b are illustratively in thermal communication with water passing through the upper and lower manifolds 1902 and 1906, respectively. Illustratively, the first thermistor 1716a is the primary detector. However, if no water is flowing past the first thermistor 1716a, then the controller 1720 receives the temperature signal from the second thermistor 1716b.

Both the upper and lower manifolds 1902 and 1906 are configured to operably couple with a conventional valve housing 1914. Illustratively, the manifolds 1902 and 1906 are threadably coupled to upper and lower outlets 1916 and 1918 of the valve housing 1914. The valve housing 1914 may be of conventional design, and illustratively of the type disclosed in U.S. patent application Ser. No. 11/107,616, filed Apr. 15, 2005, titled "PLASTER GUARD FOR A WALL MOUNTED FAUCET VALVE ASSEMBLY", which is expressly incorporated by reference herein.

The manifolds 1902 and 1906 provide for flexibility in that manual diverters may be substituted for the solenoid valves. The manual diverters may be of the type known in the art as including valves which are manually actuated by control handles.

FIGS. 75-79 show an illustrative embodiment control module 1708' in various representative modes of operation. An illustrative user interface 1950 includes a front control panel 1951 supporting the display 1742, temperature control handle 1736, and massage control handle 1738. The temperature control handle 1736 is coupled to encoder 1730 as detailed herein. An ON/OFF button 1952 is provided to activate water flow. In other words, the button 1952 replaces the flow control handle 1734 and encoder 1728 of FIGS. 61A and 61B. A low flow button 1953 is provided to reduce the rate water flow, illustratively by activating solenoid valve 1904c such that water is diverted through a flow reducing restriction prior to being discharged to the hand shower 1702 or overhead shower 1704.

Figure 75:
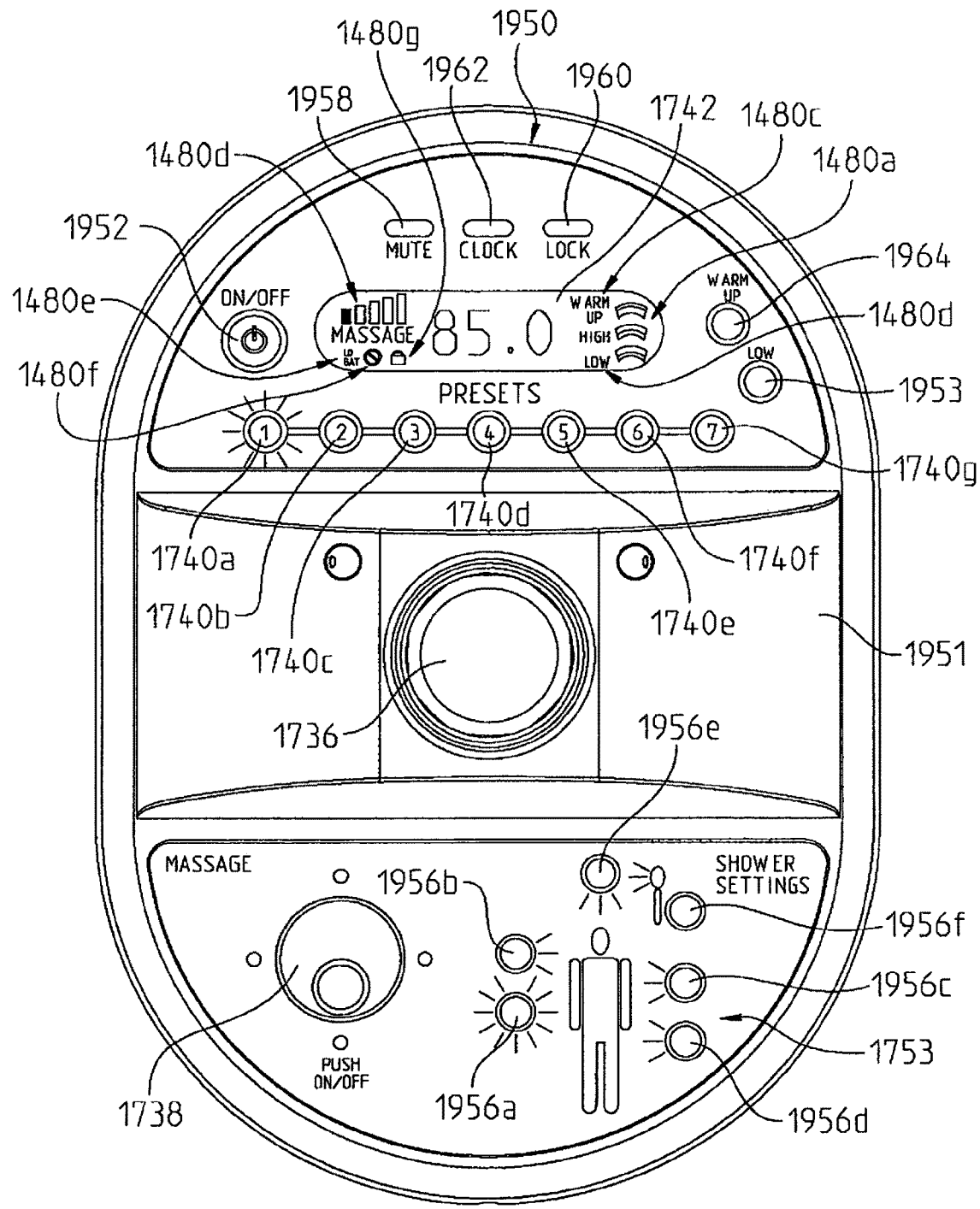
FIG. 75 is a front elevational view of an illustrative embodiment user interface for use with the control module of FIG. 66, showing the user interface in a first preset mode of operation.

With further reference to FIG. 75, each time one of the controls of the user interface 1950 is activated by a user, an audible acknowledgement may be provided. Furthermore, upon activation of the system, a tone may be provided and the lights may illuminate in a predetermined pattern to verify proper operation of the system. A mute button 1958 is disposed adjacent the display to deactivate the audible signals as desired by the user. A lock button 1960 is also provided adjacent the display for locking out or deactivating some or all of the controls, particularly the push buttons 1740, 1956 to prevent inadvertent activation during cleaning.

A clock button 1962 is provided in user interface 1950 and when successively depressed toggles the display 1742 between showing temperature and time. In other words, the clock button 1962 alternates input for the display 1742 between the temperature sensor 1716 and the clock 1786.

A warm-up button 1964 is configured to provide for automatic shower operation in order to obtain a predetermined water temperature. More particularly, upon depressing warm-up button 1964, the controller 1720 causes the valve 1714 to activate such that water flows to the valve bank 1752. Once the thermistor 1716 measures the predetermined temperature, the controller 1720 may deactivate the valve 1714 thereby stopping water flow. Alternatively, or in addition thereto, the controller 1720 may activate the enunciator 1744 thereby providing an audible signal to the user when the predetermined temperature is reached.

Desired temperature, shower/spray, flow, and massage settings are illustratively stored in individual preset buttons 1740. In operation, once a user has established the desired shower settings through controls 1736, 1956, 1953, and 1732, he depresses one of the preset buttons 1740 for a predetermined time period (e.g., 2 seconds). The shower settings are then stored in memory associated with the controller 1720 and available for recall by momentarily pressing the associated preset button 1740a-1740g. More particularly, each shower setting stored in memory by a user defines an arrangement or pattern of active water outlets (i.e. hand shower 1702, overhead shower 1704, and body sprays 1706), and a set temperature of water discharged from the active body sprays 1706.

The display 1742 is substantially identical to display 1418 detailed above in connection with FIG. 41B. As such, similar components are identified with like reference numbers.

FIG. 75 shows the user interface with a first preset button 1740a depressed and therefore illuminated. The display 1742 shows a first massage mode and a set temperature of 85.0° F. Additional buttons in the form of shower setting buttons 1956 are provided, wherein button 1956a is illuminated, thereby indicating that a single body spray 1706a is active.

Figure 76:
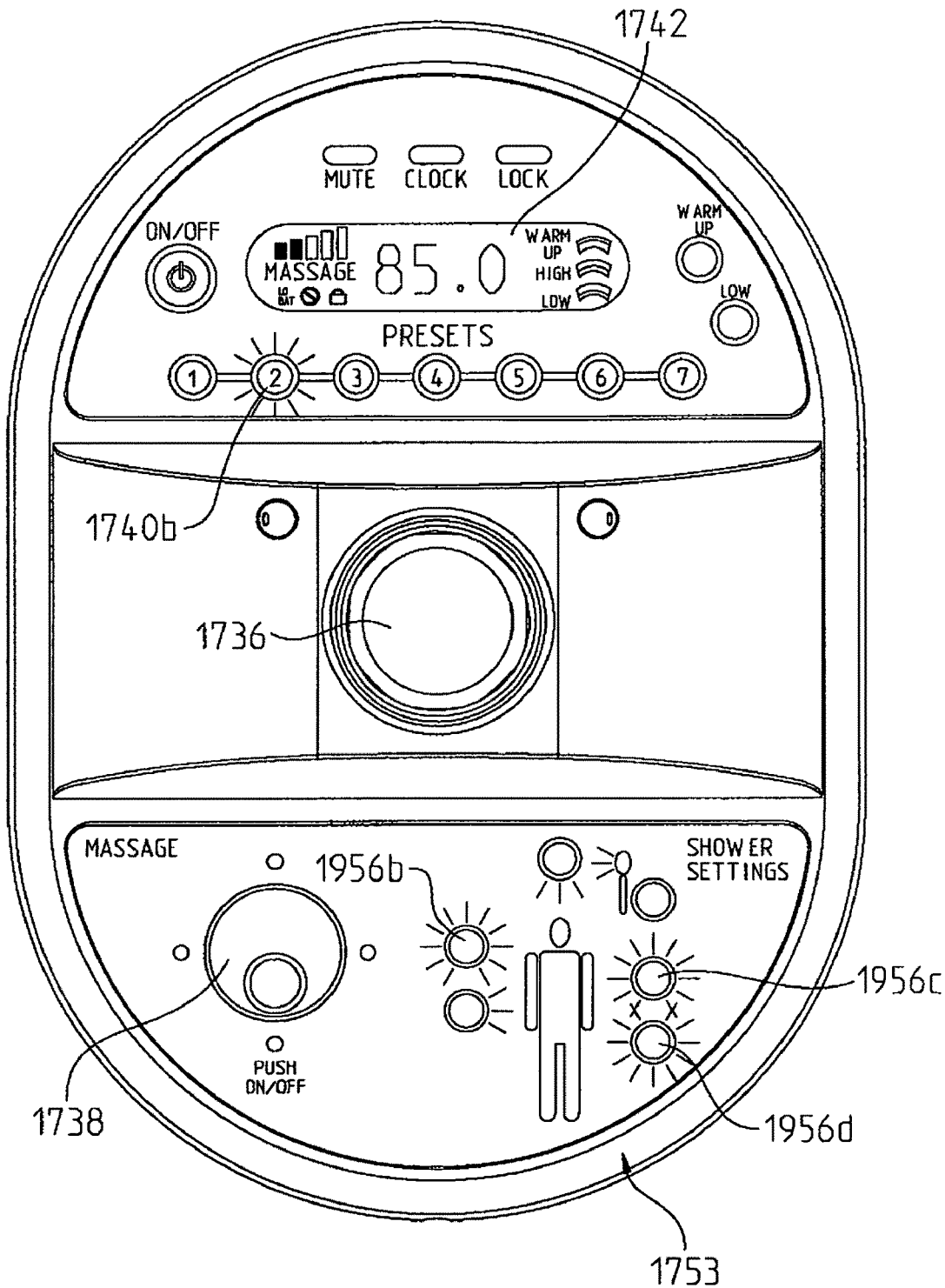
FIG. 76 is a front elevational view of the user interface of FIG. 75 in a second preset mode of operation.

FIG. 76 shows the user interface with a second preset button 1740b depressed and therefore illuminated. The display 1742 shows a second massage mode and a set temperature of 85.0° F. The shower setting portion 1954 shows buttons 1956b, 1956c, and 1956d illuminated, thereby indicating that body sprays 1906b, 1906c, and 1906d are active.

Figure 77:
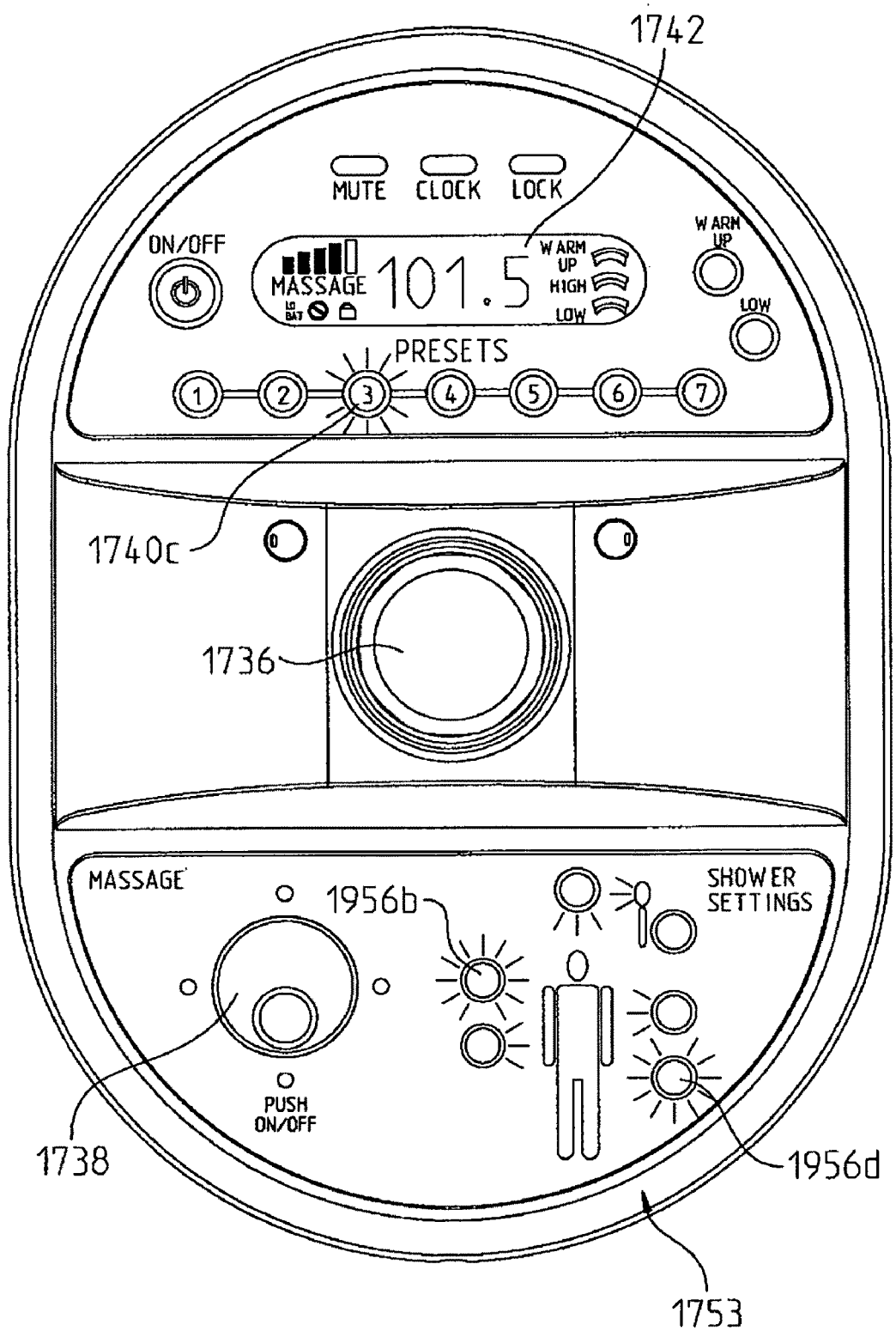
FIG. 77 is a front elevational view of the user interface of FIG. 75 in a third preset mode of operation.

FIG. 77 shows the user interface with a third preset button 1740c depressed and therefore illuminated. The display 1742 shows a fourth massage mode and a set temperature of 101.5° F. The shower setting portion 1954 shows buttons 1956b and 1956d illuminated, thereby indicating that body sprays 1906b and 1906d are active.

Figure 78:
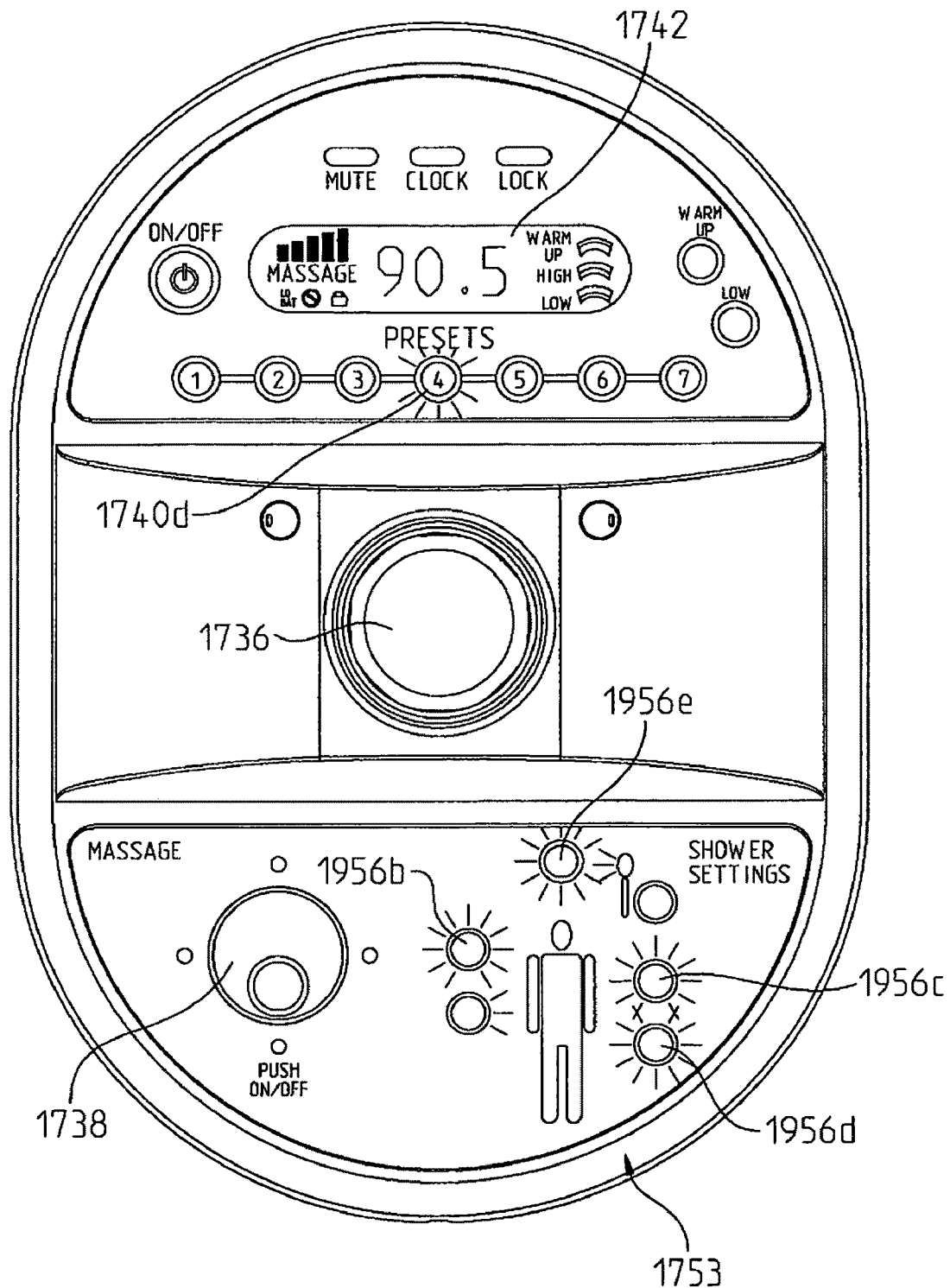
FIG. 78 is a front elevational view of the user interface of FIG. 75 in a fourth preset mode of operation.

FIG. 78 shows the user interface with a fourth preset button 1740d depressed and therefore illuminated. The display 1742 shows a fifth massage mode and a set temperature of 90.5° F. The shower setting portion 1954 shows buttons 1956b,

1956*c*, 1956*d*, and 1956*e* illuminated, thereby indicating that body sprays 1706*b*, 1706*c*, 1706*d*, and overhead shower 1704 are active.

Figure 79:
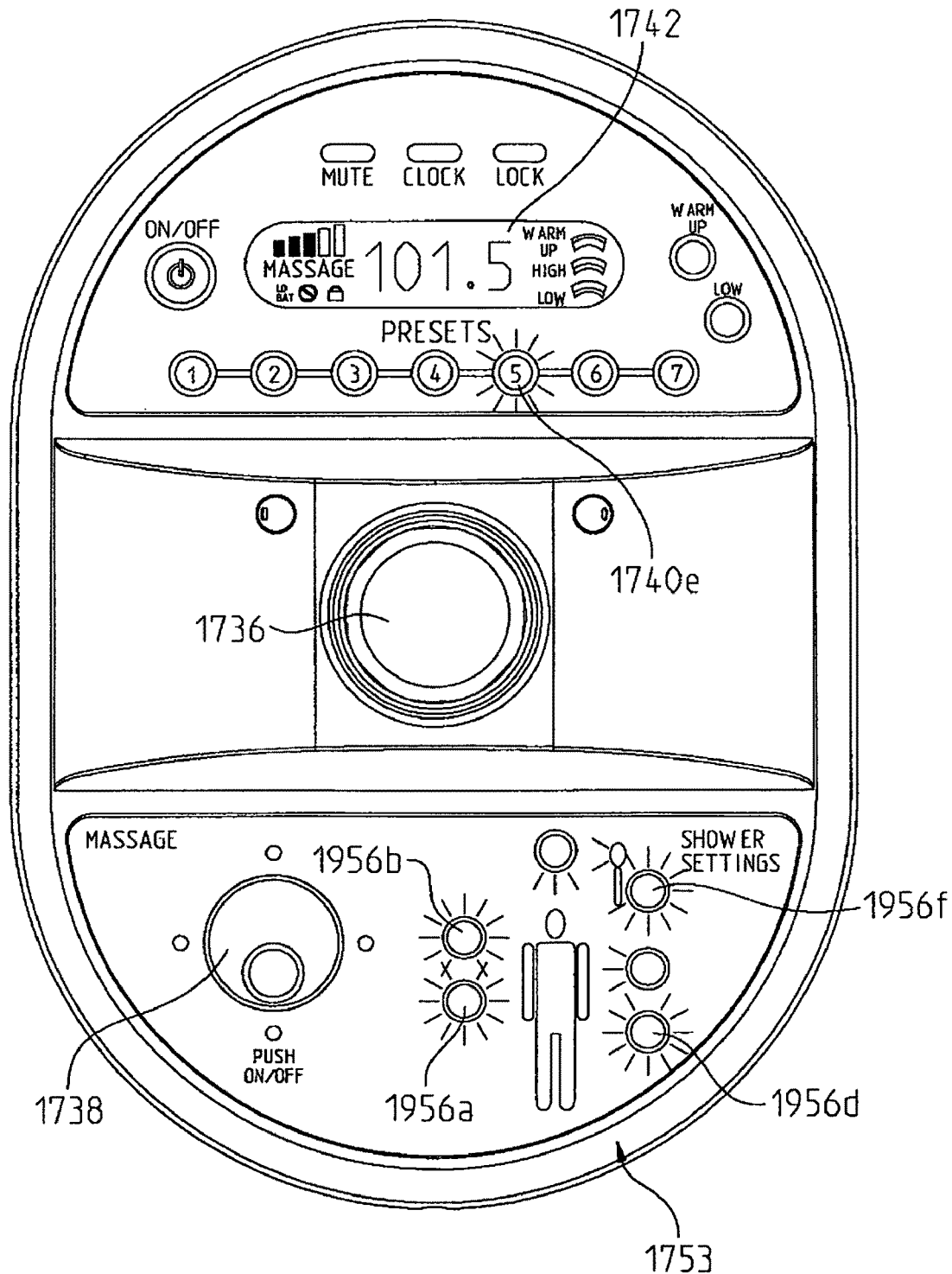
FIG. 79 is a front elevational view of the user interface of FIG. 75 in a fifth preset mode of operation.

FIG. 79 shows the user interface with a fifth preset button 1740*e* depressed and therefore illuminated. The display 1742 shows a third massage mode and a set temperature of 101.5° F. Buttons 1956*a*, 1956*b*, 1956*d*, and 1956*f* are illuminated, thereby indicating that body sprays 1706*a*, 1706*b*, 1706*d*, and hand shower 1702 are active.

During the installation of the control module 1708', an initialization process is implemented to properly map each button 1956*a*-1956*f* to a proper corresponding solenoid valve 1904*a*-1904*f* and, hence, body spray 1706*a*-1706*d*, overhead shower 1704, or hand shower 1702. During the initialization process, the controller 1720 activates the solenoid valves 1904*a*-1904*f* sequentially such that one of the body sprays 1706*a*-1706*d*, overhead shower 1704, and hand shower 1702 is active. The installer then presses a corresponding push button 1956*a*-1956*f*, whereby the controller 1720 associates the active valve 1904*a*-1904*f* with the depressed push button 1956*a*-1956*f*.

Figure 80:
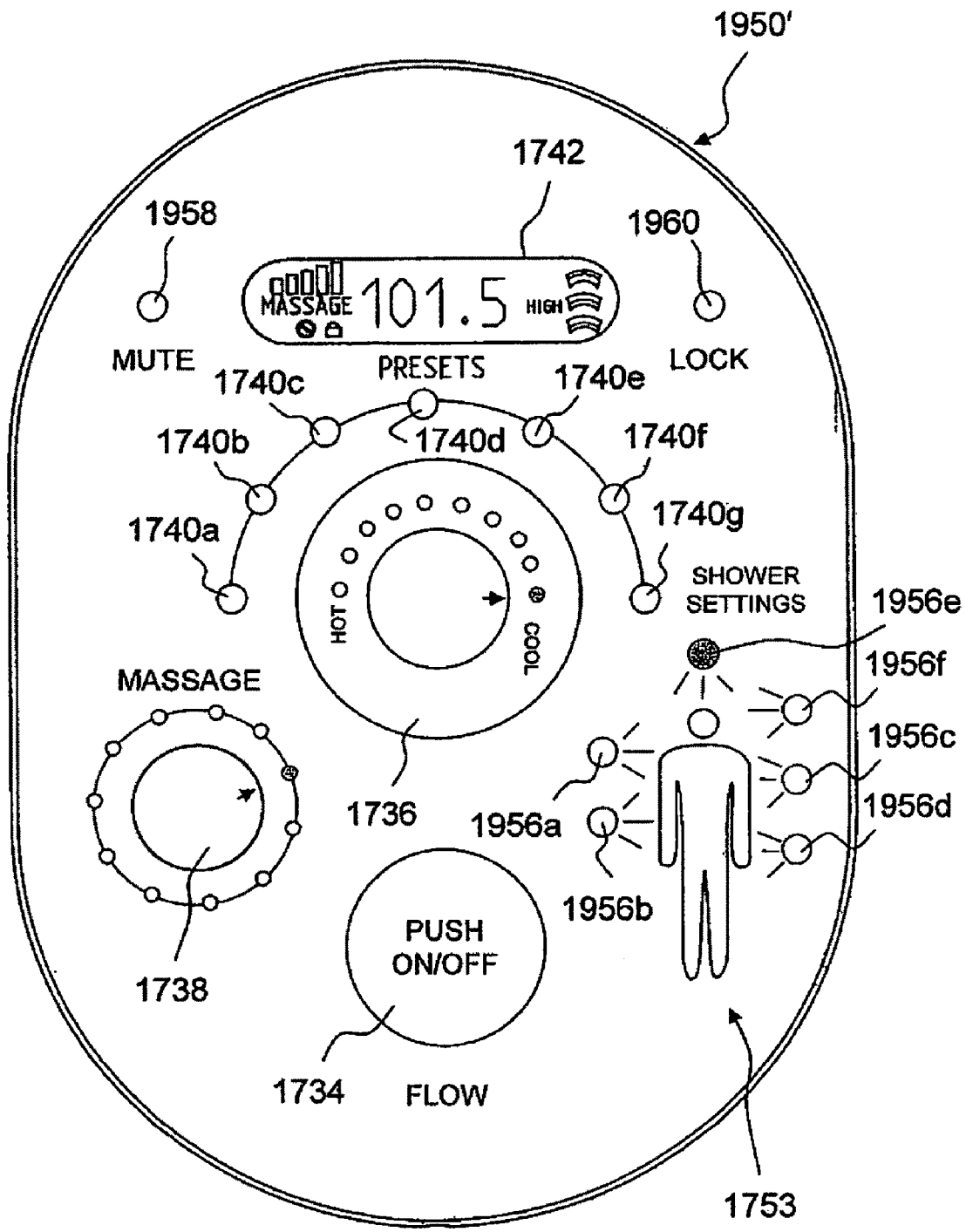
FIG. 80 is a front elevational view of a further illustrative embodiment user interface.

FIG. 80 shows a further illustrative embodiment user interface 1950' configured for use with the control module 1708'. The user interface includes a control panel supporting the display 1742, flow control handle 1734, temperature control handle 1736, and massage control handle 1738. The interface also includes a shower settings portion 1753 including a plurality of push buttons 1956. Pushing of the buttons 1956 toggles between on and off flow to the various sprayheads 1706, overhead shower 1704, and hand shower 1702. Each button 1956 may be illuminated to indicate that the respective fluid device is active. The manual override handle is accessible in the center portion of the interface through temperature control handle 1736, and may be activated in the manner detailed herein. A plurality of preset buttons 1740 are positioned in an arcuate path around a portion of the temperature control handle 1736.

Figure 81A:
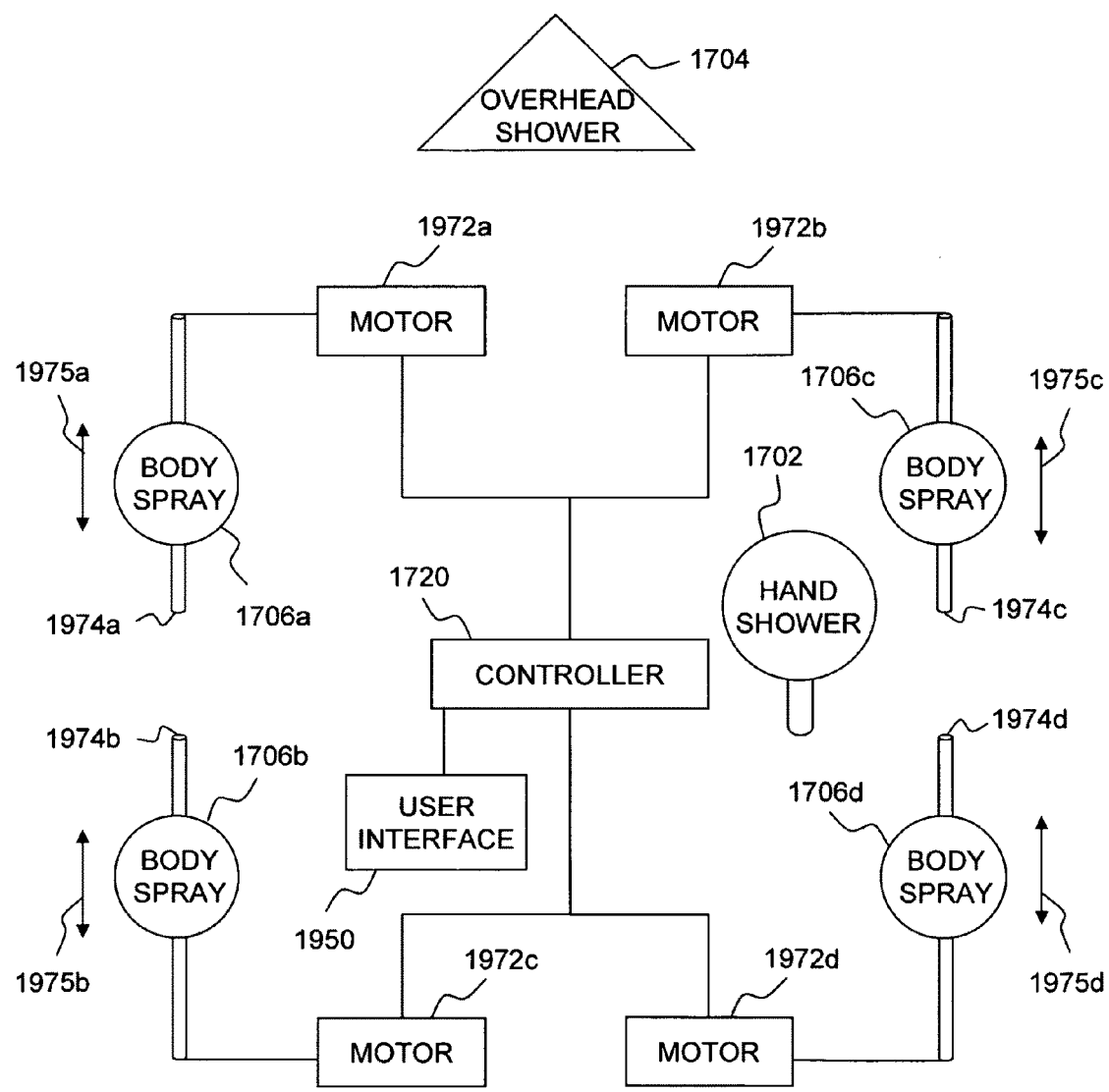
FIG. 81A is a partial schematic view of a further illustrative embodiment custom shower system.
Figure 82:
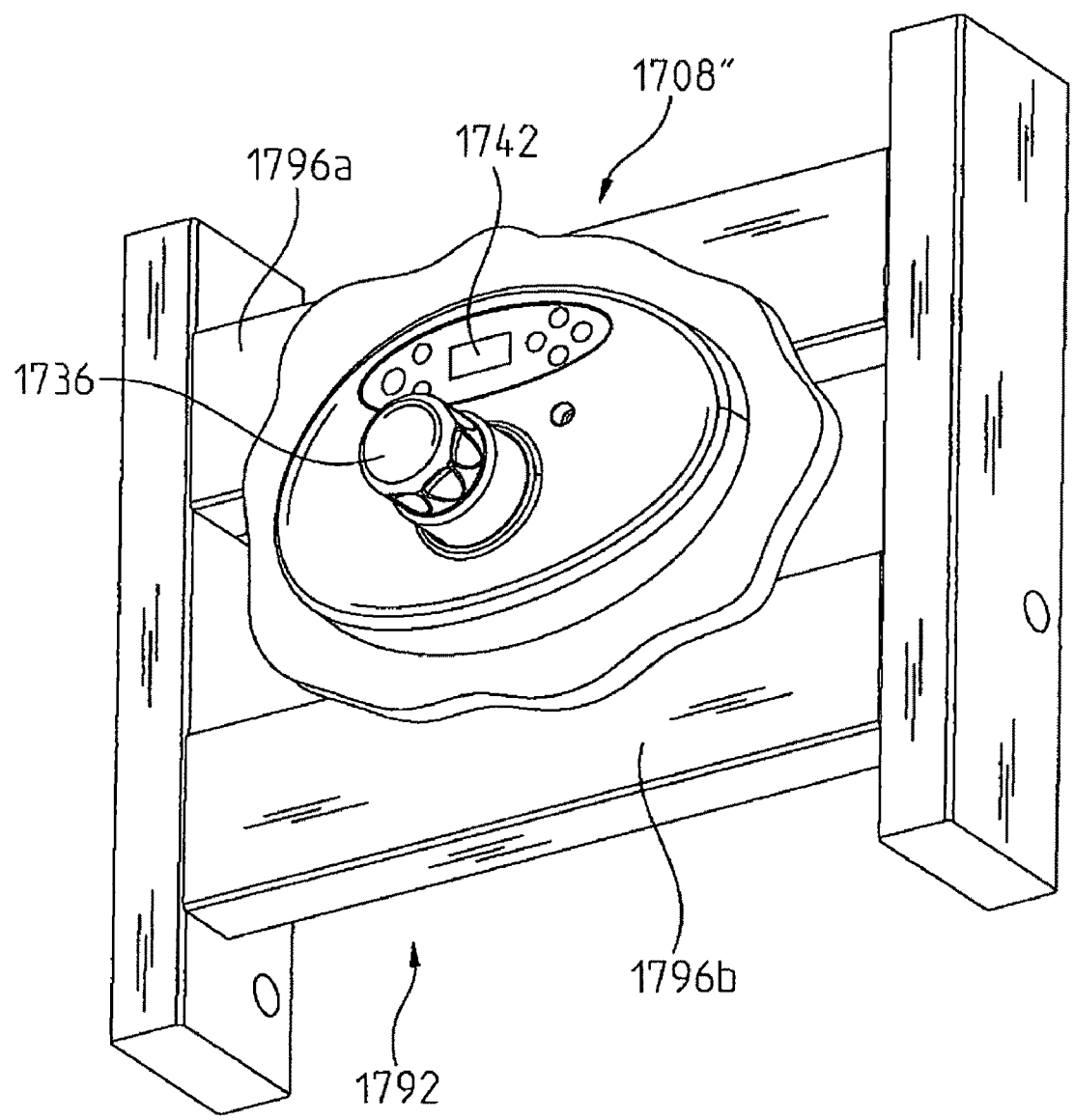
FIG. 82 is a perspective view of a further illustrative embodiment shower control module mounted within a wall.

With reference now to FIGS. 81A and 81B, a plurality of actuators 1972*a*, 1972*b*, 1972*c*, and 1972*d* may be operably coupled to the body sprays 1706*a*, 1706*b*, 1706*c*, 1706*d*, respectively. The actuators 1972 illustratively comprise one or more direct current (DC) motors in communication with the controller 1720. While DC motors are shown in the illustrative embodiment, it should be appreciated that other actuators may be substituted therefor, including solenoids, stepper motors and other rotational actuators. In the illustrative embodiment of FIG. 81A, the actuators 1972*a*, 1972*b*, 1972*c*, and 1972*d* are configured to rotate respective drive rods 1974*a*, 1974*b*, 1974*c*, and 1974*d*, illustratively jack screws. A conventional coupling, such as a worm gear arrangement (not shown), may couple the actuators 1972 to the drive rods 1974. A lifting nut (not shown) may couple the body sprays 1706 to the drive rods 1974. As such, the body sprays 1706*a*, 1706*b*, 1760*c*, and 1760*d* may be driven in translational vertical movement along the rotating rods 1974*a*, 1974*b*, 1974*c*, and 1974*d*, as represented by arrows 1975*a*, 1975*b*, 1975*c*, and 1975*d*. In other words, the controller 1720 may adjust the relative vertical positions of the body sprays 1706*a*, 1706*b*, 1706*c*, and 1706*d*. In further illustrative embodiments, the body sprays 1706 may be driven in motion by other conventional couplings, such as a rack and pinion assembly (not shown).

In the illustrative embodiment of FIG. 81B, the actuators 1972*a*, 1972*b*, 1972*c*, and 1972*d* may be configured to rotate the body sprays 1706*a*, 1706*b*, 1706*c*, and 1706*d*, respectively. More particularly, each body spray 1706 is illustratively configured to be supported by a coupling (not shown) providing for rotation about a horizontal, x-axis 1976 and a vertical, y-axis 1978 (represented in FIG. 81B by reference members 1980 and 1982, respectively). These two degrees of freedom permit the respective actuator 1972 to adjust the relative orientation of the body spray 1706 and the water discharged therefrom. In certain illustrative embodiments, movement of the body sprays 1706 may be limited to rotation 1980 about only the x-axis 1976 (to provide vertical adjustment of the water discharged) or to rotation 1982 about the y-axis 1978 (to provide horizontal adjustment of the water discharged). In a further illustrative embodiment, the translational movement shown in FIG. 81A may be combined with the rotational movement shown in FIG. 81B, thereby providing three degrees of freedom to the body sprays 1706 (one translational, two rotational).

In both embodiments of FIGS. 81A and 81B, the user interface 1950 may include controls, such as push buttons 1740 (FIGS. 75-80), for manipulation by a user for instructing the controller 1720 to activate respective actuators 1972 for adjusting the positions of the body sprays 1706 as desired. In other words, the user may customize the desired arrangement of active body sprays 1706 (i.e. spray pattern) based upon personal preferences, often based on the user's size and physical characteristics. The position of the body sprays 1706 as set by the actuators 1972 may also be stored in the memory associated with the controller 1720 as part of the shower settings corresponding to the preset buttons 1740. More particularly, once defined by the user, the desired shower setting may be recalled by pressing the associated preset button 1740 in the manner further detailed herein. As such, different users may have customized shower settings including active shower outlets (e.g. overhead shower 1704 and body sprays 1706), orientation of body sprays 1706 as determined by the actuators 1972, massage (pulse) mode, and water temperature.

With reference now to FIGS. 82-85, a further illustrative embodiment shower control module 1708" is shown for use with the shower module 1700', detailed above as not including body sprays 1706. Similar components of control modules 1708' and 1708" are identified with like reference numbers. As with the module 1708', the module 1708" is secured to cross members 1796 of a shower wall 1792 through a mounting bracket 1794 (FIGS. 83A and 83B). The gear box assembly 1802 may also be substantially the same as that detailed above.

Figure 83A:
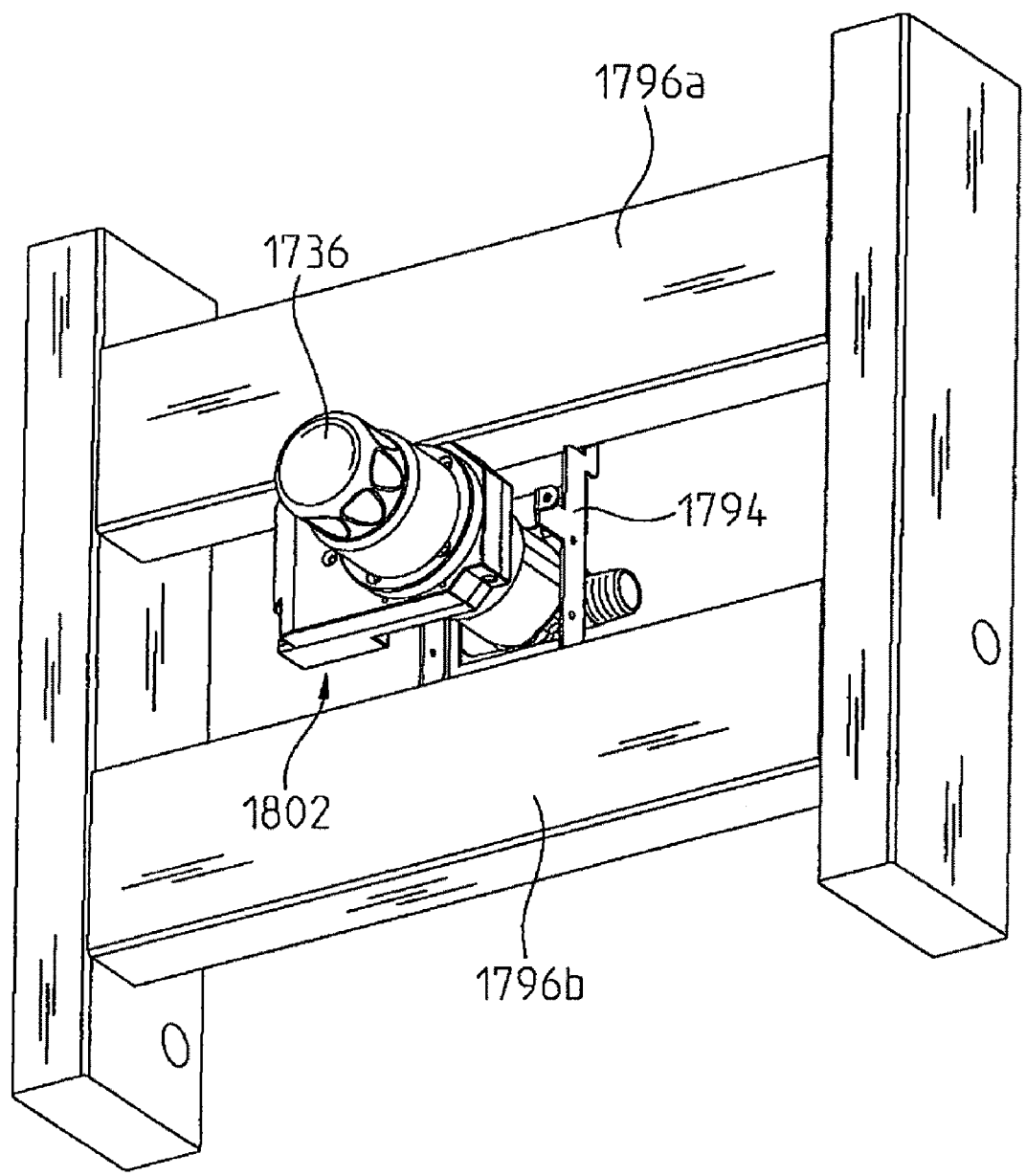
FIG. 83A is a front perspective view similar to FIG. 82, with the user interface plate and outer wall removed.
Figure 83B:
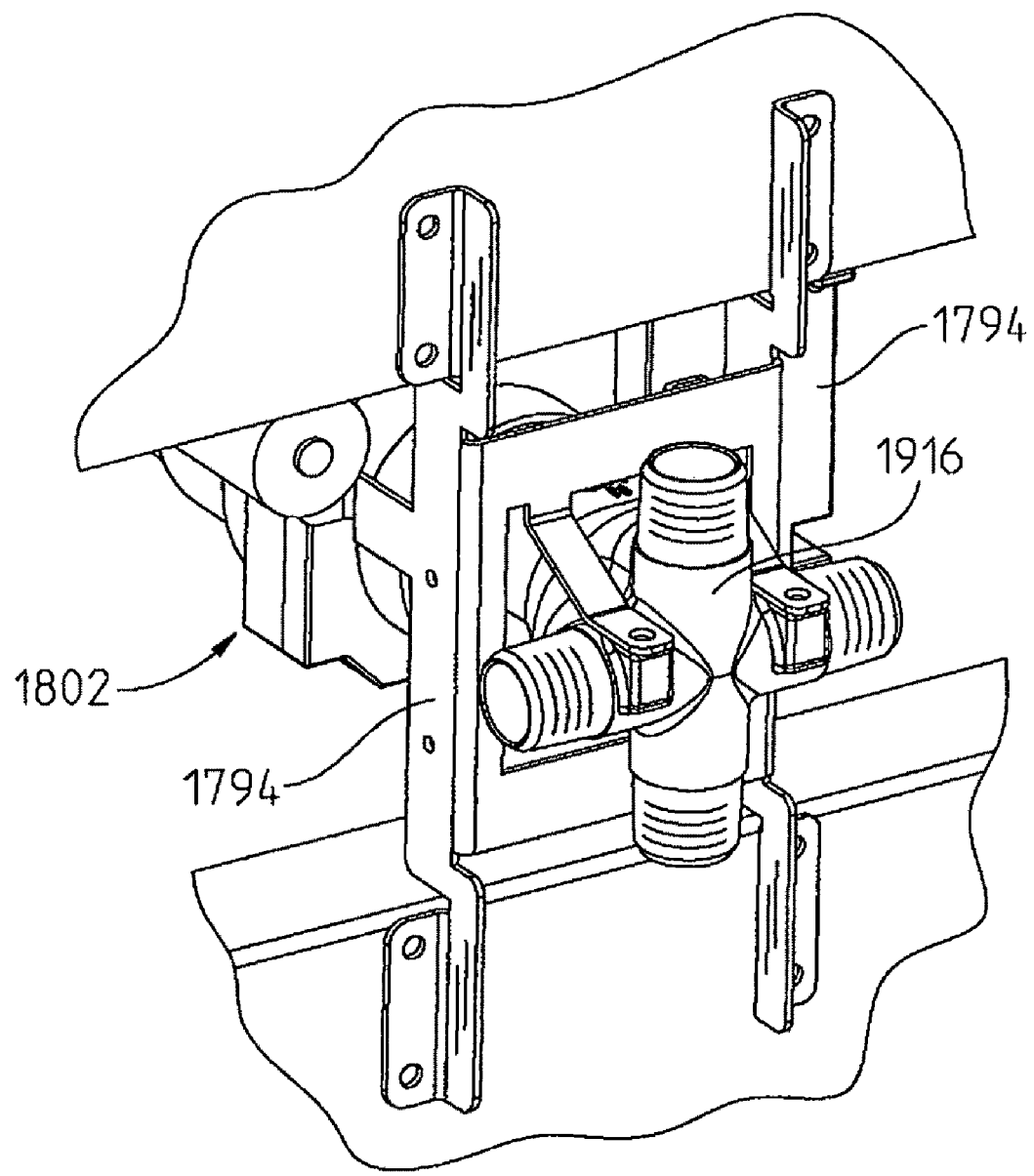
FIG. 83B is a rear perspective view of the control module of FIG. 82.
Figure 84:
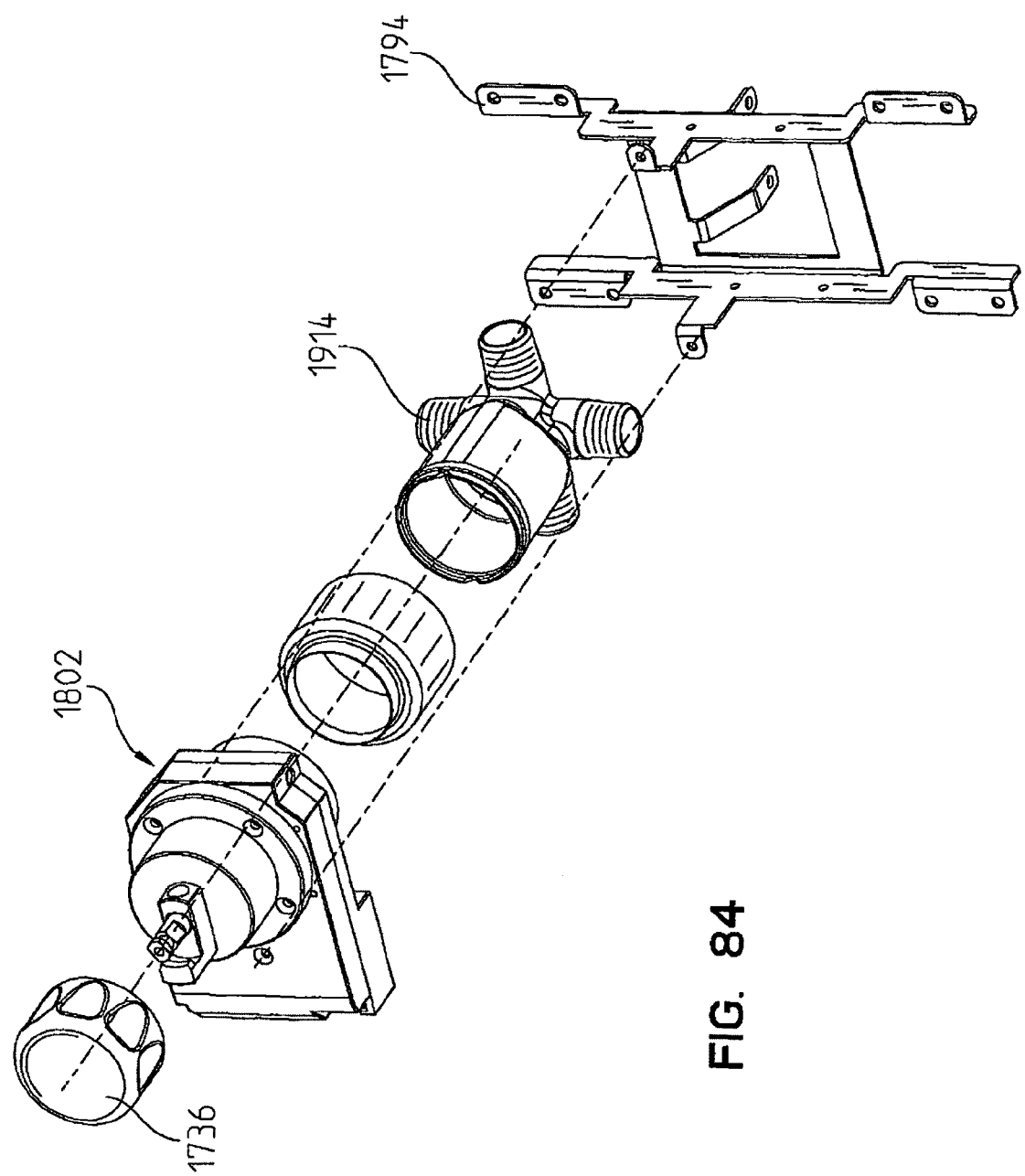
FIG. 84 is an exploded perspective view of the control module of FIG. 82.

As shown in FIG. 83B, the control module 1708' does not include solenoid valve bank 1752. A diverter valve, such as manual diverter 1758, may be included if a hand shower 1702 is added to the overhead shower 1704.

Figure 85:
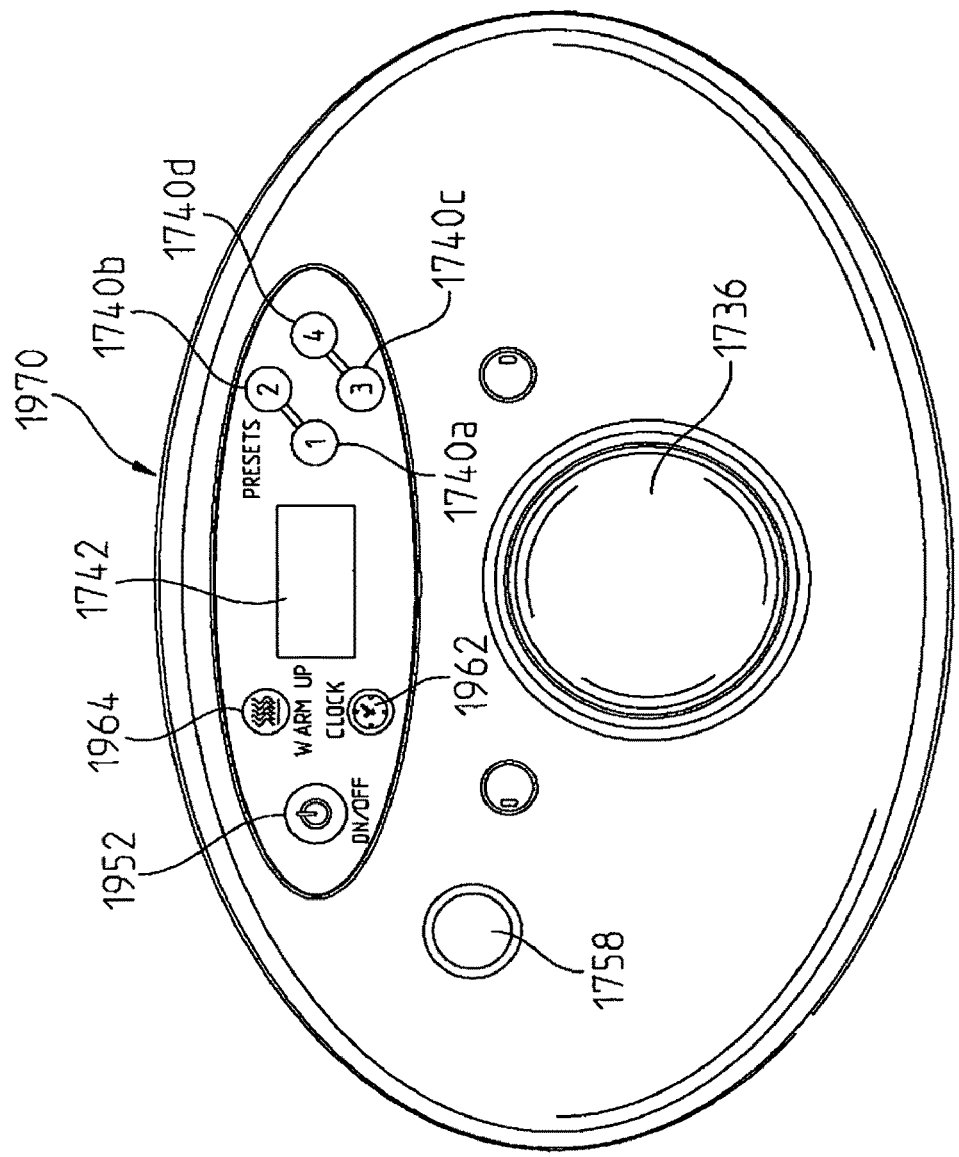
FIG. 85 is a front elevational view of an illustrative embodiment user interface for use with the control module of FIG. 82.
Figure 88:
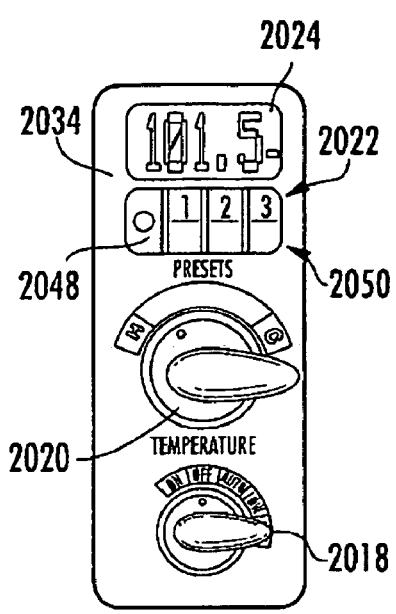
FIG. 88 is a front plan view of an illustrative embodiment user interface for use with the tub/shower control module of FIG. 87.
Figure 87:
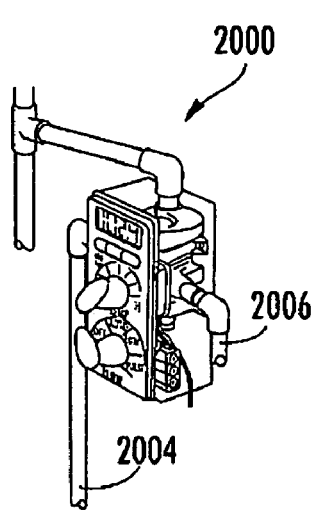
FIG. 87 is a perspective view of an illustrative embodiment control module of the tub/shower system of FIG. 86.
Figure 86:
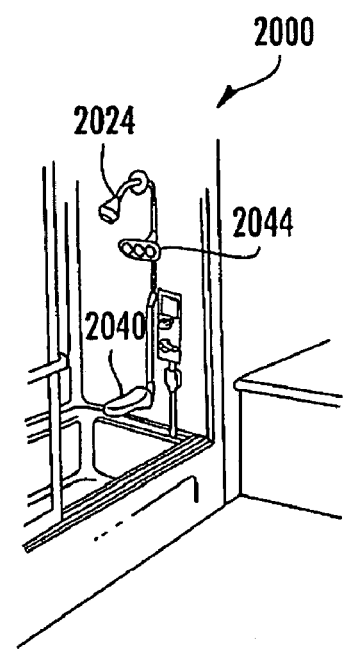
FIG. 86 is a perspective view of an illustrative embodiment tub/shower system.
Figure 89:
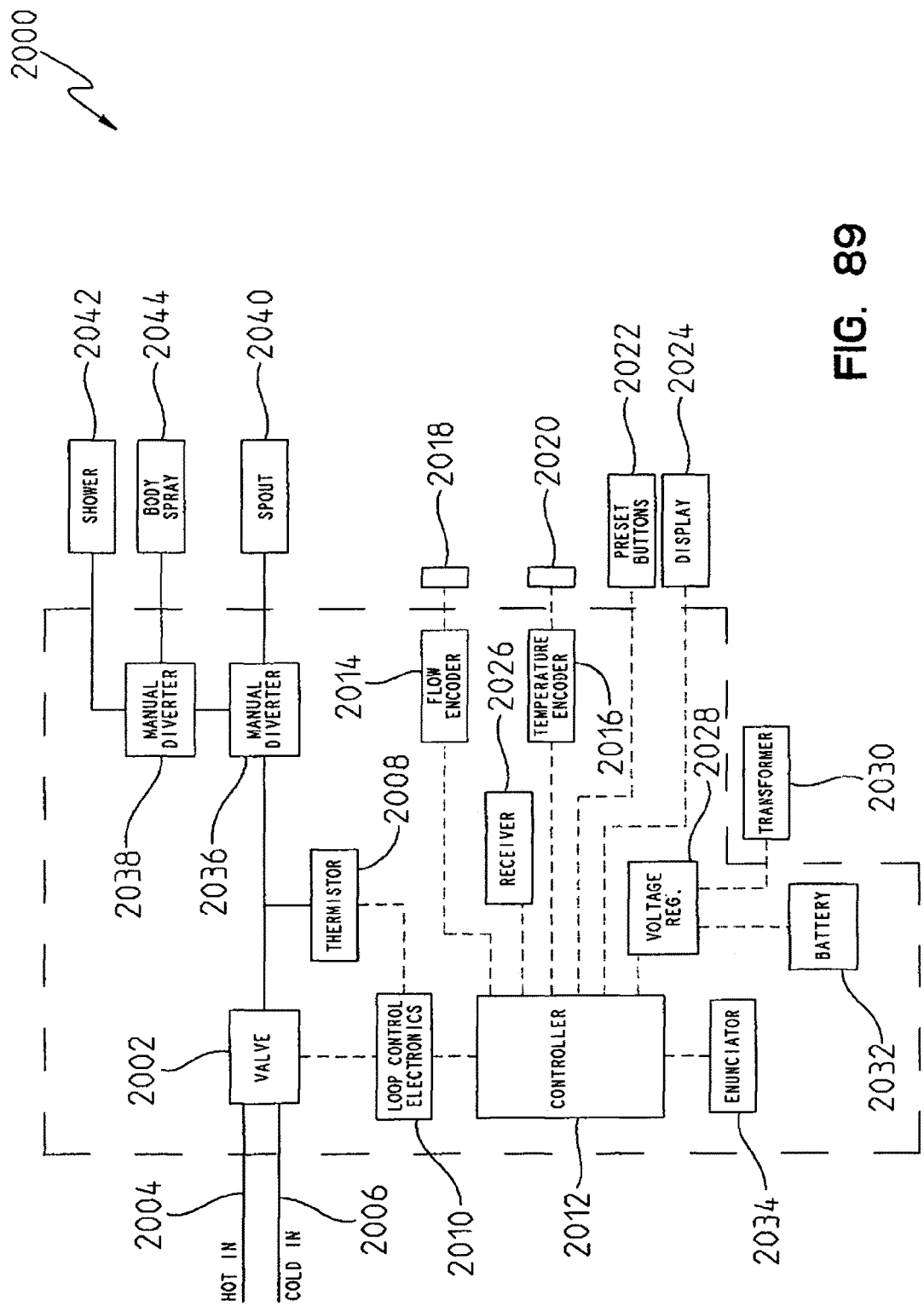
FIG. 89 is a schematic view of an illustrative embodiment tub shower system.

The user interface 1970 of FIG. 85 includes several of the same elements of the user interface 1950 of FIG. 75. As such, similar components are identified with like reference numbers. The handle for the manual diverter 1758 may be supported within the user interface 1970. It should be noted that certain preset buttons 1740 may be used to establish predetermined tub fill levels should the control module 1708' be used for a tub shower system.

Turning now to FIGS. 86-89, an illustrative embodiment tub shower module 2000 is shown. The tub shower module 2000 illustratively includes a combination of various components from the roman tub module 1400 and the custom shower module 1700 detailed above. The tub shower module 2000 includes a motorized valve 2002 in fluid communication with a hot water inlet 2004 and a cold water inlet 2006. A thermistor 2008 is in thermal communication with a mixed water outlet of the valve 2002 and is configured to detect the temperature of water exiting the valve 2002. The thermistor

2008 transmits a signal indicative of the mixed water temperature to loop control electronics 2010. The loop control electronics 2010 are in electrical communication with a controller 2012, which together control operation of the motorized valve 2002. A flow encoder 2014 and a temperature encoder 2016 are in electrical communication with the controller 2012 and are operably coupled to flow control and temperature control handles 2018 and 2020, respectively. A plurality of preset buttons 2022 and a display 2024 are also illustratively in communication with the controller 2012. A receiver 2026 is in communication with the controller 2012 and may receive signals from a remote control module, such as module 1724 detailed above.

The controller 2012 is configured to receive power from a voltage regulator 2028 in electrical communication with a transformer 2030. The transformer 2030 may be electrically coupled to a conventional power supply, such as 120 VAC. A battery 2032 may also be provided for backup power. An enunciator 2034 is in communication with the controller 2012 and is configured to provide an audible signal in response to operation of the controller 2012.

The outlet of the valve 2002 is in fluid communication with a first manual diverter valve 2036 which directs water flow to either a second manual diverter valve 2038 or a tub spout 2040. The second manual diverter valve 2038 is configured to direct water flow to either an overhead shower 2042 or a body spray 2044.

The display 2024 provides feedback on temperature, flow, tub fill, shower, and battery life settings. Memory preset buttons (1,2, and 3) 2022 are provided for storing desired temperature and flow settings. In one illustrative embodiment, the preset buttons 2022 operate such that a user can store his or her desired temperature and flow setting by pressing and holding a numbered preset button 2022 for a predetermined time period, illustratively 2 seconds. The stored preset may then be recalled by quickly pressing and releasing the preset button 2022.

The tub fill controls 2050 provide fill settings of low, medium, and high. The alarm enunciator 2034 is activated when the tub is filled to the desired setting.

The temperature control allows a user to adjust temperature with the handle 2020 while the display 2024 provides visual feedback. Tactile feedback is provided by the knob mechanism. A backlight indicator may be provided to assist in locating the handle 2020. Temperature is configured to increase with counterclockwise rotation and to decrease with clockwise rotation.

The flow control provides various settings for the handle 2018 including full flow, low flow, and auto. At full flow, the controller 2012 provides for full flow of the water. Auto pause sets the water to full flow, sounds an alarm when the set temperature has been reached, and shuts off flow until the user changes flow setting or presses on/off. A backlight indicator may be provided to facilitate in locating the handle 2018 (full flow, low flow, and auto).

A manual valve override may be provided to enable the user to manually adjust temperature and flow in the event of power or electronics failure. The temperature illustratively increases with counterclockwise rotation and decreases with clockwise rotation. Flow shuts off with full clockwise rotation. The manual valve override may be of the type detailed above.

The display 2024 is activated when the user performs any one of a variety of actions. For example, the display 2024 is activated when the user pushes the on/off button 2048 to activate flow, when the user adjusts temperature control 2020, or when the user pushes a memory preset button 2022. The display 2024 may also be activated when the user adjusts flow control, or pushes the fill control button.

The display 2024 is deactivated when the user performs certain actions or fails to act within a predetermined time period. For example, the display 2024 is deactivated if the user pushes the on/off button 2048 to turn flow off. The display 2024 also illustratively times out 15 seconds after the user adjusts temperature, flow, fill, and while the water is not on.

The set temperature and the actual temperature are displayed within a range, illustratively 60-110° F., and are shown with 4 digits having one decimal place. Indicators are provided to indicate fill settings (low, medium, and high). A low battery indicator may include an icon which illuminates to provide an indication of low battery life, illustratively less than approximately 20% of battery life remaining. Low, full, and auto modes of flow may also be indicated. The enunciator 2034, illustratively an audio transducer, sounds an audible alarm when the shower reaches the desired set temperature. The enunciator 2034 also sounds when the tub fill reaches the desired fill setting and when the tub is in an over fill condition. An overfill condition may be determined by sensors (not shown) positioned within the tub.

The temperature handle 2020 may be symmetrical, with no pointer or indicator, that is continuously adjustable (i.e., no stops). The temperature handle 2020 is configured to be rotated counterclockwise for hot and clockwise for cold. The handle 2020 provides tactile feedback and a backlight indicator is provided to facilitate handle location.

The flow control handle 2018 may have a similar appearance as the temperature control handle 2020. Push buttons may select full and auto pause modes. The handle 2018 provides tactile feedback and a backlight is provided for facilitating location of the handle 2018.

The tub/shower flow diverters 2030 and 2038 may be of conventional design and may be integrated with the user interface panel. The diverters 2036 and 2038 and body sprays 2044 are likewise of conventional design.

The valve controls illustratively include flow of 9 gpm at 60 psi. Closed loop motor control (60-118° F.) includes thermistor 2008 and a relative encoder set point.

A temperature maintain function may be provided by a combination of components, including a tub water temperature sensor and a heating device, and is further detailed herein. Illustratively, the temperature of the tub water is maintained by a recirculating pump (i.e., jetted tub), by radiated heating tubes in thermal communication with the tub water, or by recirculation of hot water from a hot water heater, all in the manner further detailed herein.

The tub/shower system illustratively includes a digital user interface with a display combined with sensors (temperature, capacitance, etc.), a gear motor driven tub/shower valve (pressure balance or thermostatic), heating element in tub, audible alarm, motor driven diverter valve(s) for: (1) setting and maintaining the temperature of water entering either the tub or shower; (2) automatically filling the tub to predetermined level and temperature and alarming when complete; (3) maintaining the temperature of the water in the tub to a pre-determined temperature; (4) remotely control the tub/shower system from hand shower or other remote user interface; (5) sensor measuring temperature of water in tub sends signal to (a) recirculation pump to keep hot water available during bathing, and (b) alarm when temperature reaches lower limit (children in tub); (6) control volume flow rate from shower head and hand shower; and (7) control flow of water to multiple jets in shower.

As detailed herein, the various modules of the system 10 are configured to communicate with each other. The system 10 can also be networked to lighting, exhaust fans, radios, or other devices in the bathroom 102 to automatically turn them on or off as individuals enter or leave the bathroom. For example, the system may be configured to activate an exhaust fan in response to a person entering the bathroom 102 or turning on water in the shower. The system may be further configured to deactivate the exhaust fan a predetermined time after the shower has been turned off or the person leaves the bathroom 102.

As detailed further herein, a sensor (IR, RF, Ultrasound, thermal, etc.) may determine when a person has entered a bathroom 102. The sensor sends a signal (IR, RF, Ultrasound, thermal, etc.) to a controller which instructs a recirculation pump to begin pumping hot water to the bathroom. The system tracks when people enter the bathroom 102 and use hot water (via shower, tub or lavatory). The system may use trend analysis to predict when hot water will be required. Thus, if the system sees Monday through Friday shower usage at 6:30 AM, the system may initiate the recirculation pump at 6:15 AM to ensure hot water is available at 6:30. Logic in the controller determines trends. Hot water is therefore accessible at the lavatory and tub shower. A temperature sensor may send a signal deactivating the pump when the predetermined water temperature is reached (for example, 98-120° F.). Either electronic hands free or manual faucets may be integrated within the system. A detecting sensor may also send a signal (IR, RF, Ultrasound, thermal, etc.) to power "light emitting devices" on the faucet and tub shower to emit light. Thus serving as "nightlight" and aid visual perception of the user interface. Lights may be timed to turn off via timer or detection sensor (IR, RF, Ultrasound, thermal, etc.) of a person leaving the bathroom. If a faucet is inadvertently left on, a detecting sensor (IR, RF, Ultrasound, thermal, etc.) determines when a person has left the bathroom and sends a signal to the faucet to deactivate. The system may be programmable to allow any or all of the features to be active or inactive.

As described herein, the system 10 may illustratively comprise a plurality of modules which have a "plug and play" configuration. Moreover, the fluid couplings and electrical connections of the modules may be arranged for simple interconnections. Further, the fluid and electrical components of each individual module may have such a "plug and play" configuration, thereby permitting customization by the user. For example, the hands free module, the quick hot modules, battery compartments, hydro-generators, and recirculation pumps may all be configured for modular interconnections. In one illustrative embodiment, a master manifold or module may be provided and each desired module plugged or inserted therein such that proper electrical and fluid couplings are automatically made. As such, a user may simply insert and remove modules and their respective components without having to make extensive electrical or plumbing connections.

Communication between the various modules, and components within each module, may be provided through RF transmissions, as detailed herein. The transmitters, receivers, and transceivers of each module may operate under the ZigBee specification. As is known, ZigBee is a set of high level communication protocols designed to use small, low power digital radios based on the IEEE 802.15.4 standard for wireless personal area networks (WPANs). As such, the system 10 may be integrated within a smart house such that the bathroom modules detailed above may talk with other smart devices, such as exhaust fans, lights, alarm clocks, kitchen appliances, radios, etc. For example, the custom shower module could communicate with an exhaust fan such that it is activated in response to shower water flow and operates for a given time after such water flow stops. As a further example, an alarm clock could communicate with the custom shower module such that water flow is initiated a predetermined time after the alarm is turned off.

Although the invention has been described in detail with reference to certain preferred embodiments, variations and modifications exist within the spirit and scope of the invention as described and defined in the following claims.

The invention claimed is:

1. A shower system comprising:
   a plurality of water outlets configured to discharge water when active;
   a controller including a memory and configured to control the discharge of water through the plurality of water outlets;
   a user interface in communication with the controller and including a plurality of user defined presets wherein each preset includes a shower setting stored in the memory by a user and defining an arrangement of active water outlets and a set temperature of water discharged from the active water outlets;
   a proximity sensor in communication with the controller; and
   a temperature sensor configured to detect the temperature of water exiting the active water outlets and in communication with the controller,
   wherein the controller is configured to stop the flow of water to the water outlets when the proximity sensor detects no user within a predetermined distance of the water outlets and the temperature sensor detects that the temperature of water exiting the active water outlets is at least as great as a predetermined value.

2. The shower system of claim 1, further comprising a plurality of electrically operable valves operably coupled to the controller and in fluid communication with the plurality of water outlets to control the discharge of water from the water outlets.

3. The shower system of claim 2, further comprising a temperature control valve operably coupled to the controller and in fluid communication with a hot water supply and a cold water supply to control the temperature of water discharged from the active water outlets.

4. The shower system of claim 1, wherein the user interface further includes a plurality of water outlets controls configured to independently control the discharge of water from the water outlets.

5. The shower system of claim 4, wherein the user interface further includes a temperature control configured to independently control the temperature of water discharged from the active water outlets.

6. The shower system of claim 5, wherein the preset configuration is stored in memory by a user manipulating the water outlets controls, to define the arrangement of active water outlets, and by a user manipulating the temperature control, to define a temperature of water discharged from the active water outlets.

7. The shower system of claim 1, further comprising at least one actuator in communication with the controller and operably coupled to at least one of the water outlets, the at least one actuator configured to adjust the position of the at least one water outlet.

8. The shower system of claim 7, wherein each preset is associated with the at least one actuator, wherein activating each preset controls the actuator and the resulting position of the at least one water outlet.

9. The shower system of claim 7, wherein the actuator is configured to drive the at least one water outlet in translational movement.

10. The shower system of claim 7, wherein the actuator is configured to drive the at least one water outlet in rotational movement.

11. The shower system of claim 1, wherein the plurality of water outlets includes a plurality of body sprays and an overhead shower.

12. The shower system of claim 1, further comprising an audible alarm in communication with the controller and configured to be activated when the temperature sensor detects a temperature at least as great as the predetermined value.

13. The shower system of claim 1, wherein the user interface further includes a temperature display in communication with the controller.

14. The shower system of claim 2, wherein the plurality of water outlets includes a plurality of body sprays, and actuating each preset controls the operational state of at least one of the electrically operable valves to provide a user defined arrangement of active body sprays.

15. The shower system of claim 14, wherein actuating one of the presets a first time activates a corresponding body spray, and actuating the one preset a second time deactivates the corresponding body spray.

16. A shower system comprising:
a water outlet configured to discharge water when active;
a controller configured to control the discharge of water through the water outlet;
a user interface in communication with the controller and including at least one user defined preset defining the active water outlet and a set temperature of water discharged from the active water outlet;
a proximity sensor in communication with the controller; and
a temperature sensor configured to detect the temperature of water exiting the active water outlet and in communication with the controller,
wherein the controller is configured to stop the flow of water to the water outlet when the proximity sensor detects no user within a predetermined distance of the water outlet and the temperature sensor detects that the temperature of water exiting the active water outlet is at least as great as a predetermined value.

17. The shower system of claim 16, further comprising a temperature control valve operably coupled to the controller and in fluid communication with a hot water supply and a cold water supply to control the temperature of water discharged from the active water outlet.

18. The shower system of claim 16, further comprising an audible alarm in communication with the controller and configured to be activated when the temperature sensor detects a temperature at least as great as the predetermined value.

19. The shower system of claim 16, wherein the user interface further includes a temperature display in communication with the controller.

* * * * *